US011384328B2

(12) United States Patent
Gannon et al.

(10) Patent No.: US 11,384,328 B2
(45) Date of Patent: Jul. 12, 2022

(54) CARTRIDGE-BASED SYSTEM FOR LONG TERM CULTURE OF CELL CLUSTERS

(71) Applicant: President and Fellows of Harvard College, Cambridge, MA (US)

(72) Inventors: Alanna R. Gannon, Medford, MA (US); Aaron L. Glieberman, Cambridge, MA (US); Kevin Kit Parker, Cambridge, MA (US); Benjamin D. Pope, Medford, MA (US); Kevin L. Shores, Virginia Beach, VA (US); Nina R. Sinatra, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1063 days.

(21) Appl. No.: 15/777,242

(22) PCT Filed: Nov. 18, 2016

(86) PCT No.: PCT/US2016/062693
§ 371 (c)(1),
(2) Date: May 18, 2018

(87) PCT Pub. No.: WO2017/087759
PCT Pub. Date: May 26, 2017

(65) Prior Publication Data
US 2018/0327702 A1    Nov. 15, 2018

Related U.S. Application Data

(60) Provisional application No. 62/411,124, filed on Oct. 21, 2016, provisional application No. 62/395,512, (Continued)

(51) Int. Cl.
*C12M 3/00*     (2006.01)
*G01N 33/50*    (2006.01)
(Continued)

(52) U.S. Cl.
CPC ............ *C12M 23/42* (2013.01); *C12M 21/08* (2013.01); *C12M 23/12* (2013.01); *C12M 23/16* (2013.01);
(Continued)

(58) Field of Classification Search
CPC ...... C12M 23/42; C12M 23/16; C12M 23/12; C12M 25/14; C12M 21/08; C40B 40/10; C12Q 1/00; G01N 33/5082; G01N 33/507
See application file for complete search history.

(56) References Cited

U.S. PATENT DOCUMENTS 6,027,694 A  * 2/2000 Boulton ............... B01J 19/0046
                                                    422/553
6,713,772 B2   3/2004 Goodman et al.
(Continued)

FOREIGN PATENT DOCUMENTS

EP    0387975 A1   9/1990
EP    1302535 A1   4/2003
(Continued)

OTHER PUBLICATIONS

Alford, P.W., et al., "Biohybrid Thin Films for Measuring Contractility in Engineered Cardiovascular Muscle." Biomaterials. 2010, 31: 3613-3621.
(Continued)

*Primary Examiner* — Michael L Hobbs
(74) *Attorney, Agent, or Firm* — McCarter & English, LLP; Maria Laccotripe Zacharakis; Anita M. Bowles

(57) ABSTRACT

Microfluidic systems including a housing configured to receive a cartridge, the cartridge including a plurality of wells for receiving one or more biological cells are described herein. The microfluidic systems include a structure with channels for introducing a medium into the housing and through channels the cartridge. Microfluidic systems
(Continued)

including a housing configured to receive a cartridge, the housing including channels for loading one or more biological cells within wells of the cartridge are described herein. Three-dimensional scaffolds, devices, and systems comprising such scaffolds that mimic the in vivo structure, physical properties, and protein composition of extracellular matrix surrounding pancreatic islet cells and adipocytes, and the use of such compositions, devices and systems for, e.g., in vitro drug screening and/or toxicity assays, disease modeling, and therapeutic applications are also described herein.

15 Claims, 59 Drawing Sheets

Related U.S. Application Data filed on Sep. 16, 2016, provisional application No. 62/332,092, filed on May 5, 2016, provisional application No. 62/262,687, filed on Dec. 3, 2015, provisional application No. 62/256,939, filed on Nov. 18, 2015.

(51) Int. Cl.
| | |
|---|---|
| *C12M 3/06* | (2006.01) |
| *C40B 40/10* | (2006.01) |
| *C12Q 1/00* | (2006.01) |
| *C12M 1/32* | (2006.01) |
| *C12M 1/12* | (2006.01) |

(52) U.S. Cl.
CPC ............... *C12M 25/14* (2013.01); *C12Q 1/00* (2013.01); *C40B 40/10* (2013.01); *G01N 33/507* (2013.01); *G01N 33/5082* (2013.01)

(56) References Cited

U.S. PATENT DOCUMENTS

| | | | |
|---|---|---|---|
| 6,821,107 B1 | 11/2004 | Hara et al. | |
| 6,829,035 B2 | 12/2004 | Yogev | |
| 7,043,292 B2 | 5/2006 | Tarjan et al. | |
| 7,115,377 B2 | 10/2006 | Yao et al. | |
| 7,122,307 B2 | 10/2006 | Rosen et al. | |
| 8,492,150 B2 | 7/2013 | Parker et al. | |
| 8,748,181 B2 | 6/2014 | Kuo et al. | |
| 8,999,378 B2 | 4/2015 | Parker et al. | |
| 9,012,172 B2 | 4/2015 | Parker et al. | |
| 9,068,168 B2 | 6/2015 | Feinberg et al. | |
| 9,383,350 B2 | 7/2016 | Parker et al. | |
| 9,669,141 B2 | 6/2017 | Parker et al. | |
| 9,719,982 B2 | 8/2017 | Parker et al. | |
| 9,857,356 B2 | 1/2018 | Parker et al. | |
| 10,997,871 B2 | 5/2021 | Parker et al. | |
| 2001/0023073 A1 | 9/2001 | Bhatia et al. | |
| 2002/0137715 A1 | 9/2002 | Mauviel | |
| 2003/0059103 A1 | 3/2003 | Shiomi et al. | |
| 2003/0059537 A1 | 3/2003 | Chilkoti et al. | |
| 2003/0134331 A1 | 7/2003 | Marks et al. | |
| 2004/0009566 A1 | 1/2004 | Okano et al. | |
| 2004/0048239 A1 | 3/2004 | Farinas et al. | |
| 2004/0078090 A1 | 4/2004 | Binette et al. | |
| 2004/0101819 A1 | 5/2004 | Montemagno et al. | |
| 2005/0048414 A1 | 3/2005 | Harnack et al. | |
| 2005/0080402 A1 | 4/2005 | Santamore et al. | |
| 2005/0085847 A1 | 4/2005 | Galdonik et al. | |
| 2005/0202569 A1 | 9/2005 | Sakaino et al. | |
| 2005/0287557 A1 | 12/2005 | Efendic | |
| 2006/0003439 A1 | 1/2006 | Ismagilov et al. | |
| 2006/0029922 A1 | 2/2006 | Van Eelen et al. | |
| 2006/0071286 A1 | 4/2006 | Axelrod et al. | |
| 2006/0134692 A1 | 6/2006 | Emmert-Buck et al. | |
| 2006/0136182 A1 | 6/2006 | Vacanti et al. | |
| 2006/0153816 A1 | 7/2006 | Brown et al. | |
| 2006/0253192 A1 | 11/2006 | Atala | |
| 2007/0053996 A1 | 3/2007 | Boyden et al. | |
| 2007/0060815 A1 | 3/2007 | Martin et al. | |
| 2007/0164641 A1 | 7/2007 | Pelrine et al. | |
| 2007/0184494 A1* | 8/2007 | McBride ............ B01D 67/0088 |
| | | | 435/7.9 |
| 2007/0190646 A1 | 8/2007 | Engler et al. | |
| 2007/0197857 A1 | 8/2007 | Palmer | |
| 2008/0031818 A1 | 2/2008 | Bush | |
| 2008/0085265 A1 | 4/2008 | Schneider et al. | |
| 2008/0118985 A1 | 5/2008 | Torres et al. | |
| 2009/0023773 A1 | 1/2009 | Vohra et al. | |
| 2009/0054954 A1 | 2/2009 | Foley et al. | |
| 2009/0061031 A1 | 3/2009 | Lee-Huang et al. | |
| 2009/0098628 A1 | 4/2009 | Ramasubramanian | |
| 2009/0317852 A1 | 12/2009 | Parker et al. | |
| 2010/0041972 A1 | 2/2010 | Mason | |
| 2010/0196432 A1 | 8/2010 | Feinberg et al. | |
| 2010/0305460 A1 | 12/2010 | Pinter et al. | |
| 2010/0330644 A1 | 12/2010 | Feinberg et al. | |
| 2011/0041935 A1 | 2/2011 | Zhou et al. | |
| 2011/0189719 A1 | 8/2011 | Kuo et al. | |
| 2011/0250585 A1 | 10/2011 | Ingber et al. | |
| 2012/0029416 A1 | 2/2012 | Parker et al. | |
| 2012/0134570 A1 | 5/2012 | Trumbull et al. | |
| 2012/0135448 A1 | 5/2012 | Parker et al. | |
| 2012/0142556 A1 | 6/2012 | Parker et al. | |
| 2013/0046134 A1 | 2/2013 | Parker et al. | |
| 2013/0053625 A1 | 2/2013 | Merc Vives | |
| 2013/0234013 A1 | 9/2013 | Patterson et al. | |
| 2013/0289675 A1 | 10/2013 | Deisseroth et al. | |
| 2013/0312638 A1 | 11/2013 | Parker et al. | |
| 2013/0330378 A1 | 12/2013 | Parker et al. | |
| 2014/0080206 A1 | 3/2014 | Dahan et al. | |
| 2014/0151224 A1* | 6/2014 | Glezer ................ B01J 19/0046 |
| | | | 204/407 |
| 2014/0235826 A1 | 8/2014 | Deisseroth et al. | |
| 2014/0236267 A1 | 8/2014 | Parker | |
| 2014/0311912 A1 | 10/2014 | Shih et al. | |
| 2014/0322515 A1 | 10/2014 | Parker et al. | |
| 2014/0342394 A1 | 11/2014 | Parker et al. | |
| 2014/0370111 A1 | 12/2014 | Boyan et al. | |
| 2014/0377320 A1 | 12/2014 | Pietramaggiori et al. | |
| 2015/0004077 A1 | 1/2015 | Wikswo et al. | |
| 2015/0182679 A1 | 7/2015 | Parker et al. | |
| 2015/0219622 A1 | 8/2015 | Hickman | |
| 2015/0253307 A1 | 9/2015 | Parker et al. | |
| 2015/0354094 A1 | 12/2015 | Parker et al. | |
| 2016/0003806 A1 | 1/2016 | Parker et al. | |
| 2016/0331528 A1 | 11/2016 | Parker et al. | |
| 2017/0016875 A1 | 1/2017 | Parker et al. | |
| 2018/0172672 A1 | 6/2018 | Parker et al. | |
| 2018/0209957 A1 | 7/2018 | Parker et al. | |
| 2018/0327702 A1 | 11/2018 | Gannon et al. | |
| 2018/0357927 A1 | 12/2018 | Parker et al. | |
| 2018/0372725 A1 | 12/2018 | Parker et al. | |

FOREIGN PATENT DOCUMENTS

| | | | |
|---|---|---|---|
| WO | WO-2004/014212 A2 | 2/2004 | |
| WO | WO-2006/068972 A2 | 6/2006 | |
| WO | WO-2008/045506 A2 | 4/2008 | |
| WO | WO-2008/051265 A2 | 5/2008 | |
| WO | WO-2010/127280 A1 | 11/2010 | |
| WO | WO-2010/132636 A1 | 11/2010 | |
| WO | WO-2011/102991 A1 | 8/2011 | |
| WO | WO-2012/006320 A1 | 1/2012 | |
| WO | WO-2012/048242 A1 | 4/2012 | |
| WO | WO-2012/131360 A2 | 10/2012 | |
| WO | WO-2013/086512 A2 | 6/2013 | |
| WO | WO-2013/115896 A2 | 8/2013 | |
| WO | WO-2016/007879 A1 | 1/2016 | |
| WO | WO-2016/045813 A1 | 3/2016 | |
| WO | WO-2016/069142 A2 | 5/2016 | |
| WO | WO-2016/191179 A1 | 12/2016 | |
| WO | WO-2017/027390 A1 | 2/2017 | |

(56) References Cited

FOREIGN PATENT DOCUMENTS

| WO | WO-2017/087759 A1 | 5/2017 |
|----|-------------------|--------|
| WO | WO-2018/027105 A1 | 2/2018 |
| WO | WO-2019079714     | 4/2019 |

OTHER PUBLICATIONS

Yang et al., "Fabrication of well-defined PLGA scaffolds using novel microembossing and carbon dioxide bonding", Biomaterials, 2005, vol. 25., pp. 2585-2594.

Bray et al., "Sarcomere Alignment is Regulated by Myocyte Shape" *Cell Motility and the Cytoskeleton*, Aug. 2008, 65(8), pp. 641-651.

Parker et al., "Extracellular matrix, mechanotransduction and structural hierarchies in heart tissue engineering." Phil Trans R. Soc B, Epub, Jun. 22, 2007, vol. 362, pp. 1267-1279.

Park et al., "Real-Time Measurement of the Contractile Forces of Self-Organized Cardiomyocytes on Hybrid Biopolymer Microcantilevers," Anal. Chem. Oct. 2005, 77:6571-6580.

Mao et al., "Capillary isoelectric focusing with whole column imaging detection for analysis of proteins and peptides," J. Biochem. Biophys. Methods, Feb. 1999, 39:93-110.

International Search Report from PCT/US2011/043027 dated Jul. 6, 2011.

Badrossamay, M.R. et al. "Nanofiber assembly by rotary jet-spinning." Nano Letters, May 2010;10(6):2257-2261.

Vandenburgh et al., "Drug-Screening Platform Based on the Contractility of Tissue-Engineered Muscle", Muscle Nerve 37:438-447, 2008.

Kim et al., "Biohybrid Microsystems Actuated by Cardiomyocytes: Microcantilever, Microrobot, and Micropump", Proceedings—IEEE International Conference on Robotics and Automation. 880-885. (2008).

Shimizu et al."Microfluidic devices for construction of contractile skeletal muscle microtissues" Journal of Bioscience and Bioengineering, vol. 119, Issue 2, Feb. 2015, pp. 212-216.

Luo, Y and Zare, RN, "Perforated membrane method for fabricating three-dimensional polydimethylsiloxane microfluidic devices", Lab Chip, 2008, 8, 1688-1694. doi: 10.1039/b807751g.

Xi et al., "Development of a Self-Assembled Muscle-Powered Piezoelectric Microgenerator", NSTI-Nanotech, 2004, vol. 1, pp. 3-6.

International Search Report from PCT/US2013/060823, dated Apr. 15, 2014.

International Search Report and Written Opinion from PCT/US2015/016395, dated Jan. 6, 2016 pp. 1-16.

International Preliminary Report on Patentability for Application No. PCT/US2015/051818, dated Apr. 6, 2017. 8 pages.

International Search Report and Written Opinion from PCT/US2015/051818 dated Jun. 2, 2016.

Bol, M., et al. "Computational modeling of muscular thin films for cardiac repair." Computational Mechanics. Sep. 13, 2009;43(4):535-44.

Feinberg, A.W., et al. "Muscular thin films for building actuators and powering devices." Science. Sep. 7, 2007;317(5843):1366-70.

Geisse, N.A., et al. "Micropatterning Approaches for Cardiac Biology." In: Khademhosseini A, Toner M, Borenstein JT, Takayama S, editors. Micro- and Nanoengineering of the Cell Microenvironment: Technologies and Applications. Boston: Artech House;2008, p. 341-357.

Nawroth et al., "A Tissue-engineered jellyfish with biomimetic propulsion", Nature Biotechnology, 2012, vol. 30, No. 8, pp. 792-800.

Johnsrude et al., "Mechanical Properties of the Myotomal Muscoskeletal System of Rainbow Trout, Salmo Gairdneri", Journal of Exp. Biol., 1985, vol. 119, pp. 71-83.

Parker, K.K.,et al. "Myofibrillar architecture in engineered cardiac myocytes. <http://diseasebiophysics.seas.harvard.edu/pdfs/017-2008AugC- ircRes.pdf>" Circ Res. Aug. 15, 2008;103(4):340-2.

Hu, S et al "Mechanical Anisotropy of Adherent Cells Probed by a Three-dimensional Magnetic Twisting Device" Am J Physiol Cell Physiol, 2004, 287(5), pp. C1184-C1191.

Anversa et al., "Morphometry of exercise-induced right ventricular hypertrophy in the rat." (1983) Circ Res 52:57-64.

Anversa et al., "Myocyte Cell Loss and Myocyte Hypertrophy in the Aging Rat Heart" (1986) J Amer Coll Cardiol 7:1140-9.

Atherton et al., "Assembly and remodeling of Myofibrils and Intercalated Discs in Cultured Neonatal Rat Heart Cells" (1986) J Cell Sci 86:233-48.

Balaban et al., "Force and focal adhesion assembly: a close relationship studied using elastic micropatterned substrates" (2001) Nat Cell Biol 3:466.

Beauchamp et al., "Relative Contributions of Connexins 40 and 43 to Atrial Impulse Propagation in Synthetic Strands of Neonatal and Fetal Murine Cardiomyocytes" (2006) Circ Res 99:1216-24.

Bershadsky et al., "Adhesion-Dependent Cell Mechanosensitivity" (2003) Annu Rev Cell Dev Biol 19:677.

Brancaccio et al., "Integrin signalling: The tug-of-war in heart hypertrophy" (2006) Cardiovasc Res 70:422-33.

Brower et al., "The relationship between myocardial extracellular matrix remodeling and ventricular function" (2006) Eur J Cardiothorac Surg 30:604-10.

Bursae et al., "Multiarm spirals in a two-dimensional cardiac substrate" (2004) Proc Natl Acad Sci USA 101:15530-4.

Camelliti et al., "Microstructured Cocuhures of Cardiac Myocylesand Fibroblasts: A Two Dimensional in Vitro Model of Cardiac Tissue" (2005) Microsc Microanal 11:249-59.

Chen et al., "Geometric Control of Cell Life and Death" (1997) Science 276:1425-8.

Chen et al., "Cell shape provides global control of focal adhesion assembly" (2003) Biochem Biophys Res Commun 307:355-61.

Chen et al., "Regional ventricular wall thickening reflects changes in cardiac fiber and sheet structure during contraction: quantification with diffusion tensor MRI" (2005) Am J. Physio.-Heart Circul Physiol 289:H1898-H1907.

Chrzanowska-Wodnicka et al., "Rho-Stimulated Contractility Drives the Formation of Stress Fibers and Focal adhesions" (1996) J Cell Biol 133:1403.

Dabiri et al., "Myofibrillogenesis visualized in living embryonic cardiomyocytes" (1997) Proc Natl Aced Sci USA 94:9493.

Danowski et al., "Costameres are Sites of Force Transmission to the Substratum in Adult Rat Cardiomyoctes" (1992) J Cell Biol 118:1411-20.

Dembo et al., "Stresses at the Cell-to-Substrate Interface during Locomotion of Fibroblasts" (1999) Biophys J 76:2307.

Ding et al., "Left Ventricular Hypertrophy in Ascending Aortic Stenosis Mice : Anoikis and the Progression to Early Failure" (2000) Circulation 101:2854-62.

Dlugosz et al. "The Relationship between Stress Riber-Like Structures and Nascent Myofibrils in Cultured Cardiac Myocytes" (1984) J Cell Biol 99:2268.

Du et al., "Myofibrillogenesis in the first cardiomyocytes formed from isolated quail precardiac mesoderm" (2003) Dev Biol 257:382.

Ehler et al., "Myofibrillogenesis in the developing chicken heart: assembly of Z-disk, M-line and the thick filaments" (1999) J Cell Sci 112 (Pt 10):1529.

Ezzell et al., "Vinculin Promotes Cell Spreading by Mechanically Coupling Integrins to the Cytoskeleton" (1997) Exp Cell Res 231:14-26.

Furuta et al., "Pulsatile Cardiac Tissue Grafts Using a Novel Three-Dimensional Cell Sheet Manipulation Technique Functionally Integrates With the Host Heart, In Vivo" (2006) Circ Res 98:705-12.

Galbraith et al., "The relationship between force and focal complex development" (2002) J Cell Biol 159:695.

Gerdes et al. (1988) Lab Invest 59:857-61.

Gerdes et al. (1992) Circulation 86:426-30.

Gopalan et al., "Anisotropic Stretch-induced Hypertrophy in Neonatal Ventricular Myocytes Micropatterned on Deformable Elastomers" (2003) Biotechnol Bioeng 81:578-87.

Harrington, et al., "Direct measurement of transmural laminar architecture in the anterolateral wall of the ovine left ventricle: new

(56) References Cited

OTHER PUBLICATIONS implications for wall thickening mechanics" (2005) Am J Physiol-Heart Circul Physiol 288:H1324-H1330.

Hilenski et al. "Myofibrillar and cytoskeletal assembly in neonatal rat cardiac myocytes cultured on laminin and collagen" (1991) Cell and Tissue Research 264:577-87.

Holtzer et al., "Independent Assembly of 1.6/an Long Bipolar MHCFilaments and 1-Z-1 Bodies" (1997) Cell Struct Funct 22:83.

Huang et al., "Control of Cyclin D1, p27Kip1, and Cell Cycle Progression in Human Capillary Endothelial Cells by Cell Shape and Cytoskeletal Tension" (1998) Mol Biol Cell 9:3179-93.

Ingber, "Integrins as Mechanochemical transducers" (1991) Current Opinion in Cell Biology 3:841-8.

Jiang et al., "Directing cell migration with asymmetric micropatterns" (2005) Proc Natl Acad Sci USA 102:975-8.

Komuro et al., "Control of Cardiac Gene Expression by Mechanical Stress" (1993) Annu Rev Physiol 55:55-75.

Legrice et al. "Laminar structure of the heart: ventricular myocyte arrangement and connective tissue architecture in the dog" (1995) Am J Physiol-Heart Circul Physiol 38:H571-H582.

Lehnert et al., "Cell behaviour on micropatterned substrata: limits of extracellular matrix geometry for spreading and adhesion" (2004) J Cell Sci 117:41-52.

Lin et al., "Polygons and Adhesions Plaques and the Disassembly and Assembly of Myofibrils in Cardiac Myocytes" (1989) J Cell Biol 108:2355-67.

Lu et al., The Vinculin/Sarcomeric-.alpha.-Actinin/.alpha.-Actin Nexus in Cultured Cardiac Myocytes: (1992) J Cell Biol 117:1007-22.

Mansour et al., "Restoration of Resting Sarcomere Length After Uniaxial Static Strain is Regulated by Protein Kinase C.sub.--and Focal Adhesion Kinase" (2004) Circ Res 94:642-9.

Maxwell et al., "The integration of tissue structure and nuclear Function" (2001) Biochemistry and Cell Biology 79:267-74.

McKenna et al., "Formation and Alignment of Z Lines in Living Chick Myotubes Microinjected with Rhodamine-Labeled Alpha-Actinin" (1986) J Cell Biol 103:2163.

O'Neill et al., "Narrow linear strips of adhesive substratum are powerful inducers of both growth and total focal contact area" (1990) J Cell Sci 95:577-86.

Novak et al., "Cooperativity between Cell Contractility and Adhesion" (2004) Phys Rev Lett 93, 268109.

Onodera et al., "Maladaptive Remodeling of Cardiac Myocyte Shape Begins Long Before Failure in Hypertension" (1998) Hypertension 32:753-7.

Parker et al., "Directional control of lamellipodia extension by constraining cell shape and orienting cell tractional forces" (2002) Faseb J 16:1195.

Pelham et al., "Cell locomotion and focal adhesions are regulated by substrate flexibility" (1997) Proc Natl Aced Sci USA 94:1366.

Rhee et al., "The Premyofibril: Evidence for Its Role in Myofi brillogenesis"(1994) Cell Motil Cytoskeleton 28:1.

Rohr et al., "Patterned growth of neonatal rat heart cells in culture. Morphological and electrophysiological characterization" (1991) Circ Res 68:114-30.

Rothen-Rutishauser et al., "Different Behaviour of the Non-sarcomeric Cytoskeleton in Neonatal and Adult Rat Cardiomyocytes" (1998) J Mol Cell Cardiol 30:19-31.

Russell et al., "Form follows function: how muscle shape is regulated by work" (2000) J Appl Physiol 88, 1127.

Samarel, "Costameres, focal adhesions, and cardiomyocyte mechanotransduction" (2006) Am J Physiol Heart Circ Physiol 289:H2291-H2301.

Sands et. al., "Automated Imaging of Extended Tissue Volumes Using Confocal Microscopy" Microscopy Research and Technique 67:227-239 (2005).

Sanger et al., "Myofibrillogenesis in Living Cells Microinjected with Fluorescently Labels Alpha-Actinin" (1986) J Cell Biol 102:2053.

Siegrist et al., "Extrinsic cues orient the cell division axis in *Drosophila* embryonic neuroblasts" (2006) Development 133:529.

Simpson et al., "Mechanical regulation of cardiac myocyte protein turnover and myofibrillar structure" (1996) Am J Physiol Cell Physiol 270:C1075-C1087.

Simpson et al. "Regulation of Cardiac Myocyte Protein Turnover and Myofibrillar Structure in Vitro by Specific Directions of Stretch" (1999) Circ Res 85:e59-e69.

Singhvi et al., "Engineering Cell Shape and Function" (1994) Science 264:696-8.

Smilenov et al., "Focal Adhesion Motility Revealed in Stationary Fibroblasts" (1999) Science 286:1172.

Smith et al., "Regional Myocyte Size in Compensated Right Ventricular Hypertrophy in the Ferret" (1985)17:1005-11.

Tan et al., "Simple Approach to Micropattern Cells on Common Culture Substrates by Tuning Substrate Wettability" (2004) Tissue Eng 10:865.

Thery et al., "Cell Distribution of Stress Fibres in Response to the Geometry of the Adhesive Environment" (2006) Cell Motil Cytoskeleton 63:341.

Tokuyasu et al., "Intermediate Filaments in Skeletal and Cardiac Muscle Tissue in Embryonic and Adult Chicken .sup.a"(1985) Ann NY Acad Sci 455:200-12.

Tokuyasu, "Immunocytochemical Studies of Cardiac Myofibrillogenesis in Early Chick Embryos. III. Generation of Fasciae Adherentes and Costamers"(1989) J Cell Biol 108:43-53.

Torsoni et al., "Focal Adhesion Kinase is Activated and Mediates the Early Hypertrophic Response to Stretch in Cardiac Myocytes" (2003) Circ Res 93:140.

Young et al., "Extended confocal microscopy of myocardial laminae and collagen network" Journal of Microscopy, vol. 192, Pt 2, Nov. 1998, pp. 139-150.

Wang. "Reorganization of Actin Filament Bundles in Living Fibroblasts", (1984) J Cell Biol 99:1478.

Wang et al., "Micropatterning Tractional Forces in Living Cells" (2002) Cell Motil Cytoskeleton 52:97.

Weiss et al., "Shape and Movement of Mesenchyme Cells as Functions of the Physical Structure of the Medium Contributions to a Quantitative Morphology" (1952) Proc Natl Acad Sci USA 38:264-80.

Zamir et al., "Dynamics and segregation of cell-matrix adhesions in cultured fibroblasts" (2000) Nat Cell Biol 2:191.

Laanilainen, Eeva "Soft Lithography for Surface Micropatterning", Thesis, Helsinki Univ. of Tech., Jun. 29, 2006, 94 pp.

McDonald, JC and Whitesides, GM "Poly(dimethylsiloxane) as a Material for Fabricating Microfluidic Devices" Acc. Chem. Res., Jul. 2002, 35(7), pp. 491-499.

Narasimhan, SV; Goodwin, RL; Borg, TK; Dawson, DM; Gao, BZ "Multiple Beam Laser Cell Micropatterning System" Optical Trapping and Optical Micromanipulation, Proc. SPIE., Oct. 18, 2004, 5514, pp. 437-445.

Grasberg et al., "Ensembles of engineered cardiac tissues for physiological and pharmacological study: Heart on a chip." Lab Chip, 2011, vol. 11, p. 4165.

Spring, "Electronic Imaging in Neuroscience," Curr. Protoc. Neurosci. 2002, 2.4.1-2.4.9.

Pilarek et al., "Biological cardio-micro-pumps for microbioreactors and analytical micro-systems", (Aug. 2011), Sensors and Actuators B: Chemical, vol. 156,Issue 2, pp. 517-526.

International Search Report and Written Opinion from PCT/US2016/062693, dated Apr. 14, 2017.

\* cited by examiner

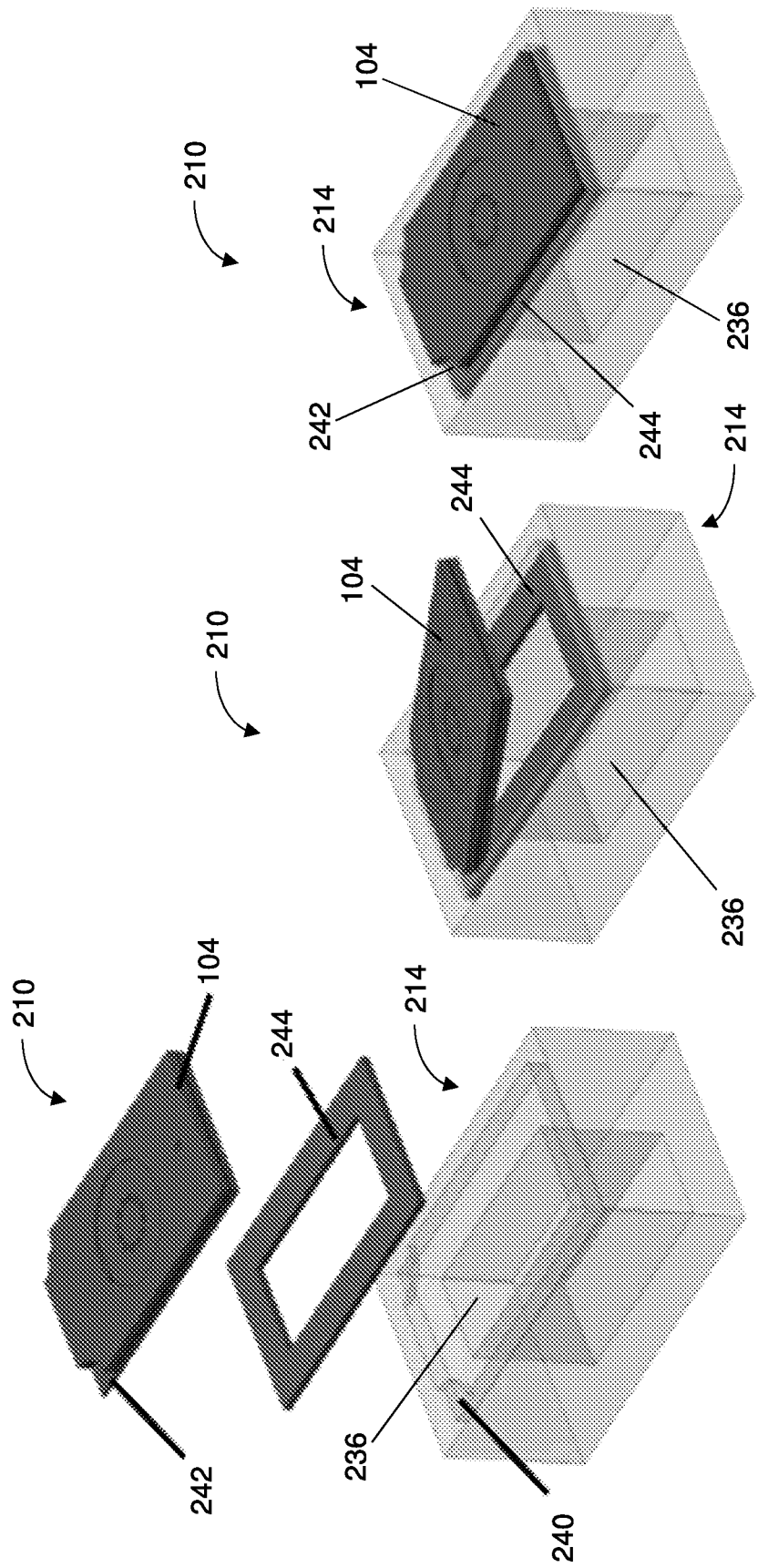

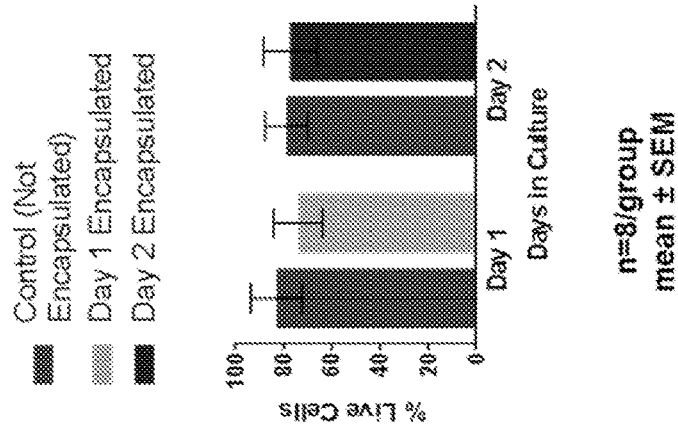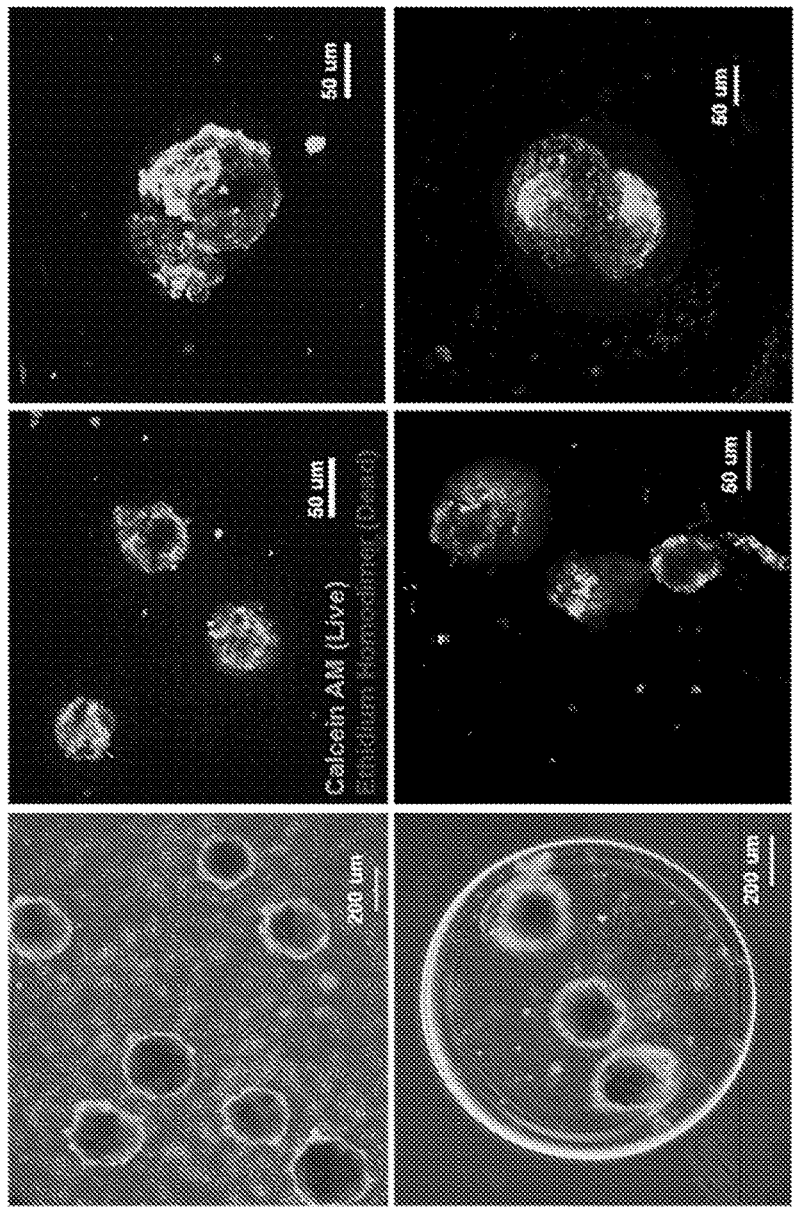
FIG. 15E, FIG. 15F, FIG. 15G, FIG. 15H, FIG. 15I, FIG. 15J, FIG. 15K SEM of Fibers Solid Support with Fibers

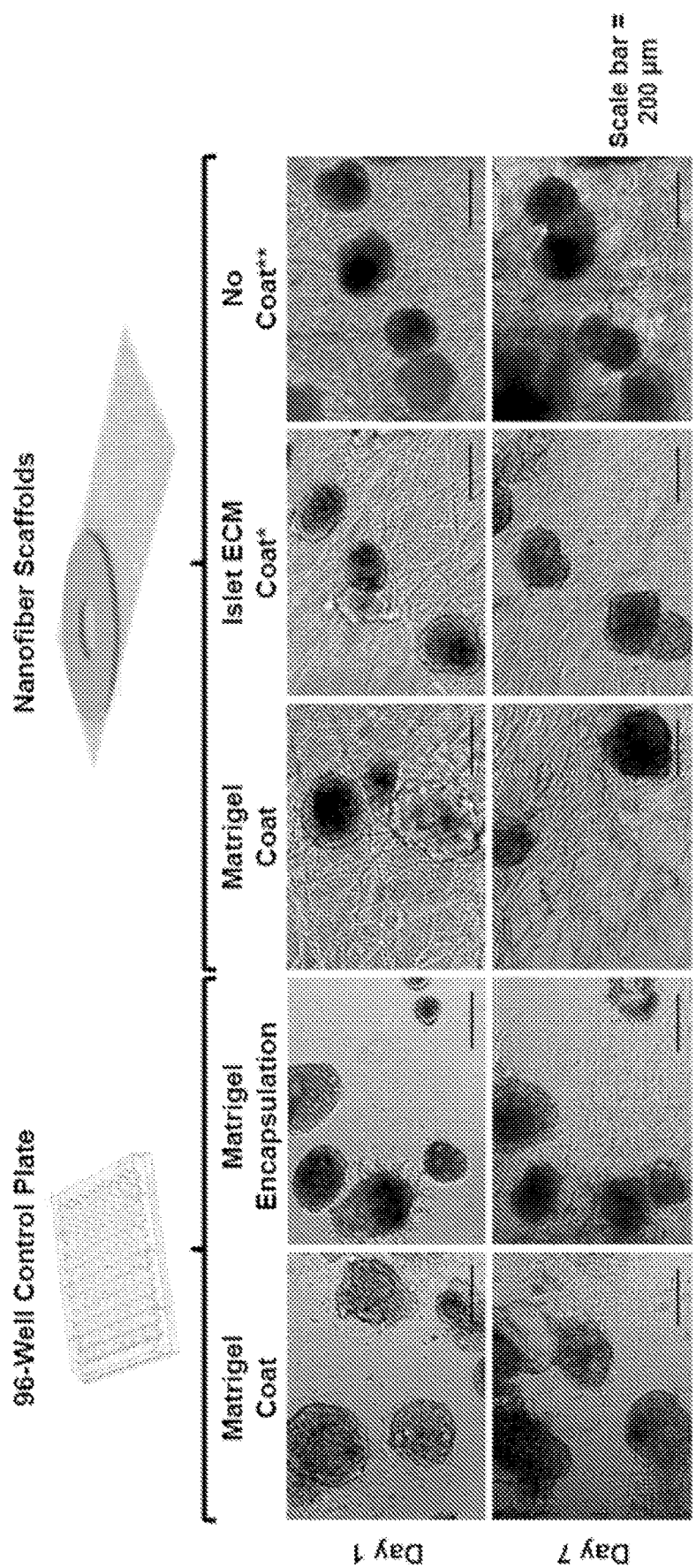

CARTRIDGE-BASED SYSTEM FOR LONG TERM CULTURE OF CELL CLUSTERS

RELATED APPLICATIONS

This application is a 35 U.S.C. § 371 national stage filing of International Application No. PCT/US2016/062693, filed on Nov. 18, 2016, which in turn claims priority to and benefit of U.S. Provisional Patent Application No. 62/411,124, entitled "Cartridge-Based System for Long Term Culture of Cell Clusters", filed on Oct. 21, 2016, U.S. Provisional Patent Application No. 62/395,512, entitled "Cartridge-Based Devices For Long-Term Culture of Cell Clusters and Methods of Use Thereof", filed on Sep. 16, 2016, U.S. Provisional Patent Application No. 62/332,092, entitled "Three-Dimensional Scaffolds For Cell Culture and Methods of Use Thereof", filed on May 5, 2016, U.S. Provisional Patent Application No. 62/262,687, entitled "Cartridge-Based Devices For Long-Term Culture of Cell Clusters and Methods of Use Thereof", filed on Dec. 3, 2015, and U.S. Provisional Patent Application No. 62/256,939, entitled "Cartridge-Based Devices For Long-Term Culture of Cell Clusters and Methods of Use Thereof", filed on Nov. 18, 2015, the entire contents of each of which are incorporated herein by reference.

GOVERNMENT SUPPORT

This invention was made with government support under grant number grant number UC4-DK104165-01, awarded by the National Institutes of Health (NIH), under grant number DK104165, awarded by the NIH, and under grant number DMR-1420570, awarded by the National Science Foundation—Materials Research Science and Engineering Center. The government has certain rights in the invention.

BACKGROUND OF THE INVENTION

Model organisms and existing human in vitro test systems do not adequately recapitulate human in vivo conditions and, therefore, are often inaccurate representations of human biology. As a result, a majority of drug candidates validated in animal or in vitro models fail in clinical trials due to toxicity and lack of efficacy in humans. Platforms that more closely mimic the human condition would help bridge this preclinical gap and more reliably model human biology. Additionally, the ability to culture, expand and differentiate target cells that make up in vivo tissue systems is clinically important for cell based therapies and tissue engineering.

Common methods and devices for maintaining differentiated cells involve plating the cells onto a generic substratum of an extracellular matrix component or suspending the cells in a medium comprised of hormones, growth factors and nutrients. More recently, microfluidic devices have been configured to enable integration and culture of living biological cells. While such culture systems may be adequate for culturing and/or propagating hematopoietic cancer cells and/or differentiated fibroblast cells, they are inadequate for maintaining the in vivo structural and functional characteristics of many cell types, e.g., pancreatic islet cells, adipocytes, or brain tissue cells, for periods of time necessary to permit relevant assays. Furthermore, such devices do not readily permit transfer of cells between different apparatuses for functional analysis.

For example, in vivo, pancreatic islet cells are surrounded by an islet capsule that is comprised of an isotropic network of collagen fibers that are approximately 50-100 nm thick. The current methods for culturing pancreatic islet cells involve the use of MATRIGEL-coated culture dishes or low attachment vessels for suspension culture. However, pancreatic islet cells cultured on MATRIGEL-coated culture dishes spread and lose their three-dimensional structure and function after about 5-7 days in culture. Similarly, islet cell mass is lost over time in suspension culture. Current methods for culturing adipocytes also involve the use of gelatin-coated culture dishes, but the use of gelatin-coated culture dishes does not permit the adipocytes to achieve or maintain in vivo structure or function. At most, adipocytes cultured on gelatin-coated culture dishes achieve a size about 8 times less than mature cells in vivo, e.g., adult human adipocytes, before floating off of the culture surface. Therefore, these cultured adipocytes do not function as they would in an in vivo environment.

Accordingly, there is a need in the art for suitable systems, devices, and methods for recapitulating human in vivo conditions of cells and cell clusters, as well as devices and methods for culturing a determined number of cells or cell clusters arranged within a predefined two-dimensional configuration such that the cells or cell clusters can be easily transferred from the culture device to different apparatuses for functional analysis, and then returned to the culture device after analysis.

SUMMARY OF THE INVENTION

Embodiments of the invention include cartridge-based systems for long term culture of cells (e.g., cell clusters), cartridges for use with such systems, and the use of such microfluidic systems and cartridges for, e.g., in vitro drug screening and/or toxicity assays, disease modeling, and therapeutic applications. In some embodiments, the systems or the cartridges include three-dimensional scaffolds that mimic the in vivo structure, physical properties, and protein composition of extracellular matrix surrounding cells, e.g., pancreatic islet cells or adipocytes, and the use of such compositions for, e.g., in vitro drug screening and/or toxicity assays, disease modeling, and therapeutic applications. In other embodiments, the use of the systems or the cartridges of the invention for, e.g., in vitro drug screening and/or toxicity assays, disease modeling, and therapeutic applications, include cells, e.g., cell clusters, e.g., pancreatic islet cells or adipocytes, encapsulated in microspheres of a polymer, e.g., a hydrogel, that promotes cell viability and functionality.

Accordingly, in one aspect, the present invention provides a system, e.g., a microfluidic system, including a housing and a cartridge. The housing includes a first housing portion and a second housing portion forming a chamber therebetween. The housing further includes an inlet for introduction of a medium into the system, an inlet channel fluidically connecting the inlet with a central portion of the chamber, an outlet, and an outlet channel fluidically connecting a peripheral portion of the chamber with the outlet.

The cartridge has a central portion and a peripheral portion and configured to be disposed within the chamber with the central portion of the cartridge disposed in the central portion of the chamber and the peripheral portion of the cartridge disposed in the peripheral portion of the chamber. The cartridge includes a cartridge body having a first surface and a second surface and defining a first plurality of channels disposed in the peripheral portion of the cartridge. Each channel of the first plurality of channels extends from the first surface to the second surface of the cartridge body. The cartridge includes at least one porous element (e.g., a filter) disposed adjacent to the second surface of the cartridge body at the first plurality of channels. The at least one porous element and the first plurality of channels form a plurality of wells disposed in the peripheral portion of the cartridge. Each well can be configured to hold one or more biological cells.

The housing and the cartridge can be configured such that when the cartridge is disposed within the housing and a medium is introduced into the inlet, the medium flows through the inlet channel and into the chamber. At least a first portion of the medium flows laterally between the first surface of the cartridge body and a chamber wall opposite the first surface of the cartridge body from the central portion of the chamber to the first plurality of channels. The first portion of the medium further flows through the first plurality of channels and the at least one porous element, and then flows through the outlet channel to the outlet of the housing.

In one embodiment, the outlet channel connects with a central portion of the chamber. The cartridge body can have a peripheral portion and a central portion that is disposed in the central portion of the chamber when the cartridge is held in the housing. The first plurality of channels can be disposed in the peripheral portion of the cartridge body. The cartridge body and housing can be configured such that when the cartridge is disposed within the housing and a medium is introduced into the inlet, the medium flows through the inlet channel and into central portion of the chamber, and at least a first portion of the medium flows radially outward between the first surface of the cartridge body and a chamber wall opposite the first surface of the cartridge body from the central portion of the cartridge body to the first plurality of channels, flows through the first plurality of channels and the at least one porous element, and then flows through the outlet channel to the outlet of the housing.

In one embodiment, the cartridge body defines a second plurality of channels extending from the first surface to the second surface of the cartridge body. Each channel in the first plurality of channels can be disposed radially outward from the central portion of the cartridge and each channel in the second plurality of channels can be disposed radially further from the central portion of the cartridge than any channel in the first plurality of channels (e.g., the second plurality of channels substantially surround the first plurality of channels).

In one embodiment, the housing and the cartridge can be configured such that when the cartridge is disposed within the housing and the medium flows through the inlet channel and into the central portion of the chamber, at least a second portion of the medium flows radially outward between the first surface of the cartridge body and the chamber wall from the central portion of the chamber past the first plurality of channels to the second plurality of channels, flows through the second plurality of channels, and then flows through the outlet channel to the outlet of the housing. In one embodiment, the housing and the cartridge can be configured such that when at least the second portion of the medium flows radially outward between the first surface of the cartridge body and the chamber wall from the central portion of the chamber past the first plurality of channels to the second plurality of channels, the medium flows into each of the second plurality of channels at substantially the same time. In one embodiment, the housing and the cartridge are configured such that when at least the first portion of the medium flows radially outward between the first surface of the cartridge body and the chamber wall opposite the first surface of the cartridge body from the central portion of the chamber to the first plurality of channels, the medium flows into each of the first plurality of channels at substantially the same time. In one embodiment, the housing defines a plurality of branched channels that fluidly connect with the inlet channel and the chamber.

In one embodiment, the first housing portion can have a surface including a recessed portion, the recessed portion fluidically connected to the inlet channel and configured such that when the cartridge is disposed within the chamber and media is introduced into the system, the recessed portion receives media that flows through the inlet channel, into the chamber, and between the surface having the recessed portion and the first surface of the cartridge body. In one embodiment, the second housing portion can have a surface including a recessed central portion configured and dimensioned to receive the cartridge. In one embodiment, the cartridge body can have a perimeter with a circular portion corresponding to a rounded edge and a straight portion corresponding to a planar edge, the planar edge orienting the cartridge within the recessed central portion of the surface of the second housing portion. In one embodiment, the cartridge body can have a perimeter with two angled linear lines extending from an endpoint and connected at an opposing end by a rounded edge. In some embodiments, the cartridge body can define different shapes, e.g., oval, square, rectangular, or the like. In one embodiment, the surface of the second housing portion can include a second recessed portion within the first recessed portion, the second recessed portion fluidically connected to the outlet channel and configured such that when the cartridge is disposed in the first recessed portion and media is introduced into the system, the second recessed portion receives media that flows through channels in the cartridge body or around the cartridge body and into the outlet channel.

In one embodiment, the system can include a first sealing element configured to be disposed between the chamber wall of the first housing portion and a sealing portion of the first surface of the cartridge body radially beyond the first plurality of channels. The chamber wall of the first housing portion opposite the sealing portion of the first surface of the cartridge body can have a first circumferential groove configured to receive or hold the first sealing element. In one embodiment, at least one of the chamber wall of the first housing portion or a chamber wall of the second housing portion can have a first circumferential groove configured to receive or hold the first sealing element (e.g., a shared groove configured and dimensioned to receive at least a portion of the first sealing element).

In one embodiment, the first sealing element can be configured to surround the cartridge. In one embodiment, the first sealing element can be configured to be disposed against the first surface of the cartridge body. In one embodiment, the system includes a second sealing element configured to be disposed against the second surface of the cartridge body. In one embodiment, the first sealing element can be a sleeve including an opening complementary to the cartridge body, the sleeve receiving the peripheral portion of the cartridge body in a circumferential groove.

In one embodiment, the system can include a second sealing element configured to be disposed between the first housing portion and the second housing portion and encircling the outlet channel. At least one of a surface of the first housing portion facing the second housing portion or a surface of the second housing portion facing the first housing portion can have a second circumferential groove surrounding the outlet channel. The second circumferential groove can be configured to receive or hold the second sealing element. The second sealing element can be configured to maintain a seal between the first housing portion, the second housing portion and the outlet channel when the first housing portion and the second housing portion are in a closed configuration.

In one embodiment, at least a portion of one or both of the first housing portion and the second housing portion can be transparent. In some embodiments, each of the plurality of wells is configured and dimensioned to receive a single cluster of cells. In some embodiments, a diameter, a width, or a length of each of the wells falls in a range of 20 μm to 500 μm, falls in a range of 100 μm to 300 μm, falls in a range of 150 μm to 250 μm, or is about 200 μm. In some embodiments, each of the plurality of wells is configured and dimensioned to receive multiple clusters of cells. In some embodiments, a diameter, a width or a length of each of the wells falls in a range of 1 mm to 10 mm, falls in a range of 5 mm to 8 mm, falls in a rage of 5.5 mm to 7.5 mm, or is about 6.4 mm. In some embodiments, a spacing between nearest neighbor wells in the plurality of wells falls in a range of 50 μm to 5 mm, falls in a range of 200 μm to 1 mm, falls in a range of 300 μm to 500 μm, or is approximately 400 μm.

In some embodiments, a diameter, a width or a length of each of the wells independently falls in a range of about 0.02 mm to about 2 mm, about 0.05 mm to about 2 mm, about 0.1 mm to about 2 mm, about 0.3 mm to about 2 mm, about 0.02 mm to about 1.5 mm, about 0.05 mm to about 1.5 mm, about 0.1 mm to about 1.5 mm, about 0.3 mm to about 1.5 mm, about 0.02 mm to about 0.7 mm, about 0.05 mm to about 0.7 mm, about 0.1 mm to about 0.7 mm, or about 0.3 mm to about 0.7 mm for a single cell cluster.

In some embodiments, a diameter, a width or a length of each of the wells independently falls in a range of about 0.05 mm to about 15 mm, about 0.1 mm to about 15 mm, about 0.5 mm to about 15 mm, about 1 mm to about 15 mm, about 3 mm to about 15 mm, about 0.05 mm to about 12 mm, about 0.1 mm to about 12 mm, about 0.5 mm to about 12 mm, about 1 mm to about 12 mm, about 3 mm to about 12 mm, about 0.05 mm to about 10 mm, about 0.1 mm to about 10 mm, about 0.5 mm to about 10 mm, about 1 mm to about 10 mm, about 3 mm to about 10 mm, about 0.05 mm to about 7 mm, about 0.1 mm to about 7 mm, about 0.5 mm to about 7 mm, about 1 mm to about 7 mm, about 3 mm to about 7 mm, for multiple cell clusters.

In some embodiments, the height of each well can independently range between about 0.02 mm to about 5 mm, about 0.05 mm to about 5 mm, about 0.1 mm to about 5 mm, about 0.5 mm to about 5 mm, about 0.02 mm to about 4 mm, about 0.05 mm to about 4 mm, about 0.1 mm to about 4 mm, about 0.5 mm to about 4 mm, about 0.02 mm to about 3 mm, about 0.05 mm to about 3 mm, about 0.1 mm to about 3 mm, about 0.5 mm to about 3 mm, or about 1 mm to about 2 mm.

In some embodiments, the interwell spacing can range between about 0.05 mm to about 5 mm, about 0.1 mm to about 5 mm, about 0.5 mm to about 5 mm, about 0.05 mm to about 4 mm, about 0.1 mm to about 4 mm, about 0.5 mm to about 4 mm, about 0.05 mm to about 3 mm, about 0.1 mm to about 3 mm, about 0.5 mm to about 3 mm, or about 1 mm to about 2 mm.

In some embodiments, a diameter or width of each of the first plurality of channels can fall in a range of about 200 μm to about 500 μm, about 100 μm to about 300 μm, about 150 μm to about 250 μm, or about 200 μm. In some embodiments, a diameter or width of each of the first plurality of channels can fall in a range of about 1 mm to about 10 mm, about 5 mm to about 8 mm, about 5.5 mm to about 7.5 mm, or about 6.4 mm. In some embodiments, a diameter or width of each of the first plurality of channels can be dimensioned substantially similarly to the diameter of the inlet and outlet channels.

In some embodiments, the inlet can include a first inlet and a second inlet (e.g., two separate inlets). In such embodiments, the first inlet can be configured to receive a first medium and the second inlet can be configured to receive a second medium, the first and second medium mixing downstream of the first and second inlets. In one embodiment, the first and second medium can mix in the inlet channel. In one embodiment, the first and second medium can mix in the chamber.

In some embodiments, the first housing portion and the second housing portion can each have elongated cutouts at opposing sides forming a step. The step can be used to engage or interlock the first and second housing portion with respective tabs of a holder. In one embodiment, the inlet channel can be a single opening through which the medium is introduced into the chamber. In one embodiment, the inlet channel can include multiple openings through which the medium is simultaneously introduced into the chamber.

In one embodiment, the first housing portion can include or be formed from a plurality of layers bonded together. For example, the first housing portion can include a first layer defining an aperture forming a portion of the inlet channel and defining an aperture forming an upward flowing portion of the outlet channel. The first housing portion can include a second layer defining a slot forming a portion of the inlet channel and defining an aperture forming an upward flowing portion of the outlet channel. The housing portion can further include a third layer defining an aperture forming a portion of the inlet channel that connects with the central portion of the chamber and defining an aperture forming an upward flowing portion of the outlet channel.

In one embodiment, the second housing portion can include or be formed from a plurality of layers bonded together. For example, the second housing portion can include a fourth layer defining a plurality of apertures forming a downward flowing portion of the outlet channel and defining an aperture forming an upward flowing portion of the outlet channel that connects with the upward flowing portion of the outlet channel in the third layer. The second housing portion can include a fifth layer defining a plurality of slots and an aperture. An end of each slot can connect with an aperture in the plurality of apertures of the fourth layer. The plurality of slots can form a lateral flowing portion of the outlet channel that connects with the downward flowing portion of the outlet channel in the fourth layer. The aperture of the fifth layer can form an upward flowing portion of the outlet channel. The second housing portion can include a sixth layer defining an aperture forming a downward flowing portion of the outlet channel and an aperture forming an upward flowing portion of the outlet channel. The second housing portion can include a seventh layer defining a slot forming a lateral flowing portion of the outlet channel that connects with the downward flowing portion of the outlet channel in the sixth layer and that connect with the upward flowing portion of the outlet channel in the sixth layer. In one embodiment, the microfluidic system can include a base layer on which the seventh layer is disposed. Although disclosed as a plurality of layers bonded together, it should be understood that the first and/or second housing portions can also be formed by different manufacturing processes, such as injection molding.

In some embodiments, the at least one porous element can be a porous membrane. The at least one porous element can include one or more bottom non-woven polymeric fiber sheets. The system can include one or more top non-woven polymeric fiber sheets configured to be disposed on the first surface of the body covering the first plurality of wells after cells have been loaded in the plurality of wells, the one or more bottom non-woven polymeric fiber sheets and the one or more top non-woven polymeric fiber sheets forming a three-dimensional scaffold for culturing cells.

In some embodiments, the one or more bottom non-woven polymeric fiber sheets and the one or more top non-woven polymeric fiber sheets can include a biogenic polymer and a synthetic polymer. In some embodiments, the one or more bottom non-woven polymeric sheets and the one or more top non-woven polymeric sheets can be the same non-woven polymeric fiber sheets with a first portion disposed on a first surface of the cartridge body and a second portion disposed on a second portion of the cartridge body. In some embodiments, the one or more bottom non-woven polymeric fiber sheets and the one or more top non-woven polymeric fiber sheet can be different non-woven polymeric fiber sheets.

In some embodiments, a thickness of the one or more bottom non-woven polymeric fiber sheets and the one or more top non-woven polymeric fiber sheets is between about 50 nm and about 5 um. In some embodiments, the three-dimensional scaffold has an elastic modulus of between about 0.1 kiloPascal (kPa) and about 25.0 kPa. For each channel in the first plurality of channels, a wall of the channel, a portion of the one or more top non-woven polymeric fiber sheets and a portion of the one or more bottom non-woven polymeric fiber sheets can define a space in which cells are enclosed. In some embodiments, the cells can include adipocytes, pancreatic islet cells, or brain tissue cells. For each channel in the plurality of channels, a thickness of the body at the channel can determine a height of the space in which the cells are enclosed. In some embodiments, for each channel in the plurality of channels, the thickness of the body at the channel is between about 10 μm and about 1 mm.

In some embodiments, the one or more bottom non-woven polymeric fiber sheets include polymeric fibers that can include a biogenic polymer and a synthetic polymer. A weight ratio of the synthetic polymer to the biogenic polymer can be between about 10:90 and about 50:50. In some embodiments, the biogenic polymer can include a polymer selected from the group consisting of poly-4-hydroxy-buyrate, collagen and gelatin, and a combination thereof. In some embodiments, the synthetic polymer can include a polymer selected from the group consisting of polycaprolactone (PCL), polyethylene glycol (PEG) and polylactide (PLA), and a combination thereof.

In some embodiments, the one or more bottom non-woven polymeric fiber sheets can include at least one extracellular matrix (ECM) protein. In one embodiment, the at least one ECM protein can be integral to the one or more bottom non-woven polymeric fiber sheets. In one embodiment, the at least one ECM protein can be coated on the one or more bottom non-woven polymeric fiber sheets. The at least one ECM protein can be selected from the group consisting of a collagen, a laminin, and a fibronectin, or a fragment thereof, and a combination thereof. The at least one ECM protein can be encoded by a gene selected from the group consisting of genes COL6A3, COL6A1, SPP1, COL6A2, LAMC2, COL1A2, FNDC3A, BGN, COL1A1, LAMB1, LAMC1, COL18A1, SPARC, LAMB3, FN1, TNC, FNDC3B, COL3A1, EMILIN1, COL6A6, AGRN, LAMA4, COL28A1, LAMA3, LAMA5, LAMC3, FBN1, LAMB2, COL5A1, or a fragment thereof, and a combination thereof. In some embodiments, the one or more bottom non-woven polymeric fiber sheets can include two or more extracellular matrix (ECM) proteins.

In another aspect, the present invention provides a system including a housing and a cartridge. The housing includes a first housing portion and a second housing portion forming a chamber therebetween. The housing also includes an inlet for introduction of a medium into the system, an inlet channel fluidically connecting the inlet with the chamber, an outlet, and an outlet channel fluidically connecting the chamber with the outlet. The system can include a cartridge configured to be disposed within the chamber. The cartridge can include a cartridge body having a first surface and a second surface. The first surface defines a plurality of channels (e.g., wells) each configured to hold one or more biological cells. The cartridge body can define a plurality of outer channels extending from the first surface to the second surface of the cartridge body.

The housing and the cartridge can be configured such that when the cartridge is disposed within the housing and a medium is introduced into the inlet, the medium flows through the inlet channel and into the chamber and at least a first portion of the medium flows laterally between the first surface of the cartridge body and a chamber wall opposite the first surface of the cartridge body to plurality of wells, flows in to and out of the plurality of wells, flows on to the plurality of outer channels, flows through the plurality of outer channels, and then flows through the outlet channel to the outlet of the housing.

The outlet channel can connect with a central portion of the chamber. The cartridge body can have a peripheral portion and a central portion that is disposed in the central portion of the chamber when the cartridge is held in the housing. The plurality of wells can be disposed in the peripheral portion of the cartridge body. The cartridge body and housing can be configured such that when the cartridge is disposed within the housing and a medium is introduced into the inlet, the medium flows through the inlet channel and into central portion of the chamber, and at least a first portion of the medium flows radially outward between the first surface of the cartridge body and a chamber wall opposite the first surface of the cartridge body from the central portion of the cartridge body to the plurality of wells, flows into and out of the first plurality of wells, flows radially outward to the plurality of outer channels, flows through the plurality of outer channels, and then flows through the outlet channel to the outlet of the housing. In one embodiment, the medium flows into each of the first plurality of wells at substantially the same time.

In some embodiments, the system can include at least one three-dimensional scaffold for culturing pancreatic islet cells, brain tissue cells or adipocytes. The three-dimensional scaffold can include a first portion of a first non-woven polymeric fiber sheet, and a second portion of a second non-woven polymeric fiber sheet overlaying the first portion. The first non-woven polymeric fiber sheet and the second non-woven polymer fiber sheet can include polymeric fibers including a biogenic polymer and a synthetic polymer. The three-dimensional scaffold can include pancreatic islet cells, brain tissue cells or adipocytes disposed between the first portion and the second portion. At least one of the plurality of wells can be configured to hold the three-dimensional scaffold.

In some embodiments, the first non-woven polymeric fiber sheet and the second non-woven polymeric fiber sheet can be a same non-woven polymeric fiber sheet and the first portion and the second portion can be different portions of the same non-woven polymeric fiber sheet. In some embodiments, the first non-woven polymeric fiber sheet and the second non-woven polymeric fiber sheet can be different non-woven polymeric fiber sheets. A weight ratio of the synthetic polymer to the biogenic polymer can be between about 10:90 and about 50:50.

The biogenic polymer can include a polymer selected from the group consisting of poly-4-hydroxybuyrate, collagen and gelatin, and a combination thereof. The synthetic polymer can include a polymer selected from the group consisting of polycaprolactone (PCL), polyethylene glycol (PEG) and polylactide (PLA), and a combination thereof. The polymeric fibers can include at least one extracellular matrix (ECM) protein. In one embodiment, the at least one ECM protein can be integral to the fibers. In one embodiment, the at least one ECM protein can be coated on the fibers. The at least one ECM protein can be selected from the group consisting of a collagen, a laminin, and a fibronectin, or a fragment thereof, and a combination thereof. The at least one ECM protein can be encoded by a gene selected from the group consisting of genes COL6A3, COL6A1, SPP1, COL6A2, LAMC2, COL1A2, FNDC3A, BGN, COL1A1, LAMB1, LAMC1, COL18A1, SPARC, LAMB3, FN1, TNC, FNDC3B, COL3A1, EMILIN1, COL6A6, AGRN, LAMA4, COL28A1, LAMA3, LAMA5, LAMC3, FBN1, LAMB2, COL5A1, or a fragment thereof, and a combination thereof. In one embodiment, the polymeric fibers can include two or more extracellular matrix (ECM) proteins.

The scaffold can have an elastic modulus of between about 0.1 kiloPascal (kPa) and about 25.0 kPa. The diameter of the polymeric fibers can be between about 50 nm and about 500 nm. The thickness of the non-woven polymeric sheet can be between about 50 nm and about 5 um. The pancreatic islet cells can maintain viability and functionality for at least about 7 days.

In some embodiments, the system can include a solid support for the three-dimensional scaffold. The solid support can include a top surface, a bottom surface, and a channel extending from the top surface to the bottom surface of the solid support. The first portion of the first non-woven polymeric fiber sheet can be disposed on the bottom surface of the solid support. The second portion of the second non-woven polymeric body can be disposed on the top surface of the solid support. The pancreatic islet cells, brain tissue cells or adipocytes can be disposed in the channel of the solid support. At least one well in the plurality of wells can be sized and configured to receive and hold the solid support.

A wall of the channel of the solid support, the first portion of the first non-woven polymeric fiber sheet, and the second portion of the second non-woven polymeric sheet can define a space in which the pancreatic islet cells, brain tissue cells or adipocytes are enclosed. A thickness of the solid support can determine a height of the space in which the cells are enclosed. In one embodiment, the thickness of the solid support can be between about 10 μm and about 1 mm. The system can include a plurality of three-dimensional scaffolds for culturing pancreatic islet cells, brain tissue cells or adipocytes.

In some embodiments, the system can include a holder configured and dimensioned to receive an assembly of the first housing portion, the second housing portion, and the cartridge. The holder can include a first holder portion and a second holder portion configured to receive the assembly therebetween. In one embodiment, the first holder portion and the second holder portion can be hingedly connected. In another embodiment, the first holder portion and the second holder portion can be connected using latches on two or more sides of the holder.

The first holder portion can include an outer surface facing away from the second holder portion when the holder is closed. The first holder portion can include an inner surface facing toward the second holder portion when the holder is closed. The first holder portion can include a protrusion extending from the inner surface. The protrusion can define an opening having a recessed edge configured to receive and engage the first housing portion of the assembly. The opening can extend through the protrusion and through the outer surface of the first holder portion, and provides access to an inlet and an outlet of the cartridge housing when the cartridge housing is disposed in the first holder portion. In some embodiments, the first holder portion can include a gasket disposed in the recessed edge of the opening. The gasket can be configured to engage the first housing portion in the recessed edge of the opening. In one embodiment, the recessed edge can include tabs on each corner forming a groove between a bottom surface of the recessed edge and the tabs, the groove configured and dimensioned to slidably engage steps of the first housing portion of the assembly. Engagement of the steps of the first housing portion with the tabs of the recessed edge ensures alignment of the first and second housing portions when the holder is positioned in a closed configuration. In one embodiment, the first holder portion can include one or more hemispherical dimples extending from the bottom surface at each corner of the opening. In some embodiments, the hemispherical dimples can be in addition to or as an alternative to the gasket.

The second holder portion can include an outer surface facing away from the first holder portion when the holder is closed. The second holder portion can include an inner surface facing toward the first holder portion when the holder is closed with the inner surface defining a recessed area. The recessed area can be configured to at least partially receive the protrusion of the first holder portion. The recessed area can define an opening having a recessed edge configured to receive and engage the second housing portion of the assembly. The opening can extend through the recessed area and through the outer surface of the second holder portion. In some embodiments, the second holder portion can include a gasket disposed around the recessed edge of the opening in the recessed area of the second holder portion. The gasket can be configured to engage and retain the second housing portion in the cutout. In one embodiment, the recessed edge can include tabs on each corner forming a groove between a bottom surface of the recessed edge and the tabs, the groove configured and dimensioned to slidably engage steps of the second housing portion of the assembly. Engagement of the steps of the second housing portion with the tabs of the recessed edge ensures alignment of the first and second housing portions. In one embodiment, the second holder portion can include one or more hemispherical dimples extending from the bottom surface at each corner of the opening. In one embodiment, the gasket and/or the dimples of the first and second holder portions can maintain the first and second housing portions raised from the bottom surface of the respective first and second holder portions to ensure proper contact, alignment and sealing between the first and second housing portions when the holder is in the closed configuration.

The housing can be configured such that introduction of the protrusion of the first holder portion into the recessed area of the second holder portion imparts a compression force on the assembly to maintain a seal between the first housing portion, the second housing portion and the cartridge. In one embodiment, the holder can include a latching mechanism disposed on the outer surfaces of the first and second holder portions and configured to interlock the first holder portion with the second holder portion to maintain the compression force on the assembly.

In one embodiment, the at least one porous element can include a porous membrane. In one embodiment, the at least one porous element can include one or more non-woven polymeric fiber sheets. In one embodiment, the microfluidic system can include at least one three-dimensional scaffold for culturing cells or cell clusters. In one embodiment, the microfluidic system can include at least one three-dimensional scaffold for culturing pancreatic islet cells. In another embodiment, the microfluidic system can include at least one three-dimensional scaffold for culturing adipocytes. The three-dimensional scaffold can include a first portion of a first non-woven polymeric fiber sheet and a second portion of a second non-woven polymeric fiber sheet overlaying the first portion. The first non-woven polymeric fiber sheet and the second non-woven polymer fiber sheet can include polymeric fibers comprising a biogenic polymer and a synthetic polymer. The three-dimensional scaffold can include cells, e.g., pancreatic islet cells or adipocytes, disposed between the first portion and the second portion. At least one of the plurality of wells can be configured to hold the three-dimensional scaffold.

In one embodiment, the first non-woven polymeric fiber sheet and the second non-woven polymeric fiber sheet can be the same non-woven polymeric fiber sheet and the first portion and the second portion can be different portions of the same non-woven polymeric fiber sheet. In one embodiment, the first non-woven polymeric fiber sheet and the second non-woven polymeric fiber sheet can be different non-woven polymeric fiber sheets. The weight ratio of the synthetic polymer to the biogenic can be between about 10:90 and about 50:50. The biogenic polymer can include a polymer selected from the group consisting of poly-4-hydroxybuyrate, collagen and gelatin, and a combination thereof.

The synthetic polymer can include a polymer selected from the group consisting of polycaprolactone (PCL), polyethylene glycol (PEG) and polylactide (PLA), and a combination thereof. The polymeric fibers can include at least one extracellular matrix (ECM) protein. In one embodiment, the at least one ECM protein can be integral to the fibers. In one embodiment, the at least one ECM protein can be coated on the fibers. The at least one ECM protein can be selected from the group consisting of a collagen, a laminin, and a fibronectin, or a fragment thereof, and a combination thereof. In one embodiment, the at least one ECM protein can be encoded by a gene selected from the group consisting of genes COL6A3, COL6A1, SPP1, COL6A2, LAMC2, COL1A2, FNDC3A, BGN, COL1A1, LAMB1, LAMC1, COL18A1, SPARC, LAMB3, FN1, TNC, FNDC3B, COL3A1, EMILIN1, COL6A6, AGRN, LAMA4, COL28A1, LAMA3, LAMA5, LAMC3, FBN1, LAMB2, COL5A1, or a fragment thereof, and a combination thereof.

In one embodiment, the polymeric fibers further can include two or more ECM proteins. The scaffold can have an elastic modulus of between about 0.1 kiloPascal (kPa) and about 25.0 kPa. The diameter of the polymeric fibers can be between about 50 nm and about 500 nm. The thickness of the non-woven polymeric sheet can be between about 50 nm and about 5 um. In one embodiment, the pancreatic islet cells can maintain viability and functionality for at least about 7 days.

The system can include a solid support for the three-dimensional scaffold. The solid support can include a top surface, a bottom surface, and a channel extending from the top surface to the bottom surface of the solid support. The first portion of the first non-woven polymeric fiber sheet can be disposed on the bottom surface of the solid support. The second portion of the second non-woven polymeric body can be disposed on the top surface of the solid support. The cells or cell clusters, e.g., pancreatic islet cells or adipocytes, can be disposed in the channel of the solid support. At least one well in the plurality of wells can be sized and configured to receive and hold the solid support.

A wall of the channel of the solid support, the first portion of the first non-woven polymeric fiber sheet, and the second portion of the second non-woven polymeric sheet can define a space in which the cells or cell clusters, e.g., pancreatic islet cells or adipocytes, are enclosed. A thickness of the solid support can determine a height of the space in which the cells or cell clusters are enclosed. The thickness of the solid support can be between about 10 μm and about 1 mm. The system can include a plurality of three-dimensional scaffolds for culturing cells or cell clusters, e.g., pancreatic islet cells or adipocytes.

In another aspect, the present invention provides a system, e.g., a microfluidic system, for loading one or more biological cells on a cartridge. The system includes a housing and a cartridge. The housing includes a first housing portion and a second housing portion forming a chamber therebetween. The housing includes an inlet for introduction of a medium including one or more biological cells into the system, an inlet channel fluidically connecting the inlet with a central portion of the chamber, an outlet, an outlet channel fluidically connecting the central portion of the chamber with the outlet, and a bypass channel fluidically connecting the inlet channel with the outlet channel bypassing the central portion of the chamber and the central portion of the cartridge.

The cartridge has a central portion and a peripheral portion and configured to be disposed within the chamber with the central portion of the cartridge in the central portion of the chamber. The cartridge includes a cartridge body having a first surface and a second surface and defining a first plurality of channels disposed in the peripheral portion of the cartridge. Each channel of the first plurality of channels extends from the first surface to the second surface of the cartridge body. The cartridge includes at least one porous element (e.g., a filter) disposed adjacent to the second surface of the cartridge body at the first plurality of channels. The at least one porous element and the first plurality of channels form a plurality of wells disposed in the peripheral portion of the cartridge, each well configured to hold the one or more biological cells.

The housing and the cartridge can be configured such that when the cartridge is disposed within the housing and the medium including the one or more biological cells or cell clusters is introduced into the inlet, at least a first portion of the medium and the one or more biological cells or cell clusters flows through the inlet channel and into the central portion of the chamber. At least one of the one or more biological cells or cell clusters lodges in a well of the plurality of wells, the first portion of the medium flows through the first plurality of channels and the at least one filter, and then flows through the outlet channel to the outlet of the housing. At least a second portion of the medium and the one or more biological cells or cell clusters flows through at least a portion of the inlet channel and into the bypass channel to bypass the plurality of wells of the cartridge and flows through the outlet channel to the outlet of the housing.

The housing and cartridge are configured such that when no cells or cell clusters are disposed in the plurality of wells, a flow resistance of a first flow path from the inlet, through the inlet channel, through the first plurality of channels, through the outlet channel and out the outlet is less than a flow resistance of a second flow path through the inlet, through inlet channel, through the bypass channel, through the outlet channel and out the outlet. The system and cartridge can be configured such that when one or more biological cells or cell clusters are lodged in the plurality of wells of the cartridge, the one or more biological cells or cell clusters at least partially block the flow path of the medium through the first plurality of channels increasing the flow resistance for the first flow path and increasing a volume of the second portion of the medium and the one or more biological cells or cell clusters that flows along the second flow path relative to a volume of the first portion of the medium and the one or more biological cells or cell clusters that flows along the first flow path.

In another aspect, the present invention provides a system, e.g., a microfluidic system, for loading one or more biological cells or cell clusters on a cartridge. The system includes a housing and a cartridge. The housing includes a first housing portion and a second housing portion forming a chamber therebetween. The housing includes an inlet for introduction of a medium including one or more biological cells or cell clusters into the system, an inlet channel fluidically connecting the inlet with a central portion of the chamber, an outlet, an outlet channel fluidically connecting a peripheral portion of the chamber with the outlet, and an alternate channel fluidically connecting the inlet channel with the outlet channel.

The cartridge has a central portion and a peripheral portion and configured to be disposed within the chamber with the central portion of the cartridge disposed in the central portion of the chamber and the peripheral portion of the cartridge disposed in the peripheral portion of the chamber. The cartridge includes a cartridge body having a first surface and a second surface and defining a first plurality of channels disposed in the peripheral portion of the cartridge. Each channel of the first plurality of channels extends from the first surface to the second surface of the cartridge body. The cartridge includes at least one filter (e.g., a porous element) disposed adjacent to the second surface of the cartridge body at the first plurality of channels. The at least one filter and the first plurality of channels form a plurality of wells disposed in the peripheral portion of the cartridge, each well configured to hold the one or more biological cells or cell clusters.

The housing and the cartridge can be configured such that when the cartridge is disposed within the housing and the medium including the one or more biological cells or cell clusters is introduced into the inlet, at least a first portion of the medium and the one or more biological cells or cell clusters flows through the inlet channel and into the central portion of the chamber. At least one of the one or more biological cells or cell clusters lodges in a well of the plurality of wells, the first portion of the medium flows through the first plurality of channels and the at least one filter, and then flows through the outlet channel to the outlet of the housing. At least a second portion of the medium and the one or more biological cells or cell clusters flows through the inlet channel into the central portion of the chamber and into the alternate channel to bypass the plurality of wells of the cartridge and flows through the outlet channel to the outlet of the housing. In one embodiment, the alternate channel substantially surrounds the central portion of the chamber. In some embodiments, due to the longer length and smaller diameter of the alternate channel relative to a flow path through the wells, a flow resistance in the alternate channel is larger than a flow resistance in the flow path through the wells when there are no cells or cell clusters in the wells. After cells have been lodged in the plurality of wells, the flow resistance through the wells increases and the alternate channel provides a flow path with less resistance than the flow path through the plurality of wells.

In another aspect, the present invention provides a cartridge for a microfluidic system. The cartridge includes a body and one or more bottom non-woven polymeric fiber sheets. The body includes a first surface and a second surface and defines a first plurality of channels extending from the first surface to the second surface. The one or more bottom non-woven polymeric fiber sheets are disposed on the second surface of the body at the first plurality of channels. The first plurality of channels and the one or more bottom non-woven polymeric fiber sheets form a plurality of wells, each well configured to receive one or more cells.

The cartridge can include one or more top non-woven polymeric fiber sheets configured to be disposed on the first surface of the body covering the first plurality of wells after the cells have been loaded in the plurality of wells. The one or more bottom non-woven polymeric fiber sheets and the one or more top non-woven polymeric fiber sheets can form a three-dimensional scaffold for culturing cells or cell clusters. In one embodiment, the one or more bottom non-woven polymeric fiber sheets and the one or more top non-woven polymeric fiber sheets include a biogenic polymer and a synthetic polymer. The one or more bottom non-woven polymeric sheets and the one or more top non-woven polymeric sheets can be the same non-woven polymeric fiber sheets with a first portion disposed on a first surface of the cartridge body and a second portion disposed on a second portion of the cartridge body. In one embodiment, the one or more bottom non-woven polymeric fiber sheets and the one or more top non-woven polymeric fiber sheet can be different non-woven polymeric fiber sheets.

In one embodiment, a thickness of the one or more bottom non-woven polymeric fiber sheets and the one or more top non-woven polymeric fiber sheets can be between about 50 nm and about 5 um. In one embodiment, the three-dimensional scaffold can have an elastic modulus of between about 0.1 kiloPascal (kPa) and about 25.0 kPa. For each channel in the plurality of channels, a wall of the channel, a portion of the one or more top non-woven polymeric fiber sheets and a portion of the one or more bottom non-woven polymeric fiber sheets can define a space in which cells or cell clusters are enclosed. In one embodiment, the cells or cell clusters can include adipocytes or pancreatic islet cells. For each channel in the plurality of channels, a thickness of the body at the channel can determine a height of the space in which the cells or cell clusters are enclosed. For each channel in the plurality of channels, the thickness of the body at the channel can be between about 10 μm and about 1 mm.

The one or more bottom non-woven polymeric fiber sheets and the one or more top non-woven polymeric fiber sheets can include polymeric fibers comprising a biogenic polymer and a synthetic polymer. In one embodiment, the weight ratio of the synthetic polymer to the biogenic polymer can be between about 10:90 and about 50:50. The biogenic polymer can include a polymer selected from the group consisting of poly-4-hydroxybuyrate, collagen and gelatin, and a combination thereof. In one embodiment, the synthetic polymer can include a polymer selected from the group consisting of polycaprolactone (PCL), polyethylene glycol (PEG) and polylactide (PLA), and a combination thereof.

In one embodiment, the one or more bottom non-woven polymeric fiber sheets and the one or more top non-woven polymeric fiber sheets can include at least ECM protein. The at least one ECM protein can be integral to the one or more bottom non-woven polymeric fiber sheets and the one or more top non-woven polymeric fiber sheets. The at least one ECM protein can be coated on the one or more bottom non-woven polymeric fiber sheets and the one or more top non-woven polymeric fiber sheets. The at least one ECM protein can be selected from the group consisting of a collagen, a laminin, and a fibronectin, or a fragment thereof, and a combination thereof. The at least one ECM protein can be encoded by a gene selected from the group consisting of genes COL6A3, COL6A1, SPP1, COL6A2, LAMC2, COL1A2, FNDC3A, BGN, COL1A1, LAMB1, LAMC1, COL18A1, SPARC, LAMB3, FN1, TNC, FNDC3B, COL3A1, EMILIN1, COL6A6, AGRN, LAMA4, COL28A1, LAMA3, LAMA5, LAMC3, FBN1, LAMB2, COL5A1, or a fragment thereof, and a combination thereof. In one embodiment, the one or more bottom non-woven polymeric fiber sheets and/or the one or more top non-woven polymeric fiber sheets can include two or more ECM proteins.

In another aspect, the present invention provides a system, e.g., a microfluidic system, including a housing and a cartridge. The housing includes a first housing portion and a second housing portion forming a chamber therebetween. The housing also includes an inlet for introduction of a medium into the microfluidic system, an inlet channel fluidically connecting the inlet with a central portion of the chamber, an outlet, and an outlet channel fluidically connecting a peripheral portion of the chamber with the outlet. The cartridge can be any of the cartridges described herein. The cartridge has a central portion and a peripheral portion and is configured to be disposed within the chamber with the central portion of the cartridge disposed in the central portion of the chamber and the peripheral portion of the cartridge disposed in the peripheral portion of the chamber. The housing and the cartridge are configured such that when the cartridge is disposed within the housing and a medium is introduced into the inlet, the medium flows through the inlet channel and into the central portion of the chamber and at least a first portion of the medium flows radially outward between the first surface of the cartridge body and a chamber wall opposite the first surface of the cartridge body from the central portion of the chamber to the first plurality of channels, flows through the first plurality of channels and the at least one porous element, and then flows through the outlet channel to the outlet of the housing.

In another aspect, the present invention provides a method for culturing cells or cell clusters in a system. The method includes providing the system, e.g., microfluidic system, described herein. The method also includes disposing one or more cells or one or more cell clusters for culturing in at least one of the plurality of wells of the cartridge and disposing the cartridge in the chamber of the housing. The method includes providing suitable culture conditions and circulating a suitable culture medium through the system, thereby culturing the one or more cells or one or more cell clusters.

In some embodiments, the one or more cells or cell clusters of any of the methods described herein can be one or more cells or cell clusters microencapsulated in a polymer. The polymer can be alginate. The one or more cells or cell clusters can be in one or more capsules of the polymer when the one or more cells or cell clusters are disposed in the at least one of the plurality of wells. Each of the one or more capsules can have a diameter in the range of about 250 µm to about 500 µm.

In another aspect, the present invention provides a method for identifying a compound that modulates cell differentiation, cell viability, and/or cell function. The method includes providing the system, e.g., microfluidic system, described herein. The system includes cells or cell clusters disposed in at least one of the plurality of wells of the cartridge. The method includes contacting the cells or cell clusters with a test compound. In some embodiments, the method includes contacting the cells or cell clusters with the test compound by introducing a medium including the test compound into the inlet of the housing. The method includes determining the effect of the test compound on cell differentiation, cell viability, and/or cell function in the presence and absence of the test compound. A modulation of cell differentiation, cell viability, and/or cell function in the presence of said test compound as compared to cell differentiation, cell viability, and/or cell function in the absence of said test compound indicates that said test compound modulates cell differentiation, cell viability, and/or function, thereby identifying a compound that modulates cell differentiation, cell viability, and/or function.

In another aspect, the present invention provides a method for identifying a compound useful for treating a disease or disorder. The method includes providing a system, e.g., a microfluidic system, described herein. The microfluidic system includes suitable cells or cell clusters disposed in at least one of the plurality of wells of the cartridge. The method includes contacting the cells or cell clusters with a test compound. In some embodiments, the method includes contacting the cells or cell clusters with the test compound by introducing a medium including the test compound into the inlet of the housing. The method includes determining the effect of the test compound on cell differentiation, cell viability, and/or cell function in the presence and absence of the test compound. A modulation of cell differentiation, cell viability, and/or cell function in the presence of said test compound as compared to cell differentiation, cell viability, and/or cell function in the absence of said test compound indicates that said test compound modulates cell differentiation, cell viability, and/or function, thereby identifying a compound useful for treating the disease or disorder.

Suitable cells or cell clusters for use in the methods of the invention for identifying a compound useful for treating a disease or disorder include cells known to be affected by or associated with the disease or disorder. For example, in the case of a muscle disease or disorder, such as muscular and neuromuscular pathologies, e.g., a muscle dystrophy, a myopathy, a disease of peripheral nerves, a metabolic muscle disorder, a vasospasm, a heart arrhythmia, and/or a cardiomyopathy, suitable cells include cardiac muscle cells, ventricular cardiac muscle cells, atrial cardiac muscle cells, striated muscle cells, smooth muscle cells, vascular smooth muscle cells, and combinations thereof. In the case of a disorder of pancreatic islet cells, e.g., impaired glucose tolerance, diabetes, insulinoma, suitable cells include pancreatic islet cells as described herein; in the case of a disorder of adipocytes, e.g., lipodystrophy, liposarcoma, suitable cells include adipocytes as described herein; in the case of a myoepithelial disorder, e.g., myoepithelial carcinoma, suitable cells include salivary gland cells, myoepithelial cells and combinations thereof; in the case of a luminal disorder, e.g., a vascular disorder, suitable cells include vascular smooth muscle cells. In one embodiment, spheroids and, more particularly, tumor spheroid cells can be used, although it should be understood that any other cell types can be used.

In one embodiment, the cells disposed in at least one of the plurality of wells of the cartridge are pancreatic islet cells, and the effect of the test compound on pancreatic islet cell differentiation, viability and/or function in the presence and absence of the test compound is determined. In one embodiment, the disease or disorder is diabetes, the cells disposed in at least one of the plurality of wells of the cartridge are pancreatic islet cells, and the effect of the test compound on pancreatic islet cell differentiation, viability and/or function in the presence and absence of the test compound is determined. In one embodiment, the cells disposed in at least one of the plurality of wells of the cartridge are adipocytes and the effect of the test compound on adipocyte differentiation, viability and/or function in the presence and absence of the test compound is determined. In one embodiment, the disease or disorder is lipodystrophy, the cells disposed in at least one of the plurality of wells of the cartridge are adipocytes, and the effect of the test compound on adipocyte differentiation, viability and/or function in the presence and absence of the test compound is determined.

In another aspect, the present invention provides a method for identifying a compound that modulates pancreatic islet cell differentiation, viability and/or function. The method includes provides a cartridge described herein, the cartridge including pancreatic islet cells. The method includes contacting the cartridge with a test compound. In some embodiments, the method includes contacting the cells with the test compound by introducing a medium including the test compound into the inlet of a housing. The method includes determining the effect of the test compound on pancreatic islet cell differentiation, viability and/or function in the presence and absence of the test compound. A modulation of pancreatic islet cell differentiation, viability and/or function in the presence of said test compound as compared to pancreatic islet cell differentiation, viability and/or function in the absence of said test compound indicates that said test compound modulates pancreatic islet cell differentiation, viability and/or function, thereby identifying a compound that modulates pancreatic islet cell differentiation, viability and/or function.

In another aspect, the present invention provides a method for identifying a compound useful for treating diabetes. The method includes providing a cartridge described herein, the cartridge including pancreatic islet cells. The method includes contacting the cartridge with a test compound. In some embodiments, the method includes contacting the cells with the test compound by introducing a medium including the test compound into the inlet of a housing. The method includes determining the effect of the test compound on pancreatic islet cell differentiation, viability and/or function in the presence and absence of the test compound. A modulation of pancreatic islet cell differentiation, viability and/or function in the presence of said test compound as compared to pancreatic islet cell differentiation, viability and/or function in the absence of said test compound indicates that said test compound modulates pancreatic islet cell differentiation, viability and/or function, thereby identifying a compound useful for treating diabetes.

In another aspect, the present invention provides a method for identifying a compound that modulates adipocyte differentiation, viability and/or function. The method includes providing a cartridge described herein, the cartridge including adipocytes. The method includes contacting the cartridge with a test compound. In some embodiments, the method includes contacting the cells with the test compound by introducing a medium including the test compound into the inlet of a housing. The method includes determining the effect of the test compound on adipocyte differentiation, viability and/or function in the presence and absence of the test compound. A modulation of adipocyte differentiation, viability and/or function in the presence of said test compound as compared to adipocyte differentiation, viability and/or function in the absence of said test compound indicates that said test compound modulates adipocyte differentiation, viability and/or function, thereby identifying a compound that modulates adipocyte differentiation, viability and/or function.

In another aspect, the present invention provides a method for identifying a compound useful for treating lipodystrophy. The method includes providing a cartridge described herein, the cartridge including adipocytes. The method includes contacting the cartridge with a test compound. In some embodiments, the method includes contacting the cells with the test compound by introducing a medium including the test compound into the inlet of a housing. The method includes determining the effect of the test compound on adipocyte differentiation, viability and/or function in the presence and absence of the test compound. A modulation of adipocyte differentiation, viability and/or function in the presence of said test compound as compared to adipocyte differentiation, viability and/or function in the absence of said test compound indicates that said test compound modulates adipocyte differentiation, viability and/or function, thereby identifying a compound useful for treating lipodystrophy.

In one aspect, the instant invention provides three-dimensional scaffolds for culturing cells or cell clusters. The scaffolds include a first portion of a first non-woven polymeric fiber sheet; a second portion of a second non-woven polymeric fiber sheet overlaying the first portion, wherein the first non-woven polymeric fiber sheet and the second non-woven polymeric fiber sheet include polymeric fibers comprising a biogenic polymer and a synthetic polymer; and cells or cells making up the clusters disposed between the first portion and the second portion.

In another aspect, the present invention provides three-dimensional scaffolds for culturing pancreatic islet cells or adipocytes. The three-dimensional scaffolds include a first portion of a first non-woven polymeric fiber sheet; a second portion of a second non-woven polymeric fiber sheet overlaying the first portion, wherein the first non-woven polymeric fiber sheet and the second non-woven polymeric fiber sheet include polymeric fibers comprising a biogenic polymer and a synthetic polymer; and pancreatic islet cells or adipocytes disposed between the first portion and the second portion.

In one embodiment, the three-dimensional scaffolds include pancreatic islet cells. In another embodiment, the scaffolds include adipocytes. The first non-woven polymeric fiber sheet and the second non-woven polymeric fiber sheet can be a same non-woven polymeric fiber sheet and the first portion and the second portion are different portions of the same non-woven polymeric fiber sheet; or the first nonwoven polymeric fiber sheet and the second non-woven polymeric fiber sheet can be different non-woven polymeric fiber sheets.

The weight ratio of the synthetic polymer to the biogenic can be between about 10:90 and about 50:50. In one embodiment, the biogenic polymer can be selected from the group consisting of poly-4-hydroxybuyrate, collagen and gelatin, and a combination thereof and a synthetic polymer. In one embodiment, the synthetic polymer can be selected from the group consisting of polycaprolactone (PCL), polyethylene glycol (PEG) and polylactide (PLA), and a combination thereof. The polymeric fibers can further include at least one ECM protein, e.g., the ECM protein can be integral to the fibers or coated onto the fibers. In some embodiments, the polymeric fibers include at least 2, at least 3, at least 4, at least 5, at least 6, at least 7, at least 8, at least 9, at least 10, or more than 10 ECM proteins.

In one embodiment, the ECM protein can be selected from the group consisting of a collagen, a laminin, and a fibronectin, or a fragment thereof, and a combination thereof. In another embodiment, the ECM protein is encoded by a gene selected from the group consisting of COL6A3, COL6A1, SPP1, COL6A2, LAMC2, COL1A2, FNDC3A, BGN, COL1A1, LAMB1, LAMC1, COL18A1, SPARC, LAMB3, FN1, TNC, FNDC3B, COL3A1, EMILIN1, COL6A6, AGRN, LAMA4, COL28A1, LAMA3, LAMA5, LAMC3, FBN1, LAMB2, COL5A1, or a fragment thereof, and a combination thereof.

The elastic modulus of the three-dimensional scaffold can be between about 0.1 kilo Pascal (kPa) and about 25.0 kPa. The diameter of the polymeric fibers can be between about 50 nm and about 500 nm. The thickness of the non-woven polymeric sheet can be between about 50 nm and about 5 µm (microns). The pancreatic islet cells or adipocytes disposed between the first portion and the second portion may maintain viability and functionality when cultured for at least about 7 days.

In one aspect, the present invention provides devices including a three-dimensional scaffold for culturing cells or cell clusters. The three-dimensional scaffold includes a first portion of a first non-woven polymeric fiber sheet, and a second portion of a second non-woven polymeric fiber sheet overlaying the first portion. The first non-woven polymeric fiber sheet and the second non-woven polymeric fiber sheet include polymeric fibers including a biogenic polymer and a synthetic polymer. The device includes cells or cells making up the clusters disposed between the first portion and the second portion. The device includes a base layer.

In one aspect, the present invention provides devices including a three-dimensional scaffold for culturing pancreatic islet cells or adipocytes. The three-dimensional scaffold includes a first portion of a first non-woven polymeric fiber sheet, and a second portion of a second non-woven polymeric fiber sheet overlaying the first portion. The first non-woven polymeric fiber sheet and the second non-woven polymeric fiber sheet include polymeric fibers including a biogenic polymer and a synthetic polymer. The device includes pancreatic islet cells or adipocytes disposed between the first portion and the second portion. The device includes a base layer.

In one embodiment, the three-dimensional scaffolds include pancreatic islet cells. In another embodiment, the three-dimensional scaffolds include adipocytes. Exemplary base layers can include a well of a tissue culture plate or a microfluidics device.

In one aspect, the present invention provides a device including a three-dimensional scaffold for culturing cells or cell clusters. The three-dimensional scaffold includes a first portion of a first non-woven polymeric fiber sheet, and a second portion of a second non-woven polymeric fiber sheet overlaying the first portion. The first non-woven polymeric fiber sheet and the second non-woven polymeric fiber sheet can include polymeric fibers including a biogenic polymer and a synthetic polymer. The three-dimensional scaffold includes cells or cells making up the clusters disposed between the first portion and the second portion. The scaffold includes a solid support including a top surface, a bottom surface, and a channel extending from the top surface to the bottom surface. The first portion of the first non-woven polymeric fiber sheet can be disposed on the bottom surface of the solid support. The second portion of the second non-woven polymeric body can be disposed on the top surface of the solid support. The cells or cell clusters can be disposed in the channel of the solid support.

In another aspect, the present invention provides a device including a three-dimensional scaffold for culturing pancreatic islet cells or adipocytes. The three-dimensional scaffold includes a first portion of a first non-woven polymeric fiber sheet, and a second portion of a second non-woven polymeric fiber sheet overlaying the first portion. The first non-woven polymeric fiber sheet and the second non-woven polymeric fiber sheet can include polymeric fibers including a biogenic polymer and a synthetic polymer. The three-dimensional scaffold includes pancreatic islet cells or adipocytes disposed between the first portion and the second portion. The three-dimensional includes a solid support including a top surface, a bottom surface, and a channel extending from the top surface to the bottom surface. The first portion of the first non-woven polymeric fiber sheet can be disposed on the bottom surface of the solid support. The second portion of the second non-woven polymeric body can be disposed on the top surface of the solid support. The pancreatic islet cells or adipocytes can be disposed in the channel of the solid support.

In one embodiment, the three-dimensional scaffolds include pancreatic islet cells. In another embodiment, the scaffolds include adipocytes. In one embodiment, the first portion of the first non-woven polymeric fiber sheet and the second portion of the second non-woven polymeric sheet can define a space in which the cells are enclosed. The thickness of the solid support can determine a height of the space in which the cells are enclosed, and can be between about 10 µm and about 1 mm. In one embodiment, the present invention provides devices including a plurality of three-dimensional scaffolds, and a plurality of solid supports.

In one embodiment, the devices further include a base layer, e.g., a well of a tissue culture plate or a microfluidics device. In one aspect, the present invention provides methods for treating a subject having diabetes. The methods include providing a three-dimensional scaffold of the invention including pancreatic islet cells, and implanting the scaffold in the subject, thereby treating the subject having diabetes. In some embodiments, the pancreatic islet cells are pancreatic islet stem cells.

In one aspect, the present invention provides methods for identifying a compound that modulates cell differentiation, viability and/or function of a pancreatic islet cell or an adipocyte. The methods include contacting a three-dimensional scaffold of the invention with a test compound. The methods include determining the effect of the test compound on cell differentiation, viability and/or function in the presence and absence of the test compound. A modulation of cell differentiation, viability and/or function in the presence of said test compound as compared to cell differentiation, viability and/or function in the absence of said test compound indicates that said test compound modulates cell differentiation, viability and/or function of the pancreatic islet cell or adipocyte, thereby identifying a compound that modulates differentiation, viability and/or function of a pancreatic islet cell or an adipocyte.

In another aspect, the present invention provides methods for identifying a compound useful for treating diabetes. The methods include contacting a three-dimensional scaffold of the invention including a pancreatic islet cell with a test compound. The methods include determining the effect of the test compound on pancreatic islet cell differentiation, viability and/or function in the presence and absence of the test compound. A modulation of cell differentiation, viability and/or function in the presence of said test compound as compared to cell differentiation, viability and/or function in the absence of said test compound indicates that the test compound is useful for treating diabetes.

In one aspect, the present invention provides methods for identifying a compound useful for treating lipodystrophy. The methods include providing a three-dimensional scaffold of the invention including an adipocyte. The methods include contacting the three-dimensional scaffold with a test compound, and determining the effect of the test compound on adipocyte differentiation, viability and/or function in the presence and absence of the test compound. A modulation of adipocyte differentiation, viability and/or function in the presence of the test compound as compared to adipocyte differentiation, viability and/or function in the absence of the test compound indicates that the test compound is useful for treating lipodystrophy.

In another aspect, the present invention provides a system (e.g., a microfluidic system) including a housing with a first housing portion and a second housing portion forming a chamber therebetween. The housing includes an inlet for introduction of a medium into the system, an inlet channel fluidically connecting the inlet with the chamber, an outlet, and an outlet channel fluidically connecting the chamber with the outlet. The system includes a cartridge configured to be disposed within the chamber. The cartridge includes a cartridge body having a first surface and a second surface and defining a first plurality of channels disposed in the cartridge, each channel of the first plurality of channels extending from the first surface to the second surface of the cartridge body. The first plurality of channels form a plurality of wells disposed in the cartridge, each well configured to hold one or more biological cells. The housing and the cartridge can be configured such that when the cartridge is disposed within the housing and a medium is introduced into the inlet, the medium flows through the inlet channel and into the chamber and at least a first portion of the medium flows laterally between the first surface of the cartridge body and a chamber wall opposite the first surface of the cartridge body to the first plurality of channels, flows through the first plurality of channels, and then flows through the outlet channel to the outlet of the housing.

In another aspect, the present invention provides a system (e.g., a microfluidic system) a housing with a first housing portion, a second housing portion, and a middle housing portion disposed between the first and second housing portions. The first housing portion and the middle housing portion form a first chamber therebetween. The middle housing portion and the second housing portion form a second chamber therebetween. The housing includes an inlet for introduction of a medium into the system, an inlet channel fluidically connecting the inlet with the first chamber and the second chamber, an outlet, and an outlet channel fluidically connecting the second chamber with the outlet. The system includes a first cartridge configured to be disposed within the first chamber. The first cartridge includes a first cartridge body having a first surface and a second surface and defining a first plurality of channels disposed in the first cartridge, each channel of the first plurality of channels extending from the first surface to the second surface of the first cartridge body. The first cartridge includes at least one first porous element disposed adjacent to the second surface of the first cartridge body at the first plurality of channels, the at least one first porous element and the first plurality of channels forming a plurality of wells disposed in the first cartridge, each well configured to hold one or more biological cells. The system includes a second cartridge configured to be disposed within the second chamber. The second cartridge includes a second cartridge body having a first surface and a second surface and defining a first plurality of channels disposed in the second cartridge, each channel of the first plurality of channels extending from the first surface to the second surface of the second cartridge body. The second cartridge includes at least one second porous element disposed adjacent to the second surface of the second cartridge body at the first plurality of channels, the at least one second porous element and the first plurality of channels forming a plurality of wells disposed in the second cartridge, each well configured to hold one or more biological cells. The housing and the first and second cartridges are configured such that when the first and second cartridges are disposed within the housing and a medium is introduced into the inlet, the medium flows through the inlet channel and into the first chamber and at least a first portion of the medium flows laterally between the first surface of the first cartridge body and a chamber wall opposite the first surface of the first cartridge body to the first plurality of channels, flows through the first plurality of channels and the at least one first porous element, and then flows through the inlet channel (located in the middle housing portion) into the second chamber, and at least a first portion of the medium flows laterally between the first surface of the second cartridge body and a chamber wall opposite the first surface of the second cartridge body to the first plurality of channels, flows through the first plurality of channels and the at least one second porous element, and then flows through the outlet channel to the outlet of the housing.

Other features and advantages of the invention will be apparent from the following description of the preferred embodiments thereof, and from the claims. References cited are hereby incorporated by reference.

BRIEF DESCRIPTION OF THE DRAWINGS

Various features and advantages of the embodiments herein described can be fully appreciated as the same becomes better understood when considered in light of the accompanying drawings:

FIGS. 10A-C show perspective, detailed views of an exemplary holder of the present invention.

FIG. 15E is an image of SC-beta cell clusters at Day 0 that were not microencapsulated in an alginate hydrogel (control).

FIG. 15F is an image of SC-beta cell clusters that were microencapsulated in an alginate hydrogel at Day 0.

FIG. 15G is an image at Day 1 of culture of SC-beta cell clusters that are not microencapsulated in an alginate hydrogel and stained with calcein and ethidium homodimer-1 (control).

FIG. 15H is an image at Day 1 of SC-beta cell clusters that were microencapsulated in an alginate hydrogel and stained with calcein and ethidium homodimer-1.

FIG. 15I is an image at Day 2 of culture of SC-beta cell clusters that are not microencapsulated in an alginate hydrogel and stained with calcein and ethidium homodimer-1 (control).

FIG. 15J is an image at Day 1 of SC-beta cell clusters that were microencapsulated in an alginate hydrogel and stained with calcein and ethidium homodimer-1.

FIG. 15K is a graph of the results of these assays.

FIGS. 21A-E show photomicrographs of islet cells cultured under the indicated conditions (scale bar: 200 μm).

DETAILED DESCRIPTION OF THE INVENTION

Figure 1:
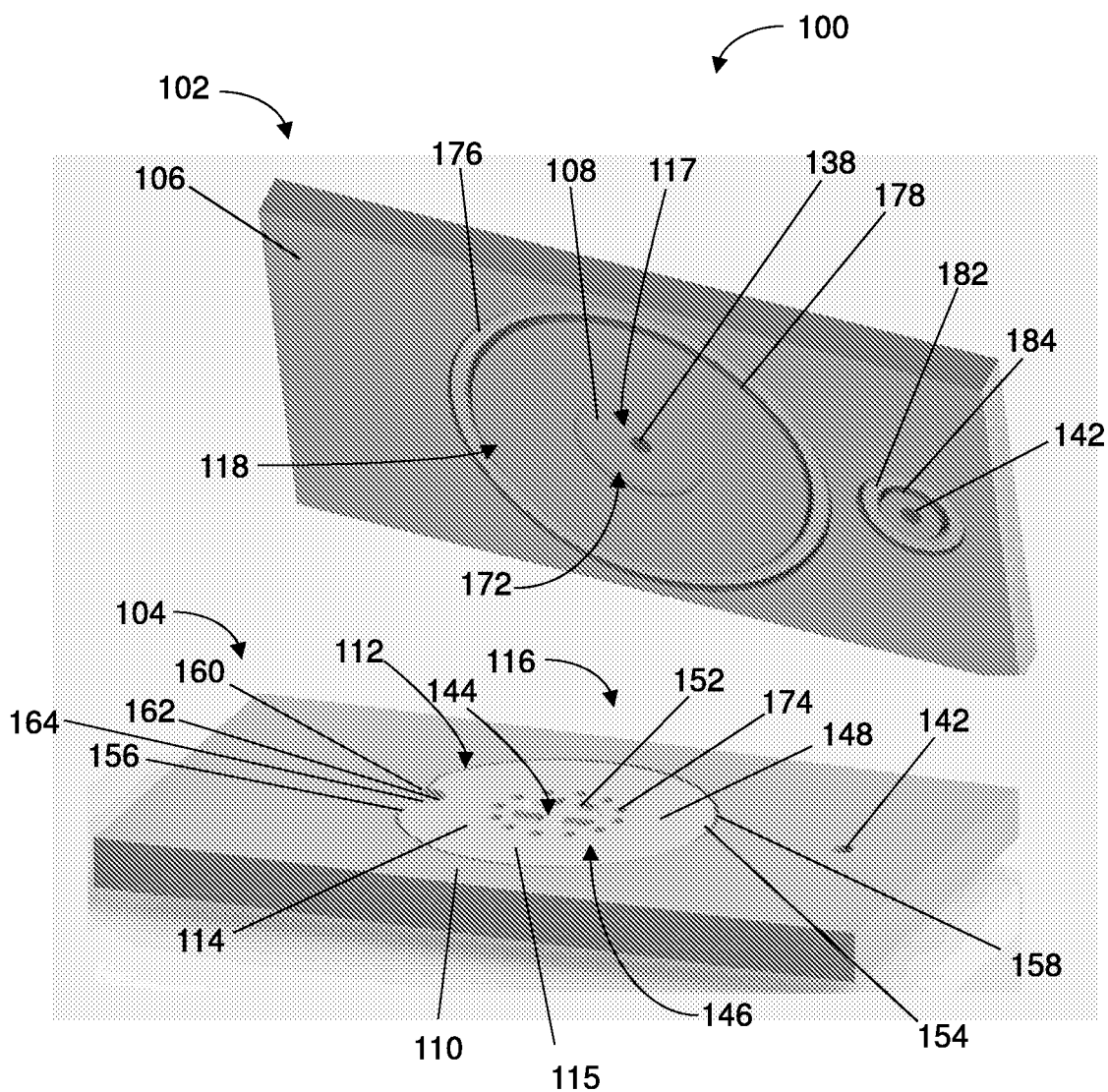
FIG. 1 is a diagrammatic perspective view of an exemplary system of the present invention, in accordance with some embodiments.

It should be understood that the relative terminology used herein, such as "front", "rear", "left", "top", "bottom", "vertical", "horizontal", "upward" and "downward" is solely for the purposes of clarity and designation and is not intended to limit the invention to embodiments having a particular position and/or orientation. Accordingly, such relative terminology should not be construed to limit the scope of the present invention. In addition, it should be understood that the invention is not limited to embodiments having specific dimensions. Thus, any dimensions provided herein are merely for an exemplary purpose and are not intended to limit the invention to embodiments having particular dimensions. In addition, different embodiments of the exemplary fluidic systems are described herein. However, certain structural elements of the different embodiments can be substantially similar in structure and/or function. As such, similar reference numbers are used herein to refer to similar structures.

The adoption of microfluidic technology in biology research is characterized by fine control over culture and experimental parameters. Some embodiments are directed to cartridge-based fluidic systems, e.g., cartridge-based microfluidic systems, for long-term culture of cells (e.g., cell clusters or individual cells). The systems include a cartridge with wells to hold cell clusters and individual cells. The systems also include a housing defining a chamber that receives the cartridge. The housing includes inlet and outlet channels for supplying media to the wells in the cartridge. In some embodiments, the cartridge enables the cells or cell clusters to be easily moved between different types of housings or other modules configured to receive the cartridge for manipulation, culturing or functional measurements. For example, cells or cell clusters may be cultured in wells in a cartridge within a housing, followed by removal of the cartridge from the housing for imaging, which may occur in another housing or module or in a transparent dish holding culture media, and then the cartridge returned to the housing for further culture of the cells or cell clusters. In some embodiments, various cartridges having different numbers of wells, different two-dimensional arrangements of wells, or different dimensions of wells may be used with the same housing for probing various spatially-dependent parameters of cells or cell clusters without requiring any modification of the housing.

Some embodiments of fluidic systems, e.g., microfluidic systems, include features that aid in the long-term culture of cells or cell clusters. For example, in some embodiments, the configuration of the housing and the cartridge is such that the flow of media to the various wells is in parallel, as opposed to being in series, exposing the cells or cells clusters in each well to about the same composition of media (e.g., similar oxygen levels and levels of other micronutrients). This prevents some wells from being exposed to fresh media while other wells are exposed to depleted media, or in the case of a screening assay, to different concentrations of test compound.

As another example, in some embodiments, the system includes one or more three-dimensional scaffolds that anchor the cells or cell clusters in place in the wells and enhance the viability of the cells or cell clusters. Such three-dimensional cell scaffolds are beneficial in the culturing of a wide variety of cells or cell clusters, but they are particularly useful in increasing cell viability of cells that are particularly difficult to culture long-term, such as pancreatic islet cells or adipocytes. In another example, in some embodiments, the cells or cell clusters are microencapsulated with a hydrogel that enhances the viability of the cells or cell clusters. Methods for the microencapsulation of cells or cell clusters are known in the art and include, for example, methods described in, e.g., U.S. Patent Publication No. 2014/0271843; Vegas et al. (2016) Nat Med, 22:3, the entire contents of each of which are incorporated herein by reference, and the examples provided herein. Suitable polymers, e.g., hydrogels, for use in microencapsulating cells or cell clusters are those described below in Section II. Non-limiting examples of such polymers include a gelatin, an alginate, a poly(ethylene glycol) (PEG) hydrogel, a chitosan, or a fragment thereof, and a combination thereof. In some embodiments, a hydrogel comprises an extracellular matrix (ECM) protein. Suitable ECM proteins, can include, e.g., ECM proteins present in a native islet capsule, e.g., a collagen, a laminin, and a fibronectin, or a fragment thereof, and a combination thereof. In one embodiment, the at least one ECM protein is encoded by a gene selected from the group consisting of genes COL6A3, COL6A1, SPP1, COL6A2, LAMC2, COL1A2, FNDC3A, BGN, COL1A1, LAMB1, LAMC1, COL18A1, SPARC, LAMB3, FN1, TNC, FNDC3B, COL3A1, EMILIN1, COL6A6, AGRN, LAMA4, COL28A1, LAMA3, LAMA5, LAMC3, FBN1, LAMB2, COL5A1, or a fragment thereof, and a combination thereof. In other embodiments, for use in the systems and cartridges of the present invention, in addition to non-woven polymeric fiber sheets and three-dimensional scaffolds, cells, such as pancreatic islet cell clusters, may be microencapsulated in a polymer, such as a hydrogel, e.g., alginate.

In some embodiments, combining these features within a fluidic system, e.g., a microfluidic system, enables more precise manipulation of the basic functional units of cell and tissue biology, and the flexibility in combining various elements ensures utility in a variety of applications in long-term cell culture and analysis. Some exemplary fluidic systems, e.g., microfluidic systems, disclosed herein include various components that combine to form a system in which biological cells or cell clusters can be cultured. The system includes a cartridge with wells to hold cells or cell clusters, the cartridge being sandwiched between first and second housing portions of a housing. Each of the first and second housing portions include microfluidic channels for introduction of a medium into the microfluidic system. The first housing portion includes an inlet and an outlet for the system, as well as an inlet channel from the inlet that leads to the cartridge disposed within a chamber between the first and second housing portions. The inlet channel leads into the chamber at a point above the top surface of the cartridge, and the medium flows laterally between the cartridge body and the chamber, thereby reducing shear stress on cells or cell clusters disposed within the wells of the cartridge.

The second housing portion includes a depression or recessed area for placement of the cartridge. The second housing portion includes a set of channels disposed underneath the peripheral portion of the cartridge that combine into a single outlet channel that travels through the second housing portion and the first housing portion to the outlet in the first housing portion. The system also includes first and second seals housed within circumferential grooves of the first housing portion, the seals maintaining a fluidic seal for the microfluidic system. The first seal surrounds the cartridge and the second seal surrounds the outlet channel when the first and second housing portions are positioned against each other.

The present invention is also directed to fluidic systems, e.g., microfluidic systems, for loading biological cells or cell clusters on the cartridge. The systems include a housing with first and second housing portions, and inlet and an outlet. An inlet channel connects the inlet with a chamber in which the cartridge is positioned, an outlet channel connects the chamber with the outlet, and a bypass channel connects the inlet channel with the outlet channel while bypassing the chamber. When the medium and cells or cell clusters are introduced into the system, some of the medium and cells or cell clusters flow through the inlet channel, into the chamber and through the channels within the cartridge. The cells or cell clusters (e.g., hydrogel microencapsulated cells or cell clusters) lodge within the wells formed by the channels in the cartridge, and the remaining medium flows out of the system through the outlet channel. As the number of cells or cell clusters lodged within the wells increases, the flow resistance through the channels in the cartridge increases and the medium and cells or cell clusters begin to flow through the bypass channel. Thus, after cells or cell clusters have been lodged or loaded into the wells of the cartridge, the remaining medium and cells or cell clusters flow through the bypass channel to exit the system.

In another embodiment, the fluidic system, e.g., microfluidic system, for loading cells or cell clusters (e.g., hydrogel microencapsulated cells or cell clusters) on the cartridge includes an alternate channel at least partially surrounding an opening over the cartridge. Initially, flow of the medium through the opening, through the channels in the cartridge, and into the outlet channel creates a suction that draws the medium and cells or cell clusters downward and through the channels in the cartridge. As cells or cell clusters lodge within the wells of the cartridge, the flow resistance through the channels in the cartridge increases, and the medium and remaining cells or cell clusters begin to flow through the alternate channel to bypass the channels in the cartridge. Thus, after cells or cell clusters have been lodged or loaded into the wells of the cartridge, the remaining medium and cells or cell clusters flow through the alternate channel to exit the system.

In some embodiments, cartridges for fluidic systems, e.g., microfluidic systems, are provided that include a body with first and second surfaces, the body including channels extending therethrough. The cartridges further include top and bottom non-woven polymeric fiber sheets forming a three-dimensional scaffold configured to receive one or more cells or one or more cell clusters. The three-dimensional scaffold assists in retaining the cells or cell clusters within the channels of the cartridge. In some embodiments, in addition to the three-dimensional scaffold or instead of the three-dimensional scaffold, a hydrogel, can be used to surround, e.g., microencapsulate, the cells or cell clusters and retain the cells or cell clusters within the channels of the cartridge.

I. Systems, Cartridges, Housings and Holders

Figure 2:
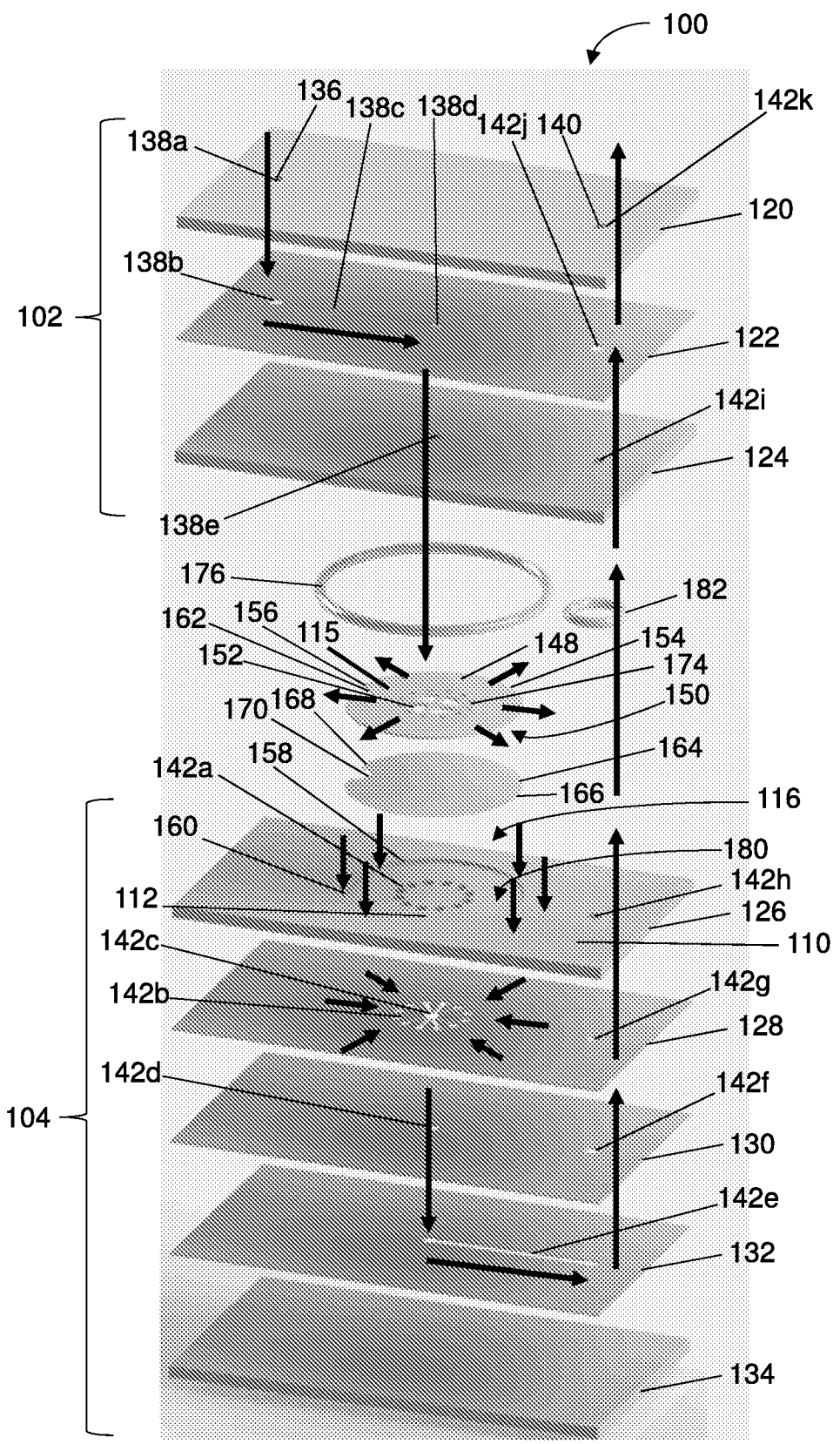
FIG. 2 is a diagrammatic, exploded perspective view of the exemplary system of FIG. 1, in accordance with some embodiments.

FIGS. 1 and 2 are diagrammatic perspective and exploded views of an exemplary fluidic system 100 (hereinafter "system 100") of the present invention. The system 100 includes a housing formed by a first housing portion 102 (e.g., a top housing) and a second housing portion 104 (e.g., a bottom housing). In some embodiments, the first and second housing portions 102, 104 each define a substantially rectangular block defining openings and channels. However, different configurations of the first and second housing portions 102, 104 are contemplated (e.g., non-rectangular configurations). In some embodiments, the first and/or second housing portions 102, 104 are transparent to provide visibility of a medium flowing through the system 100 and/or the cells or cell clusters in the system 100.

The first housing portion 102 includes a surface 106 with a recessed area 108. The second housing portion 104 includes surface 110 with a recessed area 112 configured and dimensioned to at least partially receive a cartridge 114. In particular, the recessed areas 108, 112 form a chamber 116 between the first and second housing portions 102, 104. The chamber 116 includes a central portion 117 and a peripheral portion 118 radially outward from the central portion 117.

Although the structure of the first and second housing portions 102, 104 is illustrated and will be discussed as a plurality of bonded layers, it should be understood that the first and second housing portions 102, 104 can be formed by injection molding or alternative processes, thereby each defining a single structure. In some embodiments, the first housing portion 102 can be formed by a first layer 120, a second layer 122 and a third layer 124 bonded together. The second housing portion 104 can be formed by a fourth layer 126, a fifth layer 128, a sixth layer 130 and a seventh layer 132 bonded together. In some embodiments, the second housing portion 104 can include a base layer 134 bonded to the seventh layer 132.

The first housing portion 102 includes an inlet 136 for introduction of a medium into the system 100 and an inlet channel 138 fluidically connecting the inlet 136 with the central portion 117 of the chamber. In some embodiments, the system 100 can include multiple inlets (e.g., a first inlet and a second inlet) fluidically connected to the inlet channel 138. In such embodiments, a first medium can be introduced into the system through the first inlet, a second medium can be introduced into the system through the second inlet, and the first and second mediums can mix downstream of the first and second inlets (e.g., in the inlet channel, the chamber, or the like). In some embodiments, the inlet channel is formed by apertures 138a, 138b, 138d, 138e and slot 138c (collectively referred to herein as inlet channel 138) in layers of the first housing portion 104. The first housing portion 102 also includes an outlet 140.

The second housing portion 104 and the first housing portion 102 both include portions of an outlet channel 142 fluidically connecting the peripheral portion 118 of the chamber 116 with the outlet 140. In some embodiments, the outlet channel 142 is formed by apertures 142a, 142b, 142d, 142f-k and slots 142c, 142e (collectively referred to herein as the outlet channel 142) in layers of the housing.

A medium introduced into the housing through the inlet 136 flows through the inlet channel 138 and into the central portion 117 of the chamber. Flow in the chamber 116 is described in greater detail below with respect to FIG. 3B. After flowing through the chamber 116, the medium flows through the outlet channel 142 and out of the outlet 140.

As shown in FIG. 2, the inlet channel 138 can extend through the first housing portion 102 prior to entry into the chamber 116, and the outlet channel 142 can initially extend through the second housing portion 104 and further through the first housing portion 102 prior to exit from the outlet 140. For example, the first layer 120 includes an aperture 138a forming a downward flowing portion of the inlet channel 138 and includes an aperture 142k forming an upward flowing portion of the outlet channel 142. The apertures 138a, 142k can be offset from the central portion 117 of the chamber 116.

The second layer 122 includes an aperture 138b offset from the central portion 117 of the chamber 116, an aperture 138d substantially aligned with the central portion 117 of the chamber 116, and an elongated slot 138c fluidically connecting the apertures 138b, 138d, and forming a portion of the inlet channel 138. The slot 138c forms a lateral flowing portion of the inlet channel 138. The second layer 122 also includes an aperture 142j forming an upward flowing portion of the outlet channel 142. The third layer 124 includes an aperture 138e substantially aligned with the central portion 117 of the chamber 116 and forming a downward flowing portion of the inlet channel 138, and includes an aperture 142i forming an upward flowing portion of the outlet channel 142. The apertures 138a, 138b are fluidically connected, and the apertures 138d, 138e are fluidically connected. Similarly, the apertures 142i-k are fluidically connected.

The fourth layer 126 includes a plurality of apertures 142a radially aligned with a central portion 117 of the chamber 116 and forming a downward flowing portion of the outlet channel 142. The fourth layer 126 further includes an aperture 142h offset from the central portion 117 of the chamber 116 and forming an upward flowing portion of the outlet channel 142.

The fifth layer 128 includes a plurality of slots 142b and a central aperture 142c. The slots 142b are radially disposed around the aperture 142c with one end of each slot 142b connecting with the respective aperture of the plurality of apertures 142a and the opposing end of each slot 142b connecting with the aperture 142c. The slots 142b form a lateral flowing portion of the outlet channel 142 that connects with the download flowing portion of the outlet channel 142 of the fourth layer 126 (e.g., the apertures 142a, 142b are fluidically connected). The fifth layer 128 also includes an aperture 142g offset from the central portion 117 of the chamber 116 with the aperture 142g forming an upward flowing portion of the outlet channel 142 fluidically connected to the aperture 142h.

The sixth layer 130 includes an aperture 142d aligned with a central portion 117 of the chamber forming a downward flowing portion of the outlet channel 142 and an aperture 142f offset from the central portion 117 of the chamber forming an upward flowing portion of the outlet channel 142. The aperture 142d is fluidically connected with the aperture 142c, and the aperture 142f is fluidically connected with the aperture 142g.

The seventh layer 132 includes an elongated slot 142e forming a lateral flowing portion of the outlet channel 142. One end of the slot 142e fluidically connects with the aperture 142d (e.g., the downward flowing portion of the outlet channel 142), and the opposing end of the slot 142e fluidically connects with the aperture 142f (e.g., the upward flowing portion of the outlet channel 142). Thus, in some embodiments, the second housing portion 104 include the downward flowing portions of the outlet channel (142a, 142c, 142d) the laterally flowing portions of the outlet channel (142b, 142e) and some of the upward flowing portions of the outlet channel (142f, 142g, 142h) with the remainder of the upward flowing portions of the outlet channel (142i, 142j, 142k) being in the first housing portion 102.

As noted above, the first housing portion 102 and the second housing portion 104 form a chamber 116 configured to receive and/or hold a cartridge 114. The cartridge 114 includes a central portion 144 and a peripheral portion 146. The cartridge 144 is configured and dimensioned to be disposed within the chamber 116 with the central portion 144 of the cartridge 114 disposed in and substantially aligned with the central portion 106 of the chamber 116, and the peripheral portion 146 of the cartridge 114 disposed in and substantially aligned with the peripheral portion 110 of the chamber 116. In particular, the cartridge 114 can be substantially received within the recessed area 112 of the second housing portion 104 (see FIG. 2). The cartridge 114 includes a body 115 having a first surface 148 (e.g., a top surface) and a second surface 150 (e.g., a bottom surface). In some embodiments, the cartridge body 115 has a substantially planar shape with the first surface 148 substantially parallel to the second surface 150. In some embodiments, both the first surface 148 and the second surface 150 of the cartridge body 115 have a substantially circular perimeter.

The cartridge body 115 defines a first plurality of channels 152 disposed in the peripheral portion 146 of the cartridge 114. Each channel 152 extends from the first surface 148 to the second surface 150 of the body (e.g., through the thickness of the cartridge body 115). In some embodiments, the cartridge body 115 has a keyed configuration complementary to the configuration of the recessed area 112 of the second housing portion 104 such that the orientation of the cartridge 114 within the recessed area 112 is fixed. For example, a section of the perimeter of the cartridge body 115 can define a rounded edge 154 and a section of the perimeter of the cartridge body 115 can define a straight portion 156 corresponding to a planar edge. The recessed area 112 can similarly include a perimeter with a rounded portion 158 and a straight portion 160. The straight portion 156 of the cartridge body 115 perimeter can include a radially inward directed portion or rounded notch 162 that provides a finger grip for removal of the cartridge 114 from the recessed area 112.

The cartridge 114 includes at least one porous element 164 (e.g., a filter, a porous polycarbonate membrane, one or more non-woven polymeric fiber sheets, or the like) disposed adjacent to the second surface 150 of the cartridge body 115. The one or more porous elements 164 and the plurality of channels 152 form a plurality of wells disposed in the peripheral portion of the cartridge. The porous element 164 is disposed adjacent to the second surface 150 of the cartridge body 115 such that the channels 152 form a plurality of wells having a porous bottom surface. Each well can be configured and dimensioned to receive and hold one or more biological cells (e.g., individual cells, one or more clusters of cells, or the like).

In some embodiments, the system 100 can include one or more three-dimensional scaffolds for culturing cells or cell clusters that include first and second portions of non-woven polymeric fiber sheets overlaid relative to each other, the cells or cell clusters being disposed between the fiber sheets. Such three-dimensional scaffolds can be disposed within the wells of the cartridge 114 prior to introduction of the medium into the system 100 in some embodiments. This is described in greater detail below in Section II entitled "Scaffolds for Cell Growth." In some embodiments, the at least one porous element 164 is a nonwoven polymeric fiber sheet and a second non-woven polymeric fiber sheet, or a second portion of the same nonwoven polymeric fiber sheet covers a top surface of the plurality of wells after placement of the cells or cell clusters in the wells forming the three dimensional scaffold. This is described in greater detail below with respect to below in Section II entitled "Scaffolds for Cell Growth" and depicted in the lower right side detail image of FIG. 15A. In some embodiments, the non-woven polymeric fiber sheet(s) cover most or all of the first (top) surface and the second (bottom) surface of the cartridge body. In other embodiments, the non-woven polymeric fiber sheet may cover only the portions of the top and bottom surfaces of the cartridge body (e.g., the portion of the bottom surface of the cartridge body including the first plurality of channels to form the well bottoms and the portion of the top surface of the cartridge body that includes wells that contain cells or cell clusters).

In some embodiments the porous element 164 has a perimeter matched to that of the cartridge body 115 (e.g., a rounded portion 166, a straight portion 168, an inwardly directed opening or rounded notch 170). In some embodiments, the porous element is large enough to cover the bottom of the first plurality of channels to form wells, but has a smaller area than that of the cartridge body. In some embodiments, multiple porous elements are used to cover the bottom of the first plurality of channels to form wells.

In some embodiments, the cartridge body 115 can define a second plurality of channels 174 extending from the first surface 148 to the second surface 150 of the cartridge body 115. In some embodiments, the configuration of the first plurality of channels 152 can be different than that of the second plurality of channels. For example, in some embodiments each of the first plurality of channels 152 has a wedge-shaped or pie-shaped perimeter (as shown), while each of the second plurality of channels 174 has a circular perimeter (as shown). In some embodiments, the individual channels in the first plurality of channels 152 can be of different configurations and/or sizes. In some embodiments, the individual channels in the second plurality of channels 174 can be of different configurations and/or sizes.

Each channel in the second plurality of channels 174 can be disposed radially outward from the central portion 144 of the cartridge 114. In particular, in some embodiments, each channel in the second plurality of channels 174 is disposed radially further from the central portion 144 of the cartridge 114 than any channel in the first plurality of channels 152. In some embodiments, the second plurality of channels 174 is disposed radially outward relative to the central portion 144 of the cartridge 114 and surrounds the channels 152. In some embodiments, the second plurality of channels 174 can be fluidically connected to the respective apertures 142a of the outlet channel 142. In some embodiments, the porous element 164 extends under the second plurality of channels 174 at the second surface of the cartridge body. In other embodiments, the porous element 164 does not extend under the second plurality of channels 174 at the second surface of the cartridge body.

In some alternative embodiments, the first plurality of channels is replaced with a first plurality of wells in which the cartridge body forms the sides and the bottom of the wells. In this embodiment, the medium does not flow from the first surface of the cartridge body to the second surface of the cartridge body through the wells, but instead flows into and across the wells and on to the second plurality of channels, through which it flows to the second surface of the cartridge. In such embodiments, the cartridge need not include the porous element.

In some embodiments, the system 100 includes one or more sealing elements for maintaining a fluid tight connection between the first and second housing portions 102, 104. For example, the system 100 can include a first sealing element 176 (e.g., an O-ring, polymeric or elastomeric gasket) configured to be disposed between a first chamber wall 172 corresponding to the portion of the surface 106 of the first housing portion 102 at the recess 108 and a second chamber wall 180 corresponding to the portion of the surface 110 of the second housing portion at the recess 112. In some embodiments, the first sealing element 176 encircles the first plurality of channels 152 and the second plurality of channels 174. In some embodiments, the sealing portion of the first surface 148 can be at or near the perimeter of the cartridge body 115 as shown. In some embodiments, the first chamber wall 172 includes a circumferential groove 178 configured and dimensioned to at least partially receive the first sealing element 176. In some embodiments, the circumferential groove 178 can be centered relative to the central portion 117 of the chamber 116 (e.g., the inlet channel 138 shown in FIG. 1). In some embodiments, the size and configuration of the first sealing element 176 is selected such that when the first housing portion 102 is disposed over the second housing portion 104, the sealing element 176 will be disposed against the second chamber wall 180 of the second housing portion 104 surrounding the recessed area 112 and the cartridge 114. The depth of the groove 178 can be such that a portion of the sealing element 176 extends out from the first chamber wall 172 beyond the non-groove portion of the first chamber wall 172. The extended portion of the sealing element 176 thereby creates a seal with the second chamber wall 180 of the second housing portion 104 when the first housing portion 102 is positioned against the second housing portion 104, and acts as the sealing area for the inlet channel 138 and the chamber 116.

In some embodiments, the system alternatively or additionally includes a sealing element (not shown) configured to be disposed between the first chamber wall and the 712 and the first surface 148 of the housing body radially beyond the first plurality of channels 152 and the second plurality of channels 174. In some embodiments, this takes the form of a gasket (e.g., of polydimethylsiloxane (PDMS)) at, over, or near an outer perimeter of the cartridge body. In some embodiments, this gasket is attached to the cartridge body or formed on or around the cartridge body.

In some embodiments, the system 100 includes a second sealing element 182 (e.g., an O-ring, polymeric or elastomeric gasket) configured to be disposed between the first and second housing portions 102, 104 and encircling the outlet channel 142. In some embodiments, the surface 106 of the first housing portion 102 includes a groove 184 for receiving or holding the second sealing element 182. For example, the surface 106 of the first housing portion 102 includes a circumferential groove 184 centered relative to the outlet channel 142. Similar to the groove 178, the depth of the groove 184 can be dimensioned such that a portion of the sealing element 182 extends from the first chamber wall 172 beyond a non-grooved portion of the first chamber wall. Thus, when the first housing portion 102 is positioned against the second housing portion 104, the sealing element 182 presses against the second chamber wall 180 to create a sealing area for the outlet channel 142.

Figure 3A:
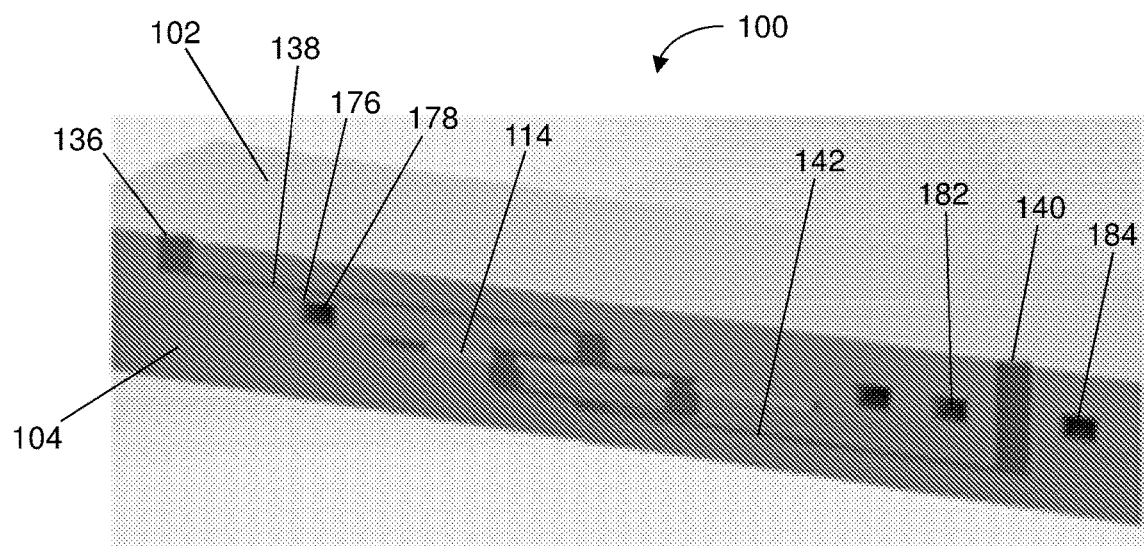
FIG. 3A is a diagrammatic, perspective, cross-sectional view of the exemplary system of FIG. 1, in accordance with some embodiments.

With reference to FIGS. 2 and 3A, after biological cells or cell clusters have been positioned within the wells of the cartridge 114, the cartridge 114 is positioned in the recessed area 112 of the second housing portion 104, and the first housing portion 102 is disposed over the second housing portion 102 with the sealing elements 176, 182 therebetween. Positioning the first and second housing portions 102, 104 against each other encloses the cartridge 114 within the chamber 116.

Figure 3B:
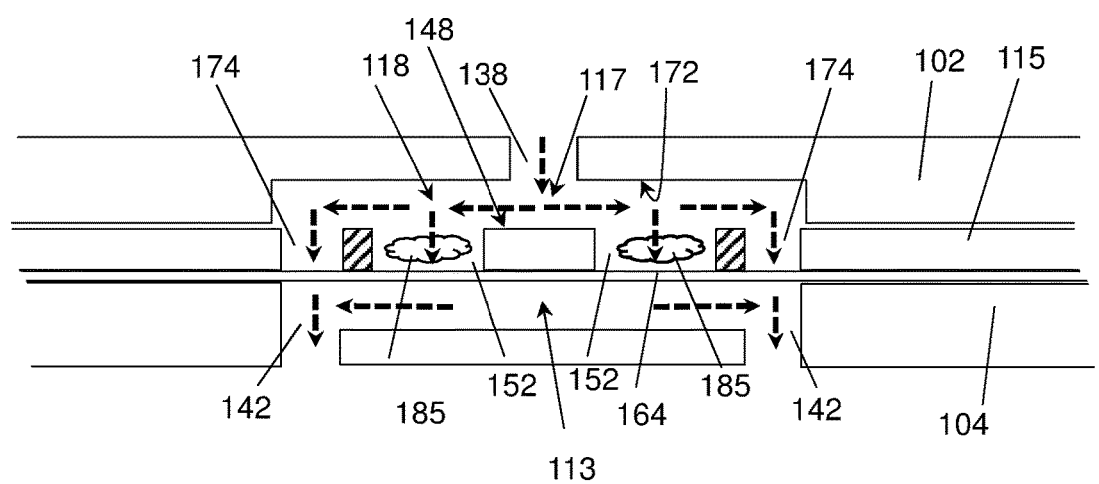
FIG. 3B is a diagrammatic, cross-sectional view of a portion of the system of FIG. 1.

A medium (e.g., culture medium) can be introduced into the system 100 to pass the medium through the cartridge 114 and over the cells or cell clusters. The arrows in FIG. 2 illustrate the flow path of the medium through the system 100, and FIGS. 3A and 3B illustrate the medium within the system 100. In FIG. 3B, the first layer and the second layer of the first housing portion 102 and the fourth layer, the fifth layer, the sixth layer, and the base of the second housing portion are omitted for ease in visualization and the thickness of various elements are exaggerated for illustrative purposes. In FIG. 3B the dotted arrows illustrate the flow path of the medium into the chamber and through the cartridge. The medium is introduced into the system 100 through the inlet 136, flows through the inlet channel 138, into the central portion 117 of the chamber. At least a portion of the medium flows radially outward between the first surface 148 of the cartridge 114 and the first chamber wall 172 (e.g., the inner wall of the first housing portion 102) opposite the first surface 148 of the cartridge 114. In some embodiments, this radially outward flow of the medium over the surface of the cartridge body ensures a uniform distribution of fluid shear for the various wells. At least a portion of the medium further flows through the first plurality of channels 152, the porous element 164, through the outlet channel 142, and out of the outlet 140. In some embodiments, the medium can flow through each of the channels 152 at substantially the same time.

Thus, media and cell stimuli can be delivered through the input 136 at the top of the first housing portion 102, which flows down onto the cartridge 114. Flow of the medium can travel radially outwards across the surface of the cartridge 114 towards channels 152 at the peripheral portion of the cartridge 114. After passing by or over the cells or cell clusters 185 disposed within the wells formed by the channels 152, the medium is focused into a common outlet channel 142 underneath the cartridge 114 before being directed back up to the outlet 140, carrying cellular secretions with it and out of the system 100. Because the arrangement of the wells and the cells or cell clusters contained within the wells on the cartridge 114 is substantially perpendicular to the flow path, a stimulus delivered through the system 100 reaches all cells or cell clusters trapped in the cartridge 114 substantially simultaneously, reducing possible time delays between them. Further, the system delivers the media to the wells in parallel, as opposed to in series, to avoid problems associated with depletion of the cell media, which is described below in Example 3 with respect to FIG. 16.

In embodiments that include the second plurality of channels 174 disposed radially outward beyond the first plurality of channels 152, when the medium is introduced into the system 100, at least a portion of the medium can flow radially outward between the first surface 148 of the cartridge 114 and the first chamber wall 172, past the channels 152 and into the channels 174. The radial flow of the medium allows some of the medium to flow over the cells 185 within the wells without flowing through the channels 152, thereby reducing the shear stress on the cells or cell clusters. This portion of the medium further flows through each of the channels 174, through the outlet channel 142 and out of the outlet 140.

In some embodiments, as shown in FIG. 3A, the medium flows directly from the channels 174 and into the outlet channels 142. In some embodiments, as shown in FIG. 3B, the recess 112 in the second housing portion may have features that direct flow. For example, as shown in FIG. 3B, the second housing portion 104 can include a second recess 113 within the recess 112 configured to receive the cartridge 114. The second recess 113 has an area smaller than that of the cartridge 114, which creates a second chamber under the cartridge body for flow of media to the outlet channel 142 from the cartridge 114 having different configurations of channels. In some embodiments that employ the second chamber, there may be only a single outlet channel leaving the chamber instead of a plurality of outlet channels leaving the chamber that join together into one outlet channel.

In embodiments in which there is no second plurality of channels, most or all of the media flows through the first plurality of channels and the porous element.

In alternate embodiments in which the first plurality of channels is replaced by a first plurality of wells with the cartridge body forming the bottom of each well, the media that flow into the wells, flows back out of the wells and flows through the second plurality of channels to the second surface of the cartridge body.

In alternate embodiments in which there is radial flow from multiple different points, the inlet channel may divide into multiple channels before connecting with various portions of the chamber (e.g., in the central and or peripheral portions of the chamber).

In alternate embodiments in which the flow is linear instead of radial, the inlet channel need not connect with a central portion of the chamber, but could connect at or near and end of the chamber, in the middle of the chamber, or both.

Figure 4:
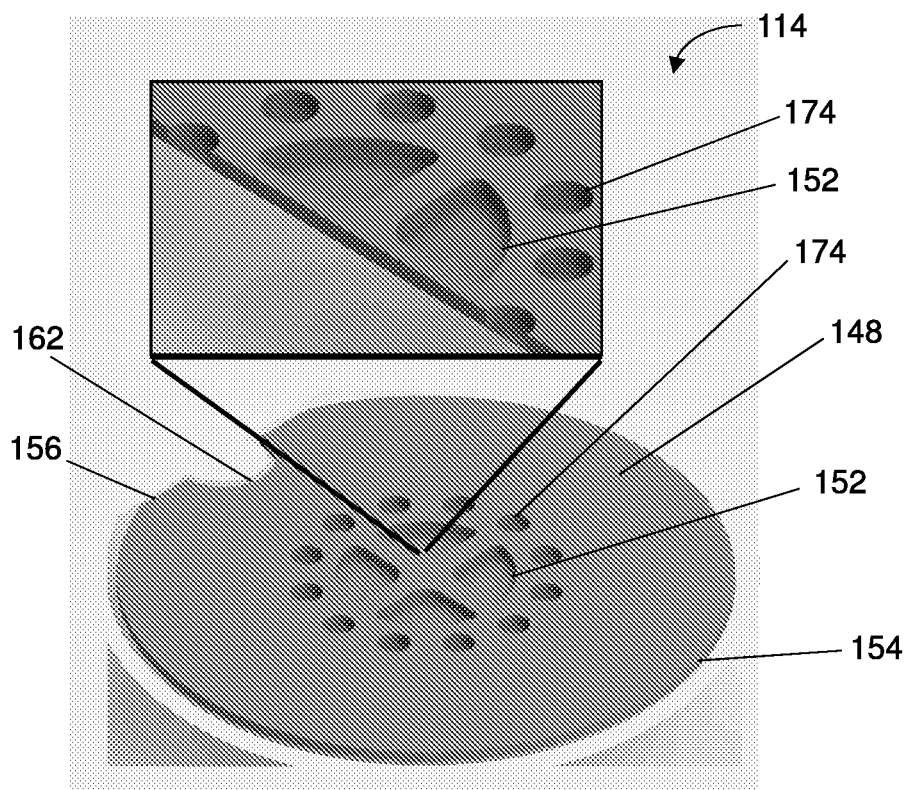
FIG. 4 is a diagrammatic perspective view and a detail view of an exemplary cartridge of the present invention, in accordance with some embodiments.
Figure 5:
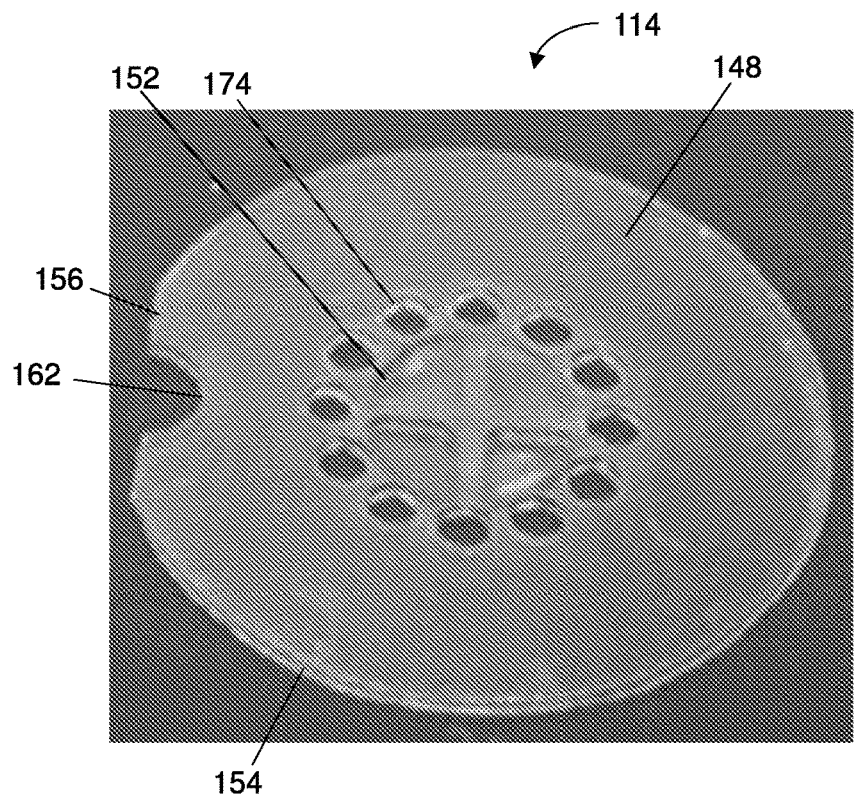
FIG. 5 is a perspective view of an example cartridge of the present invention.
Figure 6:
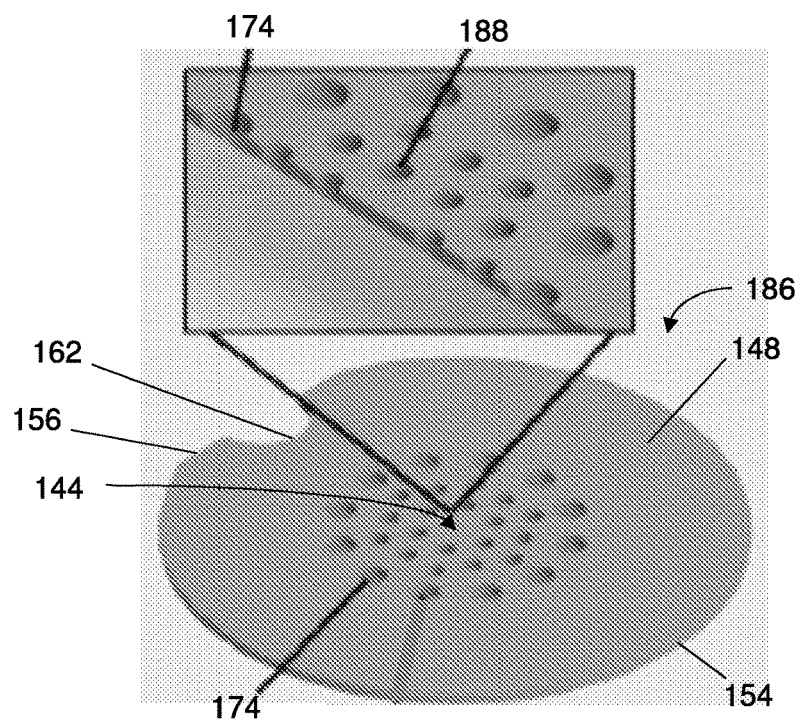
FIG. 6 is a diagrammatic perspective view and a detail view of an exemplary cartridge of the present invention having a different configuration of wells, in accordance with some embodiments.

FIGS. 4-6 show embodiments of some exemplary cartridges 114, 186 of the present invention. FIG. 4 shows the cartridge 114 of FIGS. 1 and 2. FIG. 5 is a perspective image of an example cartridge made by the Applicants based on exemplary cartridge 114 except with channels in the porous element corresponding to the second plurality of channels. With respect to FIGS. 4 and 5, the first plurality of channels 152 can be substantially wedge shaped (as shown). In some embodiments, the outer edge of the wedge can have a radius in a range of 1 mm to 7 mm, in a range of 1.5 mm to 3.5 mm, or in a range of 2 mm to 2.5 mm (e.g., approximately 2.2 mm). In some embodiments, each of the second plurality of channels 174 is substantially circular (as shown). In some embodiments, each of the second plurality of channels has a diameter that falls in a range of 100 μm to 2 mm, in a range of 600 μm to 1 mm, or in a range of 700 μm to 900 μm (e.g., approximately 800 μm). In some embodiments, the outer diameter of the cartridge 114 can be in a range of 5 mm to 50 mm, in a range of 5 mm to 20 mm, or in a range of 10 mm to 20 mm (e.g., approximately 15 mm).

FIG. 6 shows a cartridge 186 having channels of a different configuration. The cartridge 186 can include a first plurality of channels 188 each having a substantially circular configuration (as shown). In some embodiments, each of the first plurality of channels 188 has a diameter that falls in a range of 100 μm to 900 μm, falls in a range of 300 μm to 700 μm, or falls in a range of 400 μm to 700 μm (e.g., approximately 500 μm). In some embodiments, each of the first plurality of channels 188 has a diameter that falls in a range of 20 μm to 500 μm, falls in a range of 100 μm to 300 μm, falls in a range of 150 μm to 250 μm (e.g., approximately 250 μm), which may be configured to receive a single cell or a single cluster of cells. In some embodiments, each of the first plurality of channels 188 has a diameter, length or width that falls in a range of 1 mm to 10 mm, falls in a range of 5 mm to 8 mm, falls in a rage of 5.5 mm to 7.5 mm, or is about 6.4 mm, which may be configured to receive multiple cells or multiple cell clusters. In some embodiments, the first plurality of channels 188 can be formed as two rings of channels (e.g., a first ring of channels disposed near the central portion 144, and a second ring of channels disposed radially outward further from the central portion 144). However, it should be understood that the configurations, sizes, and spacing between channels can be varied based on the cells, media being used and other parameters.

Figure 7A:
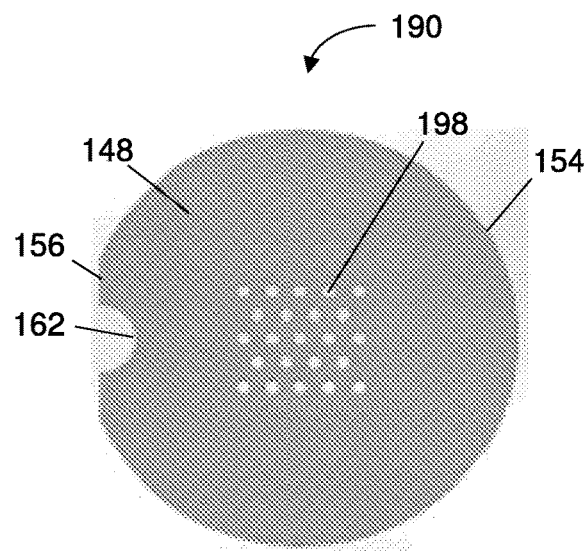
FIGS. 7A-J show exploded perspective views of exemplary cartridges of the present invention.
Figure 7B:
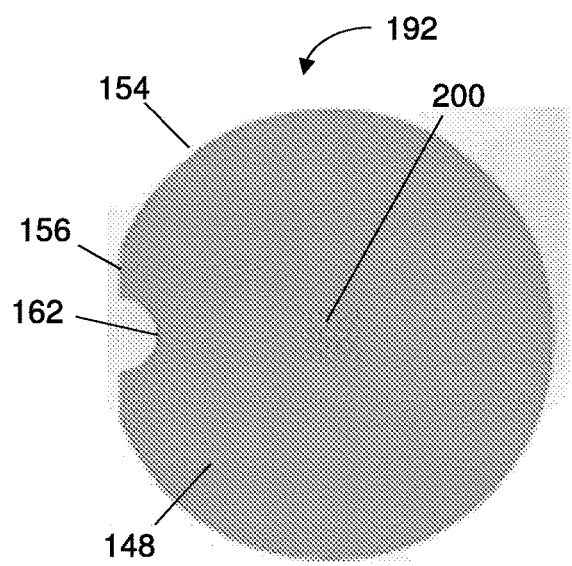
Figure 7C:
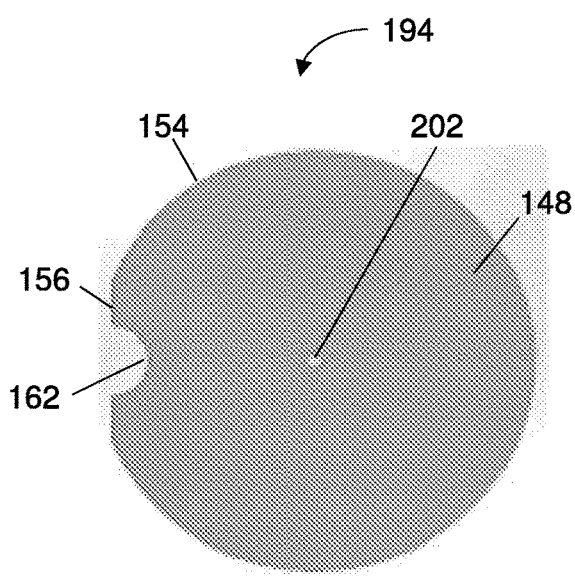
Figure 7D:
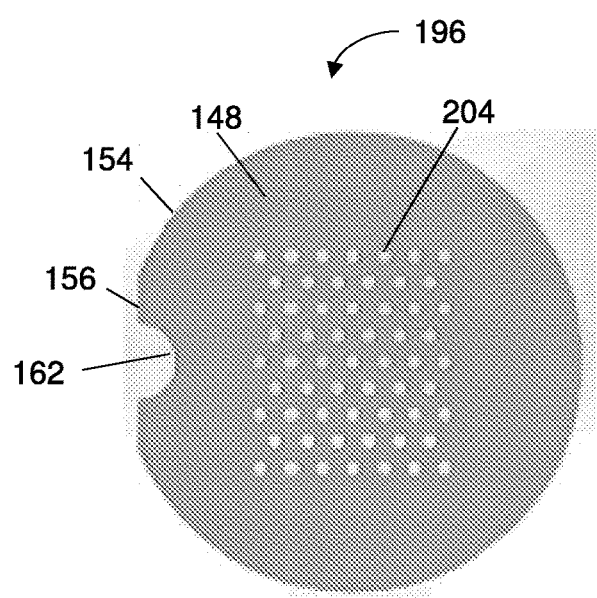

FIGS. 7A-J show alternative designs of cartridges 190, 192, 194, 196 of the present disclosure. FIGS. 7A and 7B show cartridges 190, 192 having different well diameters and interwell spacing. In particular, FIG. 7A shows the cartridge 190 including twenty-three wells 198 each having a diameter of approximately 500 μm and spaced approximately 500 μm from each other. FIG. 7B shows the cartridge 192 including twenty-three wells 200 each having a diameter of approximately 200 μm and spaced approximately 200 μm from each other. FIGS. 7C and 7D show cartridges 194, 196 with different numbers of wells. In particular, FIG. 7C shows the cartridge 194 including a single well 202 with a diameter of approximately 500 μm. FIG. 7D shows the cartridge 196 including fifty-nine wells 204 with a diameter of approximately 500 μm and spaced approximately 500 μm from each other.

Figure 7E:
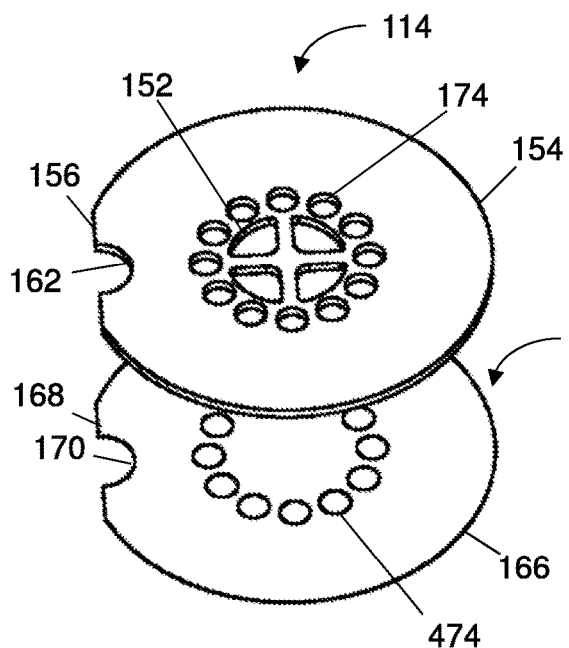
Figure 7F:
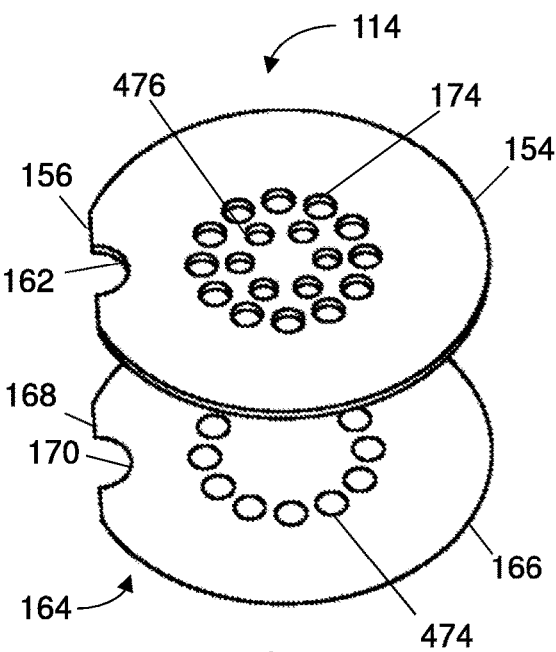
Figure 7G:
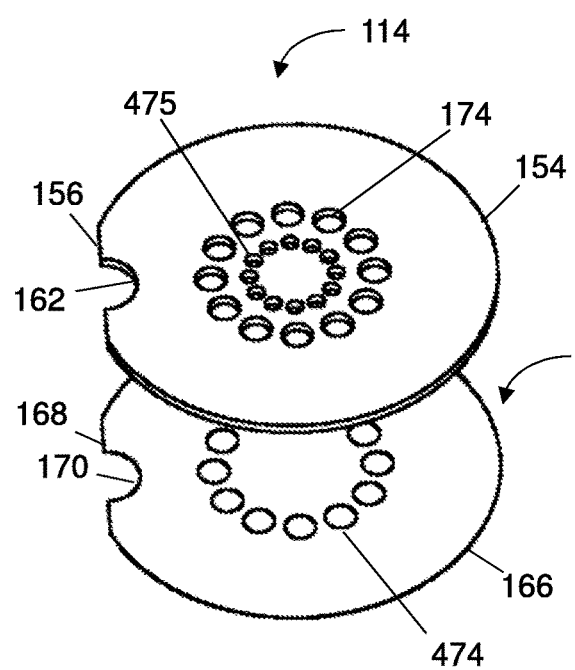
Figure 7H:
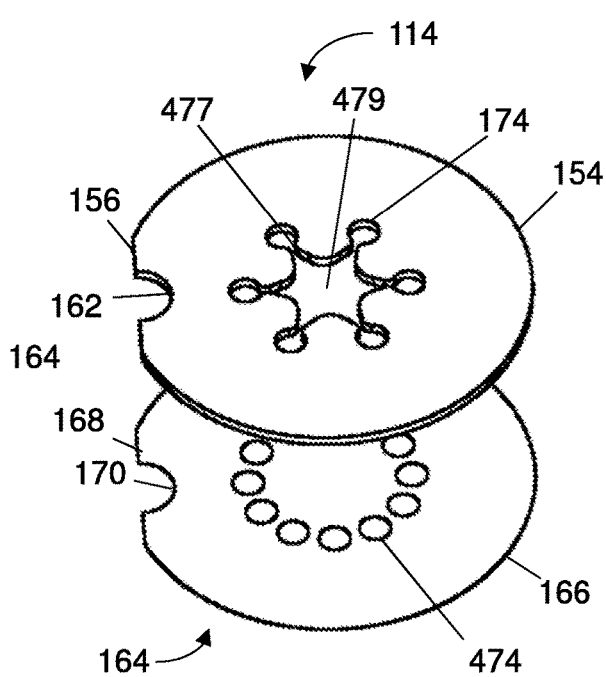

FIGS. 7E-J show cartridges 114, 566 including porous elements 164, 568. FIG. 7E shows the cartridge 114 including four wedge-shaped channels 162 surrounded by circular channels 174, and a porous element 164 including openings 474 passing therethrough and aligned with the channels 174. FIG. 7F shows the cartridge 114 including six circular channels 476 surrounded by circular channels 174, and a porous element 164 including openings 474 passing therethrough and aligned with the channels 174. FIG. 7G shows the cartridge 114 including twelve circular channels 475 surrounded by circular channels 174 each having a larger diameter that that of circular channels 475, and a porous element 164 including openings 474 passing therethrough and aligned with the channels 174. FIG. 7H shows the cartridge 114 including a central channel 479, six constrictions 477 leading outwardly from the central channel 479 and connecting with circular channels 174, and a porous element 164 including openings 474 passing therethrough and aligned with the channels 174. With the cartridges shown in FIGS. 7A-H, the media can flow from a central portion of the cartridge radially or laterally outward into the channels 174.

Figure 7I:
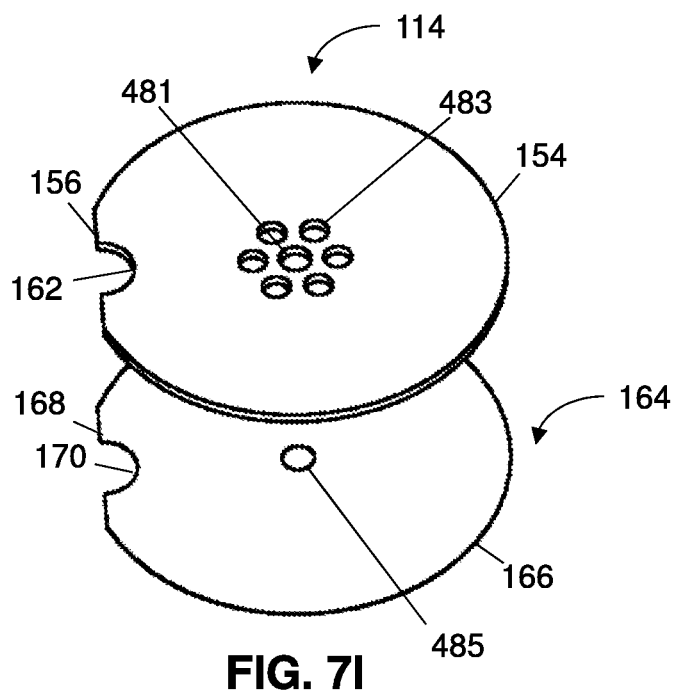
Figure 7J:
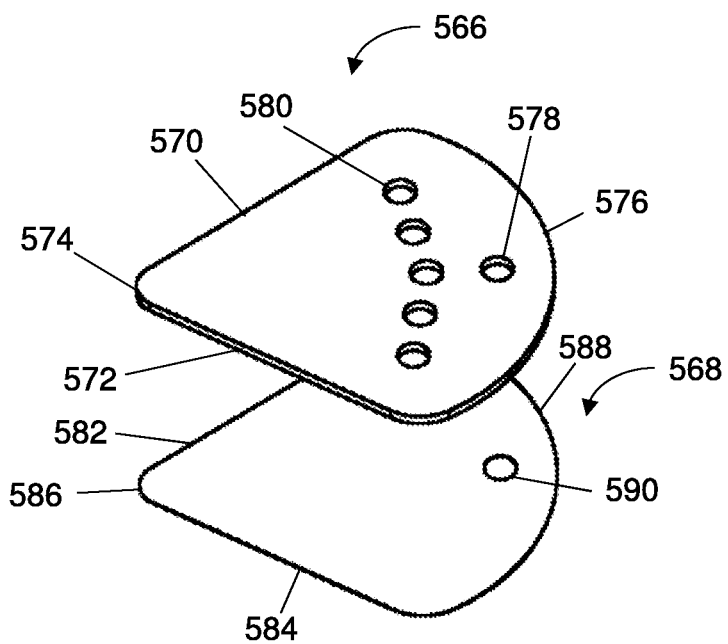

FIG. 7I shows the cartridge 114 including a central channel 481 surrounded by circular channels 483, and a porous element 164 including a central opening 485 passing therethrough and aligned with the channel 481. In such embodiment, the media can flow from a peripheral portion of the cartridge 114 radially or laterally inward into the channel 481. FIG. 7J shows a wedge-shaped cartridge 566 and porous element 568, the details of which are discussed below with respect to FIGS. 50-52. In the embodiment of FIG. 7J, the media can flow from one end of the cartridge 566, over the channels 580, and through the channel 578.

Thus, the different configurations of cartridges allow for flow of media radially or laterally inward from the periphery of the cartridge, radially or laterally outward from a central portion of the cartridge, or linearly from one side to another over the cartridge. In each configuration, the media can flow directly through the wells or first channels containing the cell or cell clusters, can flow into and across the wells and further into and through the adjacent channels, or a combination of the two. The number, shape and configuration of the wells and channels can vary depending on the cells being tested. In some embodiments, a diameter, a width or a length of each of the wells independently falls in a range of about 0.02 mm to about 2 mm, about 0.05 mm to about 2 mm, about 0.1 mm to about 2 mm, about 0.3 mm to about 2 mm, about 0.02 mm to about 1.5 mm, about 0.05 mm to about 1.5 mm, about 0.1 mm to about 1.5 mm, about 0.3 mm to about 1.5 mm, about 0.02 mm to about 0.7 mm, about 0.05 mm to about 0.7 mm, about 0.1 mm to about 0.7 mm, or about 0.3 mm to about 0.7 mm for a single cell cluster. In some embodiments, a diameter, a width or a length of each of the wells independently falls in a range of about 0.05 mm to about 15 mm, about 0.1 mm to about 15 mm, about 0.5 mm to about 15 mm, about 1 mm to about 15 mm, about 3 mm to about 15 mm, about 0.05 mm to about 12 mm, about 0.1 mm to about 12 mm, about 0.5 mm to about 12 mm, about 1 mm to about 12 mm, about 3 mm to about 12 mm, about 0.05 mm to about 10 mm, about 0.1 mm to about 10 mm, about 0.5 mm to about 10 mm, about 1 mm to about 10 mm, about 3 mm to about 10 mm, about 0.05 mm to about 7 mm, about 0.1 mm to about 7 mm, about 0.5 mm to about 7 mm, about 1 mm to about 7 mm, about 3 mm to about 7 mm, for multiple cell clusters. In some embodiments, the height of each well independently can range between about 0.02 mm to about 5 mm, about 0.05 mm to about 5 mm, about 0.1 mm to about 5 mm, about 0.5 mm to about 5 mm, about 0.02 mm to about 4 mm, about 0.05 mm to about 4 mm, about 0.1 mm to about 4 mm, about 0.5 mm to about 4 mm, about 0.02 mm to about 4 mm, about 0.05 mm to about 3 mm, about 0.1 mm to about 3 mm, about 0.5 mm to about 3 mm, or about 1 mm to about 2 mm. In some embodiments, the interwell spacing can range between about 0.05 mm to about 5 mm, about 0.1 mm to about 5 mm, about 0.5 mm to about 5 mm, about 0.05 mm to about 4 mm, about 0.1 mm to about 4 mm, about 0.5 mm to about 4 mm, about 0.05 mm to about 3 mm, about 0.1 mm to about 3 mm, about 0.5 mm to about 3 mm, or about 1 mm to about 2 mm. The diameter of the wells and the interwell spacing may be selected based on the size of cells to be disposed in the wells and/or the amount or speed of the media flowing through the cartridge.

In some embodiments, each of the plurality of wells is configured and dimensioned to receive a single cluster of cells. For example, in some embodiments, a diameter, a width, or a length of each of the wells falls in a range of 20 μm to 500 μm, falls in a range of 100 μm to 300 μm, falls in a range of 150 μm to 250 μm, or is about 200 μm. In some embodiments, each of the plurality of wells is configured and dimensioned to receive multiple clusters of cells. For example, in some embodiments, a diameter, a width or a length of each of the wells falls in a range of 1 mm to 10 mm, falls in a range of 5 mm to 8 mm, falls in a rage of 5.5 mm to 7.5 mm, or is about 6.4 mm. In some embodiments, a spacing between nearest neighbor wells in the plurality of wells falls in a range of 50 μm to 5 mm, falls in a range of 200 μm to 1 mm, falls in a range of 300 μm to 500 μm, or is approximately 400 μm.

In some alternate embodiments, the flow occurs radially outward simultaneously from multiple different areas, as opposed to just radially outward from the central portion of the chamber.

In some alternate embodiments, the system need not employ radial flow. For example, in some embodiments, the cartridge and system may be arranged for linear parallel flow along the surface of the cartridge. In such embodiments, the cartridge body may have a substantially rectangular plate configuration, as opposed to a substantially disk shaped configuration.

Because the portions 102, 104 of the housing and the cartridge 114 that holds the cells or cell clusters are all separate from one another, they can be manipulated independently and may benefit from a modular design process. FIGS. 7A-D offer demonstrations of this modularity by changing features within a cartridge. For example, a single rectangular array of wells evenly spaced apart can be altered in terms of well diameter and interwell spacing (FIGS. 7A-B) or the overall number of wells (FIGS. 7C-D). Any subset of the parameters can be changed with ease. While all cartridge designs displayed in FIGS. 7A-D are a rectangular grid with equidistant wells, it is equally possible to alter the well configuration to accomplish other patterns of cell or cell cluster arrangements.

The wells within a cartridge may be further patterned by changing the cellular content contained within each one. Instead of individual cells or cell clusters, the cartridge could contain small monolayers of cells grown upon the membrane. More complex configurations can involve two or more different populations of cells (or cell clusters) contained within the same cartridge but in distinct wells, their placement dictated by the cartridge geometry. Changing the location and spacing of the wells relative to one another allows for an assessment of behaviors between neighboring cell or cell clusters of the same cell type or different cell types.

In some embodiments, after the cartridge 114 has been disposed between the first and second housing portions 102, 104, the first and second housing portions 102, 104 can be bonded together to maintain the cartridge 114 sealed therebetween. Bonding the first and second housing portions 102, 104 maintains a pressure between the components to fluidically seal the components of the system 100 together.

Figure 24:
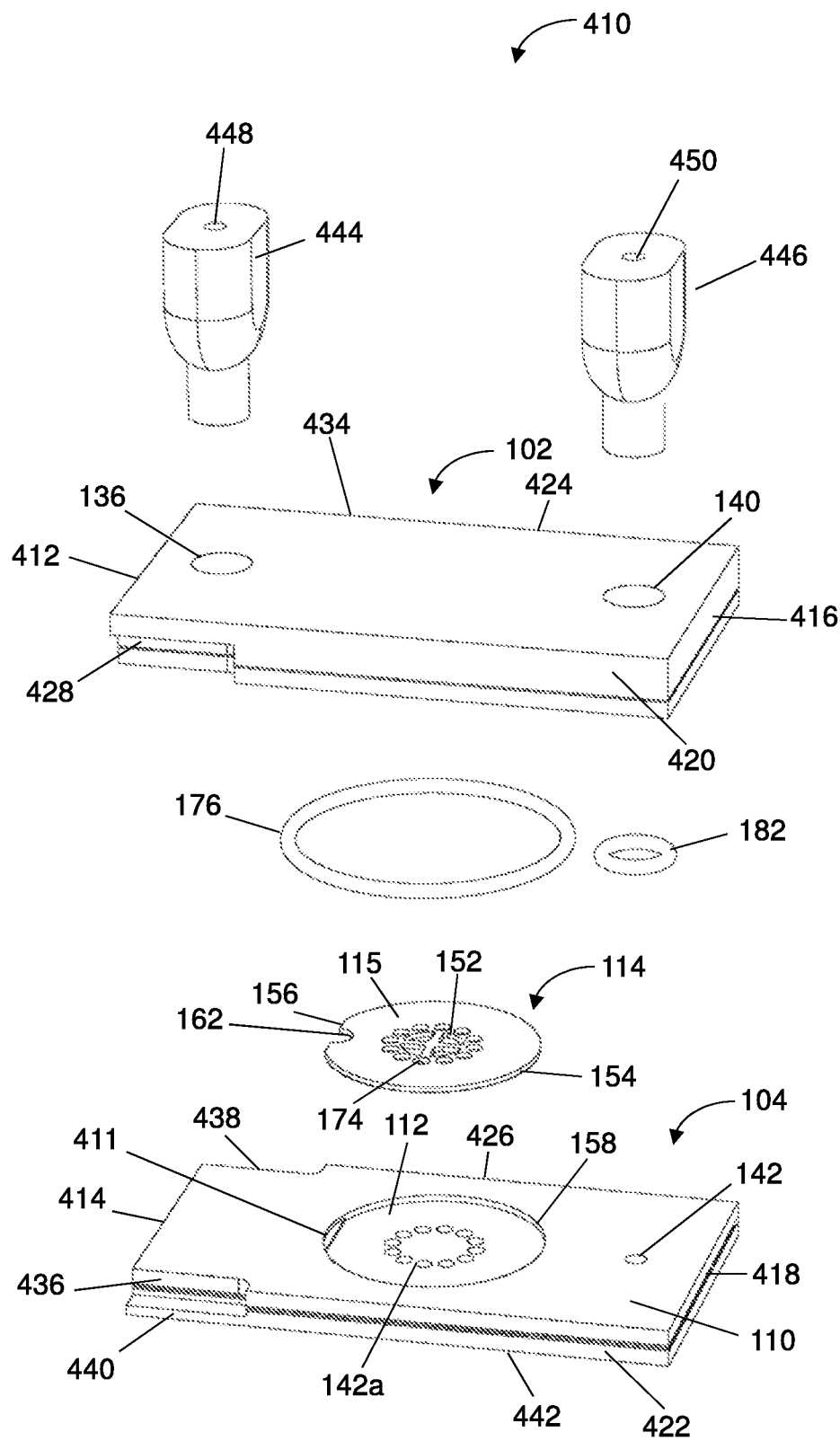
FIG. 24 is a diagrammatic exploded perspective view of an exemplary system of the present invention, in accordance with some embodiments.
Figure 25:
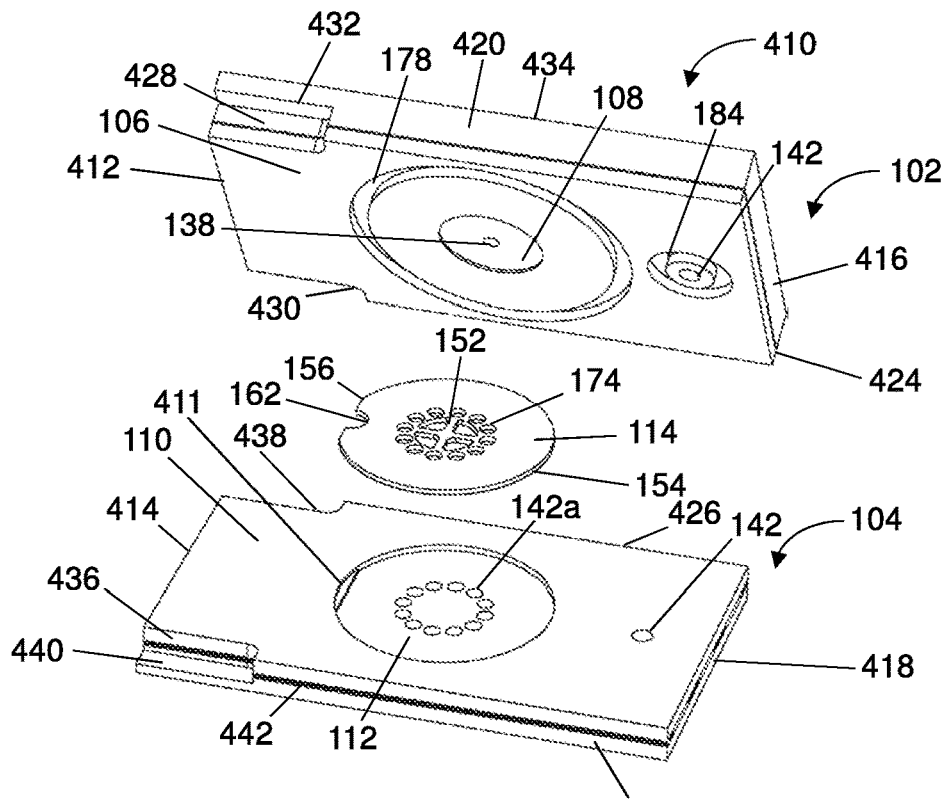
FIG. 25 is a diagrammatic perspective view of the exemplary system of FIG. 24 illustrating a chamber formed by two housing portions and a cartridge to be received in the chamber.
Figure 26:
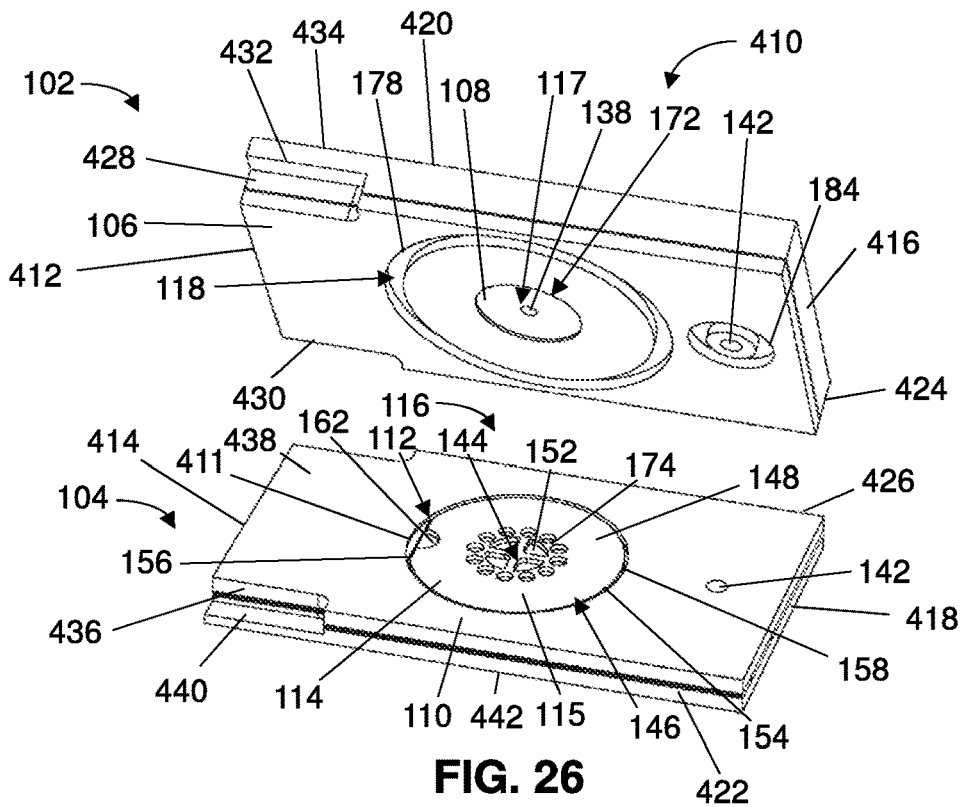
FIG. 26 is a diagrammatic perspective view of the exemplary system of FIG. 24 illustrating the cartridge positioned in a recess of the second housing portion.

FIGS. 24-26 are diagrammatic perspective views of another exemplary fluidic system 410 (hereinafter "system 410") of the present invention. The system 410 can be substantially similar in structure and function to the system 100, except for the distinctions noted herein. Therefore, like reference numbers represent like structures. In particular, rather than defining a substantially rectangular configuration with planar sides, the first and second housing portions 102, 104 can include additional features for engaging the housing with a holder.

For example, first housing portion 102 includes a first side 412 opposing a second side 416 and a third side 420 opposing a further side 426. In some embodiments, the intersection of the first side 412 and the third side 420 in the first housing portion 102 includes an elongated groove or cutout 428 extending a partial distance from the first side 412 towards the second side 416. In some embodiments, the first housing portion 102 can include an elongated slit extending along the sides 420, 424 to assist in alignment of the first housing portion 102 in the holder. In some embodiments, the intersection of the first side 412 and the fourth side 424 also includes an elongated groove or cutout 430 extending a partial distance from the first side 412 towards the second side 416. In some embodiments, the cutout 428, 430 can define a substantially rectangular shape. In some embodiments, an inner corner of the cutout 428, 430 can be chamfered or curved. The cutouts 428, 430 form steps 432 adjacent to the top surface 434 on opposing sides of the first housing portion 102.

The second housing portion 104 includes a first side 414 opposing a second side 418, and a third side 422 opposing a fourth side 426. In some embodiments, the intersection of the first side 414 and the third side 422 and the intersection of the first side 414 and the fourth side 426 in the second housing portion 104 similarly each include an elongated groove or cutout 436, 438 (respectively) extending a partial distance from the first side 414 towards the second side 418. In some embodiments, the second housing portion 104 can include an elongated slit extending along the sides 422, 426 to assist in alignment of the second housing portion 104 in the holder. The cutouts 436, 438 can be substantially similar to the cutouts 428, 430, and can be located in a complementary position relative to the cutouts 428, 430. The cutouts 436, 438 form steps 440 adjacent to the bottom surface 442 on opposing sides of the second housing portion 104. As will be discussed in greater detail below, the cutouts 428, 430, 436, 438 and steps 432, 440 can be used to engage a tab of a holder (e.g., tab 240 of holder 210) to interlock the system 410 with the holder.

In some embodiments, rather than including a straight portion 160, the recessed area 112 in the second housing portion 104 can include a rounded portion 158 extending the entire perimeter, and further includes an inner step 411 configured to align with the rounded notch 162 of the cartridge 114. The inner step 411 assists in removal of the cartridge 114 from the recessed area 112. In some embodiments, the diameter of the inlet 136 and outlet 140 can be greater than the diameter of most of the inlet channel 138 and outlet channel 142. In such embodiments, push-in adapters 444, 446 (e.g., PDMS adapters) can be used to connect inlet and outlet tubing to the system 410. The adapters 444, 446 can define tapering configurations including openings 448, 450 having diameters dimensioned substantially similar to the diameter of the inlet and outlet channels 138, 142. One end of the adapter 444 can be inserted into the inlet 136 and the inlet tubing can be inserted into the opening 448 at the opposing end of the adapter 444. One end of the adapter 446 can be inserted into the outlet 140 and the outlet tubing can be inserted into the opening 450 at the opposing end of the adapter 446.

FIGS. 27-30 are diagrammatic perspective views of another exemplary fluidic system 452 (hereinafter "system 452") of the present invention. The system 452 can be substantially similar in structure and function to the system 100, 410, except for the distinctions noted herein. Therefore, like reference numbers represent like structures. For clarity, some reference numbers have been omitted. Cutouts 428*a-c*, 430*b-c*, 436*a-c*, 438*a-c* collectively form the cutouts 428, 430, 436, 438.

In some embodiments the surfaces of the first and second housing portions 102, 104 that face each other may both have similar features for receiving sealing elements In particular, rather than having a single circumferential groove 178 in the first housing portion 102 to receive a sealing element, the system 452 includes a first housing portion 102 including a first circumferential groove half 458 and a second housing portion 104 including a second circumferential groove half 460 surrounding the chamber 116. The first circumferential groove half 458 can be configured to receive substantially half of the first sealing element 176 such that when the first housing portion 102 is positioned over the second housing portion 104, the remaining portion of the first sealing element 176 is received within the second circumferential groove half 460. Similarly, the first housing portion 102 includes a first circumferential groove half 462 and the second housing portion 104 includes a second circumferential groove half 464 surrounding the outlet channel 142. The first circumferential groove half 462 can be configured to receive substantially half of the second sealing element 182 such that when the first housing portion 102 is positioned over the second housing portion 104, the remaining portion of the second sealing element 182 is received within the second circumferential groove half 164. Thus, the groove for the sealing elements is split between the first and second housing portions 102, 104.

The first housing portion 102 includes the recessed area 108 centered around the inlet 136. A circumferential step 466 can be formed adjacent to the first circumferential groove half 458 and surrounding the recessed area 108 to form a top half of the chamber 116. The second housing portion 104 includes a complementary recessed area 468 centered around a single outlet channel 470. In particular, rather than including multiple individual outlet openings in the recessed area 468 and a fifth layer 128 with outlet channels for converging the flow into a single outlet channel, the second housing portion 104 of the system 452 includes a single outlet channel 470 formed directly in the recessed area 468. The second housing portion 104 further includes a circumferential step 472 formed adjacent to the second circumferential groove half 460 and surrounding the recessed area 468 to form a bottom half of the chamber 116.

When the first and second housing portions 102, 104 are positioned against each other, the circumferential steps 466, 472 can be positioned against each other to enclose the chamber 116 and the cartridge 114, and the first sealing element 176 seals the perimeter of the chamber 116 and the cartridge 114 to prevent leakage of the media. The porous element 164 includes a plurality of openings 474 extending therethrough. The openings 474 can be substantially aligned with the channels 174 of the cartridge 114. The media is introduced into the system 452 through the inlet 136, flows through the inlet channel 138 and into the chamber 116. In some embodiments, the media flows into and through the channels 152 into the recessed area 468 of the second housing portion 104. In some embodiments, a portion of the media flows into and through the channels 152, and the remaining portion of the media flows radially outward and through the channels 174 into the recessed area 468 of the second housing portion 104. In some embodiments, the media flows into the channels 152, fills the channels 152, flows out of the channels 152, and flows radially outward and through the channels 174 into the recessed area 468 of the second housing portion 104. The media can initially collect in the chamber 116 (e.g., the recessed area 108 and/or the recessed area 468), and further flows through the outlet channel 470 into the outlet channel 142 to exit the system 452 through the outlet 140. Converging of the media within the recessed area 468 of the chamber 116 reduces the need for multiple openings in the second housing portion 104 for guiding the media into the outlet channel 142.

Figure 31:
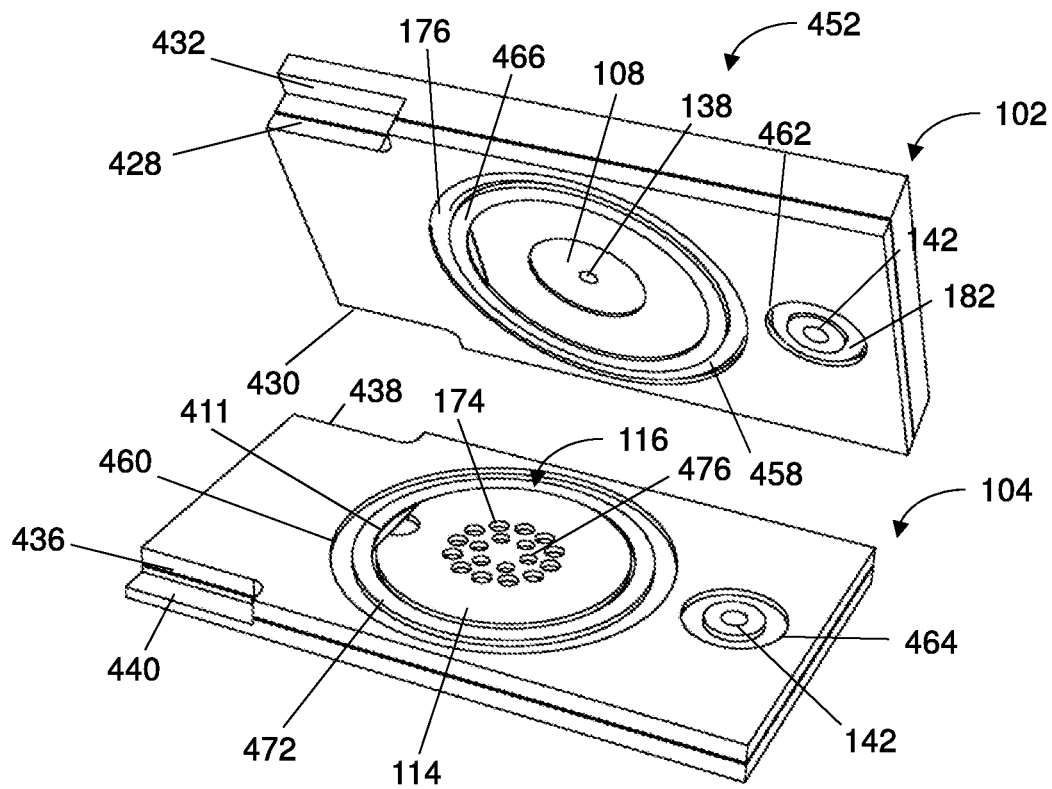
FIG. 31 is a diagrammatic, perspective view of an exemplary system of FIG. 27 including a cartridge with a first plurality of channels that includes six channels.
Figure 32:
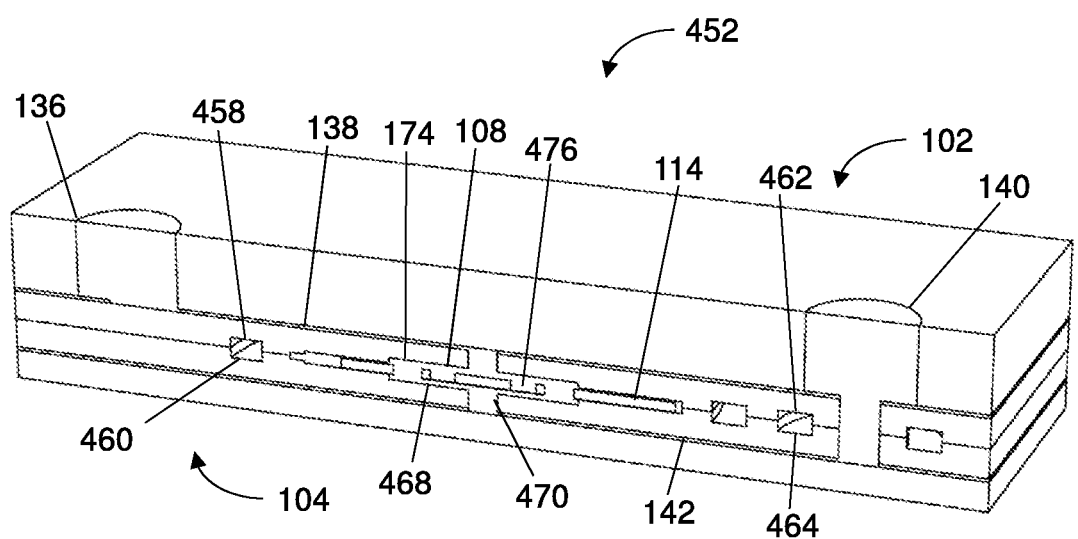
FIG. 32 is a diagrammatic, cross-sectional view of the exemplary system of FIG. 31 showing flow of media through inlet and outlet channels.
Figure 33:
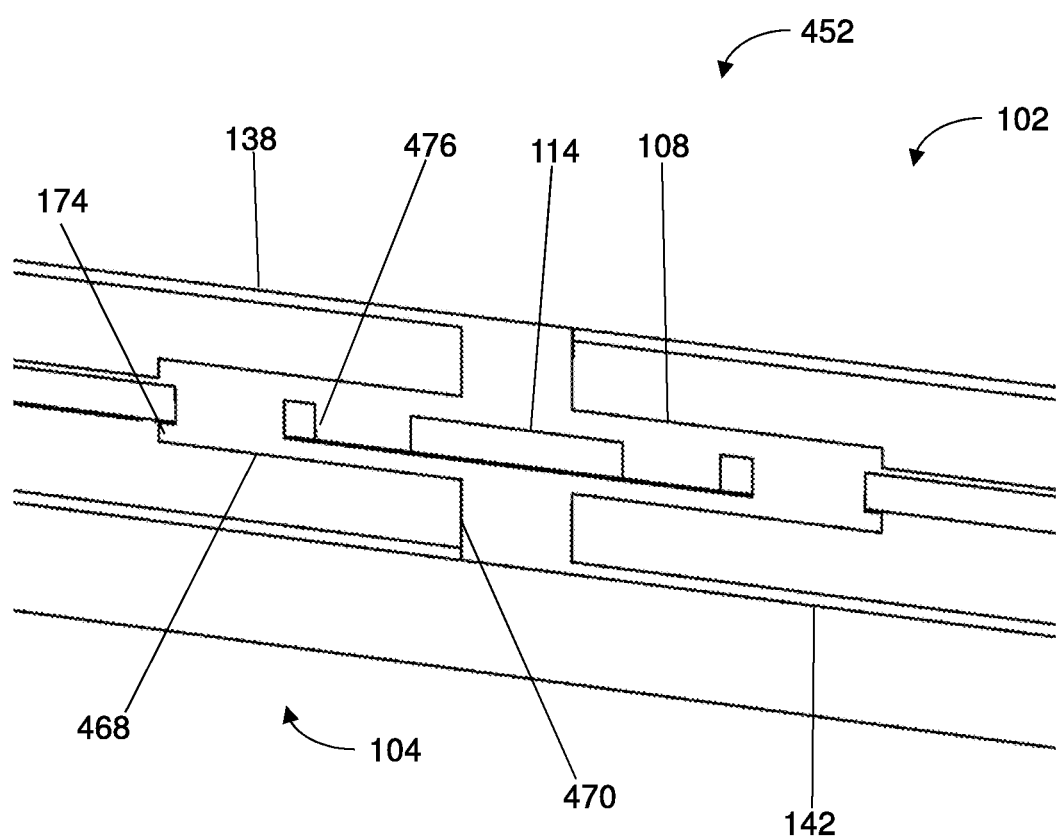
FIG. 33 is a diagrammatic, cross-sectional detailed view of the exemplary system of FIG. 31 showing flow of media through inlet and outlet channels.

FIGS. 31-33 are diagrammatic perspective and cross-sectional views of the system 452 including a cartridge 114 with a first plurality of channels 476 that includes six circular channels. As shown in FIG. 32, the media flows through the inlet 136, into the inlet channel 138, and exits the inlet channel 138 directly above the center of the cartridge 114. The media flows radially outward over the cartridge 114 with a portion of the media traveling through the first plurality of channels 476 and a portion of the media traveling further radially outward and through the second plurality of channels 174. The media collects in the recessed areas 108, 468. The media collected in the recessed area 468 flows out of the single outlet channel 470 that is fluidically connected to the outlet channel 142. The media further flows through the outlet channel 142 and out of the system 452 through the outlet 140.

FIGS. 34-38 are diagrammatic perspective and cross-sectional views of another exemplary fluidic system 478 (hereinafter "system 478") of the present invention. The system 478 can be substantially similar in structure and function to the systems 100, 410, 452, except for the distinctions noted herein. Therefore, like reference numbers represent like structures. For clarity, some reference numbers have been omitted. Cutouts 428a-e, 430b-e, 436a-c, 438a-c collectively form the cutouts 428, 430, 436, 438.

Rather than including a single inlet channel 138 leading into the chamber 116, the system 478 includes layers 480, 482 that distribute the media across a plurality of inlet channels 484. Although illustrated as layers, it should be understood that the first and second housing portions 102, 104 can be formed as single, structural components. The inlet aperture 138e in layer 124 is fluidically connected with a central aperture 486. The central aperture 486 is fluidically connected with a plurality of radially extending slots 488 that fluidically connect with respective apertures 490. The apertures 490 are fluidically connected to the plurality of inlet channels 484 that introduce the media into the chamber 116 directly over the cartridge 114. The layers 480, 482 also include apertures 492, 494 that fluidically connect with the remaining apertures and/or slots of the outlet channel 142.

The cartridge 114 includes a central channel 496 and the porous element 164 includes a corresponding central channel 498. The central channels 496, 498 align with channel 470 of the second housing portion 104. The cartridge 114 further includes a first plurality of channels 500 circumferentially disposed around the central channel 496. In some embodiments, the channels 500 extend through the cartridge 114 and the porous element 164 provides support for cells disposed within the channels 500 with the channel walls and the porous element 164 defining wells. In some embodiments, the channels 500 extend only a partial distance through the cartridge 114 (e.g., the cartridge 114 has a solid bottom surface except for the central channel 496) forming wells for supporting cells, and the porous element 164 is omitted from the system 478.

Figure 37:
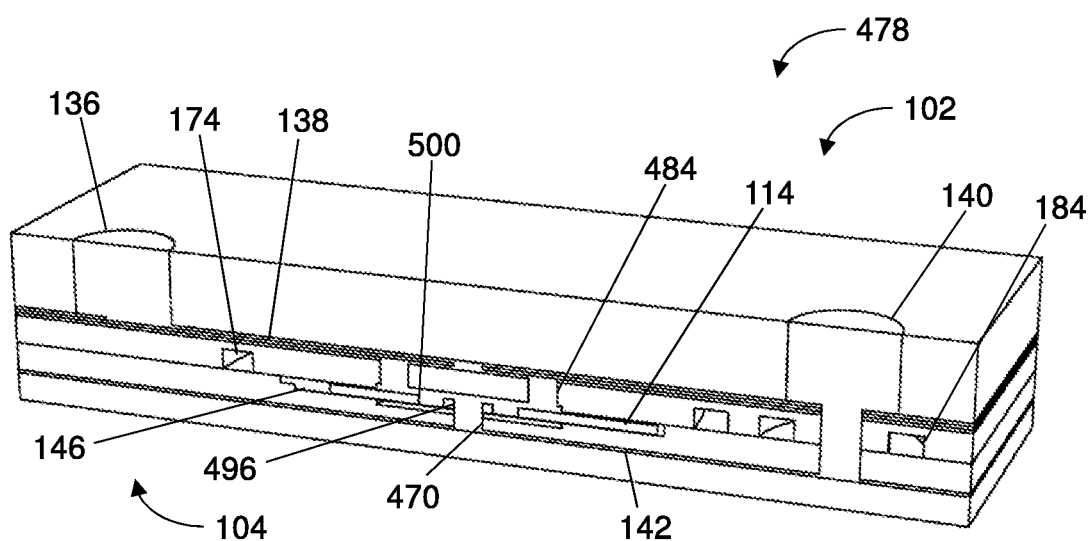
FIG. 37 is a diagrammatic, cross-sectional view of the exemplary system of FIG. 34 showing flow of media through inlet and outlet channels.
Figure 38:
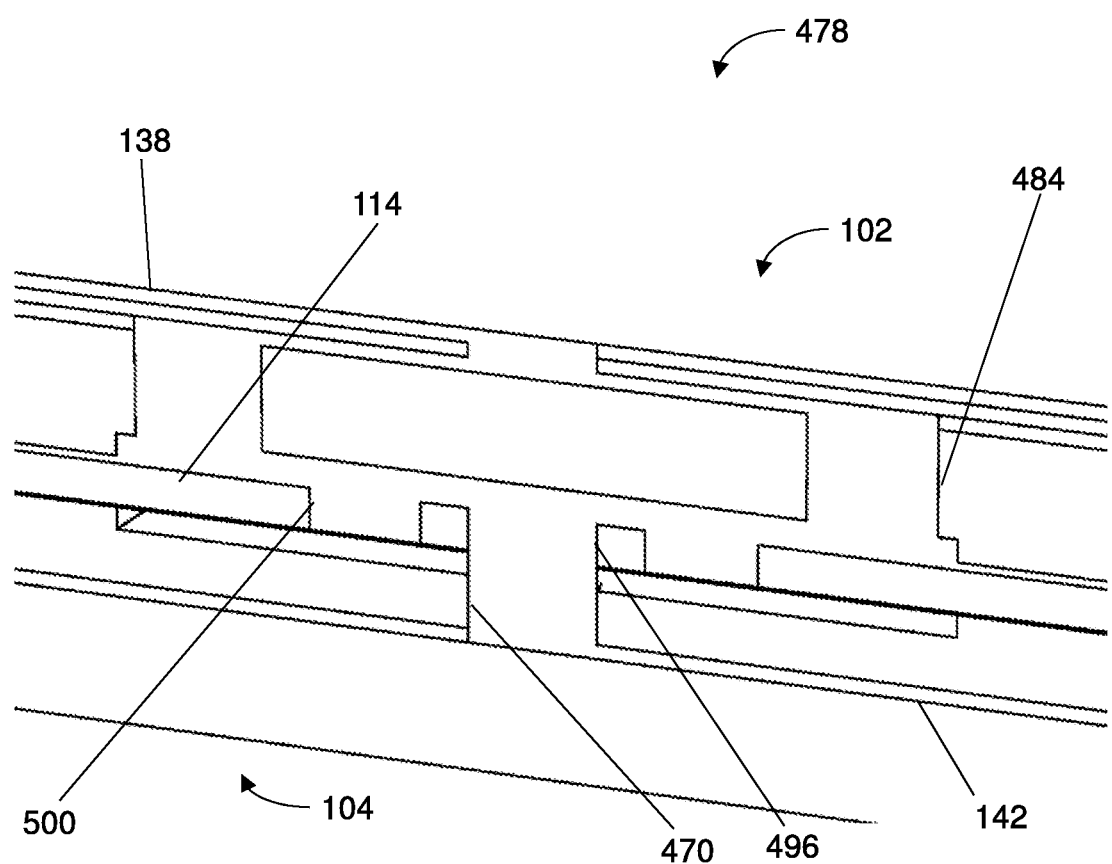
FIG. 38 is a diagrammatic, cross-sectional detailed view of the exemplary system of FIG. 34 showing flow of media through inlet and outlet channels.

The radial distance of the channels 500 from the central channel 496 is smaller than the radial distance of the inlet channels 484 relative to the central channel 496. Thus, as shown in FIGS. 37 and 38, the media flows through the inlet 138, along the inlet channel 138, is distributed outward into the inlet channels 484 within the first housing portion 102, and is introduced into the chamber 116 via multiple inlets in the form of the inlet channels 484. Upon entry into the chamber 116, the media flows laterally from a peripheral portion 146 of the cartridge 114, across and/or into the channels 500, and through the central channel 496. In some embodiments, at least a portion of the media flows through the channels 500 and converges with the media flowing through the central channel 496 before flowing into the channel 470 and the outlet channel 142. In some embodiments, all of the media introduced into the chamber 116 flows through the central channel 496, through the channel 470 and the outlet channel 142, and out of the outlet 140. In some embodiments, the second housing portion 104 can include a recessed area (e.g., recessed area 468 of FIG. 27) in which the media can collect prior to flowing through the outlet channel 142.

Figure 39:
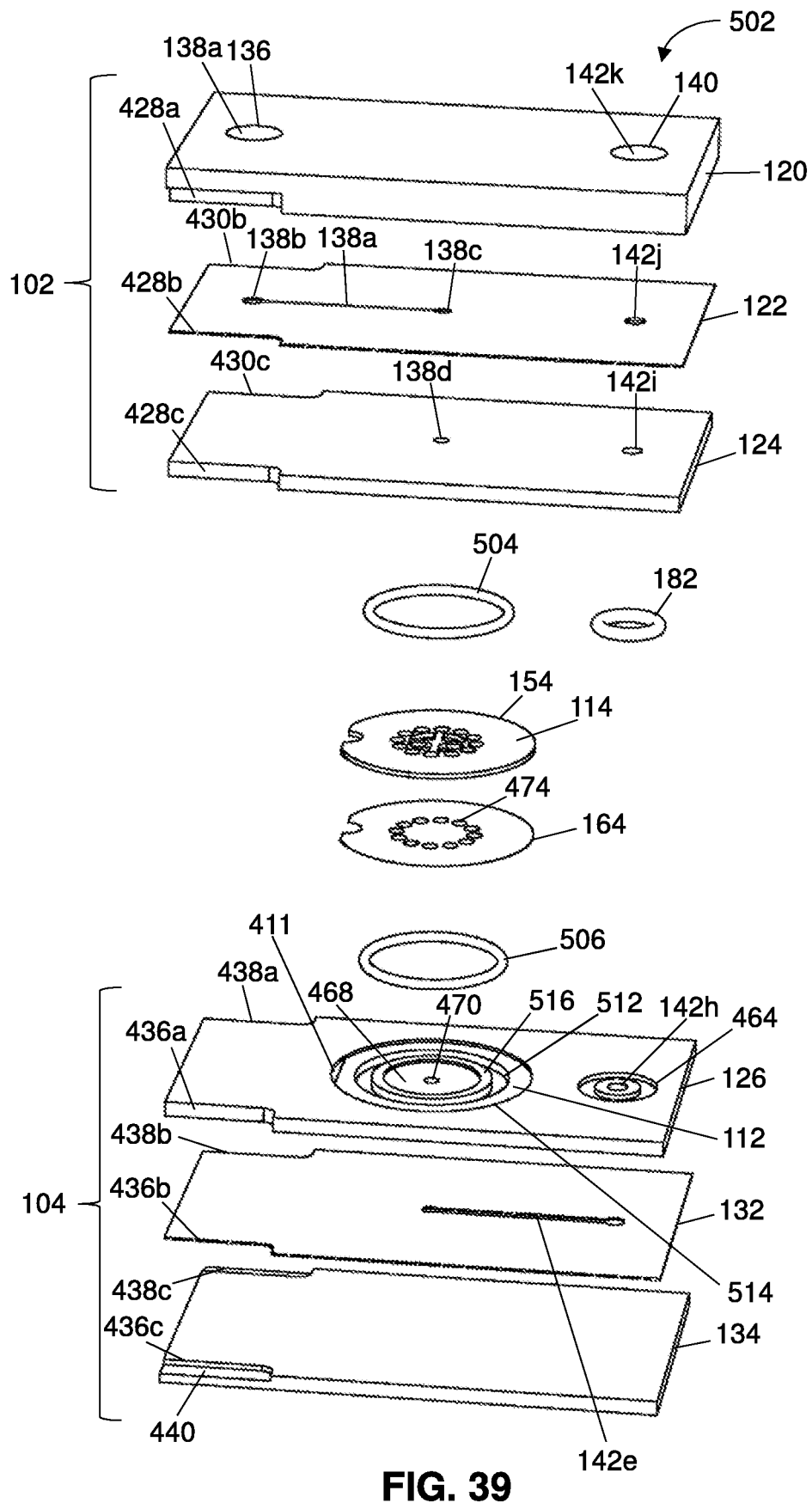
FIG. 39 is a diagrammatic exploded perspective view of an exemplary system of the present invention, in accordance with some embodiments.
Figure 40:
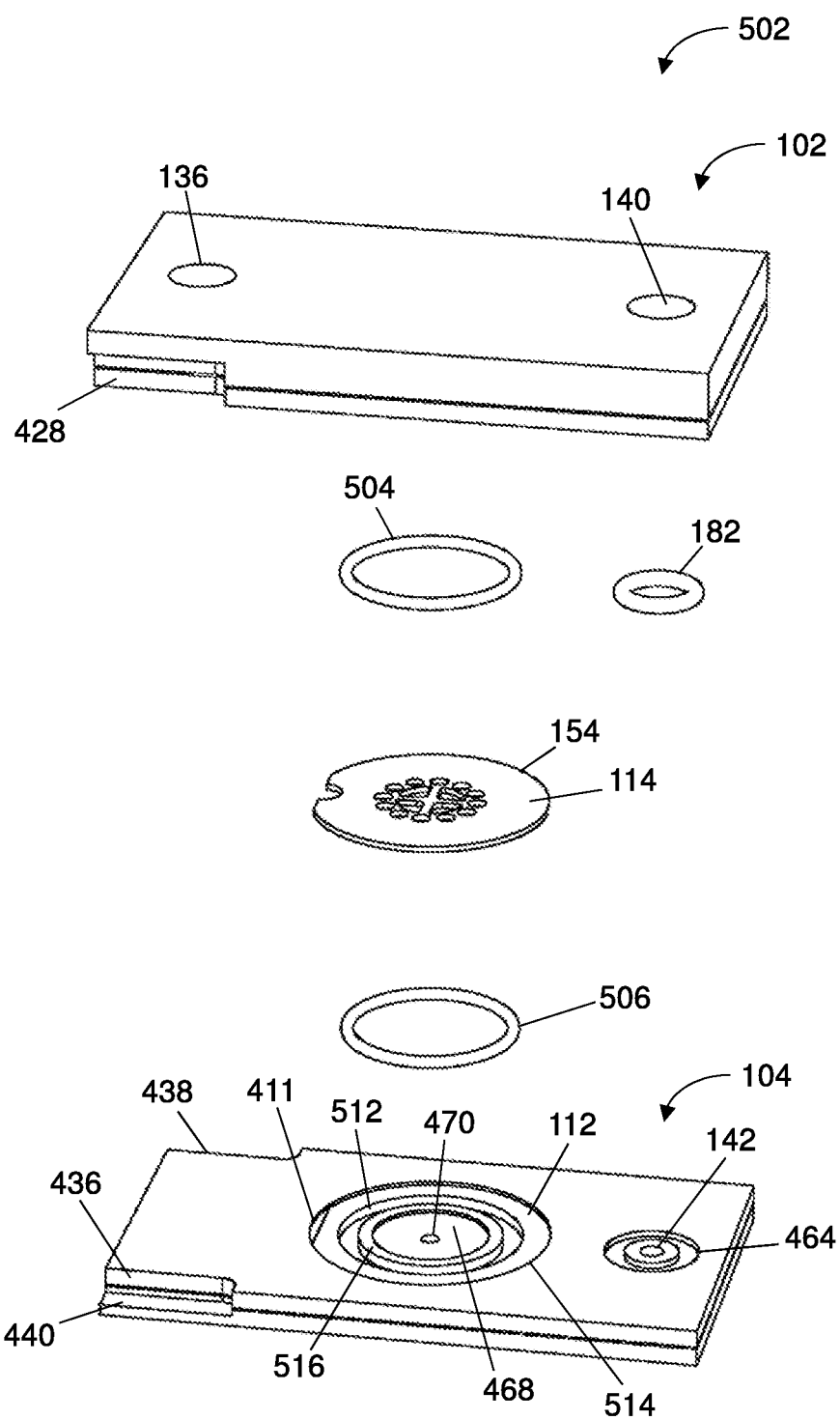
FIG. 40 is a diagrammatic perspective view of the exemplary system of FIG. 39.
Figure 41:
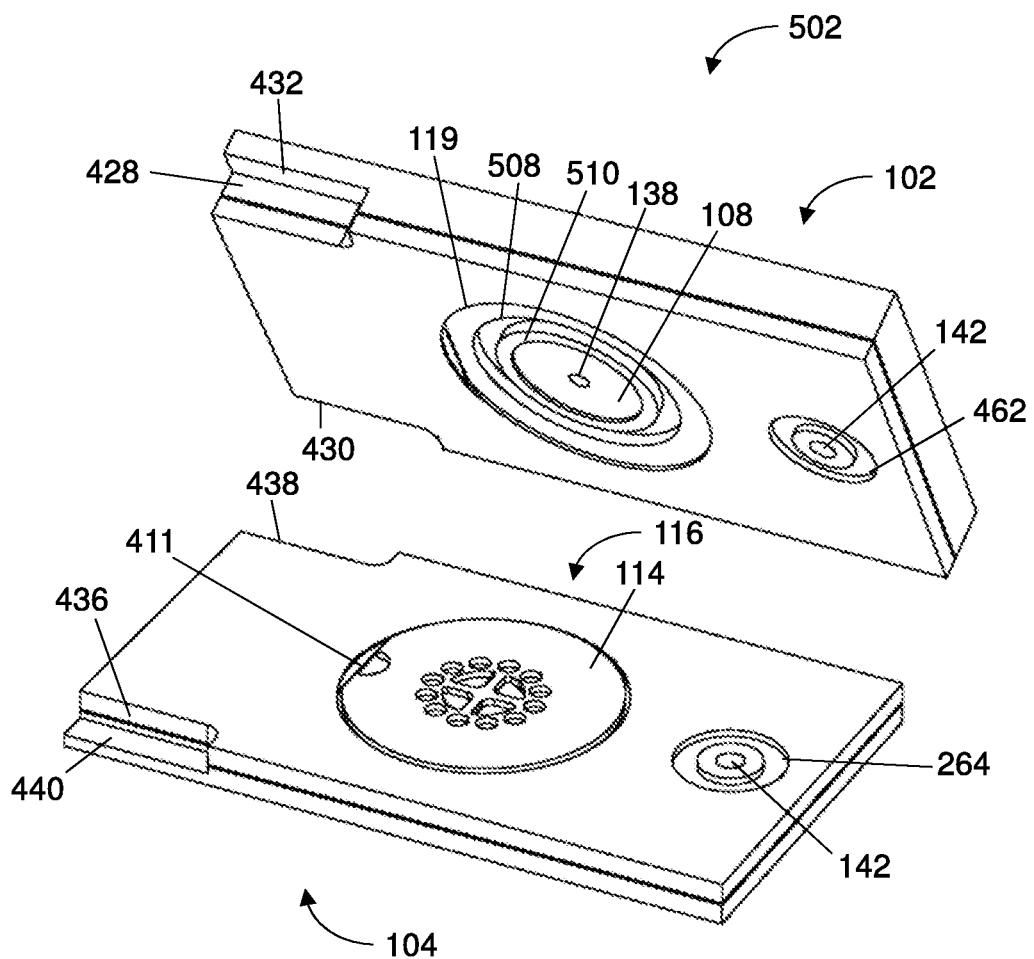
FIG. 41 is a diagrammatic perspective view of the exemplary system of FIG. 39.

FIGS. 39-41 are diagrammatic perspective and cross-sectional views of another exemplary fluidic system 502 (hereinafter "system 502") of the present invention. The system 502 can be substantially similar in structure and function to the system 100, 410, 452, 478, except for the distinctions noted herein. Therefore, like reference numbers represent like structures. For clarity, some reference numbers have been omitted. Cutouts 428a-c, 430b-c, 436a-c, 438a-c collectively form the cutouts 428, 430, 436, 438.

Rather than including a single, first sealing element 176 surrounding the chamber 116 and cartridge 114, the system 502 includes a top sealing element 504 configured to be disposed over and against the top surface of the cartridge 114, and a bottom sealing element 506 configured to be disposed under and against the bottom surface of the cartridge 114 (or the porous element 164). Thus, the sealing elements 504, 506 rest directly on the opposing faces of the cartridge 114 to maintain the media within the chamber 116. The diameter of the sealing elements 504, 506 is dimensioned smaller than the diameter of the rounded edge 154 of the cartridge 114.

The first housing portion 102 includes a circumferential groove 508 inwardly spaced from a peripheral edge portion 119 of the recessed area 108. The first housing portion 102 includes a circumferential step 510 extending from the recessed area 108 immediately adjacent to the circumferential groove 508 and separating the groove 508 from the inlet channel 138. The elevated step 510 forms a barrier for the media entering the chamber 116 and defines the top half of the chamber 116. The groove 508 at least partially receives the top sealing element 504 such that when the first housing portion 102 is positioned against the second housing portion 104, the top sealing element 504 rests against the top surface of the cartridge 114 and maintains the chamber 116 within the step 510 fluidically sealed.

The second housing portion 104 similarly includes a circumferential groove 512 inwardly spaced from a peripheral edge portion 514 of the recessed area 112. The second housing portion 104 includes a circumferential step 516 extending from the recessed area 112 immediately adjacent to the circumferential groove 512 and separating the groove 512 from the channel 470. The elevated step 516 forms a barrier for the media entering the bottom half of the chamber 116 after flowing through the cartridge 114. The groove 512 at least partially receives the bottom sealing element 506 such that when the cartridge 114 is inserted into the recessed area 112, the bottom sealing element 506 rests against the bottom surface of the cartridge 114 and maintains the chamber 116 within the step 516 fluidically sealed. The chamber 116 therefore has top and bottom media collecting areas within the steps 510, 516.

Figure 42:
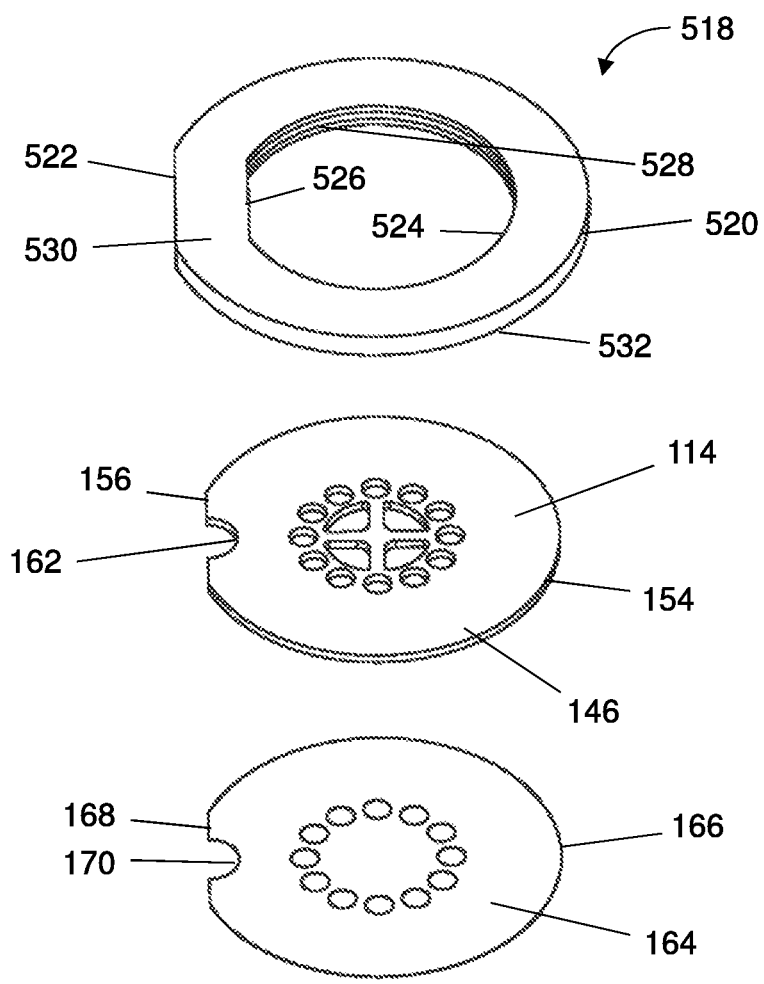
FIG. 42 is a diagrammatic exploded perspective view of an exemplary sealing element of the present invention and a cartridge with which it can be used, in accordance with some embodiments.
Figure 43:
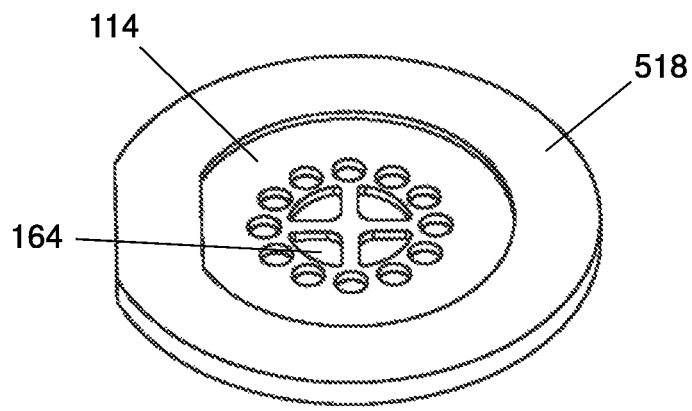
FIG. 43 is a diagrammatic perspective view of the exemplary sealing element of FIG. 42 positioned on a cartridge.

FIGS. 42 and 43 are diagrammatic perspective views of another exemplary sealing element 518 for the cartridge 114 and/or the porous element 164. Rather than including a sealing element in the form of an O-ring that surrounds the cartridge 114 or is positioned against a surface of the cartridge 114, the sealing element 518 is in the form of a gasket or sleeve that fits around the cartridge 114 and/or the porous element 164. The sealing element 518 can be fabricated from a flexible yet durable material (e.g., rubber) such that the sealing element 518 can be stretched to insert the cartridge 114 including the porous element 164, and returns to the original configuration to maintain a fluidic seal between the cartridge 114 and the sealing element 518.

The sealing element 518 includes an outer surface with a rounded edge 520 and a straight portion 522 complementary to the rounded edge 154 and straight portion 156 of the cartridge 114. The sealing element 518 includes an opening passing therethrough with a rounded edge 524 and a straight portion 526 aligned with the rounded edge 520 and the straight portion 522. While the rounded edge 520 and straight portion 522 are dimensioned at a greater diameter or size relative to the rounded edge 154 and straight portion 156 of the cartridge 114, the rounded edge 524 and straight portion 526 have a smaller diameter or size than the cartridge 114 such that the cartridge 114 can be received within the sealing element 518 in a tight manner.

The sealing element 518 includes an inner circumferential groove 528 configured to receive the peripheral portion 146 of the cartridge 114. The cartridge 114 can thereby be received within the circumferential groove 528 such that at least an outer edge of the peripheral portion 146 of the cartridge 114 is continuously covered to maintain a seal between the cartridge 114 and the sealing element 518. The opposing surfaces 530, 532 (e.g., top and bottom surfaces) of the sealing element 518 can be substantially planar.

Figure 44:
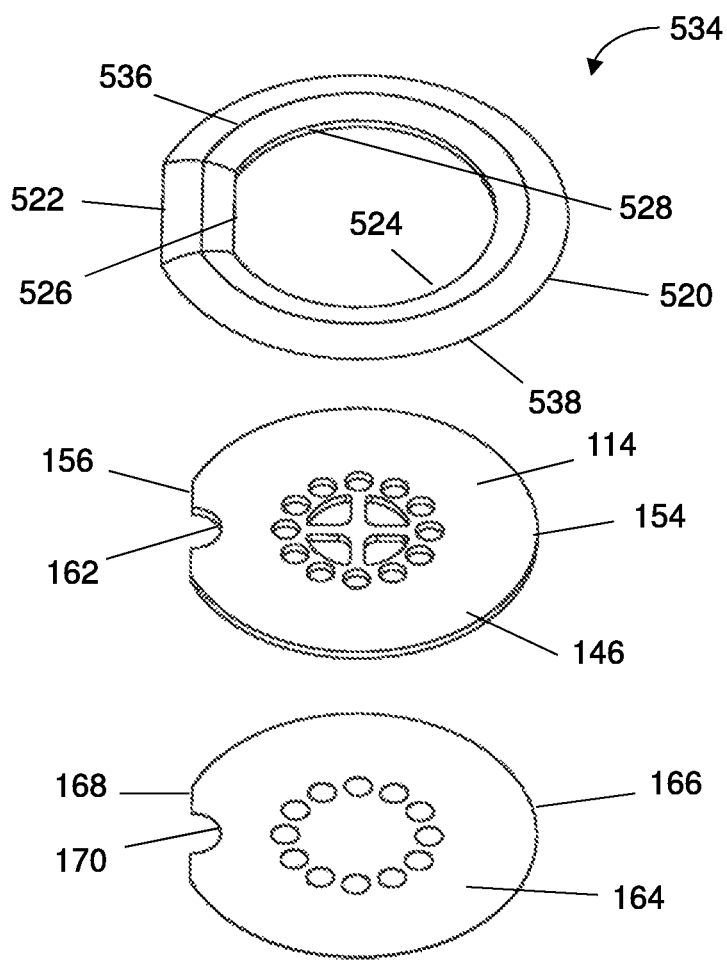
FIG. 44 is a diagrammatic exploded perspective view of an exemplary sealing element of the present invention and a cartridge with which it can be used, in accordance with some embodiments.
Figure 45:
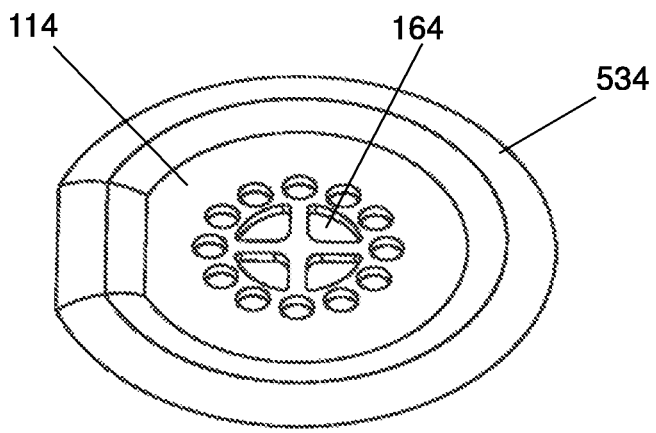
FIG. 45 is a diagrammatic perspective view of the exemplary sealing element of FIG. 44 positioned on a cartridge.

FIGS. 44 and 45 are diagrammatic perspective views of another exemplary sealing element 534 for the cartridge 114 and/or the porous element 164. The sealing element 534 can be substantially similar in structure and function to the sealing element 518, except for the distinctions noted herein. Therefore, like reference numbers represent like structures. In particular, rather than having substantially planar surfaces, one or both of the opposing surfaces 536, 538 can define a rounded, curved, or beveled configuration.

Figure 46:
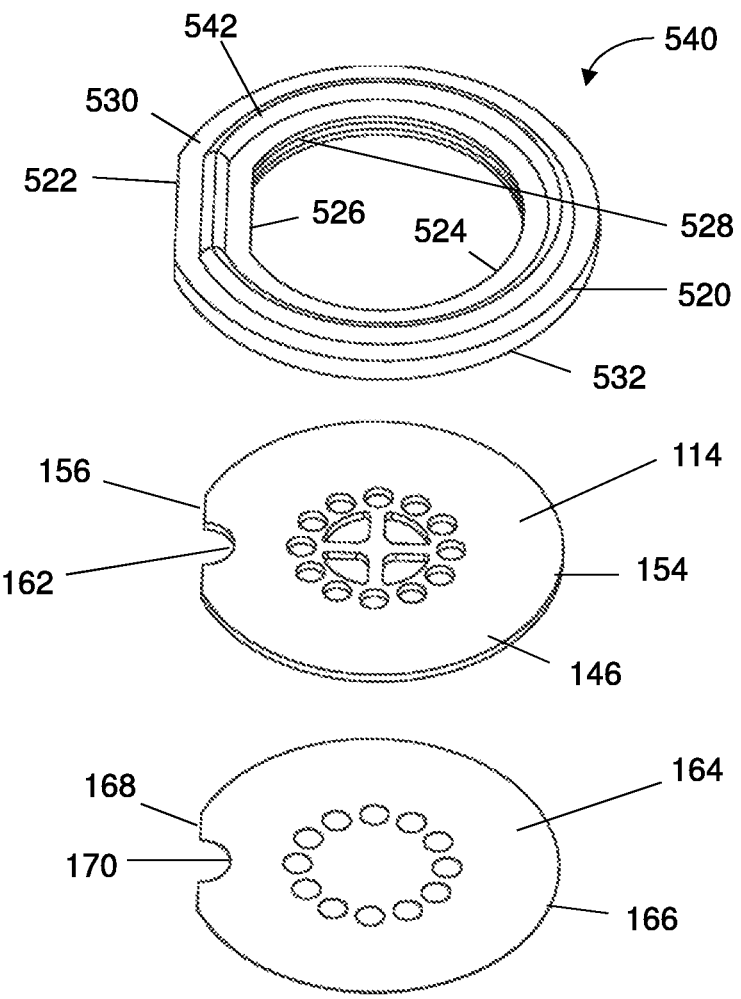
FIG. 46 is a diagrammatic exploded perspective view of an exemplary sealing element of the present invention and a cartridge with which it can be used, in accordance with some embodiments.
Figure 47:
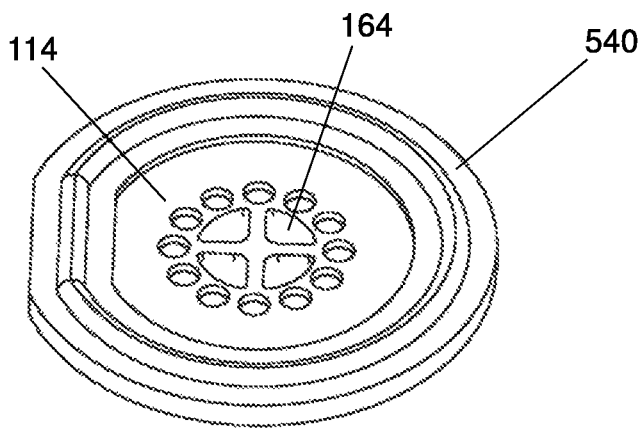
FIG. 47 is a diagrammatic perspective view of the exemplary sealing element of FIG. 46 positioned on the cartridge.

FIGS. 46 and 47 are diagrammatic perspective views of another exemplary sealing element 540 for the cartridge 114 and/or the porous element 164. The sealing element 534 can be substantially similar in structure and function to the sealing element 518, 534, except for the distinctions noted herein. Therefore, like reference numbers represent like structures. In particular, rather than having substantially planar surfaces, one or both of the opposing surfaces 530, 532 can include a circumferential ridge 542. The ridge 542 provides additional sealing surfaces positioned against the first and second housing portions 102, 104 for fluidically sealing the cartridge 114 therebetween.

Figure 48:
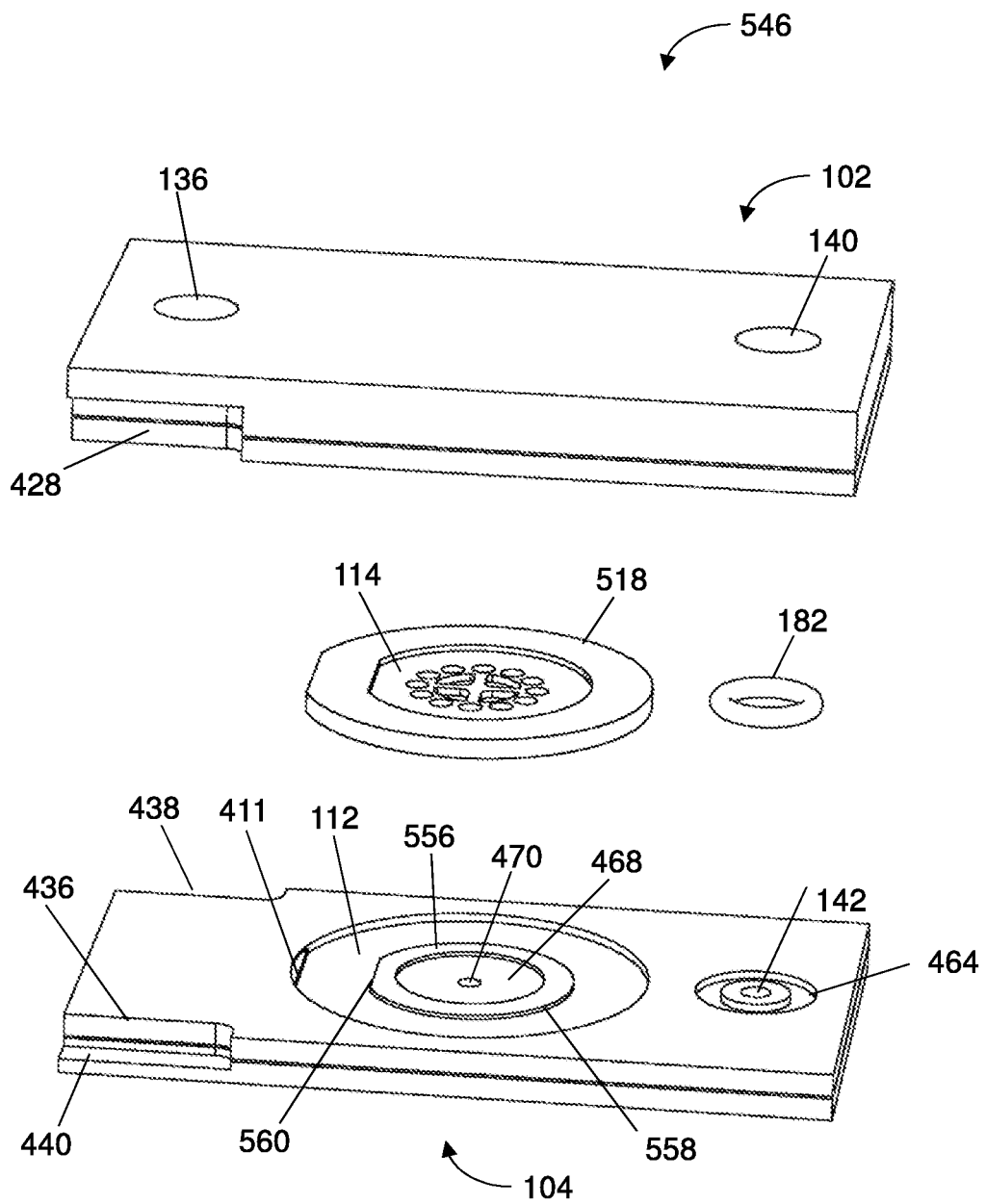
FIG. 48 is a diagrammatic perspective view of an exemplary system of the present invention, in accordance with some embodiments.
Figure 49:
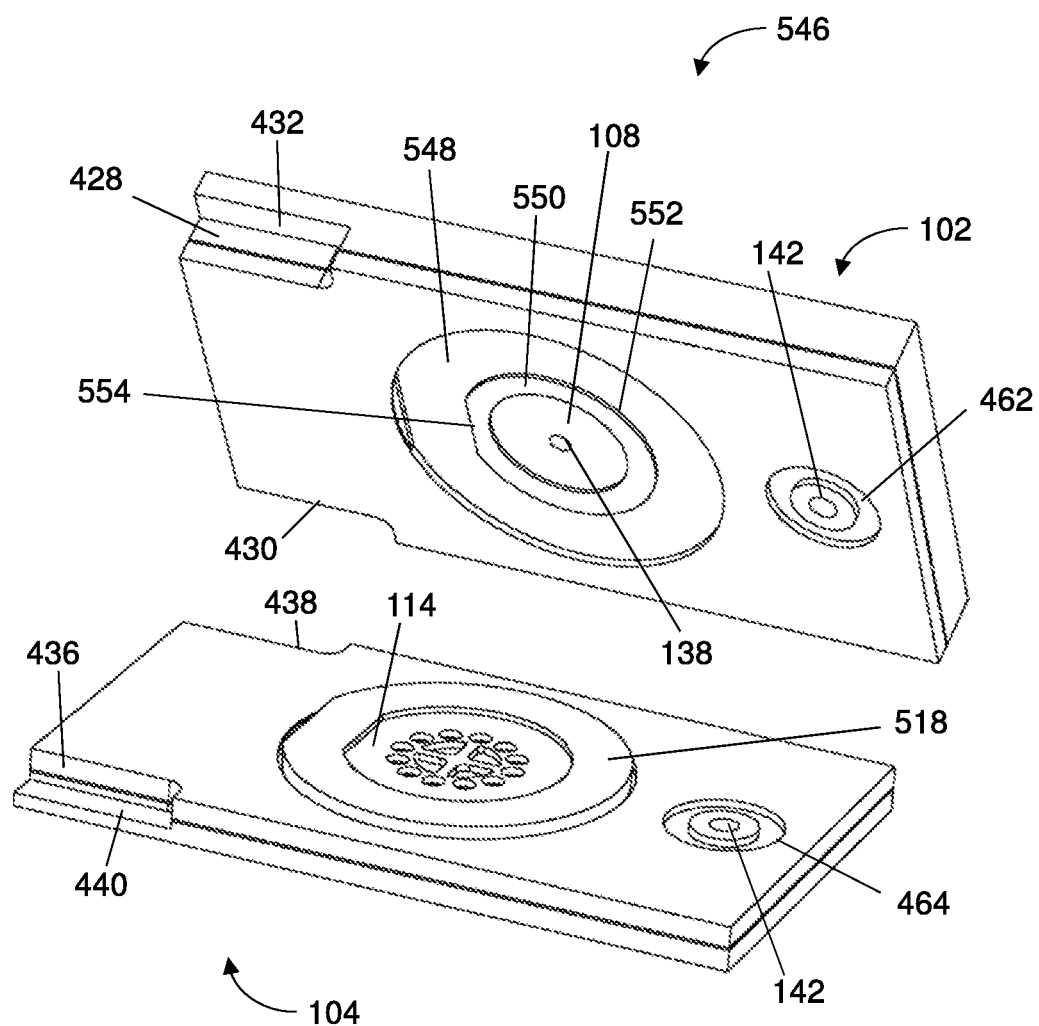
FIG. 49 is a diagrammatic perspective view of the exemplary system of FIG. 48 with the sealing element positioned on the cartridge and the cartridge received in a recess of the second housing portion.

FIGS. 48-49 are diagrammatic perspective views of another exemplary fluidic system 546 (hereinafter "system 546") of the present invention. The system 546 can be substantially similar in structure and function to the system 100, 410, 452, 478, 502, except for the distinctions noted herein. Therefore, like reference numbers represent like structures. For clarity, some reference numbers have been omitted.

The first and second housing portions 102, 104 of the system 546 are configured and dimensioned to receive therein the sealing element 518 of FIGS. 42-43. However, it should be understood that the system 546 can receive any one of the sealing elements 518, 534, 540. The first housing portion 102 includes a peripheral recessed area 548 separated from the central recessed area 108 by a circumferential step 550 configured dimensioned complementary to the central opening of the sealing element 518. In particular, the step 550 includes a rounded edge 552 and a straight portion 554 configured to mate against the rounded edge 524 and straight portion 526 of the sealing element 518.

The second housing portion 104 similarly includes a peripheral recessed area 112 separated from a central recessed area 468 by a circumferential step 556 including a rounded edge 558 and a straight portion 560. As shown in FIG. 49, the sealing element 518 can be mated with the recessed areas 112, 468 of the second housing portion 104, and positioning the first housing portion 102 over the sealing element 518 mates the sealing element 518 with the recessed areas 548, 108. The recessed areas of the first and second housing portions 102, 104 assist in aligning the cartridge 114 within the system 546.

Figure 50:
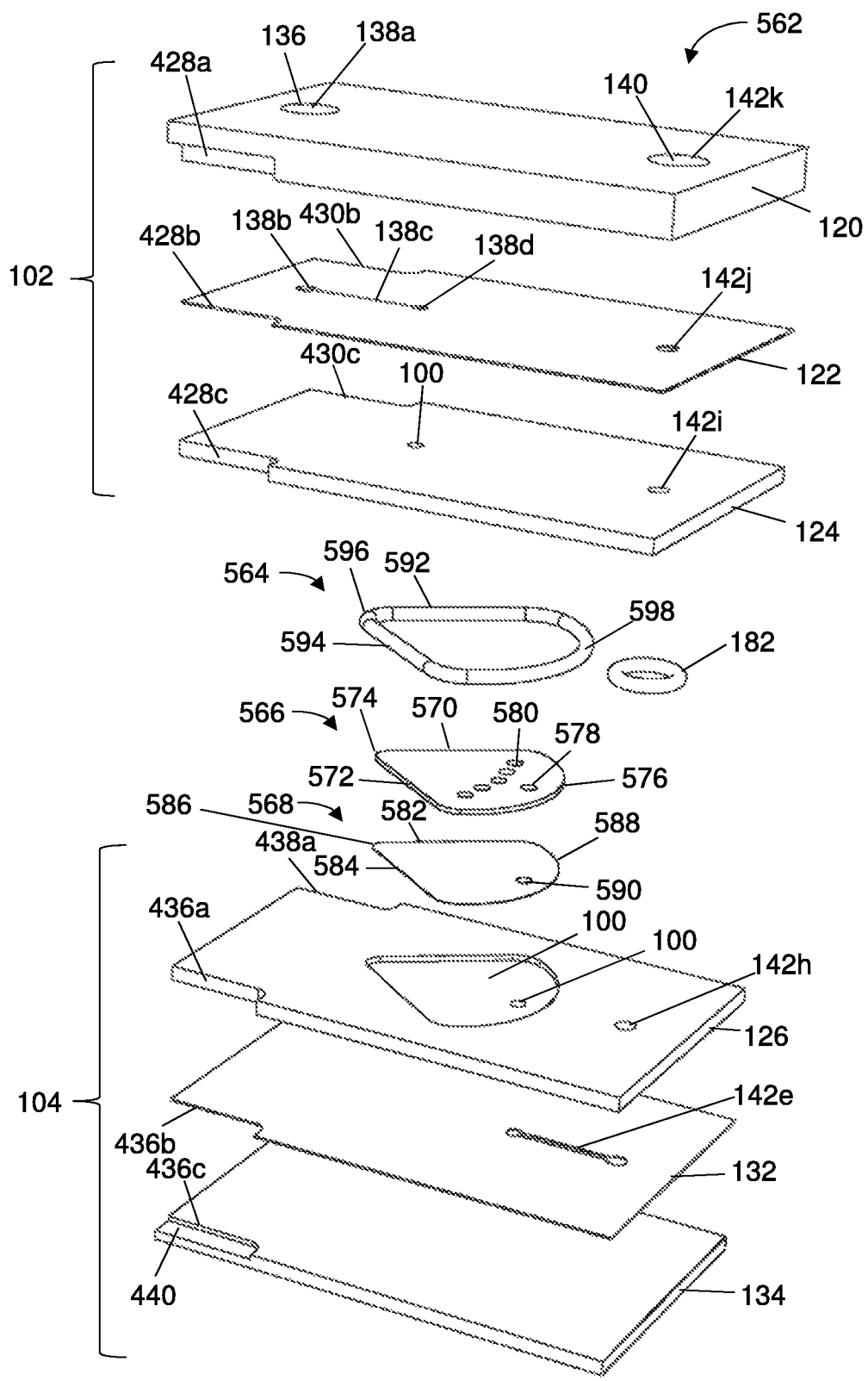
FIG. 50 is a diagrammatic exploded perspective view of an exemplary system of the present invention, in accordance with some embodiments.
Figure 51:
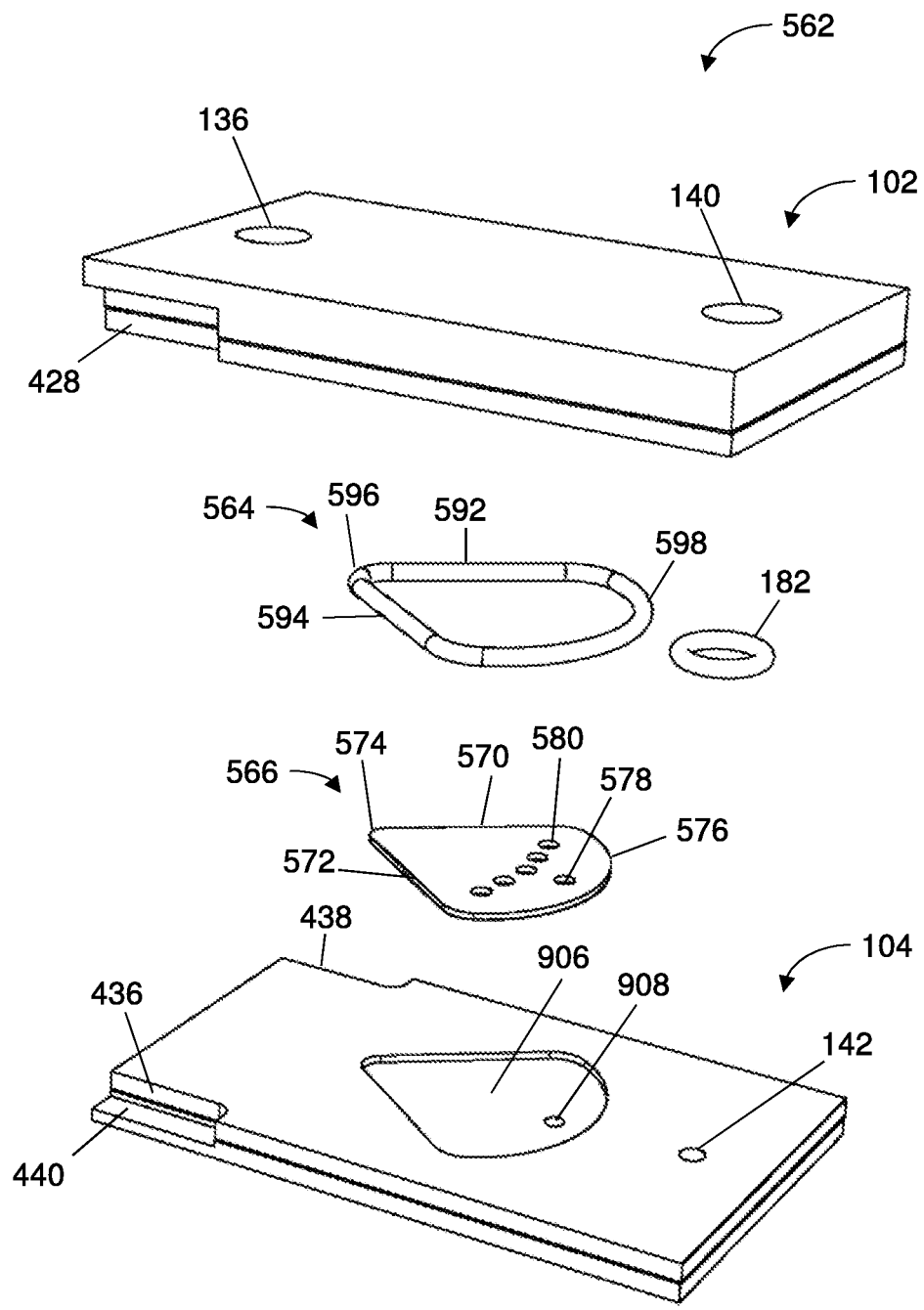
FIG. 51 is a diagrammatic perspective view of the exemplary system of FIG. 50.
Figure 52:
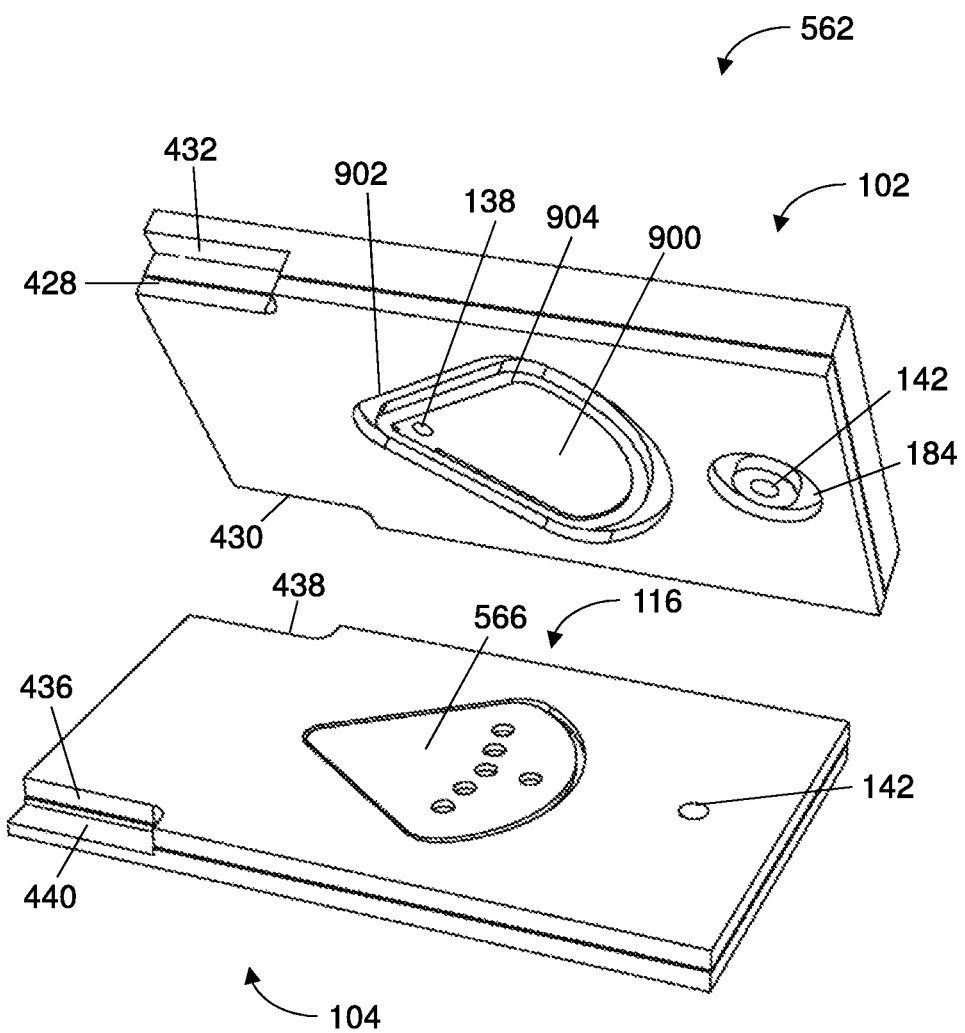
FIG. 52 is a diagrammatic perspective view of the exemplary system of FIG. 50 showing the cartridge positioned in a recess of the first housing portion.
Figure 53:
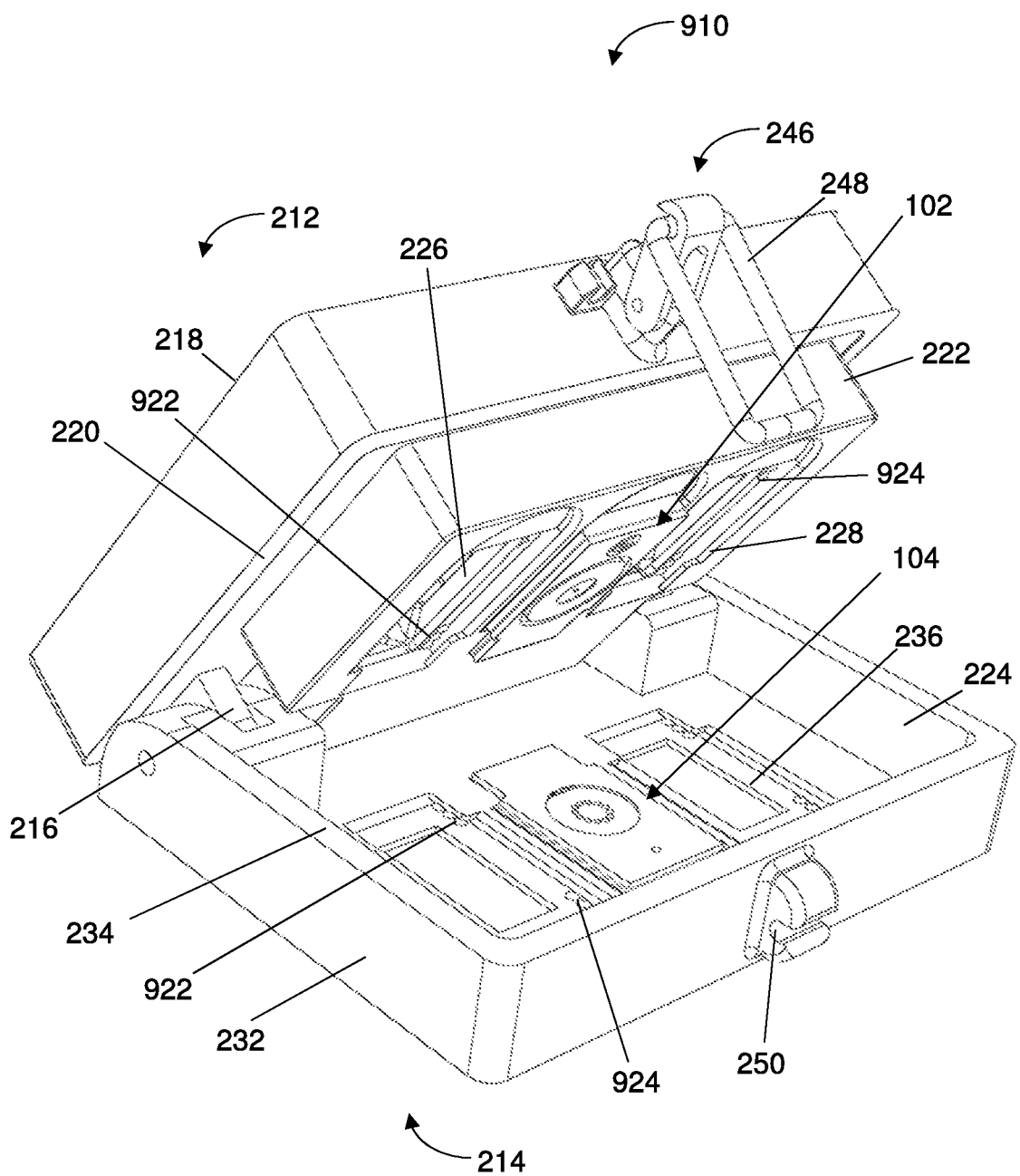
FIG. 53 shows a perspective view of an exemplary holder of the present invention.
Figure 54:
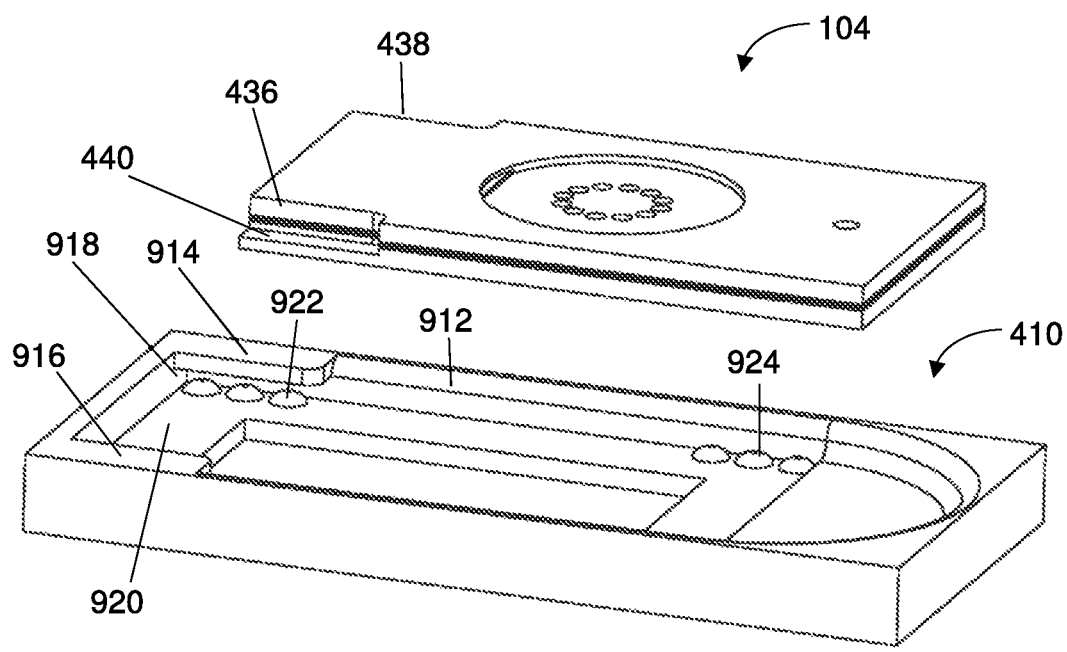
FIG. 54 shows a perspective, detail view of a portion of the exemplary holder of FIG. 53 and a portion of a housing to be used with the holder.
Figure 55:
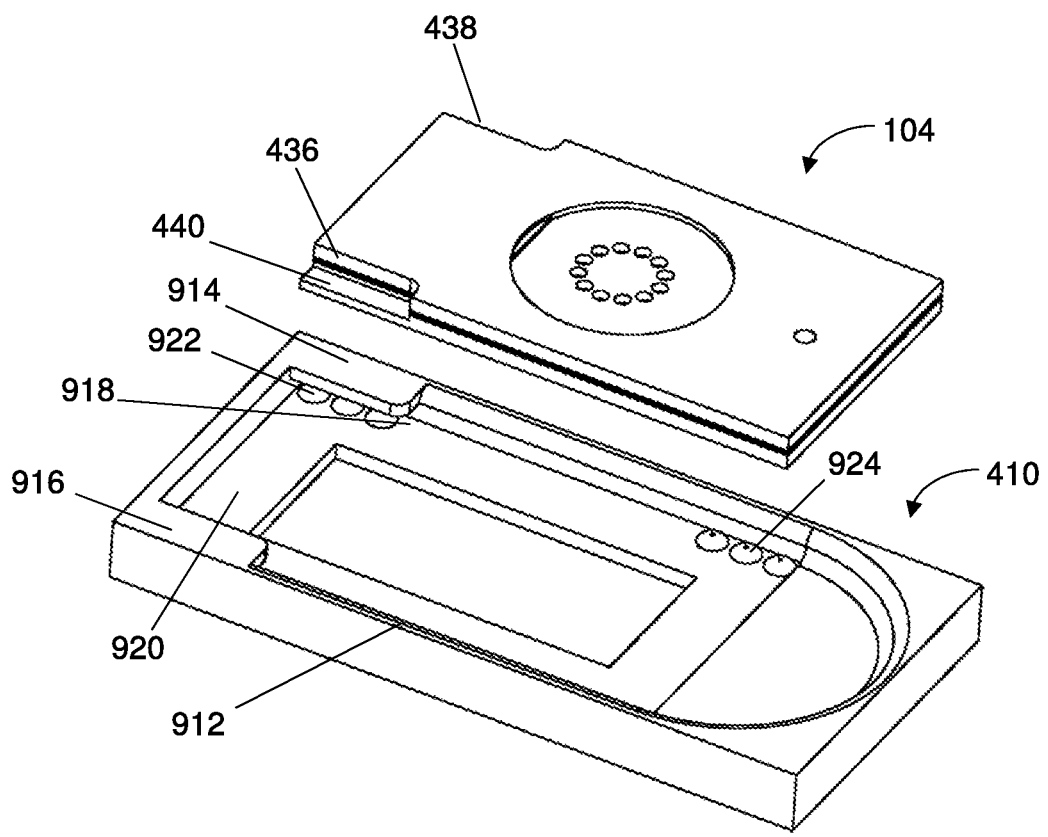
FIG. 55 shows a perspective, detail view of the portion of the exemplary holder of FIG. 53 and the portion of the housing to be used with the holder.
Figure 56:
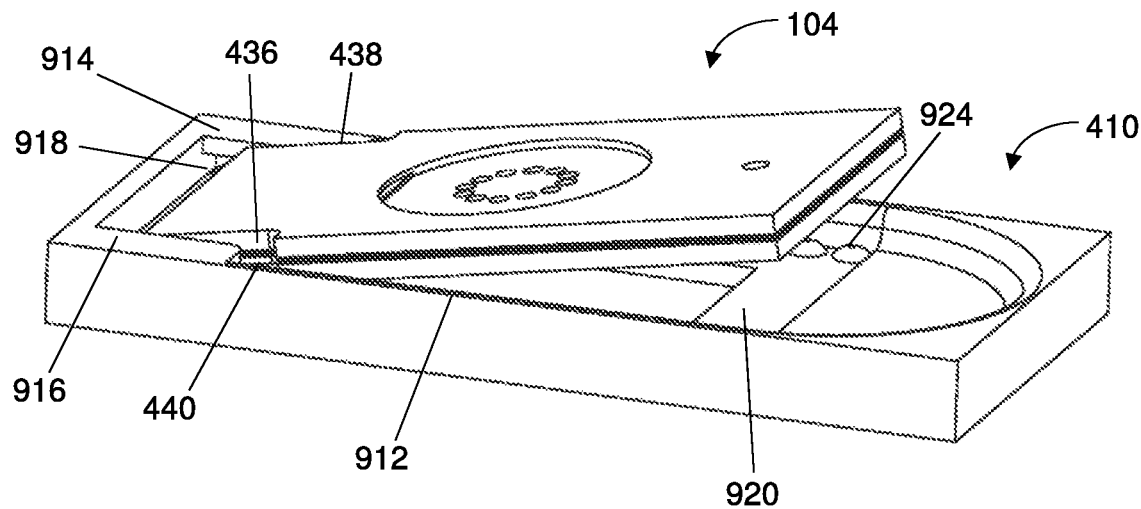
FIG. 56 shows a perspective, detail view of the portion of the exemplary holder of FIG. 53 receiving the portion of the housing.
Figure 57:
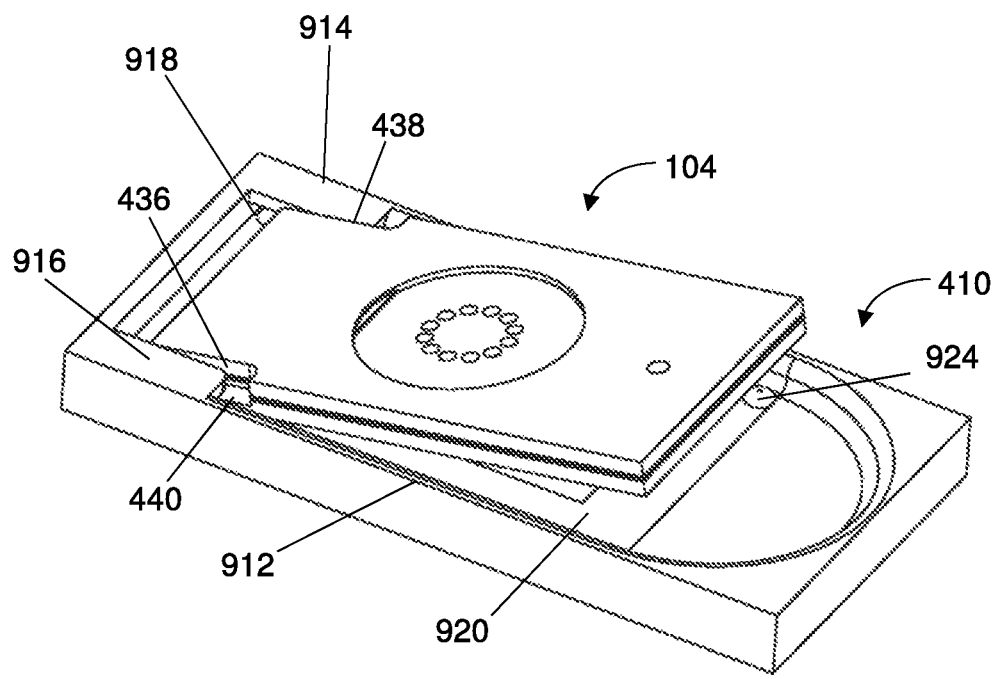
FIG. 57 shows a perspective, detail view of the portion of the exemplary holder of FIG. 53 receiving the portion of the housing.
Figure 58:
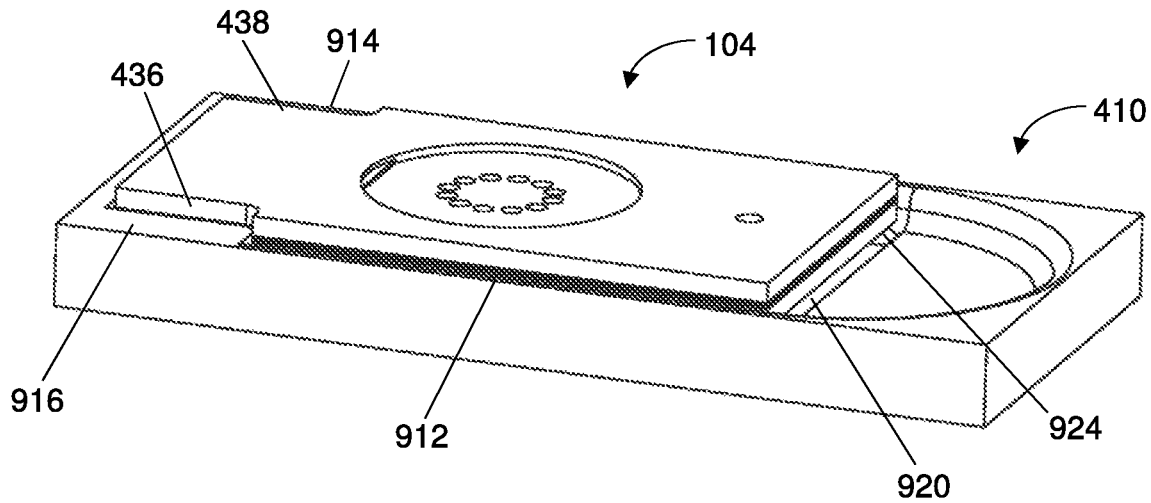
FIG. 58 shows a perspective, detail view of the portion of the exemplary holder of FIG. 53 having received the portion of the housing.
Figure 59:
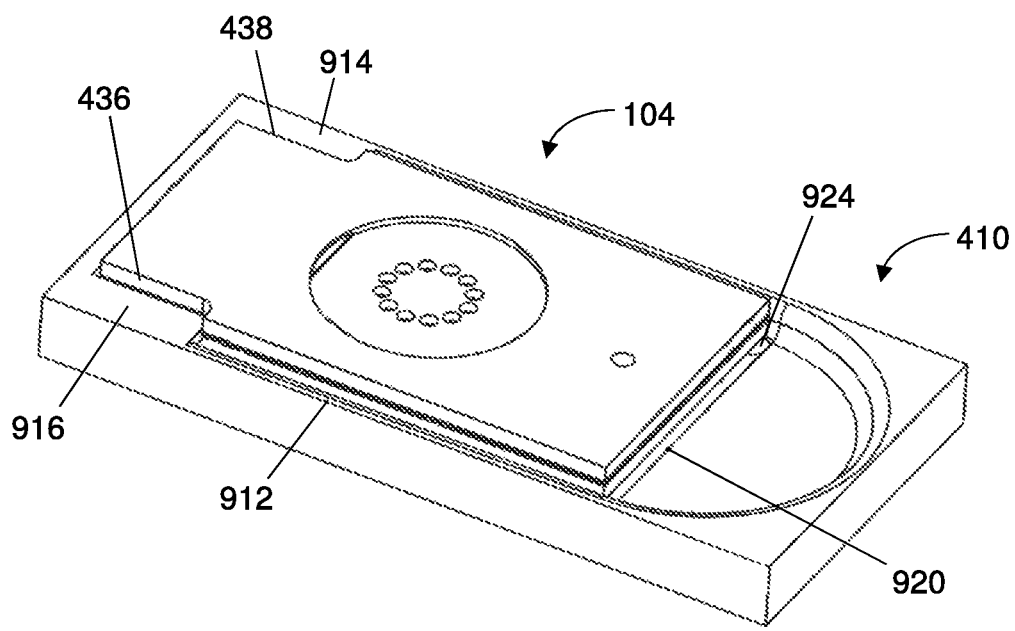
FIG. 59 shows a perspective, detail view of the portion of the exemplary holder of FIG. 53 having received the portion of the housing.
Figure 60:
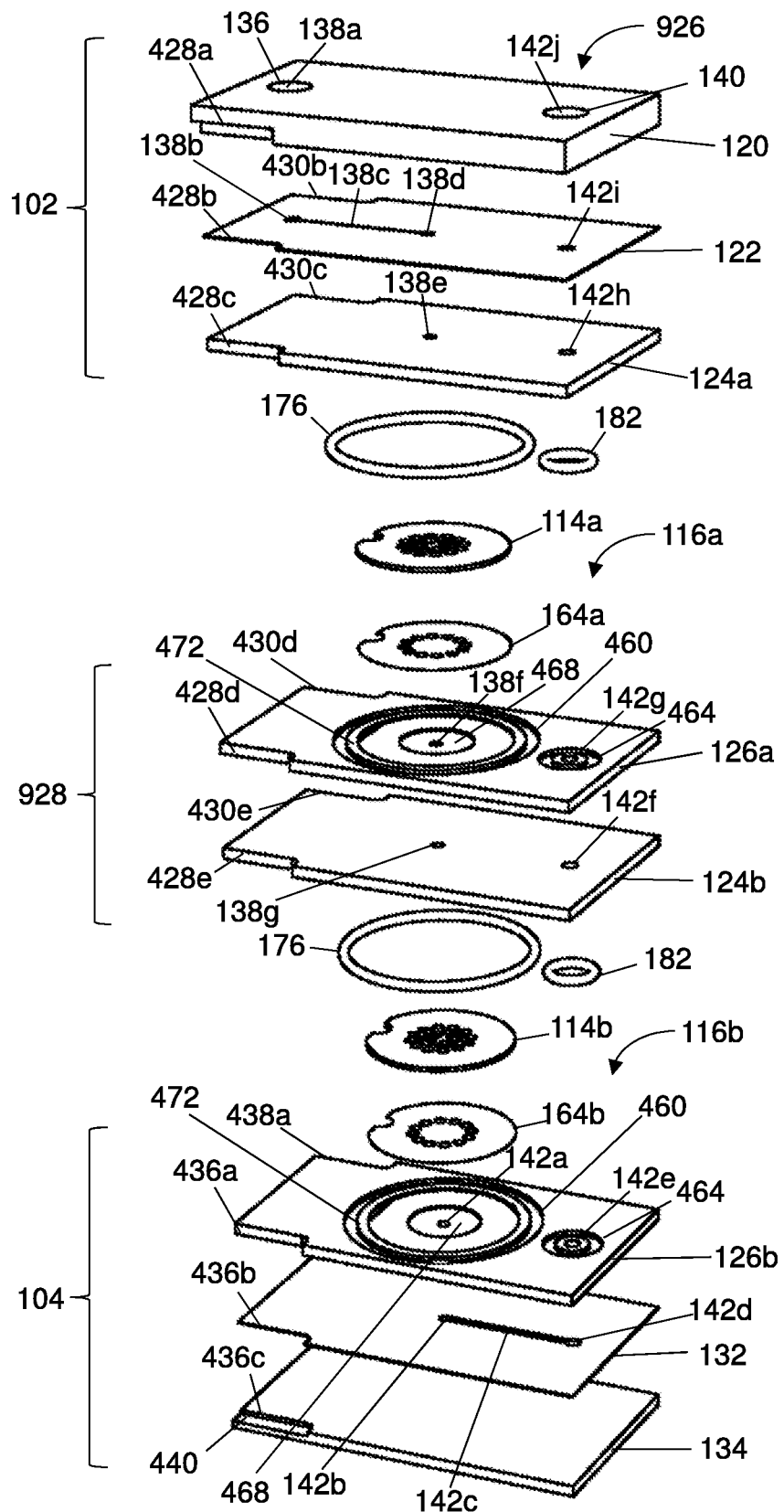
FIG. 60 is a diagrammatic exploded perspective view of an exemplary system of the present invention, in accordance with some embodiments.
Figure 61:
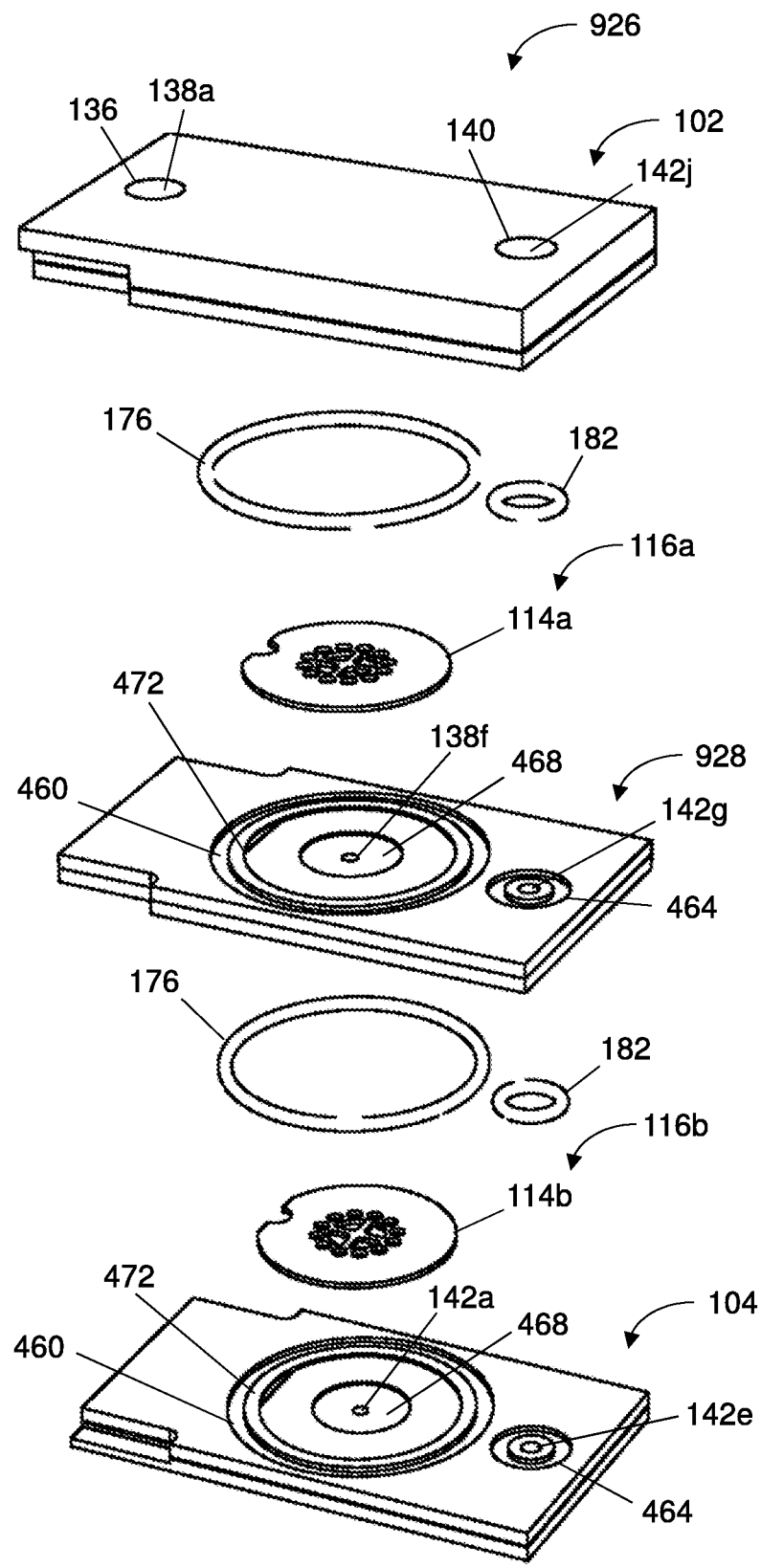
FIG. 61 is a diagrammatic exploded perspective view of the exemplary system of FIG. 60.
Figure 62:
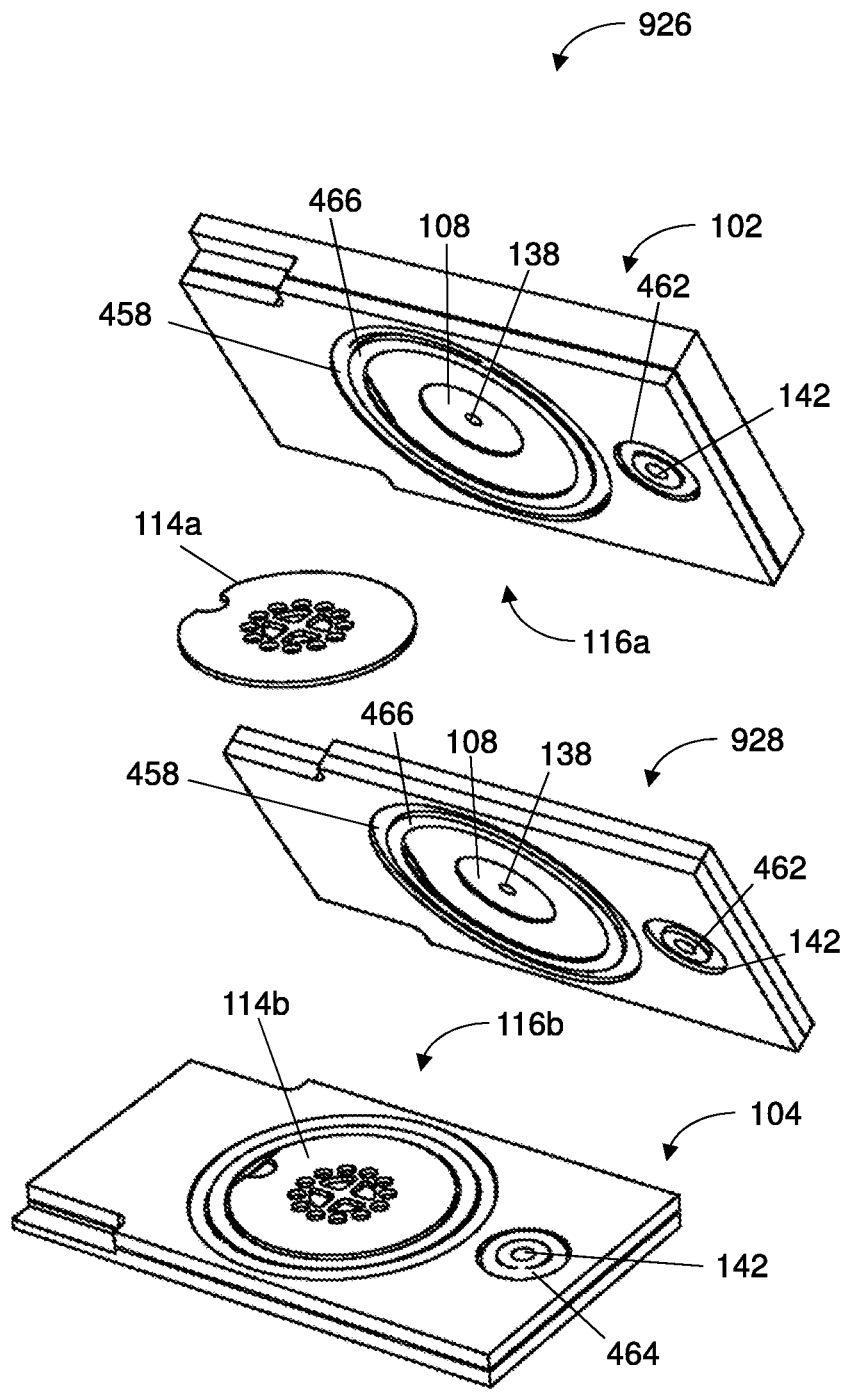
FIG. 62 is a diagrammatic, partially exploded perspective view of the exemplary system of FIG. 60.
Figure 63:
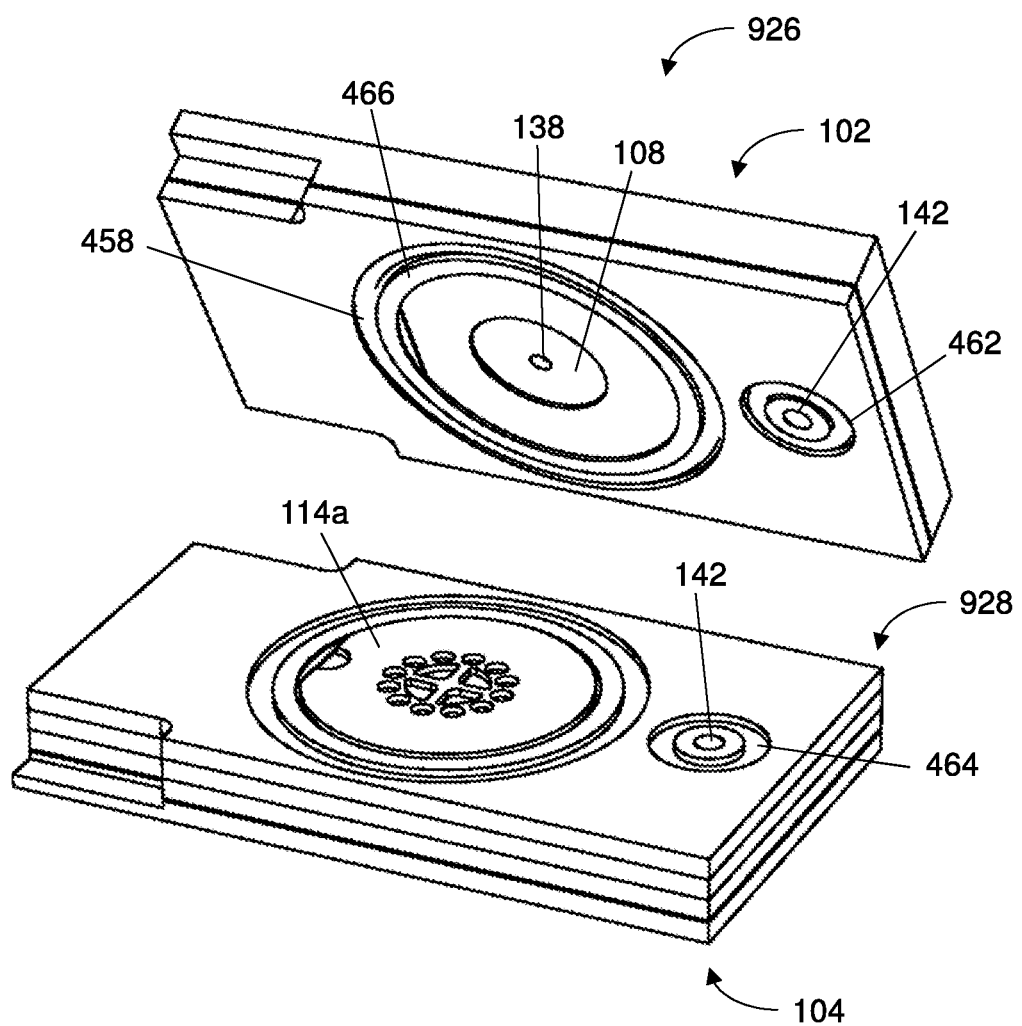
FIG. 63 is a diagrammatic perspective view of the exemplary system of FIG. 60.
Figure 64:
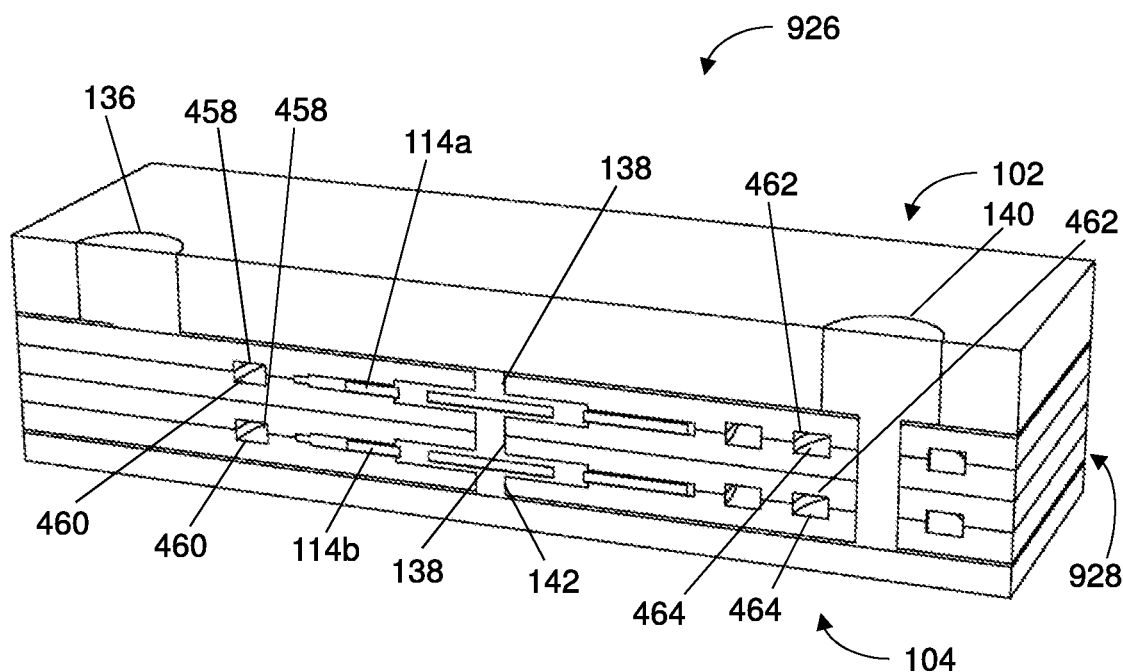
FIG. 64 is a diagrammatic cross-sectional view of the exemplary system of FIG. 60.
Figure 65:
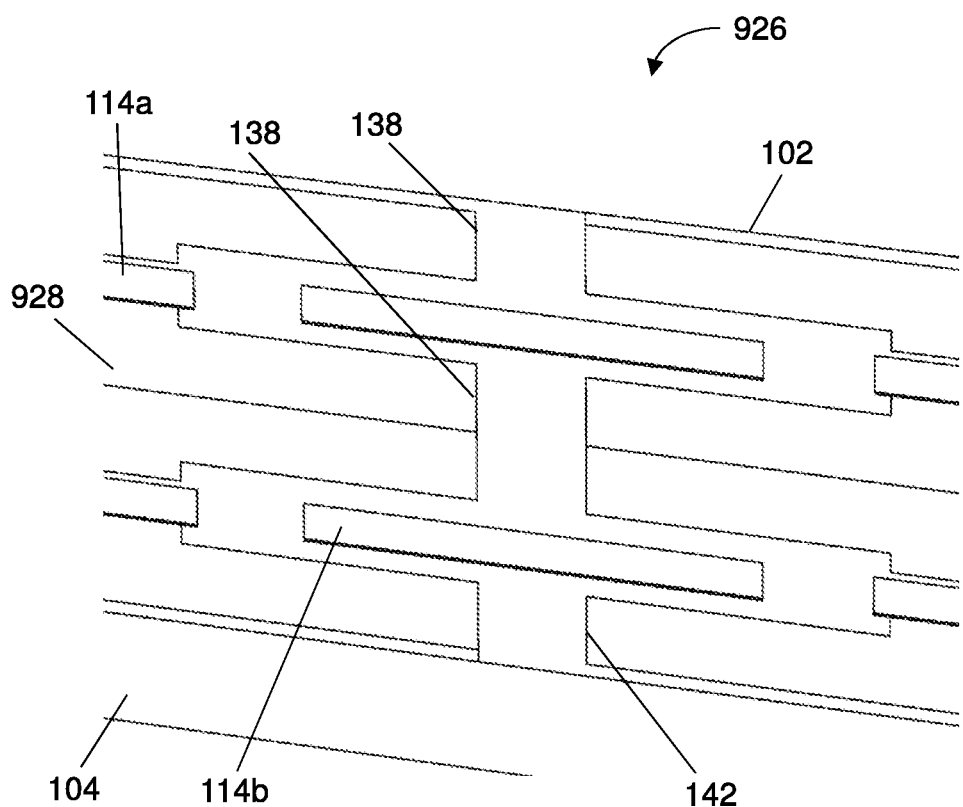
FIG. 65 is a diagrammatic cross-sectional view of the exemplary system of FIG. 60.

FIGS. 50-52 are diagrammatic perspective views of another exemplary fluidic system 562 (hereinafter "system 562") of the present invention. The system 562 can be substantially similar in structure and function to the system 100, 410, 452, 478, 502, 546, except for the distinctions noted herein. Therefore, like reference numbers represent like structures. For clarity, some reference numbers have been omitted. Cutouts 428a-c, 430b-c, 436a-c, 438a collectively form the cutouts 428, 430, 436, 438.

Rather than including a substantially circular cartridge 114, porous element 164 and first sealing element 176, the system 562 includes a substantially wedge-shaped cartridge 566, porous element 568, and first sealing element 564. The cartridge 566 includes two linear sides 570, 572 connected at an endpoint 574 and angled away from each other. The linear sides 570, 572 connect at an opposing end of the cartridge 566 at a rounded edge 576. The cartridge 566 includes a channel 578 near the rounded edge 576, and includes a plurality of channels 580 spaced from the channel 578 in the direction of the endpoint 574.

The porous element 568 similarly includes two linear sides 582, 584 connected at an endpoint 586 and angled away from each other. The linear sides 582, 584 connect at an opposing end of the porous element 568 at a rounded edge 588. The porous element 568 includes a channel 590 formed near the rounded edge 588. The channel 590 is aligned with the channel 578, and is in fluid communication with the channel 578. The sealing element 564 also defines a wedge-shaped configuration configured to be positioned over or around the cartridge 566. The sealing element 564 includes two linear extensions 592, 594 connected at an endpoint 596 and angled away from each other. The linear sides 592, 594 connect at an opposing end of the sealing element 564 at a rounded portion 598. Thus, cartridge 566, porous element 568 and first sealing element 564 define complementary configurations.

The first housing portion 102 includes a wedge-shaped recessed area 900, a wedge-shaped groove 902 configured to receive the sealing element 564, and a wedge-shaped step 904 separating the recessed area 900 from the groove 902 (see FIG. 52). The recessed area 900 surrounded by the step 904 defines a top half of the chamber 116 and the sealing element 564 maintains a fluidic seal around the cartridge 566. The inlet channel 138 enters the recessed area 900 such that the media is introduced into the chamber 116 at a point adjacent to the endpoint 574 of the cartridge 566.

The second housing portion 104 includes a wedge-shaped recessed area 906 complementary to the cartridge 566 such that the cartridge 566 can be at least partially positioned in the recessed area 906 (see FIGS. 50 and 51). An outlet channel 908 in the recessed area 906 is in a position aligned with the channel 578 of the cartridge 566. Media is introduced into the system 562 through the inlet 136, flows through the inlet channel 138, and enters the chamber 116 at or near the endpoint 574 of the cartridge 566. Rather than flowing from a center outward, the media flows linearly from one end of the cartridge 566 to the opposing end (e.g., in the direction of the rounded edge 576), passing into and/or over the channels 580 such that the channels 580 receive the media in a substantially parallel manner.

In some embodiments, the media flows through the channels 580 and into the recessed area 906. In some embodiments, the media flows into and out of the channels 580, and further flows through the channel 578 and the outlet channel 908. In some embodiments, the media flows through both the channels 580 and the channel 578, and converges in the recessed area 906 to flow through the outlet channel 908. In some embodiments, the recessed area 906 can include a centrally disposed, wedge-shaped recessed area and step (similar to the first housing portion 104) to define a bottom half of the chamber 116 and encourage flow of the media through the channels 580.

FIGS. 60-65 are diagrammatic perspective views of another exemplary fluidic system 926 (hereinafter "system 926") of the present invention. The system 926 can be substantially similar in structure and function to the system 100, 410, 452, 478, 502, 546, except for the distinctions noted herein. Therefore, like reference numbers represent like structures. For clarity, some reference numbers have been omitted. Cutouts 428a-e, 430b-e, 436a-c, 438a collectively form the cutouts 428, 430, 436, 438.

Figure 27:
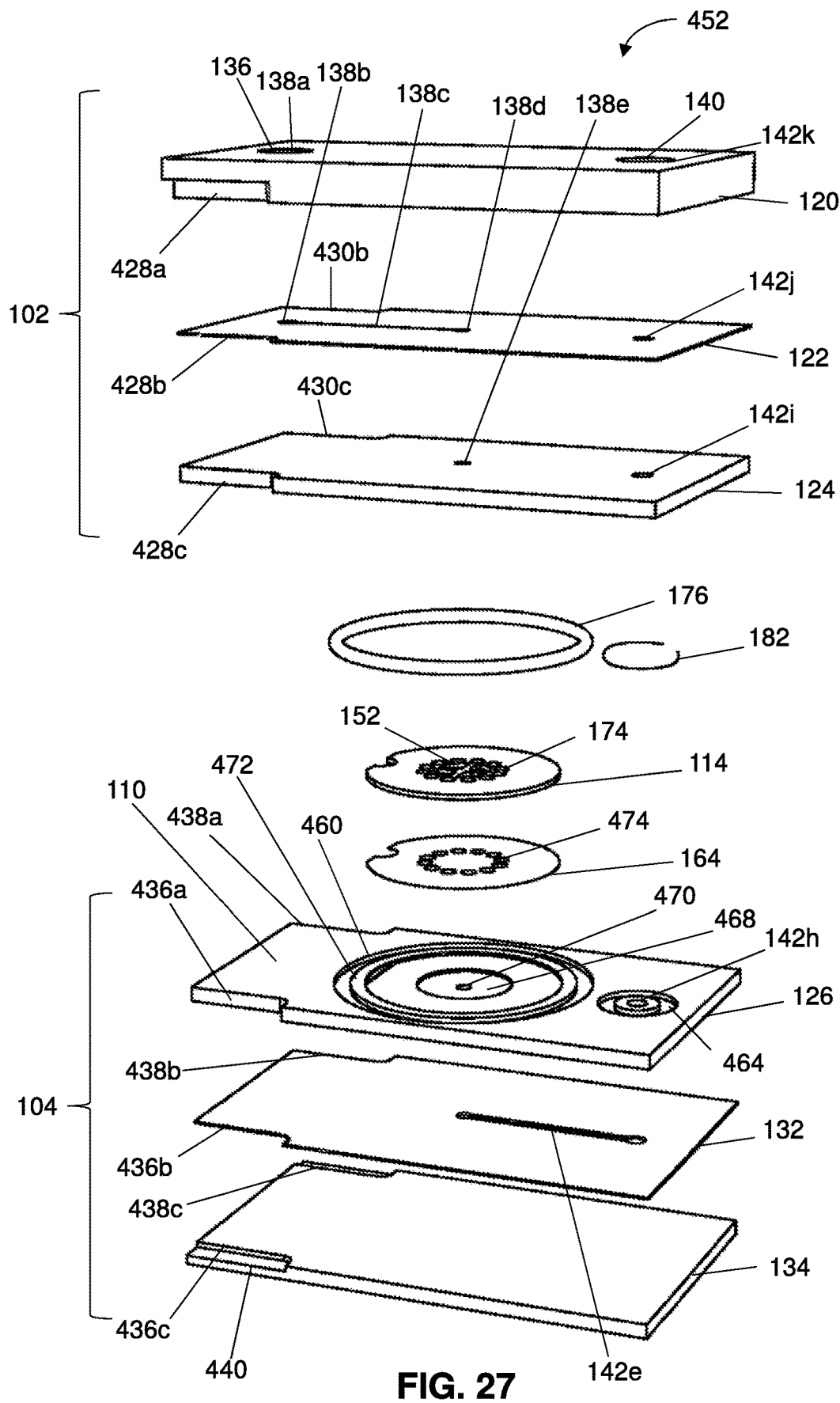
FIG. 27 is a diagrammatic exploded perspective view of an exemplary system of the present invention, in accordance with some embodiments.
Figure 28:
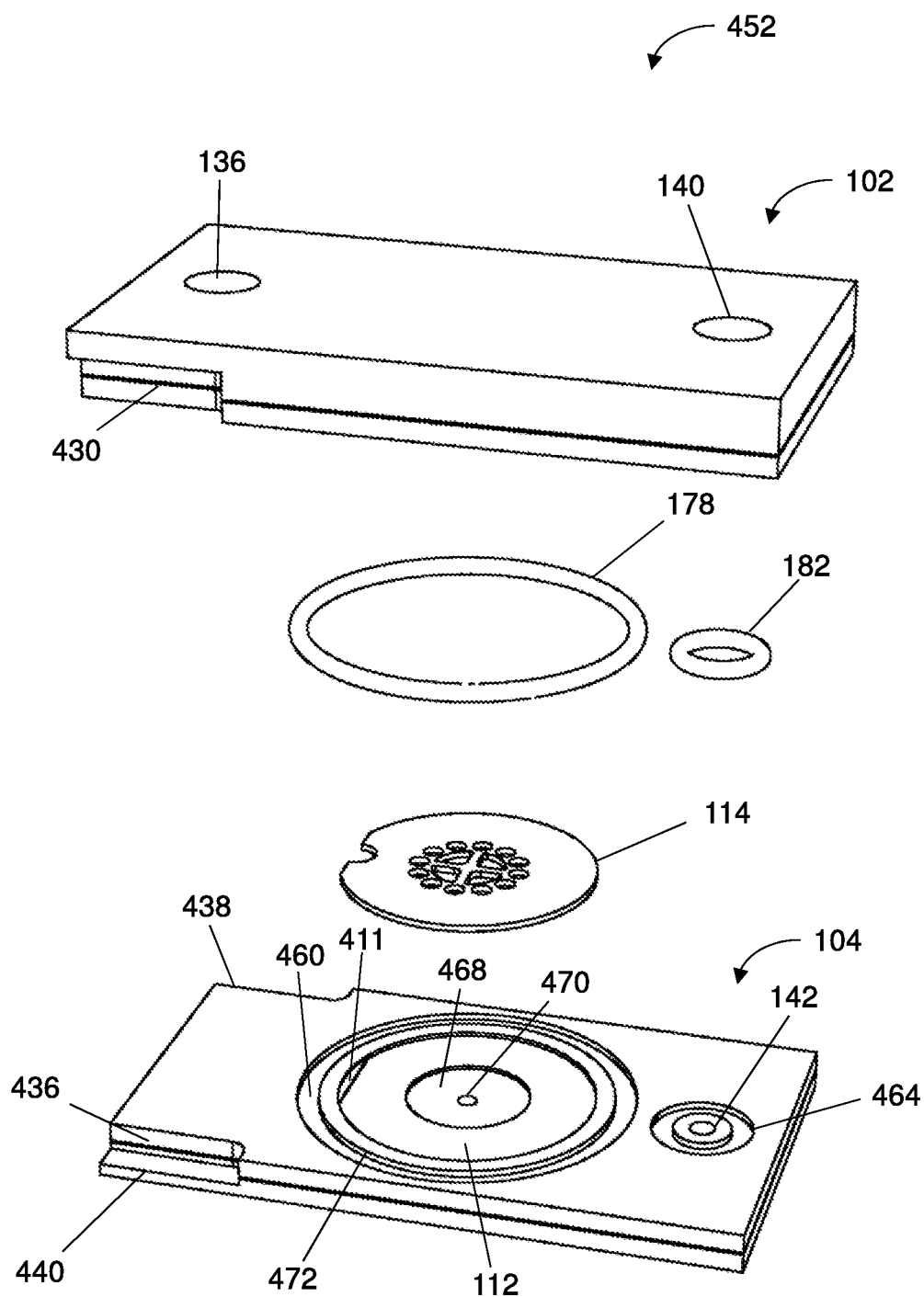
FIG. 28 is a diagrammatic perspective view of the exemplary system of FIG. 27.
Figure 29:
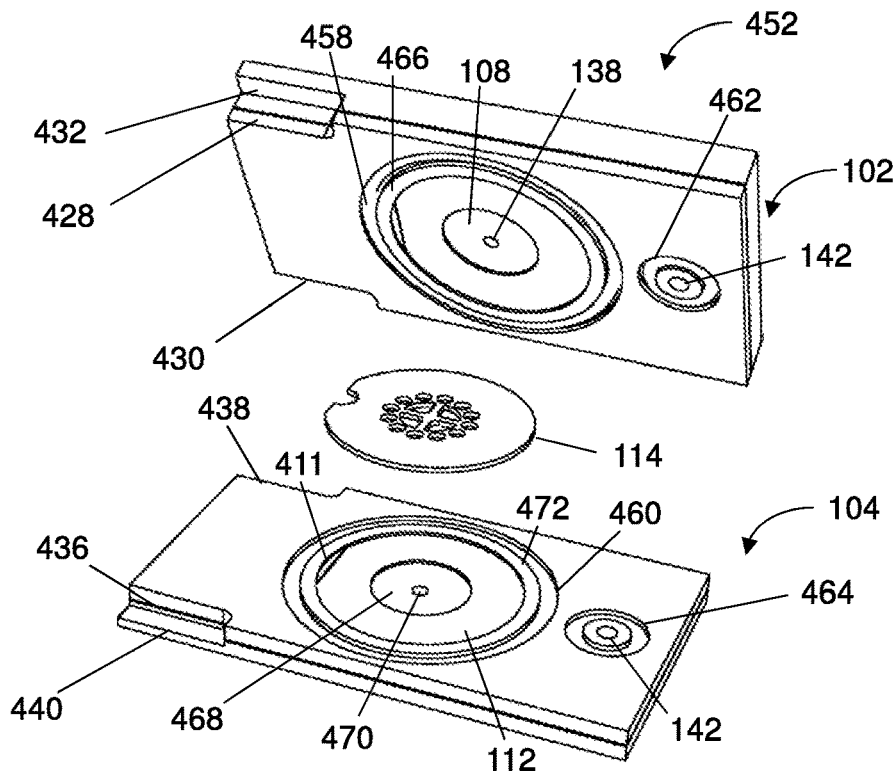
FIG. 29 is a diagrammatic perspective view of the exemplary system of FIG. 27 illustrating a chamber formed by two housing portions and a cartridge to be received in the chamber.
Figure 30:
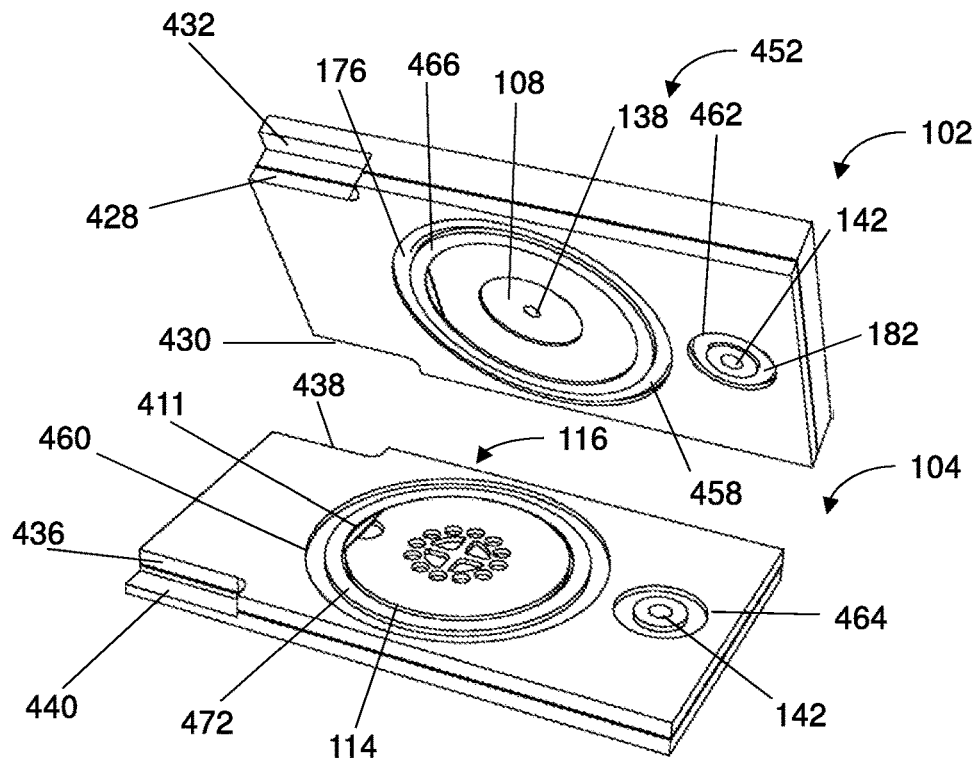
FIG. 30 is a diagrammatic perspective view of the exemplary system of FIG. 27 including a cartridge positioned in a recess of the second housing portion.

Rather than using the system for a single cartridge 114 and porous element 164, the system 926 can be used for multiple cartridges 114a, 114b and porous elements 164a, 164b. As an example, the configuration of the system 452 of FIG. 27 is used. However, it should be understood that other system configurations can be used. For example, rather than a single output channel 142, the system 926 can incorporate layers having multiple output channels 142 that converge within the body of the housing portions. In particular, the layer 124a can be duplicated and disposed below layer 126a. The layer 124b and layer 126a can form a middle housing portion 928 disposed between the first and second housing portions 102, 104. The duplicated layer 124b forms the top half of the second chamber 116b in which the second cartridge 114b can be disposed. The duplicated design results in a substantially continuous flow path between the first cartridge 114a disposed in the first chamber 116a, through the first instance of the layer 126a and the duplicated layer 124b, through the second cartridge 114b, and through the second instance of the layer 126b. Thus, multiple cartridges 114a, 114b can be tested at one time. In an embodiment, rather than including multiple layers, the first, middle and second housing portions 102, 928, 104 can be formed as solid structures with openings or channels formed therein.

Medium is introduced through the inlet 136, flows through the aperture 138a, aperture 138b, slot 138c, aperture 138d, aperture 138e (in layer 124a) and into the first chamber 116a. The medium flows through at least some of the channels of the first cartridge 114a and out of the first chamber 116a through the aperture 138f. Aperture 138f acts as the outlet channel for the first chamber 116a and the inlet channel for the second chamber 116b. In particular, the medium flows through the aperture 138f, the aperture 138g and into the second chamber 116b. The medium flows through at least some of the channels of the second cartridge 114b and out of the second chamber 116b through the aperture 142a. The medium flows out of the system 926 through the aperture 152b, slot 142c, aperture 142d, aperture 142e, aperture 142f, aperture 142g, aperture 142h, aperture 142i, and aperture 142j.

In an embodiment, the system 926 can include a diversion channel between the two cartridge 114a, 114b such that at least a portion of the medium flowing from the first cartridge 114a connects with the outlet channel 142 and does not flow into the second cartridge 114b. In an embodiment, the system 926 can include an input channel between the two cartridge 114a, 114b such that a new medium can be introduced into the system 926 for flow through the second cartridge 114b without flowing through the first cartridge 114a. In an embodiment, rather than a stacked configuration, the first and second cartridges 114a, 114b can be disposed adjacent to each other in separate chambers oriented at the same elevation. For example, the length of the first and second housing portions 102, 104 can be dimensioned longer to accommodate two or more cartridges 114 in separate chambers, and can include multiple inlets or inlet channels to introduce the medium into each chamber. In an embodiment, multiple cartridges 114 resulting in 24 or 96 well plate formats can be tested at one time for high throughput testing.

Figure 34:
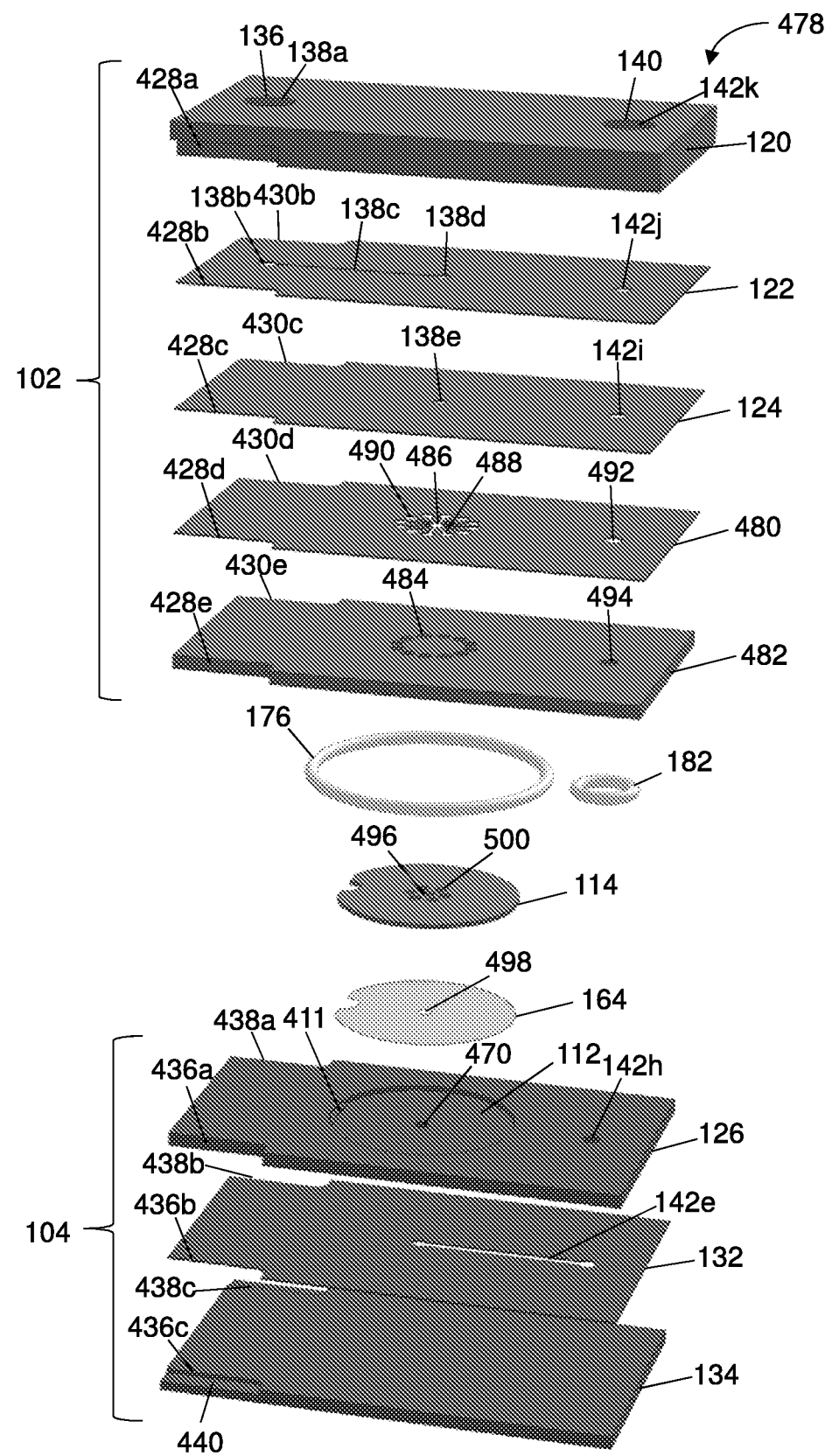
FIG. 34 is a diagrammatic perspective view of an exemplary system of the present invention including an inlet channel that branches into a plurality of inlet channels prior to connecting with the chamber, in accordance with some embodiments.
Figure 35:
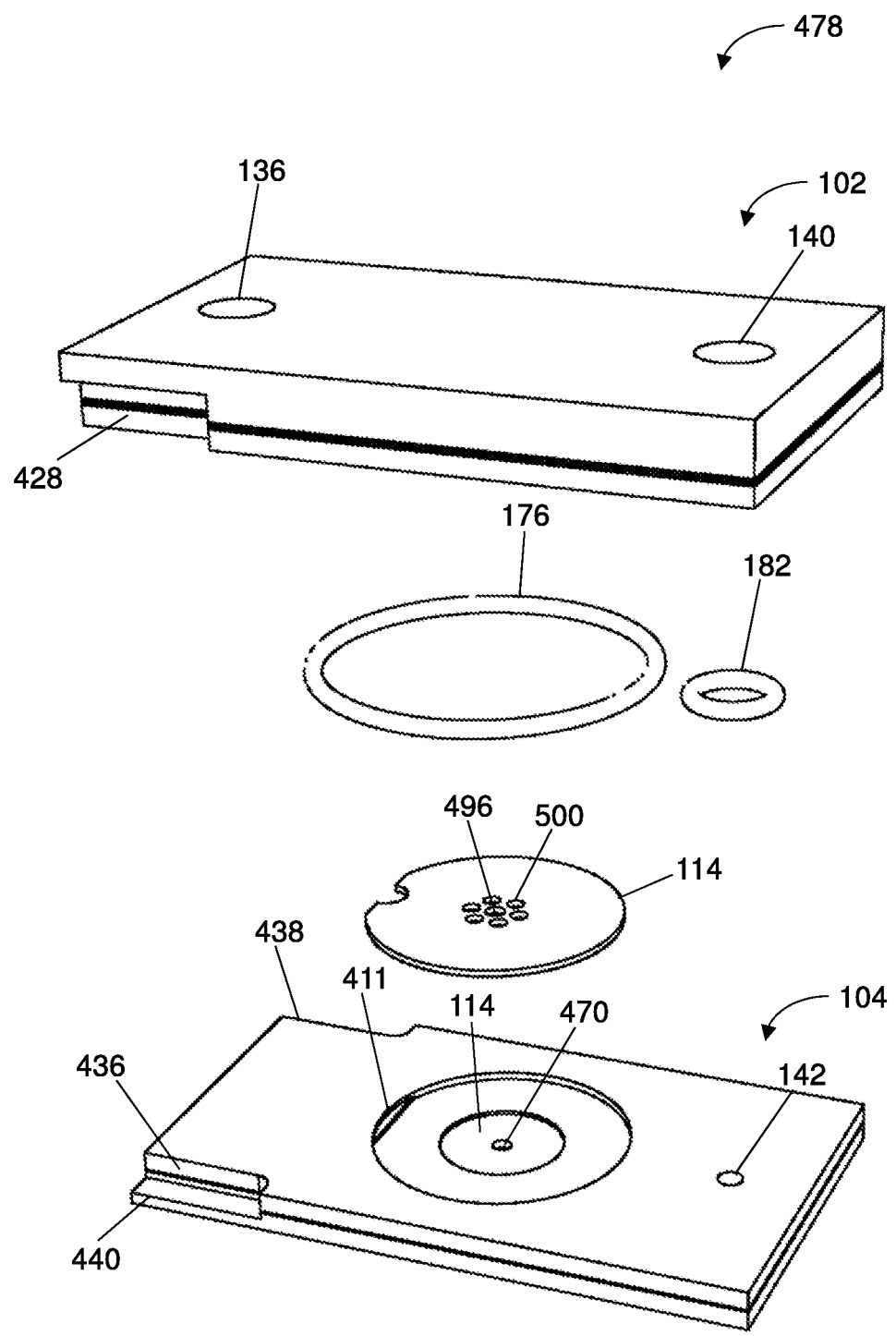
FIG. 35 is a diagrammatic exploded perspective view of the exemplary system of FIG. 34.
Figure 36:
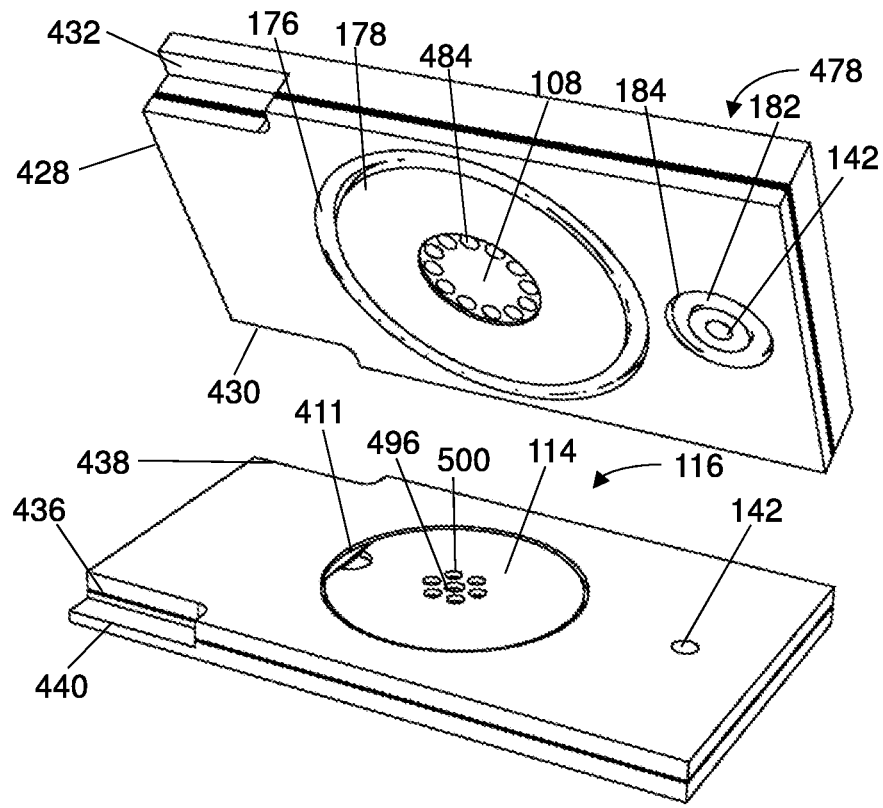
FIG. 36 is a diagrammatic perspective view of the exemplary system of FIG. 34 with the cartridge positioned in a recess of the second housing portion.

The first housing portion 102 can include a single inlet channel 138 for introduction of the media into a central portion of the cartridge 114 for flow of the media radially or laterally outward from the center portion of the cartridge 114 (see, e.g., FIG. 2) or the first housing portion 102 can include a spoke of channels (apertures 486, 490 and slots 488) for introduction of the media radially offset from the central portion of the cartridge 114 for flow of the media radially or laterally inward towards the center portion of the cartridge 114 (see, e.g., FIG. 34). In an embodiment, the height or thickness of each layer 122, 124, 480 can be in the range of about 0.005 mm to about 5 mm. In an embodiment, the width of the slots or apertures forming the inlet channel 138 can be in the range of about 0.005 to about 5 mm. In an embodiment, the cumulative length of the inlet channel 138 can be in the range of about 0.5 mm to about 1,000 mm.

The recessed area 108 of the first housing portion 102 allows for flow of media on the cartridge surface after introduction of the media into the chamber 116 through an individual or multiple inlet channels 138 (see, e.g., FIG. 25). In an embodiment, the first housing portion 102 and the second housing portion 104 can be symmetrically configured, each having a recessed portion for flow of the media above and below the cartridge 114, respectively. In an embodiment, the first housing portion 102 can include a peripheral recessed area and a central recessed area (e.g., similar to the recessed areas 112, 468 of FIG. 28). In an embodiment, the depth of the recessed area 108 in the first housing portion 102 can be in the range of about 0.005 mm to about 5 mm. In an embodiment, the area of the chamber 116 formed by the first housing portion 102 can be in the range of about $3 \times 10^{-4}$ mm$^2$ to about 125 mm$^2$.

The second housing portion 104 can include a single outlet channel 142 for converging of the media within the chamber 116 and flow into the outlet channel 142 removal of the media from the system (see, e.g., channel 470 and slot 142e of FIG. 27) or the second housing portion 104 can include a spoke of channels (aperture 142b and slots 142c) for converting of the media within the structure of the second housing portion 104 and removal of the media from the system (see, e.g., FIG. 2). In an embodiment, the height or thickness of each layer 128, 130, 132 can be in the range of about 0.005 mm to about 5 mm. In an embodiment, the width of the slots or apertures forming the outlet channel 142 can be in the range of about 0.005 to about 5 mm. In an embodiment, the cumulative length of the outlet channel 142 can be in the range of about 0.5 mm to about 1,000 mm.

The recessed area 112 of the second housing portion 104 is configured to receive a portion of the cartridge 114 and includes channels fluidically connecting the chamber 116 to the outlet channel 142 (see, e.g., FIG. 2). In an embodiment, the second housing portion 104 can include a central recessed area 468 configured to receive media flowing through the cartridge 114 such that the media converges and flows through the outlet channel 142 (see, e.g., FIG. 28). In an embodiment, the depth of the recessed area 112, 468 in the second housing portion 104 can be in the range of about 0.005 mm to about 5 mm. In an embodiment, the area of the chamber 116 formed by the second housing portion 104 can be in the range of about $3 \times 10^{-4}$ mm$^2$ to about 125 mm$^2$.

FIGS. 53-59 are diagrammatic perspective and detailed views of another exemplary holder 910 of the present invention. The holder 910 can be substantially similar in structure and function to the holder 210, except for the distinctions noted herein. Therefore, like reference numbers represent like structures. The holder 910 can be configured to receive and hold housing portions of any of the microfluidic systems described herein. The holder can also be configured to align the housing portions and to impart a compressive force on the housing portions to seal a cartridge between the housing portions. Although the detailed views of FIGS. 54-59 illustrate interlocking of the second housing portion 104 with the holder 910, it should be understood that the first housing portion 102 can be similarly interlocking with the opposing side of the holder 910.

Each of the openings 226, 236 include a first section 912 defining a substantially rectangular area configured and dimensioned to receive the first and second housing portions 102, 104, respectively. One end of the openings 226, 236 includes tabs 914, 916 extending on opposing sides limiting the side of the opening 226, 236. The tabs 914, 916 define grooves 918 configured and dimensioned to receive the steps 432, 440 of the first and second housing portions 102, 104. For example, the cutouts 436, 438 can be configured and dimensioned to accommodate and mate with the tabs 914, 916, while the step 440 slides into the groove 918 between the bottom surface 920 the tabs 914, 916, thereby interlocking the second housing portion 104 with the holder 410.

In some embodiments, each of the openings 226, 236 can include one or more raised dimples 922, 924 (e.g., hemispherical dimples) extending from the bottom surface 920 at corners of the openings 226, 236. The dimples 922 can extend from the bottom surface 920 directly underneath the tabs 914, 916, and the dimples 924 can extend from the bottom surface 920 at the opposing side of the openings 226, 236 at a distance dimensioned to support the first and second housing portions 102, 104 thereon. For example, the dimples 922 support the corners of the second housing portion 104 having the steps 440, while the dimples 924 support the opposing corners of the second housing portion 104. The dimples 922, 924 maintain the first and second housing portions 102, 104 raised and level relative to the bottom surface 920 of the openings 226, 236. In some embodiments, the dimples 922 can maintain the first and second housing portions 102, 104 raised from the bottom surface 920 of the respective first and second holder portions 212, 214 to ensure proper contact, alignment and sealing between the first and second housing portions 102, 104 when the holder 910 is in the closed configuration.

Figure 8:
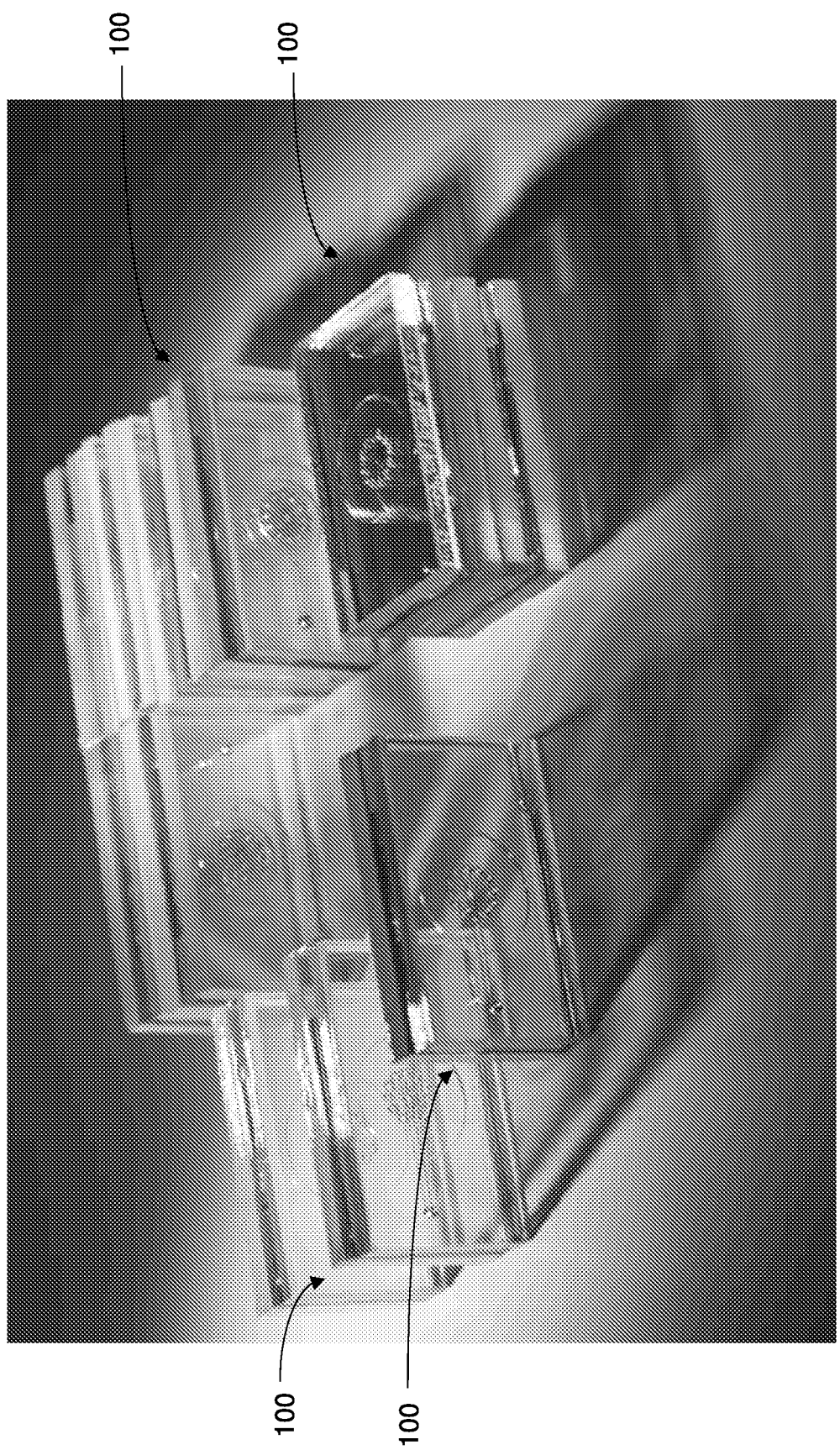
FIG. 8 shows a perspective view of a plurality of housing components sandwiched between glass layers in preparation for bonding, in accordance with some embodiments.

In some embodiments, rather than bonding the first and second housing portions 102, 104, an exemplary holder 210 of the present invention can be used to temporarily maintain a pressure between the components to fluidically seal the components of the system 100 during culturing or testing. FIGS. 9, 10A-C and 11A-B show perspective and detailed views of an exemplary holder 210 of the present invention. The holder 210 is configured and dimensioned to receive therein an assembly of the first housing portion 102, the second housing portion 104, and the cartridge 114. For ease in visualization, the first housing portion 102, the second housing portion 104 and the cartridge 114 are shown as opaque in FIGS. 9, and 10A-C; however, they are transparent or translucent in some embodiments, as shown in the images in FIG. 5 and FIG. 8.

The holder 210 generally includes a first holder portion 212 (e.g., a top holder half) and a second holder portion 214 (e.g., a bottom holder half) configured to receive the assembly therebetween. The first and second holder portions 212, 214 can be hingedly connected (e.g., using one or more hinges 216) such that the holder 210 can transition between an open configuration (shown in FIG. 9) and a closed configuration. In some embodiments, each of the first and second holder portions 212, 214 has a substantially rectangular perimeter with chamfered corners. The first holder portion 212 includes an outer surface 218 and an inner surface 220. The outer surface 218 faces away from the second holder portion 214 when the holder 210 is closed, and the inner surface 220 faces toward the second holder portion 214 when the holder 210 is closed.

The first holder portion 212 includes a protrusion 222 extending from the inner surface 220. When the holder 210 is positioned in the closed configuration, the protrusion 222 is substantially received by a recessed area 224 of the second holder portion 214. In some embodiments the protrusion 222 has a substantially rectangular perimeter with chamfered corners. The perimeter of the protrusion 222 is dimensioned smaller than and sits within the perimeter of the inner surface 220. The protrusion 222 includes one or more openings 226 having a recessed edge 228 configured and dimensioned to receive and releasably engage the first housing portion 102 of the system 100. In some embodiments, the recessed edge 228 can include a tab into which a complementary extension or groove of the first housing portion 102 can be inserted for engagement of the first housing portion 102 with the opening 226 (e.g., substantially similar to the configuration of the second holder portion 214 shown in FIGS. 10A-C).

Figure 9:
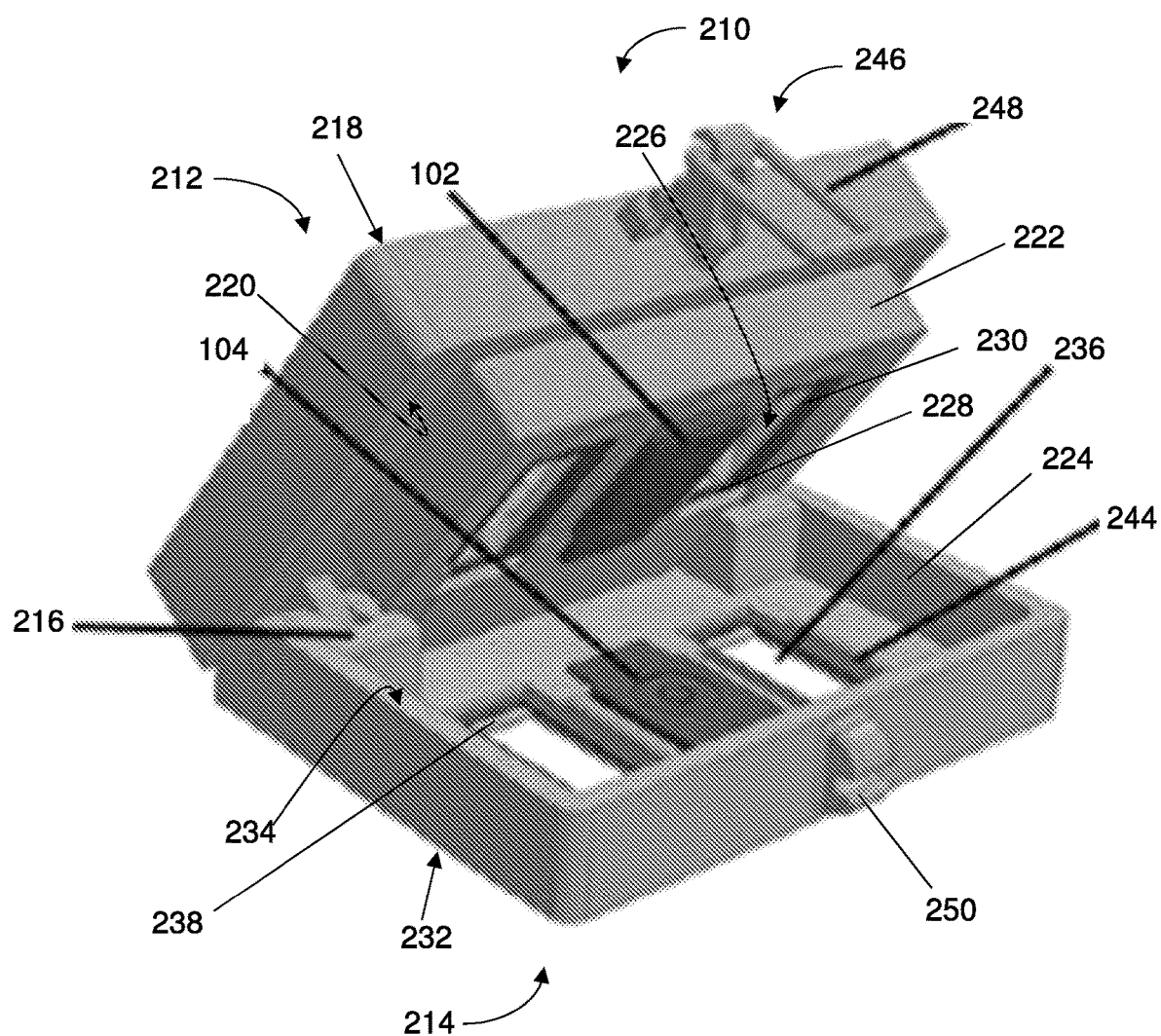
FIG. 9 shows a perspective view of an exemplary holder of the present invention.

In the embodiment shown in FIG. 9, the holder 210 includes three openings 226 for retaining up to three assemblies each including a cartridge and first and second housing portions within the holder 210. However, it should be understood that the holder 210 can have any number of openings 226 based on the desired number of assemblies to be retained therein. Each opening 226 extends through the protrusion 222 and the outer surface 218 of the first holder portion 212 providing access to the inlet 138 and outlet 140 on the first holder portion 102 of the assembly. In some embodiments, fluidic connections can be passed through the opening 226 and connected to the inlet 138 and outlet 140 for introduction of the medium into the assembly and removal of the medium from the assembly, respectively. In some embodiments, the holder 210 can include a gasket 230 disposed in the recessed edge 228 of the opening 226. The gasket 230 can assist in engagement and retaining of the first housing portion 102 within the opening 226, and in preventing damage to the first housing portion 102.

The second holder portion 214 also includes an outer surface 232 and an inner surface 234. The outer surface 232 faces away from the first holder portion 212 when the holder 210 is closed, and the inner surface 234 faces toward the first holder portion 212 when the holder 210 is closed. The inner surface 234 includes the recessed area 224 configured and dimensioned to at least partially receive the protrusion 222 of the first holder portion 212. In particular, the recessed area 224 can be complementary to the protrusion 222 such that during closure of the holder 210, the protrusion 222 gradually enters and rests within the recessed area 224.

The recessed area 224 includes one or more openings 236 with a recessed edge 238 configured to receive and releasably engage the second housing portion 104 of the system 100. The openings 236 can be aligned with the openings 226 of the first holder portion 212 such that the first and second housing portions 102, 104 align when the holder 210 is closed. The openings 236 extend through the recessed area 224 and the outer surface 232 of the second holder portion 214, and provide windows through which the system 100 can be monitored. In some embodiments, the recessed edge 238 can include a tab 240 into which a complementary extension or groove 242 of the second housing portion 104 can be inserted for engagement of the second housing portion 104 with the opening 236 (see, e.g., FIGS. 10A-C). In some embodiments, the holder 210 can include a gasket 244 disposed in the recessed edge 238 of the opening 236. The gasket 244 can assist in engagement and retaining of the second housing portion 104 within the opening 236, and in preventing damage to the second housing portion 104. In some embodiments, the gaskets 230, 244 can maintain the first and second housing portions 102, 104 raised from the bottom surface of the respective first and second holder portions 212, 214 to ensure proper contact, alignment and sealing between the first and second housing portions 102, 104 when the holder 210 is in the closed configuration.

As noted above, introduction of the protrusion 222 of the first holder portion 212 into the recessed area 224 of the second holder portion 214 positions the first and second housing portions 102, 104 against each other, and imparts a compression force on the assembly to maintain a seal between the first housing portion 102, the second housing portion 104, and the cartridge 114. In some embodiments, the holder 210 can include one or more latching mechanisms 246 for maintaining the holder 210 in the closed position, thereby maintaining the compression force on the system 100. For example, the first holder portion 212 can include a hingedly movable latch 248, and the second holder portion 214 can include a retaining groove 250 configured to receive and interlock with the latch 248. After the holder 210 is positioned in the closed configuration, the latch 248 can be engaged with the groove 250 and the latching mechanism 246 can be locked to prevent the holder 210 from opening.

Once secured, the holder 210 can be manipulated to connect inlet and/or outlet tubes or connectors to the system 100 and view the system 100 from the openings 226, 236. In addition, the openings 226, 236 allow a microscope to be disposed immediately adjacent to the system 100, allowing for viewing of the cells while disposed within the holder 210.

The holder 210 orients and anchors the portion of the cartridge housing, and delivers necessary compression to seal the housing and cartridge without the use of screws. The design of FIG. 9 features locations for three assemblies to run triplicate conditions in parallel, with openings above and below each assembly to allow for imaging directly within the holder 210. As noted above, each portion of the holder 210 can be designed to accommodate a portion of the cartridge housing, with tabs that fit around the housing component to keep it in place (FIG. 5). A hinge 216 connects the top and bottom halves of the holder 210, which swivel together to enclose the cartridge housing with the cartridge 114 between them. The latch mechanism 246 secures the holder 210 in the closed position, ensuring that the clamping force is maintained. This platform facilitates assembly of the cartridge within the housing for experimentation and allows for easy manipulation of the cartridge 114.

In some embodiments, the first and second housing portions 102, 104 of the system 100 can be secured to each other with one or more other securing elements (e.g., screws, clips, etc.) instead of the holder. In some embodiments, the system 100 can be held together by a customized latch or clip that matches the dimensions and forces required, such as the clips described in U.S. Provisional Application No. 62/202,216, filed on Aug. 7, 2015, the entire contents of which are hereby incorporated herein by reference.

The system is configured to incorporate different versions of the cartridge design. For example, one configuration can accommodate a collection of cell clusters within a single well, which facilitates loading of the cell clusters onto the housing, while another has individual wells for each cell cluster. In some embodiments, a cartridge that has individual wells for each cell cluster can be used for purposes of defining the number of cell clusters being cultured within the system, a number that can be altered by changing the number of wells on the cartridge. The systematic arrangement of individual clusters on the cartridge can also assist with tracking the state of each cluster over the course of long-term culture. In addition to variations in the well pattern, the cartridge includes channels (e.g., second plurality of channels 174 in FIGS. 1-5) that facilitate flow around the clusters instead of through them, as might be the case when the resistance to flow is too high. The configuration of these wells can also be altered to improve the flow profile within the cartridge, or may be removed as necessary. Without changing the flow path, however, all modifications to the cartridge to achieve different experimental objectives can be made while keeping the overall dimensions unchanged, meaning that the same housing can be used for different cartridges with different cell culture configurations.

In addition, the same cartridge can be transferred between multiple housings. Because the cells are wholly contained within the cartridge, it is feasible to culture cells for a designated period of time in a first housing, remove the cartridge from the housing, and transfer it to another housing, possibly to achieve a different culture environment or to place the cells in series with another cartridge containing a different cell type. In some embodiments, a housing can accommodate multiple cartridges, either to increase the number of cells under study in parallel or to couple different cell types arranged on separate cartridges.

Figure 12A:
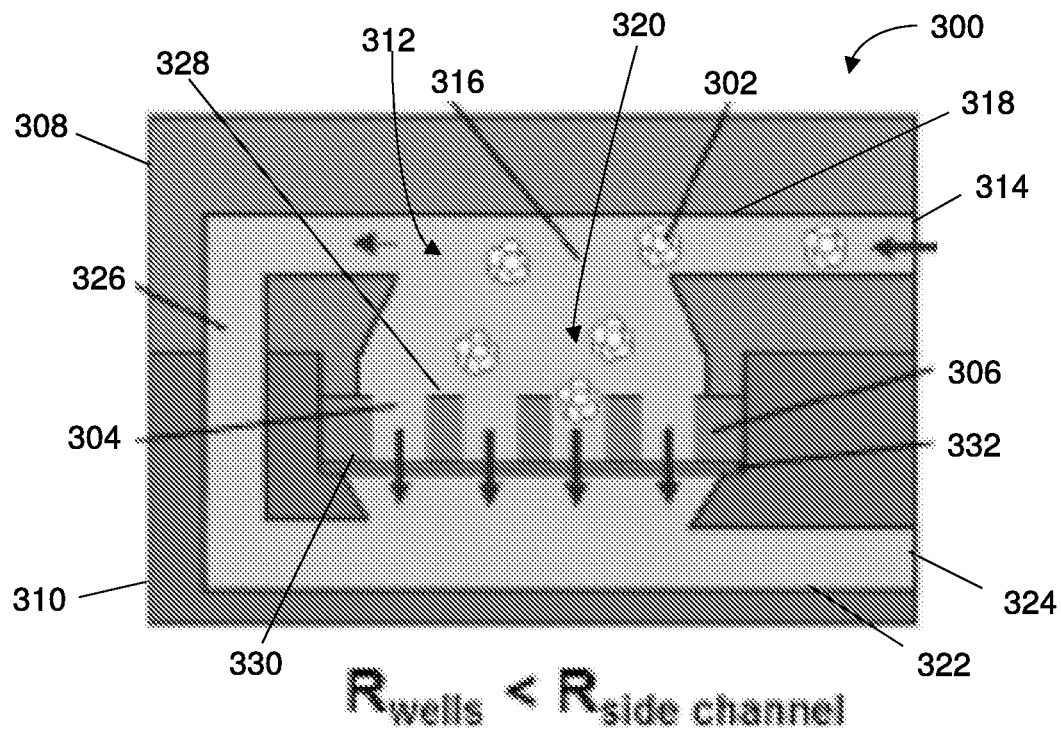
FIGS. 12A-B show diagrammatic, cross-sectional views of an exemplary system of the present invention for loading a cartridge with one or more biological cells.
Figure 12B:
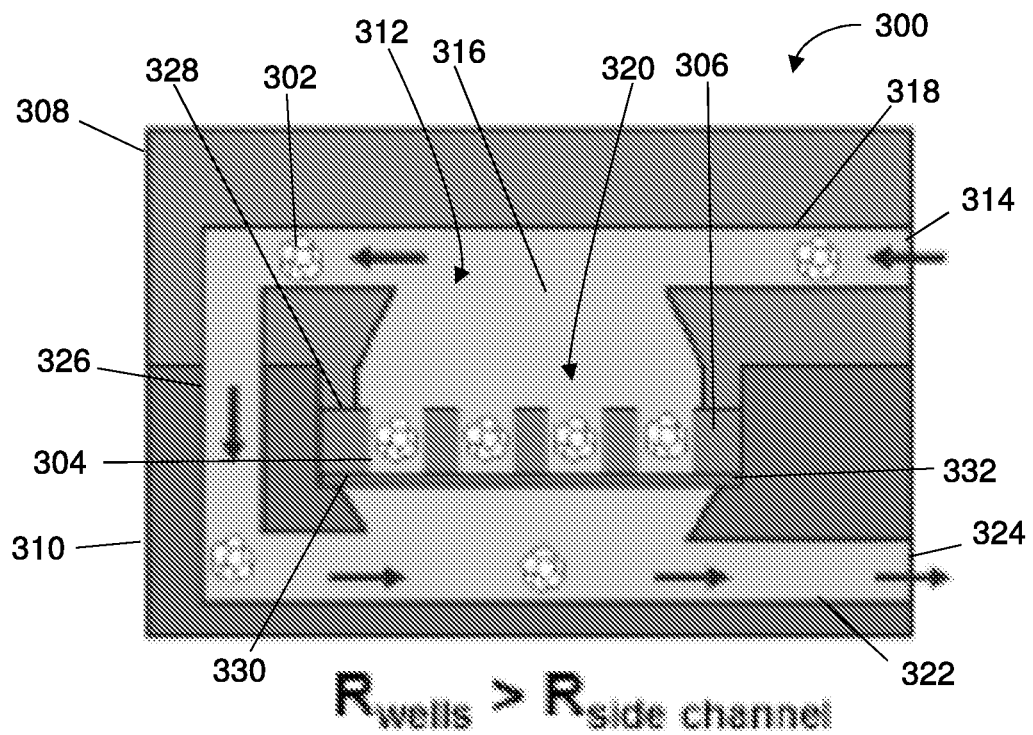

Another important example of where housing modularity may come into effect is when loading cells or cell clusters into the cartridge to fill individual wells. FIGS. 12A-B show diagrammatic, cross-sectional views of an exemplary microfluidic system 300 for loading cells or cell clusters 302 into wells 304 of a cartridge 306. The system 300 includes a housing with a first housing portion 308 and a second housing portion 310. The first and second housing portions 308, 310 form a chamber 312 therebetween. The housing includes an inlet 314 for introduction of a medium 316 including one or more biological cells 302 into the system 300. The housing includes an inlet channel 318 fluidically connecting the inlet 314 with a central portion 320 of the chamber 312 (e.g., in which the cartridge 306 is disposed). The housing includes an outlet channel 322 fluidically connecting the central portion 320 of the chamber 312 with an outlet 324. The housing further includes a bypass channel 326 fluidically connecting the inlet channel 318 with the outlet channel 322, and bypassing the central portion 320 of the chamber 312. In particular, rather than flowing from the inlet channel 318, through the central portion 320, the wells 304 of the cartridge 306, into the outlet channel 322, and out of the outlet 324, the medium 316 that enters the bypass channel 326 flows directly from the bypass channel 326, into the outlet channel 322, and out of the outlet 324.

Similar to the cartridge 114, the cartridge 306 can include a central portion and a peripheral portion configured to be disposed within the chamber 312 with the central portion of the cartridge 306 in the central portion 320 of the chamber 312. The cartridge 306 includes a first surface 328 and an opposing second surface 330 with a plurality of channels forming the wells 304. The cartridge 114 includes at least one porous element 332 disposed adjacent to the second surface 330 and forming the wells 304 extending through the cartridge 306.

The system 300 can be configured such that when the cartridge 306 is disposed between the first and second housing portions 308, 310 and the medium 316 with the cell clusters 302 is introduced into the inlet 314, at least a first portion of the medium 316 and cell clusters 302 flows through the inlet channel 318 and into the central portion 320 of the chamber 312. At least one or more of the cell clusters 302 enter into and lodge within the wells 304. The medium 316 continues to flow around the cell clusters 302, through the wells 304, into the outlet channel 322 and out of the outlet 324. As shown in FIG. 12A, while the wells 304 are not filled with cell clusters 302, the flow resistance of the medium 316 through the central portion 320 and the wells 304 is less than the flow resistance of the medium 316 through the bypass channel 326.

As shown in FIG. 12B, when cell clusters 302 lodge within the wells 304 and partially block the flow path through the wells 304, the flow resistance of the medium 316 through the central portion 320 and the wells 304 increases and becomes greater than the flow resistance of the medium 316 through the bypass channel 326. Thus, at least a portion of the medium 316 and the cell clusters 302 flows through the inlet channel 318, into the bypass channel 326 to bypass the wells 304, and flows through the outlet channel 322 to the outlet 324. Cell clusters 302 are thereby loaded into the wells 304 of the cartridge 306 and, once loaded, the remaining medium 316 and cell clusters 302 bypass the cartridge 306 and flow out of the system 300 along the bypass channel 326.

Thus, placing the cartridge 306 inside of the housing creates a trap for the cells or cell clusters 302. A suspension of cell clusters 302 introduced at the inlet 314 of the loading system 300 flows to the chamber 312 above the cartridge 306. At this point, there are two different directions in which flow occurs. Although the system 300 includes the bypass channel 326 that could accommodate movement of the cell clusters 302, this channel 326 is designed such that the resistance is greater than for flow directed down through the wells 304 in the cartridge 306. As a result, the cell clusters 302 preferentially fill the wells 304 first. However, as the wells 304 in the cartridge 306 become blocked with cell clusters 302, the resistance to flow through the cartridge increases, necessitating a diversion through the bypass channel 326. Once all or most of the wells 304 are filled with cell clusters 302, the excess cell clusters 302 can be flushed from the system 300, the first and second housing portions 308, 310 can be separated, and the cartridge 306 is removed and transferred to another microfluidic system (e.g., such as system 100) for long-term culture. In some embodiments, non-woven polymeric fiber sheet over the wells may be used to trap the cell clusters in the wells. In some embodiments, a hydrogel material can be used to anchor cell clusters in the wells 304.

Figure 13A:
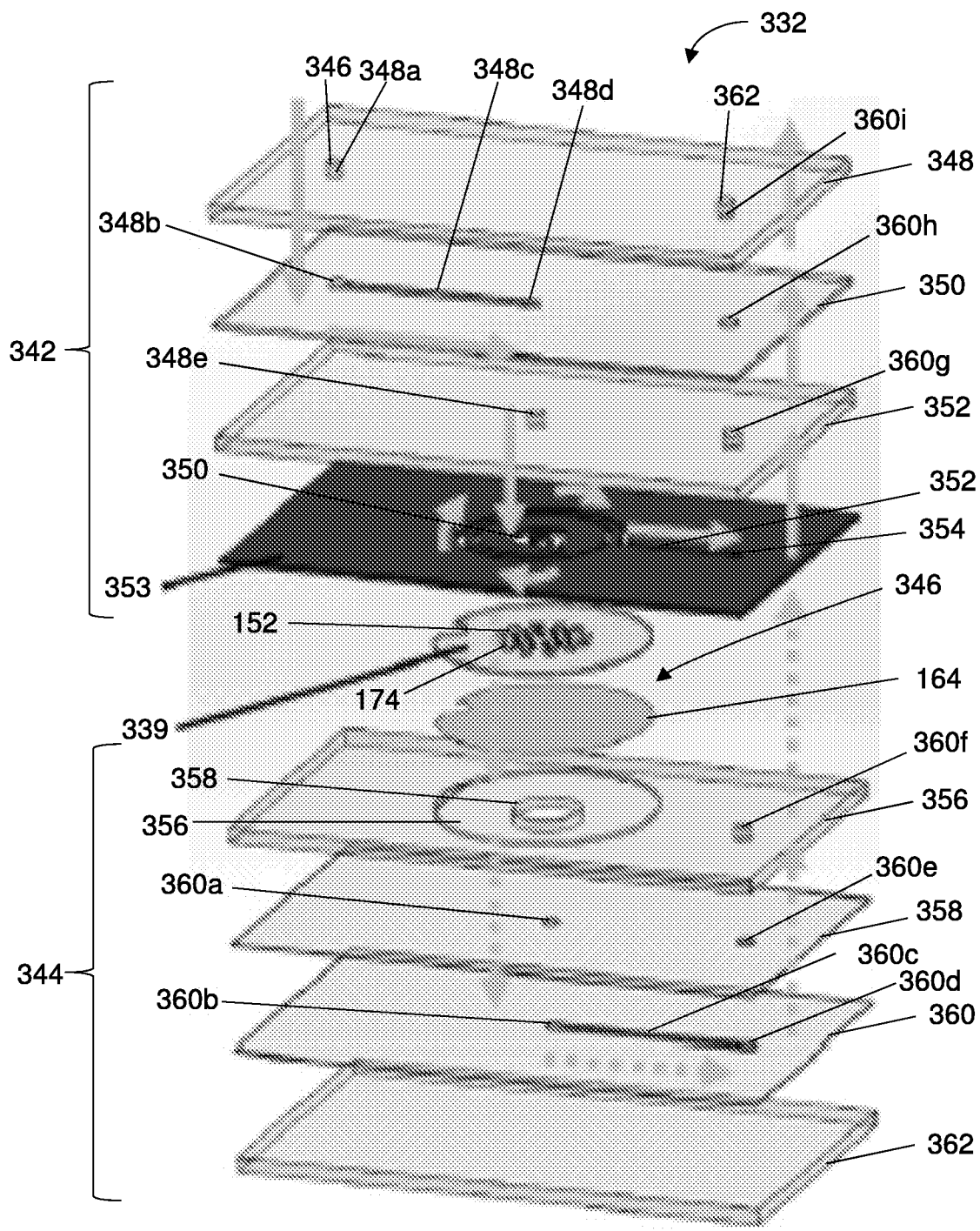
FIGS. 13A-C show diagrammatic, exploded and cross-sectional views of an exemplary system of the present invention for loading a cartridge with one or more biological cells.
Figure 13B:
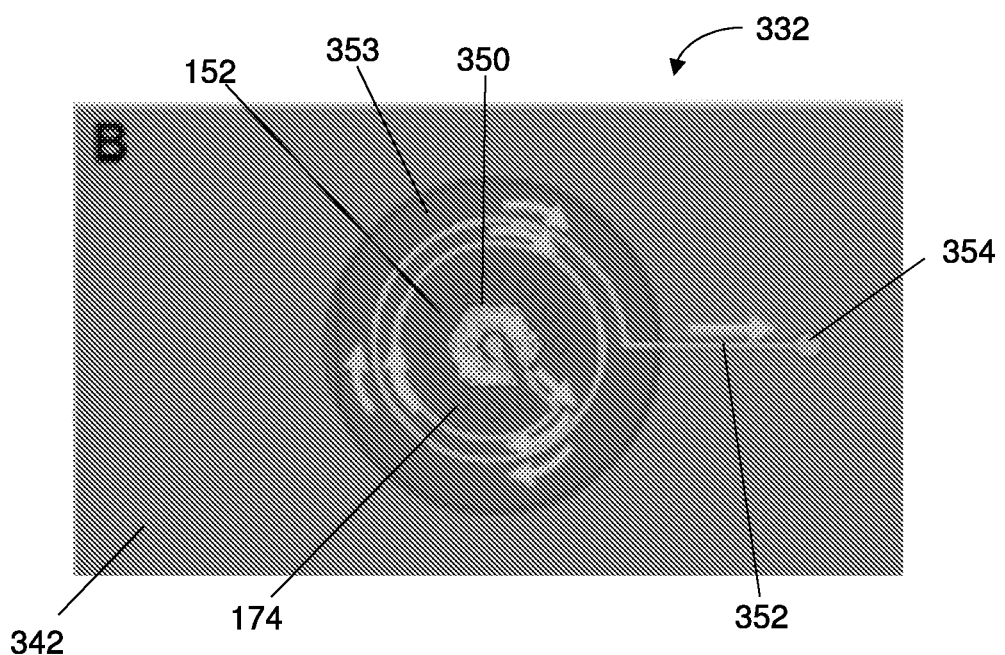
Figure 13C:
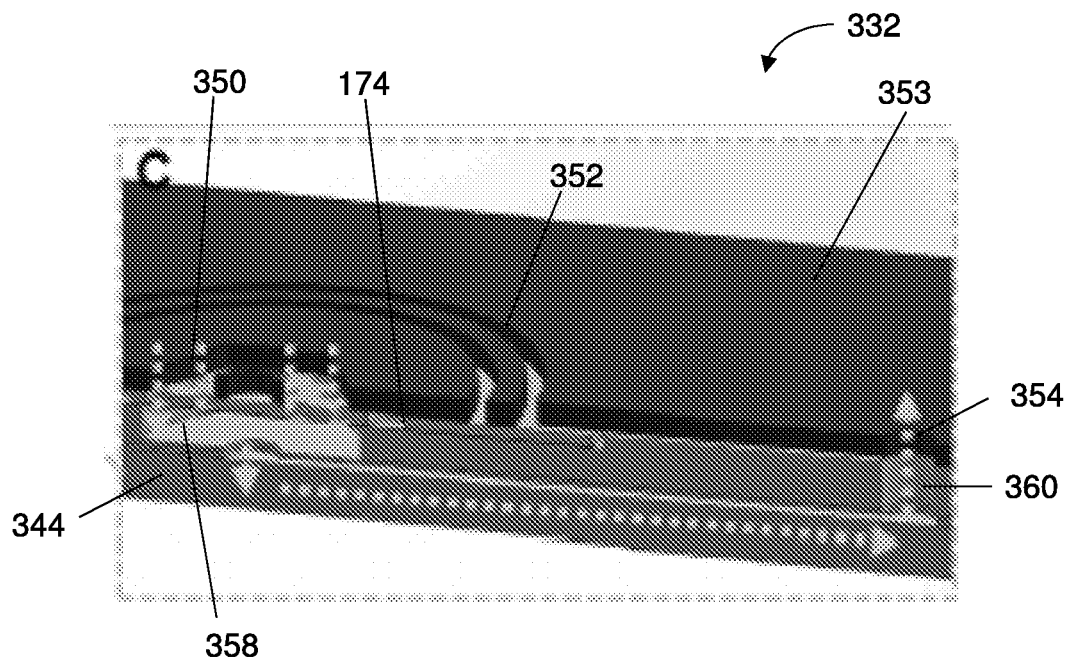

FIGS. 13A-C are diagrammatic, exploded and cross-sectional views of another exemplary fluidic system 332 of the present invention for loading a cartridge 334 with one or more biological cells or cell clusters. The system 332 includes a housing formed by a first housing portion 342 and a second housing portion 344, and a chamber 346 disposed therebetween. In some embodiments, the first housing portion 342 can be formed from a plurality of layers 348-354 bonded together, and the second housing portion 344 can be formed from a plurality of layers 356-362 bonded together. In some embodiments, each of the first and second housing portions 342, 344 can be fabricated by, for example, injection molding such that the first and housing portions 342, 344 define a single, structural component.

The system 332 includes an inlet 364 (e.g., in the first layer 348) for introduction of the medium including one or more biological cells or cell clusters into the system 332. The system 340 includes an inlet channel including apertures 348a, 348b, 348d, 348e and an elongated slot 348c (collectively referred to herein as inlet channel 348) fluidically connected for flow of the medium through the first, second and third layers 348-352. The inlet channel 348 fluidically connects the inlet 364 with the chamber 346. The fourth layer 353 can include a central aperture 350 and an alternate channel 352 fluidically connected to the central aperture 350, circling the central aperture 350 one or more times, extending toward the outlet channel, and connecting with the outlet channel at an aperture 354. Thus, the alternate channel 352 fluidically connects the inlet channel 348 with the outlet channel 360.

The fifth layer 356 includes a central recessed area 356 configured and dimensioned to receive the cartridge 332 and porous element 164. The central recessed area 356 further includes a central aperture 358 for passage of the medium and cells therethrough. The system 340 includes an outlet 362 (e.g., in the first layer 348) for exit of the medium and cells from the system 340. The system 340 includes an outlet channel including apertures 360a, 360b, 360d-i and 354 and an elongated slot 360c (collectively referred to herein as outlet channel 360). The outlet channel 360 fluidically connects the peripheral portion of the chamber 346 with the outlet 362.

The channels 338 and the porous element 164 disposed against the cartridge body 336 form a plurality of wells configured and dimensioned to receive one or more biological cells or cell clusters. With the cartridge 334 disposed between the first and second housing portions 342, 344, the medium with the cells can be introduced through the inlet 364. At least a portion of the medium and cells flows through the inlet channel 348 and into the chamber 346 with some of the cells dropping into and lodging within the wells of the cartridge 334. The layer 353 is positioned against the top surface of the cartridge 334 and blocks flow of the medium through the channels 174, thereby ensuring that the medium flows through the wells of the cartridge 334 or through the alternate channel 352. In one embodiment, the layer 353 can be formed from PDMF to act as a gasket to seal the layer 353 against the channel 174. In one embodiment, the layer 353 can be a removable layer and can be removed from the first housing portion 342 to allow flow through the channels 174. The remaining medium flows around the cells in the wells, through the aperture 358 and into the outlet channel 360 to exit the system 340 via the outlet 362. The solid arrows shown in FIGS. 13A-C indicate the medium with cells flowing through the system 340, while the dashed arrows indicate the medium without cells flowing through the system 340. Thus, once cells are lodged within the wells, the medium without the cells flows downward into the outlet channel 360.

Initially, the flow of the medium through the cartridge 334 and into the outlet channel 360 creates a suction force in the system 340 below the cartridge 334 that urges the medium and cells to travel through the channels 152 in the cartridge 114, thereby ensuring that cells are loaded into the wells. The alternate channel 352 is substantially longer than a flow path through the wells, which results in the alternate channel 352 having a higher flow resistance than flow through the wells when there are no cells or cell clusters in the wells resulting in a faster flow of medium through the wells than through the alternate channel. The faster flow of medium through the wells relative to flow through the alternate channel creates the suction force that aids in loading the cells in the wells. As cells lodge in the wells, the flow resistance through the wells increases due to partial blocking of flow through the wells, which reduces the suction force as a greater proportion of the medium is flowing through the alternate channel and the medium with the cells is urged to flow through a path of least resistance, i.e., the alternate channel 352. In particular, as the medium and cells flow into the opening 350 in the fourth layer 353, the medium and cells enter the alternate channel 352 and into the outlet channel 360, thereby allowing excess medium and cells to exit through the outlet 362.

In some embodiments, the fourth layer 353 can be formed from a malleable (e.g. PDMS) layer that rests above the cartridge 334 to define the alternate flow path for the cell clusters. Initially, negative pressure applied at the outlet 362 drives movement of the cell clusters through the alternate channel 352, and also results in suction from the wells underneath. The spiral pattern in the alternate channel 352 adds resistance to flow due to its length, biasing cell clusters to be drawn into wells of the cartridge 334 as they pass. When a well is filled, the influence of suction diminishes, and cells continue to flow along the alternate channel 352. It should be noted that different methods of loading cells into the cartridge 334 can be used. For example, a simpler form of suction can be implemented to achieve the same outcome, or cartridges with larger wells can be used into which a suspension of clusters is pipetted directly. However, these alternative methods may require more manual manipulation of the cell clusters, or may be limited in their ability to load clusters into individual wells.

In some embodiments, after the cells or cell clusters are disposed in the wells, one more non-woven polymeric fiber sheets may be disposed over the wells may be used to trap the cell clusters in the wells. In some embodiments, the one or more porous element is a non-woven polymer fiber sheet forming the bottom of the wells. In some embodiments the non-woven polymeric fibers sheets over the wells and forming the bottom of the well provide a three-dimensional scaffold for growth of the cells, as described below in below in Section II entitled "Scaffolds for Cell Growth" and depicted in the lower right side detail image of FIG. 15A. In some embodiments, cells are contained in a three-dimensional scaffold that is placed into a well. In some embodiments, the three-dimensional-scaffold scaffold surrounds a solid support with a channel in which the cells are disposed, as described below in below in Section II entitled "Scaffolds for Cell Growth" and depicted in FIG. 19, and the well is configured to hold the three-dimensional scaffold and the solid support.

Figure 14A:
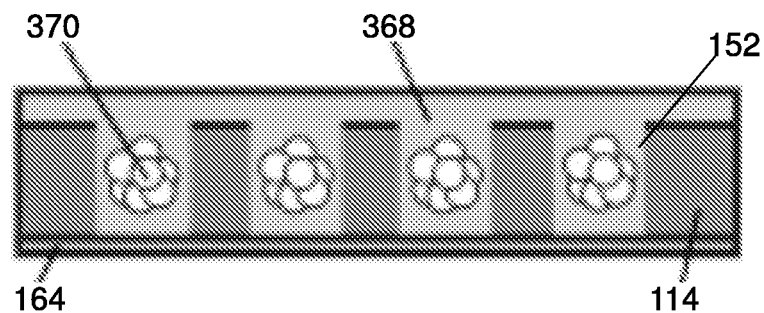
FIG. 14A shows a diagrammatic, cross-sectional view of an exemplary cartridge of the present invention in which cell clusters are loaded into the wells of a cartridge of the invention are seeded within a hydrogel such that the hydrogel captures and surrounds the cell clusters to, e.g., provide adequate nutrient delivery to the cells, relevant environmental cues, and provide additional longevity to the cells in the cluster. After the desired number of cell clusters has been loaded and any excess removed, the surface above the cartridge may be compressed to achieve a thin film of hydrogel above the wells.
Figure 14B:
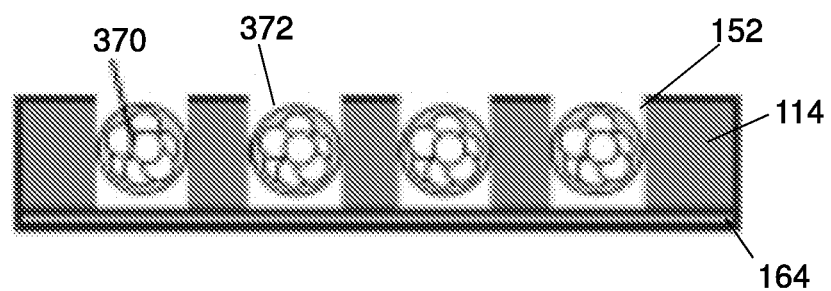
FIG. 14B shows a diagrammatic, cross-sectional view of an exemplary cartridge of the present invention in which each cell cluster is encased within its own conformal hydrogel shell, e.g., by an emulsion droplet process, and the encased cell clusters are loaded into a well of cartridge of the invention to, e.g., provide adequate nutrient delivery to the cells, relevant environmental cues, and provide additional longevity to the cells in the cluster.

In some embodiments, the cartridge-based systems described herein can be used for encasing the cells within a hydrogel material, such that they are fixed in place and also benefit from the additional longevity afforded by the microenvironment of the hydrogel. A hydrogel layer that is thinner is generally more likely to provide adequate nutrient delivery to the cells. Two different methods of hydrogel encapsulation are shown in FIGS. 14A-B. In the first case shown in FIG. 14A, cell clusters 370 are loaded onto the cartridge 114 within a hydrogel mixture 368, such that clusters 370 within the channels 152 (e.g., wells) are also surrounded by the hydrogel mixture 368. After the desired number of cell clusters 370 have been isolated and the excess removed, the surface above the cartridge 114 can be compressed to achieve a thin film above the wells 152. An alternative option is shown in FIG. 14B, and involves encasing each cluster 370 with its own conformal hydrogel shell 372 through the use of, e.g., emulsion droplets. Each microencapsulated cluster 370 can then be loaded into the wells 152 of the cartridge 114 as described above. In some embodiments, wells 152 of larger sizes can be used to load encapsulated clusters 370. The encapsulated clusters depicted in FIG. 14B may enable greater diffusion of nutrients to cells, as compared to the hydrogel-filled wells depicted in FIG. 14A.

Aside from long-term culture, different designs of the system may allow for collection of functional readings from the cells within the housing, by moving the cartridge to a different device, or even through integration of components within the cartridge itself. For instance, protein secretions of the cells may be siphoned off downstream of the cartridge and assayed at a separate site within the housing. Cell clusters within a cartridge can be imaged either directly while resting within the system under culture conditions or after the cartridge has been removed from the housing. In the latter case, the cells can be immuno-stained in situ on the cartridge. Because of the segregation between individual cell clusters, additional information can be obtained by extracting a cluster of interest and running genetic or expression analyses on the cells for that specific cluster. In cases where electrophysiology data is relevant, a cartridge may also be placed onto a microelectrode array where the well pattern is aligned with the location of the electrodes, such that each cluster has its own electrical readout. To facilitate on-chip electrical recordings, one might also consider embedding electrodes within the cartridge itself, such that they are positioned adjacent to the cell clusters as they rest in the wells of the cartridge.

Various methods and materials may be employed for forming the cartridge body, the housing portions and the holder portions. In some embodiments, the cartridge is fabricated from two layers bonded together, including a planar cartridge body material with holes cut into a pattern in or through the cartridge body material bonded to a membrane material layer with pore sizes small enough to exclude individual cells from passing through. In some embodiments, the porous element can be thermally bonded to the second surface of the cartridge. In some embodiments, the cartridge is fabricated from non-woven polymeric fiber material bonded to or adhered to the cartridge body. In some embodiments, the cartridge body is fabricated from a polymeric material (e.g., polycarbonate). In some embodiments, the cartridge body is fabricated by laser cutting. In some embodiments, the channels or wells can be cut into the cartridge body using ultraviolet (UV) laser patterning.

In some embodiments, the housing is fabricated from a polymeric material (e.g., polycarbonate). In some embodiments, layers for forming the housing can be cut out of bulk material using a mill or a laser cutter.

In some embodiments, the porous element is a membrane. In some embodiments, porous element is a non-woven polymeric sheet as described below.

Methods for fabricating cartridges, housings and holder are described in further detail below in Example 1.

While the methods described in the Examples section enabled the fabrication of cartridges, housings and holders for testing, the possible fabrication methods are not limited to what has been described above. Other plastics amenable to laser cutting, milling, and bonding (either thermally or with solvent), are also feasible alternatives. In line with another common medium for microfluidics, one may also consider making some or all of the components out of PDMS. Furthermore, the components can be 3D printed, hot embossed, injection molded, or fabricated in a number of other approaches. The methods outlined here merely represent some examples of how to fabricate cartridges, housings and holder.

In some embodiments, the holder is fabricated at least in part from a polymer material. In some embodiments, the holder is fabricated, at least in part, using 3D printing. In some embodiments, the holder is fabricated, at least in part, using a molding technique, such as injection molding.

Additional functional features may be incorporated into or used with the system. The system 100 can be augmented by adding additional inputs for the cells. For instance, two or more solutions driven by separate pumps can be connected to the system 100. These inlets could intersect at a T-junction, and the relative flow rates would dictate the concentration of a stimulus that is delivered to the cells downstream. A programmed system for quickly changing flow conditions can be used to generate timed pulses of stimuli.

II. Scaffolds for Cell Growth

As noted above, some embodiments of systems and cartridges include three-dimensional scaffolds for cellular growth. In some embodiments, a porous element that forms a bottom surface of each well in a cartridge is a non-woven polymeric fiber sheet and a non-woven polymeric fiber sheet (e.g., another portion of the same sheet or a different sheet) covers the top of the wells after cells are loaded into the cartridge. As described below, the non-woven polymeric fiber sheet on the top and the bottom of the cartridge body can form a three-dimensional scaffold for cell growth. In other embodiments, the non-woven polymeric fiber sheet may be used only on the top of the wells or only on the bottom of the wells. In some embodiments, the three-dimensional scaffolds described herein mimic the in vivo structure, physical properties, and protein composition of extracellular matrix surrounding cells (e.g., pancreatic islet cells and adipocytes). In some embodiments, a well of a cartridge may be dimensioned and configured to receive a cell or cell cluster that is enclosed in or encapsulated by polymeric fibers that form a three-dimensional scaffold. In some embodiments, the cell or cell cluster is disposed in a channel of a solid support with one or more non-woven polymeric fiber sheets covering the ends of the channel of the solid support forming a three-dimensional scaffold. In some embodiments, a well of a cartridge body may be configured and dimensioned to receive the solid support and non-woven polymeric sheet holding the cell cluster. The exemplary three-dimensional scaffolds can be positioned on surfaces of the cartridge body discussed above (e.g., cartridge 114 of FIGS. 1-3) for receiving and retaining one or more cells or one or more cell clusters, and maintaining the cells or cell clusters over or within the channels of the cartridge.

In some embodiments, a three-dimensional scaffold is suitable for use in devices other than the systems and cartridges described above and such compositions are suitable for use in, e.g., in vitro drug screening and/or toxicity assays, disease modeling, and therapeutic applications, and the like. In particular, the present invention provides three-dimensional non-woven polymeric scaffolds that, e.g., can be used to suspend cells or cell clusters, e.g., pancreatic islet cells or adipocytes, off of the bottom of a culture dish that has a relatively high stiffness and that does not mimic in vivo conditions in other ways as well.

Accordingly, in some aspects, the present invention provides three-dimensional scaffolds for culturing cells or cell cluster, e.g., pancreatic islet cells or adipocytes. The three-dimensional scaffolds include a first portion of a first non-woven polymeric fiber sheet; a second portion of a second non-woven polymeric fiber sheet overlaying the first portion, wherein the first non-woven polymeric fiber sheet and the second non-woven polymeric fiber sheet include polymeric fibers comprising a biogenic polymer and a synthetic polymer; and cells or cell cluster, e.g., pancreatic islet cells or adipocytes, disposed between the first portion and the second portion.

In one aspect, the present invention provides devices including a three-dimensional scaffold for culturing cells or cell clusters, e.g., pancreatic islet cells or adipocytes. The three-dimensional scaffold includes a first portion of a first non-woven polymeric fiber sheet, and a second portion of a second non-woven polymeric fiber sheet overlaying the first portion. The first non-woven polymeric fiber sheet and the second non-woven polymeric fiber sheet include polymeric fibers including a biogenic polymer and a synthetic polymer. The device includes cells or cell clusters, e.g., pancreatic islet cells or adipocytes, disposed between the first portion and the second portion. The device includes a base layer.

In another aspect, the present invention provides three-dimensional scaffold for culturing cells or cell clusters, e.g., pancreatic islet cells or adipocytes. The three-dimensional scaffold includes a first portion of a first non-woven polymeric fiber sheet, and a second portion of a second non-woven polymeric fiber sheet overlaying the first portion. The first non-woven polymeric fiber sheet and the second non-woven polymeric fiber sheet can include polymeric fibers including a biogenic polymer and a synthetic polymer. The three-dimensional scaffold includes cells or cells clusters disposed between the first portion and the second portion. In some embodiments, the scaffold includes a solid support including a top surface, a bottom surface, and a channel extending from the top surface to the bottom surface. The first portion of the first non-woven polymeric fiber sheet can be disposed on the bottom surface of the solid support. The second portion of the second non-woven polymeric body can be disposed on the top surface of the solid support. The cells or cell cluster, e.g., pancreatic islet cells or adipocytes, can be disposed in the channel of the solid support.

In one aspect, the present invention provides three-dimensional scaffolds for culturing cells or cell clusters, including pancreatic islet cells and their precursor cell types, or adipocytes e.g., white, brown, or "beige"/"brite" adipocytes, and their precursor cell types. The three-dimensional scaffold includes a first portion of a first non-woven polymeric fiber sheet, and a second portion of a second non-woven polymeric fiber sheet overlaying the first portion. The first non-woven polymeric fiber sheet and the second non-woven polymeric fiber sheet include polymeric fibers including a biogenic polymer and a synthetic polymer. Cells can be disposed between the first portion and the second portion of the polymeric fiber sheets. The cells with the three-dimensional scaffold can further be disposed within the wells of the cartridges described herein.

In some embodiments, the first non-woven polymeric fiber sheet and the second non-woven polymeric fiber sheet can be the same non-woven polymeric fiber sheet and the first portion and the second portion are different portions of the same non-woven polymeric fiber sheet. In some embodiments, the first non-woven polymeric fiber sheet and the second non-woven polymeric fiber sheet can be different non-woven polymeric fiber sheets.

As used herein, the term "three-dimensional scaffold" includes a porous, three-dimensional network, or mesh, of a plurality of polymeric fibers of any orientation including random orientation which are capable of supporting cells therein. The three-dimensional network or mesh of a plurality of randomly orientated polymeric fibers can be in the form of non-woven polymeric fiber sheets which are held together by fiber-to-fiber interactions and have a desired size and shape, e.g., a desired size and shape suitable for the use thereof. The term "sheet" as used herein refers to a structure having a third dimension substantially less than that of the other two dimensions.

The terms "fiber" and "polymeric fiber" are used herein interchangeably, and both terms refer to fibers having micron, submicron, and nanometer dimensions. The polymeric fibers for use in the scaffolds and devices of the present invention are "chemically and physically stable polymeric fibers", e.g., they show substantially no signs of loss of strength measured by uniaxial tensile testing, and/or degradation rate in culture with media or cells measured by weight of the fibers over time.

The weight ratio of the synthetic polymer to the biogenic for use in the claimed scaffolds can be tuned to mimic the native stiffness of, e.g., pancreatic islet cells or adipocytes and in some embodiments, can be between about 10:90 and about 50:50, e.g., about 10:90, 15:85, about 20:80, about 25:75, about 30:70, about 35:65, about 40:60, about 45:55, or about 50:50. Ranges and values intermediate to the above recited ranges and values are also contemplated to be part of the invention.

Suitable synthetic polymers include, for example, poly (urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly (methacrylic acid), polylactides (PLA), polyglycolides (PGA), poly(lactide-co-glycolides) (PLGA), polyanhydrides, polyphosphazenes, polygermanes, polyorthoesters, polyesters, polyamides, polyolefins, polycarbonates, polyaramides, polyimides, polycaprolactone (PCL), and copolymers and derivatives thereof, and combinations thereof.

In one embodiment, the synthetic polymer can include a polymer selected from the group consisting of polycaprolactone (PCL), polyethylene glycol (PEG) and polylactide (PLA), and a combination thereof.

Suitable biogenic polymers (or bio-derived polymers), e.g., proteins, polysaccharides, lipids, nucleic acids or combinations thereof, include, but are not limited to, silk (e.g., fibroin, sericin, etc.), keratins (e.g., alpha-keratin which is the main protein component of hair, horns and nails, beta-keratin which is the main protein component of scales and claws, etc.), elastins (e.g., tropoelastin, etc.), fibrillin (e.g., fibrillin-1 which is the main component of microfibrils, fibrillin-2 which is a component in elastogenesis, fibrillin-3 which is found in the brain, fibrillin-4 which is a component in elastogenesis, etc.), fibrinogen/fibrins/thrombin (e.g., fibrinogen which is converted to fibrin by thrombin during wound healing), fibronectin, laminin, collagens (e.g., collagen I which is found in skin, tendons and bones, collagen II which is found in cartilage, collagen III which is found in connective tissue, collagen IV which is found in vascular basement membrane, collagen V which is found in hair, etc.), collagen VI which is found in pancreatic islets and adipose, vimentin, neurofilaments (e.g., light chain neurofilaments NF-L, medium chain neurofilaments NF-M, heavy chain neurofilaments NF-H, etc.), amyloids (e.g., alpha-amyloid, beta-amyloid, etc.), actin, myosins (e.g., myosin I-XVII, etc.), titin which is the largest known protein (also known as connectin), gelatin, chitin which is a major component of arthropod exoskeletons, hyaluronic acid which is found in extracellular space and cartilage (e.g., D-glucuronic acid which is a component of hyaluronic acid, D-N-acetyl-glucosamine which is a component of hyaluronic acid, etc.), etc., and combinations thereof. Exemplary biogenic polymers, e.g., glycosaminoglycans (GAGs) (carbohydrate polymers found in the body), for use in the present invention include, but are not limited to, heparan sulfate founding extracellular matrix, chondroitin sulfate which contributes to tendon and ligament strength, keratin sulfate which is found in extracellular matrix, etc.

In one embodiment, the biogenic polymer can be selected from the group consisting of poly-4-hydroxybuyrate, a collagen and a gelatin, and a combination thereof.

The polymeric fibers or non-woven polymeric fiber sheets for use in the present invention can further include at least one extracellular matrix (ECM) protein, e.g., in order to mimic the in vivo microenvironment of the cells. In some embodiment, the polymeric fibers or non-woven polymeric fiber sheets of thee three-dimensional scaffolds of the invention include a plurality of extracellular matrix (ECM) proteins, e.g., two or more, three or more, four or more, five or more, or six or more ECM proteins. The ECM protein can be integral to the fibers (e.g., included in a polymer solution used to prepare the non-woven polymeric sheets (described below) or the ECM protein may be coated on the fibers or coated on the non-woven polymeric fiber sheet.

In some embodiments, the polymeric fibers or non-woven polymeric fiber sheet can include a plurality of ECM proteins. For example, the polymeric fibers or non-woven polymeric fiber sheet may include at least 2, at least 3, at least 4, at least 5, at least 6, at least 7, at least 8, at least 9, at least 10, at least 11, at least 12, at least 13, at least 14, at least 15, at least 20, at least 25, or greater number of the proteins (or fragments thereof) listed in Table 1 below. In related embodiments, the devices can include all the proteins (or fragments thereof) listed in Table 1.

Suitable ECM proteins, e.g., for culturing pancreatic islet cells, can include, e.g., ECM proteins present in a native islet capsule, e.g., a collagen, a laminin, and a fibronectin, or a fragment thereof, and a combination thereof. In one embodiment, the at least one ECM protein is encoded by a gene selected from the group consisting of genes COL6A3, COL6A1, SPP1, COL6A2, LAMC2, COL1A2, FNDC3A, BGN, COL1A1, LAMB1, LAMC1, COL18A1, SPARC, LAMB3, FN1, TNC, FNDC3B, COL3A1, EMILIN1, COL6A6, AGRN, LAMA4, COL28A1, LAMA3, LAMA5, LAMC3, FBN1, LAMB2, COL5A1, or a fragment thereof, and a combination thereof.

TABLE 1

Abbreviated and complete names of ECM proteins, including, NCBI accession numbers of the associated mRNA and protein sequences of human and in mouse orthologs

| Genes | Full name | Human protein | Human mRNA | Mouse protein | Mouse mRNA |
| --- | --- | --- | --- | --- | --- |
| COL6A3 | Collagen, type VI, alpha 3 | NP_004360 | NM_004369 | NP_001229937 | NM_001243008 |
| COL6A1 | Collagen, type VI alpha 1 | NP_001839 | NM_001848 | NP_034063 | NM_009933 |
| SPP1 | Secreted Phosphoprotein 1 | NP_000573 | NM_000582 | NP_001191130 | NM_001204201 |
| COL6A2 | Collagen type VI alpha 2 | NP_001840 | NM_001849 | NP_666119 | NM_146007 |
| LAMC2 | Laminin, gamma 2 | NP_005553 | NM_005562 | NP_032511 | NM_008485 |
| COL1A2 | Collagen, type I alpha 2 | NP_000080 | NM_000089 | NP_031769 | NM_007743 |
| FNDC3A | Fibronectin-III domain-containing protein 3a | NP_001073141 | NM_001079673 | NP_997519 | NM_207636 |
| BGN | Biglycan | NP_001702 | NM_001711 | NP_031568 | NM_007542 |
| COL1A1 | Collagen, type I, alpha 1 | NP_000079 | NM_000088 | NP_031768 | NM_007742 |
| LAMB1 | Laminin subunit beta-1 | NP_002282 | NM_002291 | NP_032508 | NM_008482 |
| LAMC1 | Laminin subunit gamma-1 | NP_002284 | NM_002293 | NP_034813 | NM_010683 |
| COL18A1 | Collagen, type XVIII, alpha 1 | NP_085059 | NM_030582 | NP_001103461 | NM_001109991 |
| SPARC | Secreted protein acidic and rich in cysteine | NP_001296372 | NM_001309443 | NP_001277746 | NM_001290817 |
| LAMB3 | Laminin subunit beta-3 | NP_000219 | NM_000228 | NP_001264857 | NM_001277928 |
| FN1 | Fibronectin 1 | NP_001293058 | NM_001306129 | NP_001263337 | NM_001276408 |
| TNC | Tenascin C | NP_002151 | NM_002160 | NP_035737 | NM_011607 |
| FNDC3B | Fibronectin type III domain containing 3B | NP_073600 | NM_022763 | NP_775274 | NM_173182 |
| COL3A1 | Collagen, type III, alpha 1 | NP_000081 | NM_000090 | NP_034060 | NM_009930 |
| EMILIN1 | Elastin microfibril interfacer 1 | NP_008977 | NM_007046 | NP_598679 | NM_133918 |
| COL6A6 | Collagen, type VI, alpha 6 | NP_001096078 | NM_001102608 | NP_766515 | NM_172927 |
| AGRN | Agrin | NP_001292204 | NM_001305275 | NP_067617 | NM_021604 |
| LAMA4 | Laminin subunit alpha-4 | NP_001098676 | NM_001105206 | NP_034811 | NM_010681 |
| COL28A1 | Collagen, type XXVIII, alpha 1 | NP_001032852 | NM_001037763 | NP_001032954 | NM_001037865 |
| LAMA3 | Laminin subunit alpha-3 | NP_000218 | NM_000227 | NP_034810 | NM_010680 |
| LAMA5 | Laminin subunit alpha-5 | NP_005551 | NM_005560 | NP_001074640 | NM_001081171 |
| LAMC3 | Laminin subunit gamma-3 | NP_006050 | NM_006059 | NP_035966 | NM_011836 |
| FBN1 | Fibrillin-1 | NP_000129 | NM_000138 | NP_032019 | NM_007993 |
| LAMB2 | Laminin subunit beta-2 | NP_002283 | NM_002292 | NP_032509 | NM_008483 |

Representative examples of fragments of ECM proteins include, but are not limited to, Ser-Ile-Lys-Val-Ala-Val (SIKVAV) sequence in the laminin α1 chain as well as corresponding sequence Ala-Ser-Lys-Val-Lys-Val (ASKVKV) in the laminin α5 chain. (see, e.g., Adair-Kirk et al., The International Journal of Biochemistry & Cell Biology, 40(6-7), 2008).

Without listing all of the possible permutations and combinations, purely as representative embodiments, the fibers or sheets can include a composition of ECM proteins selected from: (1) a composition containing COL6A3 and COL6A1; (2) a composition containing COL6A3, COL6A1 and SPP1; (3) a composition containing COL6A3, COL6A1, SPP1 and COL6A2; (4) a composition containing COL6A3, COL6A1, SPP1, COL6A2 and LAMC2; (5) a composition containing COL6A3, COL6A1, SPP1, COL6A2, LAMC2 and COL1A2, or the like.

In one embodiment, the ECM proteins of Table 1 are differentially distributed in or on the polymeric fibers or sheets, e.g., in order to mimic the distribution of an in vivo pancreatic islet capsule. Under this embodiment, the differential distribution includes differential abundance of the ECM proteins, wherein the relative abundance is COL6A3≥COL6A1≥SPP1≥COL6A2≥LAMC2≥COL1A2≥ FNDC3A≥BGN≥COL1A1≥LAMB1≥LAMC1≥COL18A1≥ SPARC≥LAMB3≥FN1≥TNC≥FNDC3B≥COL3A1≥ EMILIN1≥COL6A6≥AGRN≥LAMA4≥COL28A1≥ LAMA3≥LAMA5≥LAMC3≥FBN1≥LAMB2. Under this embodiment, it may be preferable to employ ECM compositions comprising highly abundant proteins, e.g., a collagen and a laminin, e.g., COL6A3 and LAMC2.

In some embodiments, the sheets, fibers, and/or three-dimensional scaffolds can be supplemented with various additional agents and/or biological molecules, which can be coated onto, or which can be integral to the sheets, fibers and/or three-dimensional scaffolds. In one embodiment, the biological molecule can be a protein, a polypeptide, a lipid, a carbohydrate, a proteoglycan, a polynucleotide, an amino acid, a sugar, a nucleic acid, or a combination thereof.

The elastic modulus of the three-dimensional scaffold (i.e., the scaffold in tissue culture media) can be tuned to mimic the native stiffness of cells, e.g., pancreatic islet cells or adipocytes, and may be between about 0.1 kiloPascal (kPa) and about 25.0 kPa; between about 0.1 kPa and about 20 kPa; between about 0.1 kPa and about 15 kPa; between about 0.1 kPa and about 10 kPa; between about 0.1 kPa and about 5 kPa; between about 1.0 kPa and about 25.0 kPa; between about 1.0 kPa and about 20 kPa; between about 1.0 kPa and about 15 kPa; between about 1.0 kPa and about 10 kPa; between about 1.0 k Pa and about 5 kPa, e.g., about 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, or about 25.0 kPa. Ranges and values intermediate to the above recited ranges and values are also contemplated to be part of the invention.

A polymeric fiber forming the non-woven polymeric sheet can be a single, continuous polymeric fiber or a plurality of polymeric fibers of the same or different diameters, e.g., diameters of about 500 nanometers to about 100 micrometers, about 100 nanometers to about 1 micrometer, about 50 nanometers to about 500 nanometers, about 50 nanometers to about 300 nanometers, about 50 nanometers to about 200 nanometers, or about e.g., 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 33, 340, 350, 360, 370, 380, 390, 400, 410, 420, 430, 440, 450, 460, 470, 480, 490, or about 500. Sizes and ranges intermediate to the recited diameters are also part of the invention.

In one embodiment, the diameter of the polymeric fibers forming the non-woven polymeric sheet can be substantially uniform. The diameter of the substantially uniform polymeric fibers forming the non-woven polymeric sheet can be between about 50 nm and about 500 nm; about 50 nm and about 450 nm; about 50 nm and about 400 nm; about 50 nm and about 350 nm; about 50 nm and about 300 nm; about 50 nm and about 250 nm; about 50 nm and about 200 nm; or about 50 nm and about 150 nm; or about e.g., 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 33, 340, 350, 360, 370, 380, 390, 400, 410, 420, 430, 440, 450, 460, 470, 480, 490, or about 500. Diameters and ranges intermediate to the recited diameters are also part of the invention.

The polymeric fibers can be of any length. In one embodiment, the length of the polymeric fibers can be dependent on the length of time the device used to generate the fibers is in motion and/or the amount of polymer fed into the system. For example, the polymeric fibers can be about 1 nanometer, about 10 feet, or about 500 yards. Additionally, the polymeric fibers can be cut to a desired length using any suitable instrument.

The thickness of the non-woven polymeric fiber sheet can be between about 75 nm and about 5 μm; between about 75 nm and about 1 μm; between about 70 nm and about 5 μm; between about 70 nm and about 1 μm; between about 65 nm and about 5 μm; between about 65 nm and about 1 μm; between about 60 nm and about 5 μm; between about 60 nm and about 1 μm; between about 55 nm and about 5 μm; between about 55 nm and about 1 μm; between about 50 nm and about 5 μm; between about 50 nm and about 1 μm; between about 45 nm and about 5 μm; between about 45 nm and about 1 μm; between about 40 nm and about 5 μm; between about 40 nm and about 1 μm; between about 35 nm and about 5 μm; between about 35 nm and about 1 μm; between about 30 nm and about 5 μm; between about 30 nm and about 1 μm; between about 25 nm and about 5 μm; between about 25 nm and about 1 μm; between about 20 nm and about 5 μm; between about 20 nm and about 1 μm, e.g., about 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 33, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 900, 910, 920, 930, 940, 950, 960, 970, 980, 990, or about 1000 nm, or about 0.5, 1, 1.5, 2, 2.5, 3, 3.5, 4, 4.5, or about 5 microns thick.

The non-woven polymeric fiber sheets of the invention can have a variety of dimensions. In an exemplary embodiment, the non-woven polymeric fiber sheet can be 0.1 mm to 50 cm long. In another exemplary embodiment, the non-woven polymeric fiber sheet can be 0.1 mm to 1 mm long. In another exemplary embodiment, the non-woven polymeric fiber sheet can be 1 mm to 1 cm long. In another exemplary embodiment, the non-woven polymeric fiber sheet can be 1 cm to 10 cm long. In another exemplary embodiment, the non-woven polymeric fiber sheet can be 10 cm to 50 cm long. In another exemplary embodiment, the non-woven polymeric fiber sheet can be 1 cm to 5 cm long. In another exemplary embodiment, the non-woven polymeric fiber sheet can be 2.5 cm to 15 cm long. In another exemplary embodiment, the non-woven polymeric fiber sheet can be 5 mm to 6 cm long. In another exemplary embodiment, the non-woven polymeric fiber sheet can be 8 mm to 3 cm long. In another exemplary embodiment, the non-woven polymeric fiber sheet can be 10 cm to 25 cm long. In another exemplary embodiment, the non-woven polymeric fiber sheet can be 0.5 cm to 2 cm long. In another exemplary embodiment, the non-woven polymeric fiber sheet can be 0.1 cm to 2 cm long.

Any suitable method can be used to prepare the non-woven polymeric fiber sheets. For example, a method for generating the non-woven polymeric fiber sheet can include configuring micron, submicron or nanometer dimension polymeric fibers in a desired shape using a collection device, such as a glass coverslip, a multi-well plate, a mandrel or a mandrel assembly.

In one embodiment, non-woven polymeric fiber sheets can be formed by ejecting a polymer solution from a reservoir onto a multi-well plate. In another embodiment, non-woven polymeric fiber sheets can be formed by ejecting a polymer solution from a reservoir onto a rotating mandrel or mandrel assembly. In exemplary embodiments, rotary jet spinning (RJS) can be used to create the non-woven polymeric fiber sheets. Suitable RJS devices and uses of the devices for fabricating the non-woven polymeric fiber sheets are described in U.S. Patent Publication No. 2012/0135448, U.S. Patent Publication No. 2013/0312638, U.S. Patent Publication No. 2014/0322515, the entire contents of each of which are incorporated in their entirety by reference.

Figure 17:
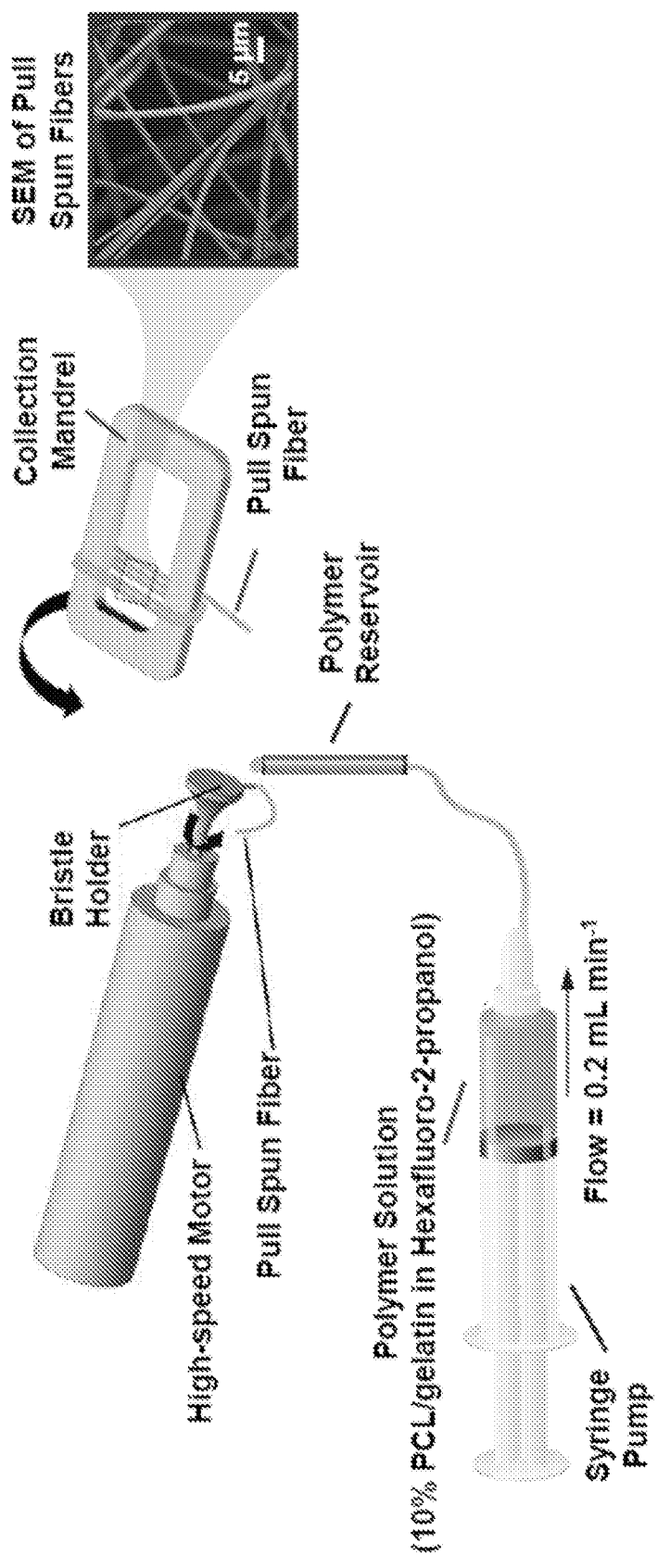
FIG. 17 schematically depicts an exemplary pull spinning device, exemplary rotating collection mandrel, and exemplary method for fabrication of the non-woven polymeric fibers sheets for use in the scaffolds and devices of the invention.

In other exemplary embodiments, the polymeric fibers can be flung using a pull spinning technique onto a collection device, such as a glass coverslip, a multi-well plate, a mandrel or a mandrel assembly. In one embodiment, non-woven polymeric fiber sheets can be formed by flinging a polymer solution from a reservoir onto a multi-well plate. In another embodiment, non-woven polymeric fiber sheets can be formed by flinging a polymer solution from a reservoir onto a rotating mandrel or mandrel assembly. Suitable pull spinning devices and uses of the devices for fabricating the non-woven polymeric fiber sheets are described in U.S. Patent Publication No. 2014/0322515, the entire contents of which are incorporated in its entirety by reference, and an exemplary device and method of preparing the sheets are depicted in FIG. 17.

In some embodiment, e.g., when a rotating mandrel collection device is used to prepare the non-woven polymeric fiber sheet in a tubular structure, the resulting tubular structure can be cut to form into a sheet using any suitable instrument, e.g., scalpel, scissors, or the like.

The three-dimensional scaffold can be shaped into any number of desirable configurations to satisfy any number of overall system, geometry or space restrictions, e.g., a well of a multi-well tissue culture dish, a chamber of a microfluidics device, a well of a cartridge, or a covering or coverings for at least portions of top and bottom surfaces of a well body, as described above.

Seeding of cells can be performed according to standard methods. Any number of cells can be seeded into the three-dimensional scaffolds. In one embodiment, in the range of 1 million to 50 million cells can be suspended in medium and applied to each square centimeter of a surface of a three-dimensional scaffold. Preferably, between 1 million and 50 million cells, and more preferably, between 1 million and 10 million cells can be suspended in media and applied to each square centimeter of a surface of a three-dimensional scaffold. The three-dimensional scaffold and cells can be incubated under standard culturing conditions, such as, for example, 37° C., 5% $CO_2$, for a suitable period of time.

Although it should be understood that any cell type can be used in the systems and methods of the invention, non-limiting examples of suitable cells or cell clusters for use in the present invention include, for example, cardiac muscle cells, ventricular cardiac muscle cells, atrial cardiac muscle cells, striated muscle cells, smooth muscle cells, vascular smooth muscle cells, pancreatic islet cells, adipocytes, salivary gland cells, myoepithelial cells spheroids, and tumor spheroid cells, and combinations thereof.

Suitable cells for use in the invention can be normal cells, abnormal cells (e.g., those derived from a diseased tissue, or those that are physically or genetically altered to achieve an abnormal or pathological phenotype or function), normal or diseased pancreatic islet cells, normal or diseases adipocytes, stem cells (e.g., embryonic stem cells), or induced pluripotent stem cells.

Cells for seeding can be cultured in vitro, derived from a natural source, genetically engineered, or produced by any other means. Any natural source of eukaryotic cells can be used. Embodiments in which a scaffold is implanted in an organism can use cells from the recipient, cells from a conspecific donor or a donor from a different species.

The term "progenitor cell" is used herein to refer to cells that have a cellular phenotype that is more primitive (e.g., is at an earlier step along a developmental pathway or progression than is a fully differentiated cell) relative to a cell to which it can give rise by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "progenitor cell" is used herein synonymously with "stem cell."

The term "stem cell" as used herein, refers to an undifferentiated cell that is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation".

The term "embryonic stem cell" is used to refer to the pluripotent stem cells of the inner cell mass of the embryonic blastocyst (see, e.g., U.S. Pat. Nos. 5,843,780, 6,200,806, the entire contents of which are incorporated herein by reference). Such cells can similarly be obtained from the inner cell mass of blastocysts derived from somatic cell nuclear transfer (see, e.g., U.S. Pat. Nos. 5,945,577, 5,994, 619, 6,235,970, the entire contents of which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells.

As used herein, the term "pancreatic islet cell" includes pancreatic islet cells derived from an adult organism or an embryonic organism, pancreatic islet cell precursor cell types or stem cells that will develop into pancreatic islet cells. Similarly, the term "adipocyte" includes adipocytes e.g., white, brown, or "beige"/"brite" adipocytes derived from an adult organism or an embryonic organism, adipocyte precursor cell types or stem cells that will develop into adipocytes.

Exemplary cells that can be used include stem cells, pancreatic acinar cells, islets of Langerhans, adipocytes, preadipocytes, biliary epithelial cells, and the like. In some embodiments, the cells can be adult stem cells, such as, in some embodiments, adipose-derived stem cells, pancreatic stem cells, and the like. In some particular embodiments, the adult stem cells can be adipose-derived stem cells which may differentiate to pancreatic progenitor cells.

In one embodiment, the cells can be pancreatic beta-cells. Suitable pancreatic beta-cells can be, for example, from species such as mouse, rat, human, guinea pig, hamster, pig, dog, sheep, goat, donkey or cow, and are used either in the form of islets of Langerhans or isolated cells. The cell line can be, for example, selected from the rat insulinoma (RIN) cell lines such as INS-1 (see, e.g., Asfari et al. *Endocrinol.*, 130, 167 (1992)), INS-2 (see, e.g., Asfari et al., *Endocrinol.*, 130, 167 (1992)), RIN-r (see, e.g., Philippe et al., *Endocri-* *nol.* 119, 2833 (1986)), and RIN-m (see, e.g., Bathena et al., *Diabetes* 31, 521 (1982); Praz et al., *Biochem. J.* 210, 345 (1983); Philippe et al. *J. Clin. Invest.* 79, 351(1987)) or from the hamster insulinoma (HIT) cell lines such as HIT-T15 (see, e.g., Santerre et al., *Proc. Natl. Acad. Sci. U.S.A.* 78, 4339 (1981)) or from mouse beta-cell lines expressing the SV40 large T-antigen (beta-TC lines) such as betaTC1, betaTC2, betaTC3 (see, e.g., Efrat et al., *Proc. Natl. Acad. Sci. U.S.A.* 85, 9037(1988)), betaTC6 (see, e.g., Poitout et al., *Diabetes* 44, 306 (1995)), betaTC7 (see, e.g., Efrat et al., *Diabetes* 42, 901(1993)), betaTCtet (see, e.g., Efrat et al., *Proc. Natl. Acad. Sci. U.S.A.* 92, 3576 (1995)) or from mouse insulinoma (MIN) cell lines such as MIN6 (see, e.g., Myazaki et al., *Endocrinol.* 127, 126(1990)).

Suitable adipocytes include, isolated adipose tissue (such as brown adipose tissue or white adipose tissue), isolated cells (such as primary adipocytes or adipocyte cell lines), or a combination thereof. In some embodiments, an adipose cell-line can be employed. Exemplary cells include, but are not limited to, 3T3-L1 cells, PAZ6 cells, T37i cells, 3T3-F442A cells, and/or HIB-1B cells. Any of a variety of isolated cells (such as cell lines) can be used.

The aforementioned cells/cell-lines can be optionally transformed to express a variety of growth factors and/or agents. The reagents and markers useful for such purposes are known in the art (see, e.g., U.S. Pat. No. 8,389,207, the contents of which are incorporated by reference herein).

In one embodiment, the instant invention provides for compositions, devices, and systems comprising the non-woven polymeric fiber three-dimensional scaffolds and the cells, wherein the cells maintain their viability and functionality for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 18 days, at least 20 days, at least 22 days, at least 24 days, at least 26 days, at least 28 days, at least 30 days or more.

In one embodiment, the present invention provides devices comprising the aforementioned three-dimensional scaffolds and a base layer. A base layer can be formed of a rigid or semi-rigid material, such as a metal, ceramic, or a combination thereof. In particular embodiments, the Young's modulus of the base material used to form the base layer is greater than 1 mega-pascal (MPa). The base layer material can also be transparent, so as to facilitate observation. Examples of suitable base layer material include polymethylmethacrylate, polystyrene, polycarbonate, polyethylene terephthalate film, silicon wafer, or gold. In one embodiment, the base layer is a silicon wafer, a glass cover slip, a multi-well plate, tissue culture plate, or a chamber of a microfluidic device. The exemplary three-dimensional scaffolds can be positioned on the cartridges discussed above (e.g., cartridge 114 of FIGS. 1-3) for receiving and retaining one or more cells, and maintaining the cells over or within the channels of the cartridge.

Figure 19:
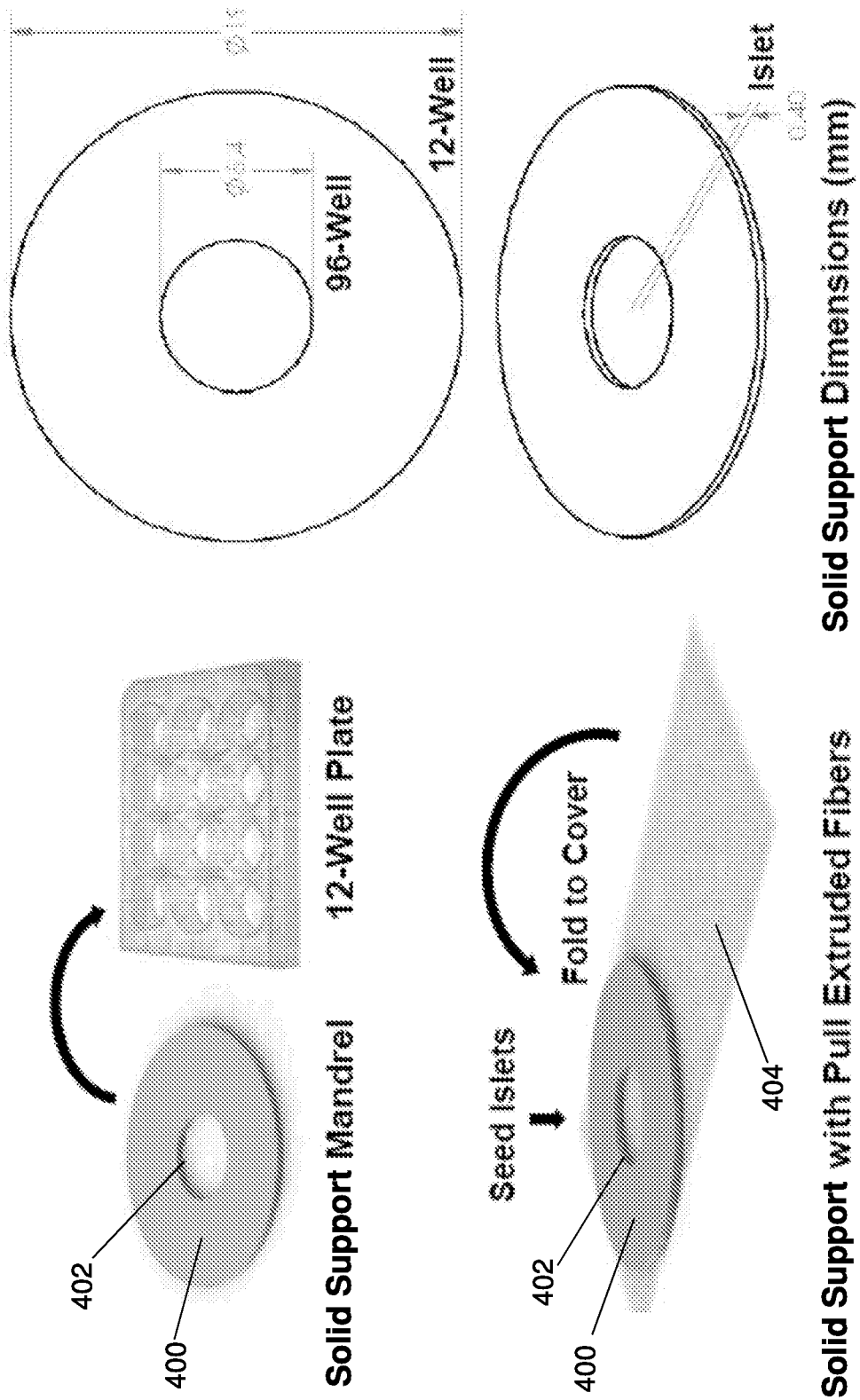
FIG. 19 schematically depicts an exemplary solid support having a top surface, a bottom surface, and a channel extending from the top surface to the bottom surface and an exemplary method to create a scaffold by folding a non-woven polymeric fiber sheet over the solid support.

In one embodiment, the base layer includes the well of a tissue culture plate. A schematic representation of such device is shown in FIG. 19.

The present invention also provides devices including the aforementioned three-dimensional scaffolds and a solid support. The wells of the cartridges discussed above (e.g., cartridge 114 of FIGS. 1-3) can be configured and dimensioned to receive and hold the solid support. The solid support includes a top surface, a bottom surface, and a channel extending from the top surface to the bottom surface. The first portion of the first non-woven polymeric fiber sheet can be disposed on the bottom surface of the solid support. The second portion of the second non-woven polymeric body can be disposed on the top surface of the solid support. The cells or cell clusters can be disposed in the channel of the solid support. The first portion of the first non-woven polymeric fiber sheet and the second portion of the second non-woven polymeric sheet can define a space in which the cells or cell clusters, e.g., pancreatic islet cells or adipocytes, are enclosed.

The solid support can facilitate positioning of the non-woven polymeric sheet onto a base layer or into wells of a cartridge, and, in some embodiments, can be used as a rotating mandrel for preparation of a non-woven polymeric fiber sheet. The solid support can be formed of a rigid or semi-rigid material, such as polystyrene or acrylic.

In certain embodiments, the thickness of the solid support of the invention can be adjusted so as to correspond to the height of the cells or cell clusters cultured therein. In one embodiment, the thickness of the solid support (e.g., clearance) corresponds to the height of adipose cells. In other embodiments, the thickness of the solid support (e.g., clearance) corresponds to the height of pancreatic islet cells. For example, the thickness of the solid support can be between about 10 µm and about 1 mm, between about 10 µm and 750 µm, between about 10 µm and 500 µm, between about 10 µm and 250 µm, between about 10 µm and 100 µm, between about 25 µm and about 1 mm, between about 25 µm and 750 µm, between about 25 µm and 500 µm, between about 25 µm and 250 µm, between about 25 µm and 225 µm, between about 25 µm and 200 µm, between about 25 µm and 175 µm, between about 25 µm and 150 µm, between about 25 µm and 125 µm, between about 25 µm and 100 µm, between about 10 µm and 750 µm, between about 10 µm and 500 µm, between about 10 µm and 250 µm, between about 10 µm and 225 µm, between about 10 µm and 200 µm, between about 10 µm and 175 µm, between about 10 µm and 150 µm, or between about 10 µm and 125 µm, e.g., about 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 33, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 900, 910, 920, 930, 940, 950, 960, 970, 980, 990, or about 1000 µm. Ranges and values intermediate to the aforementioned ranges and values are also encompassed by the invention.

In embodiments in which non-woven polymeric fiber sheets are disposed on at least portions of the first surface and the second surface of the cartridge body, the thickness of the cartridge body can be adjusted so as to correspond to the height of the cells or cell clusters cultured therein. In such embodiments, the values and ranges presented above with respect to the thickness of the solid support are also applicable to the thickness of the cartridge body.

In certain embodiments, the present invention relates to a plurality of the three-dimensional scaffolds and a corresponding plurality of solid supports, and a device including a plurality of the three-dimensional scaffolds and a corresponding plurality of solid supports. The plurality of three-dimensional scaffolds and plurality of solid supports can include about 1, 2, 3, 4, or about 5, or more three-dimensional scaffolds and solid supports which can be, e.g., stacked on top of one another.

The three-dimensional scaffolds and devices (e.g., a solid support) are suitable for use in, among other things, culturing cells or cell clusters, and forming engineered tissue. Such tissue can be useful not only for the production of prosthetic devices and regenerative medicine, but also for investigating tissue developmental biology and disease pathology, as well as in drug discovery and toxicity testing. In some embodiments, the three-dimensional scaffolds with cells can be disposed within the wells of the cartridges described herein (e.g., cartridge 114 of FIGS. 1-3) such that the three-dimensional scaffolds retain the cells within the wells. The three-dimensional scaffolds and devices of the invention can also be combined with other substances, such as, therapeutic agents, in order to deliver such substances to the site of application or implantation of the three-dimensional scaffolds and devices.

In one aspect, the three-dimensional scaffolds and devices (e.g., a solid support), and systems of the invention are useful for culturing cells or cell clusters in a microfluidic system. The methods include, providing a microfluidic system of the invention, disposing one or more cells or one or more cell clusters for culturing in at least one of the plurality of wells of the cartridge and disposing the cartridge in the chamber of the housing; and providing suitable culture conditions and circulating a suitable culture medium through the microfluidic system, thereby culturing the one or more cells.

In another aspect, the three-dimensional scaffolds and devices (e.g., a solid support), and systems of the invention are useful for screening compounds that modulate a property of the cells contained therein. The methods include providing a three-dimensional scaffold, device, or system according to the instant invention, contacting the three-dimensional scaffold, device, or system with a test compound, and monitoring a parameter in the absence of the compound (negative control) and in the presence of the compound. A change in the parameter in the presence of the test compound compared to the parameter in absence of the test compound indicates that the test compound is effective in modulating the property.

In one embodiment, the parameter can be growth, division, differentiation, or viability of the cells, e.g., adipocytes or pancreatic islet cells. In an embodiment, the property can be insulin secretion, oxygen consumption, and extracellular acidification rates in response to secretagogue treatment, or presence/absence of c-peptide and glucagon-like peptide 2 co-stained cells. In another embodiment, the property can be expression of certain genes, e.g., PAX-6.

Identification of a test compound that modulates the cell property can also be made by evaluating various physiological parameters such as cell morphology, cell structure, cell agglutination, formation of cell clusters, cell size, presence or absence of vesicles/granules, or the like. The cell can be an adipose cell, in certain embodiments, a test compound's activity can be assayed by measuring cellular uptake of labeled sugars, cellular assimilation of glycogen, or the like. In other instances, the assays an include analyzing adipose-specific enzymes, e.g., hormone-sensitive lipase activity.

The three-dimensional scaffolds and devices (e.g., a solid support), and systems of the invention can be also useful for screening compounds useful for treating a disease or disorder of the cells contained therein. The methods include providing a scaffold, device, or system according to the instant invention, contacting the scaffold, device, or system with a test compound, and monitoring a parameter in the absence of the compound (negative control) and in the presence of the compound. A change in the parameter in the presence of the test compound compared to the parameter in absence of the test compound indicates that the test compound is useful for treating the disease or disorder.

As used herein, the various forms of the term "modulate" are intended to include stimulation (e.g., increasing or upregulating a particular response or activity) and inhibition (e.g., decreasing or downregulating a particular response or activity).

As used herein, the term "contacting" (e.g., contacting a scaffold including pancreatic islet cells or adipocytes with a test compound) is intended to include any form of interaction (e.g., direct or indirect interaction) of a test compound and a scaffold or cells. The term contacting includes incubating a compound and scaffold or tissue together (e.g., adding the test compound to scaffold including pancreatic islet cells or adipocytes in culture).

Test compounds can be any agents including chemical agents (such as toxins), small molecules, pharmaceuticals, peptides, proteins (such as antibodies, cytokines, enzymes, and the like), nanoparticles, and nucleic acids, including gene medicines and introduced genes, which may encode therapeutic agents, such as proteins, antisense agents (i.e., nucleic acids comprising a sequence complementary to a target RNA expressed in a target cell type, such as RNAi or siRNA), ribozymes, and the like.

The test compound can be added to the scaffold by any suitable means. For example, the test compound can be added drop-wise onto the surface of a device of the invention and allowed to diffuse into or otherwise enter the device, or it can be added to the nutrient medium and allowed to diffuse through the medium. In the embodiment where the device of the invention includes a multi-well plate, each of the culture wells being contacted with a different test compound or the same test compound. In one embodiment, the screening platform includes a microfluidics handling system to deliver a test compound and simulate exposure of the microvasculature to drug delivery.

In some embodiments, the three-dimensional scaffolds and devices of the invention can be used for the culture of three-dimensional tissues in tissue engineering application as, e.g., synthetic pancreatic tissue or adipose tissue. For example, a three-dimensional scaffold or plurality of three-dimensional scaffolds of the invention can be implanted or grafted in a subject, using standard surgical techniques, for the treatment of a pancreatic disease, e.g., diabetes or lipodystrophy.

Accordingly, the present invention provides methods of treating a subject having diabetes or lipodystrophy, or a subject needing reconstructive or cosmetic surgery. The methods include providing a scaffold of the invention and implanting the scaffold in the subject.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. (See, e.g., *Molecular Cloning A Laboratory Manual* (1989), 2nd Ed., ed. by Sambrook, Fritsch and Maniatis, eds., Cold Spring Harbor Laboratory Press, Chapters 16 and 17; U.S. Pat. No. 4,683,195; *DNA Cloning, Volumes I and II*, Glover, ed., 1985; Oligonucleotide Synthesis, M. J. Gait, ed., 1984; *Nucleic Acid Hybridization*, D. Hames & S. J. Higgins, eds., 1984; *Transcription and Translation*, B. D. Hames & S. J. Higgins, eds., 1984; Culture Of Animal Cells, R. I. Freshney, Alan R. Liss, Inc., 1987; *Immobilized Cells And Enzymes*, IRL Press, 1986; Perbal (1984), *A Practical Guide To Molecular Cloning*; See Methods In Enzymology (Academic Press, Inc., N.Y.); *Gene Transfer Vectors For Mammalian Cells*, J. H. Miller and M. P. Calos, eds., Cold Spring Harbor Laboratory, 1987; *Methods In Enzymology*, Vols. 154 and 155, Wu et al., eds., Academic Press Inc., N.Y.; *Immunochemical Methods In Cell And Molecular Biology* (Mayer and Walker, eds., Academic Press, London, 1987; *Handbook Of Experimental Immunology*, Volumes I-IV, D. M. Weir and C. C. Blackwell, eds., 1986).

Portions of the present invention are illustrated by the following examples which should not be construed as limiting. The entire contents of all references, patents and published patent applications cited throughout this application, as well as the Figures, are hereby incorporated herein by reference.

EXAMPLES

Example 1: Fabrication of Cartridges, Housings, and Holders

Fabrication of a first generation of example cartridges involved laser cutting a few cartridge bodies out of a 254 µm thick polycarbonate sheet, and then subsequently manually bonding each cartridge body to a 24 µm thick membrane having 1 µm pore size and $2*10^6$ pores/cm$^2$. However, this approach was limited in manufacturing capacity and the wells were not sufficiently deep.

A second generation of example cartridges were fabricated from a 372 µm thick sheet of polycarbonate to provide deeper wells for holding cells. Further, the laser cutting was divided into two sessions, one for forming the inner quadrants to be used as wells prior to bonding to the membrane, and a second session for forming the outer channels and cutting the outer border/perimeter of the cartridge body and filter after the materials for cartridge body and filter were bonded together. First, the inner well quadrant patterns were laser cut out of a 109 mm×109 mm square of polycarbonate stock. A laser power of 0.6 W was used with a laser frequency of 50 kHz, a laser speed of 20 mm/s, and 30 repetitions, resulting in a significant improvement in cut quality and speed over other settings. After sonicating in a 9:1 mixture of distilled water and isopropanol for 20 minutes and cleaning with isopropanol, the square was bonded to a similarly-sized piece of membrane between panes of glass to obtain smooth top and bottom cartridge surfaces. The bonding was performed thermally, where the layers were preheated to 160° C., compressed at 0.35 MPa for 30 minutes, and then allowed to cool to 55° C. over the course of 4 hours under the same pressure. Afterwards, the bonded layers were realigned on the laser cutter and the outer channels and border of each cartridge body was cut out. The cartridges were then sonicated in a bath and dried with compressed air. A resulting second generation cartridge is shown in FIG. 5. The disclosed second generation process reduced the time of fabrication per cartridge, while improving the overall quality of the cartridge.

An example housing was fabricated from a combination of thicker (e.g., approximately 1 mm) and thinner (e.g., approximately 0.127 mm) layers that were been bonded together. Layers of 1 mm in thickness were cut using Roland ModelaProII CNC mill out of polycarbonate stock material. After sanding down the faces of the layers on a flat surface, the layers were cleaned in a process identical to that described above with respect to the laser-cut cartridges. Following cleaning, the layers were polished with heated dichloromethane vapor and left to sit overnight. The thinner layers were cut out of polycarbonate films using the UV laser cutter, and subsequently cleaned in the same process as that described above for the laser-cut cartridges. Layers of each respective housing portion 102, 104 were aligned and taped together along one edge. These stacks of layers, which correspond to the different housing portions 102, 104, were bonded in a press under identical conditions used for bonding the cartridge body to the membrane, with the exception that the bonding temperature was 135° C.

The 127 μm thick layers (which compose the main channel layers in the housing) were fabricated using the same laser cutter settings as those for the cartridges (described above), but with six repetitions. An additional cut at 0.5 W focused on the bottom of the material was also included. As with the cartridges, this change facilitated efficient production of the housing, speeding up manufacturing of these parts at least fivefold. The 1 mm thick layers that form the cartridge chamber, chip base and aperture/channel layers were cut on a CNC mill. Both milled and laser cut housing layers were cleaned in a sonicating bath of isopropanol for 20 minutes, and dried with compressed air. Layers of each respective housing portion were aligned and sandwiched between custom-sized glass pieces (see FIG. 8). These stacks of layers are bonded in parallel in a press under identical conditions to the cartridges, with the exception that the bonding temperature should be 138° C. The increased temperature generally yields a consistently better bond.

Figure 11A:
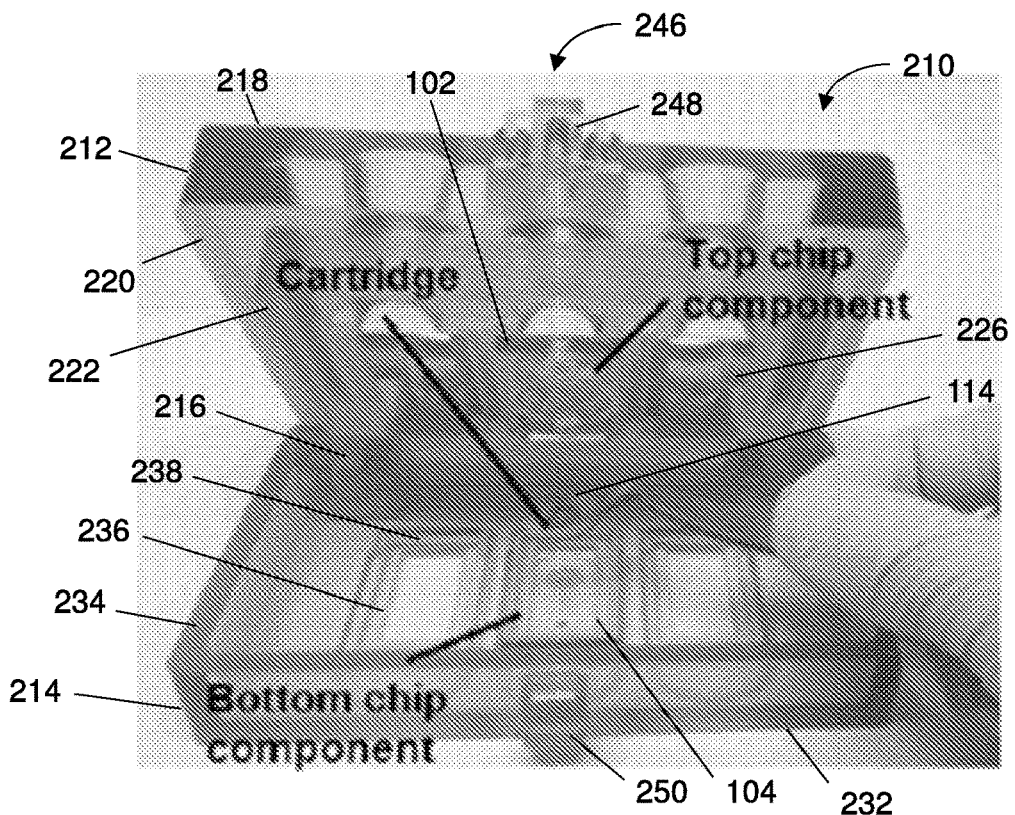
FIGS. 11A-B show perspective views of an exemplary holder of the present invention.
Figure 11B:
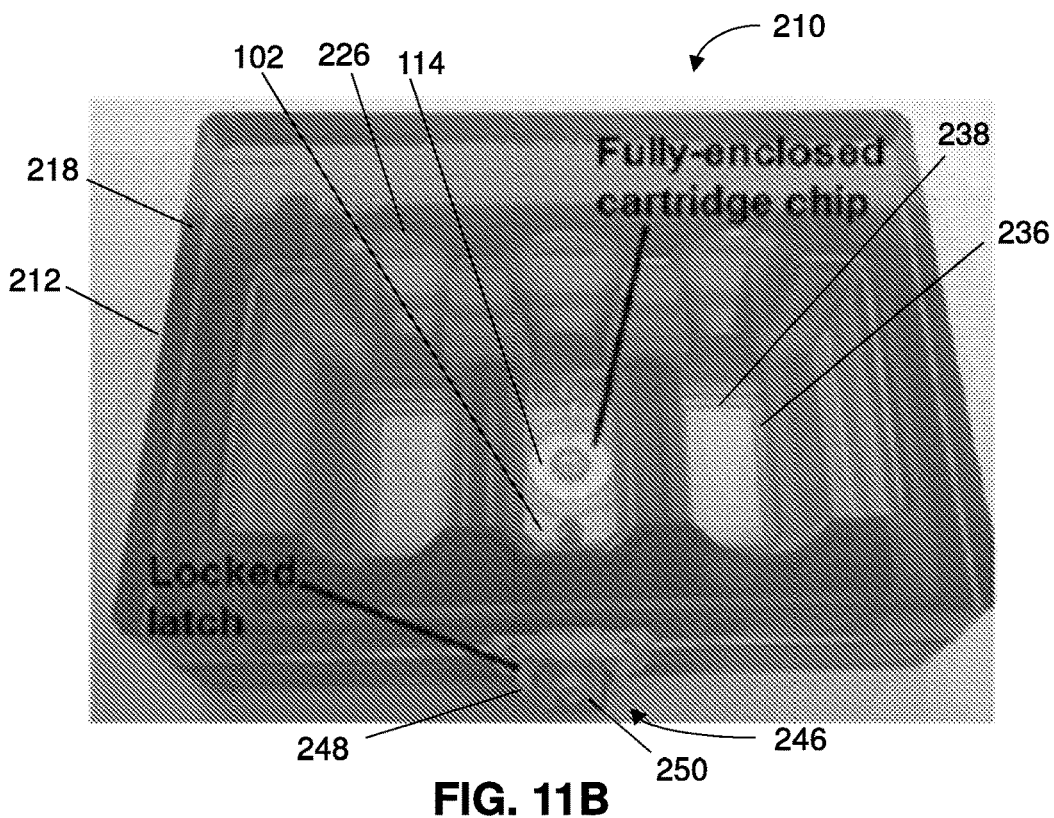

An example holder was fabricated using a 3D printing system. Specifically, a holder was 3D printed out of a transparent photo-setting Veroclear material, aside from a single steel dowel employed affix the latch 248 to the main body of the holder 210. FIGS. 11A and 11B show the example holder.

Example 2: Maintenance of a Mature and Functional Adult Human Beta Cell Phenotype for Long Periods of Time in Culture in the Cartridges and Devices of the Invention One approach for housing and culturing SC-beta cell clusters in an exemplary cartridge based fluidics system, e.g., microfluidics system, as described herein may include hydrogel macroencapsulation (see, e.g., FIG. 14A). Initial results of cultured macroencapsulated SC-beta cell clusters suggested that cell viability may not remain optimal after extended periods of time in culture. Less than optimal viability of such macroencapsulated cell clusters after extended periods of time may be due to cell necrosis at the center of the cell clusters as a result of insufficient oxygen transport caused by, e.g., a lack of control of the cell cluster position within the hydrogel.

One alternative, hydrogel microencapsulation of SC-beta cell clusters in an exemplary cartridge based fluidics system, e.g., microfluidics system, as described herein was explored and is described below in Example 8.

Figure 15A:
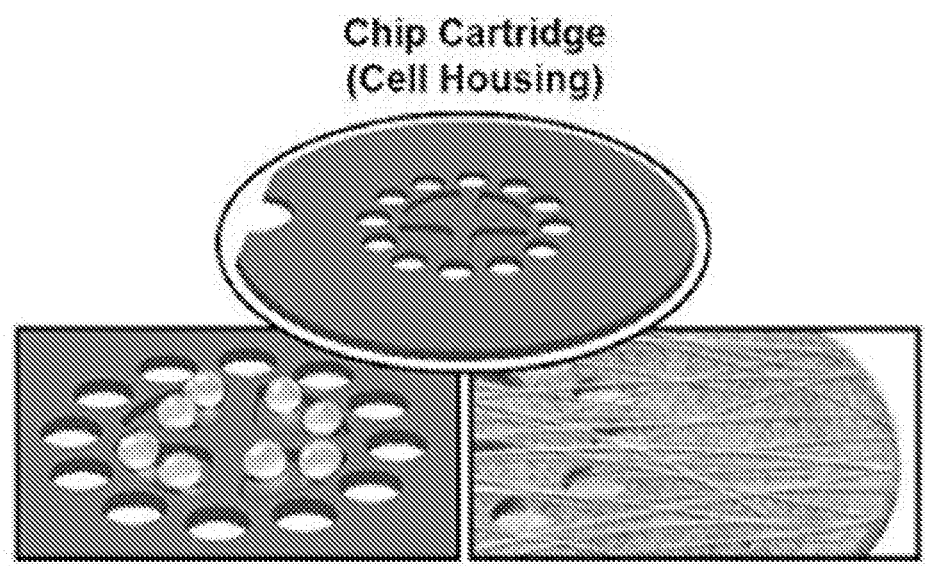
FIG. 15A includes a schematic of an exemplary cartridge of the invention (upper image) with detail views depicting two different exemplary approaches for containing cells in the wells of a cartridge: a hydrogel micro-encapsulation of individual cell clusters (lower left) and containment using a non-woven polymeric sheet (lower right).
Figure 15B:
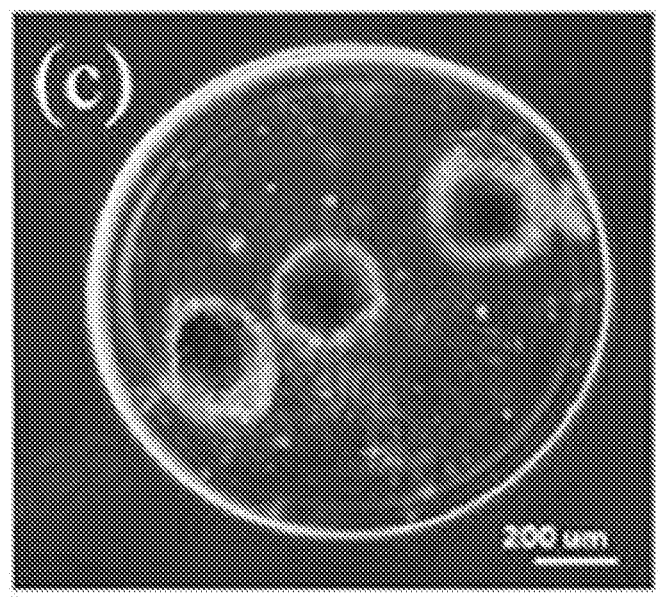
FIGS. 15B-C includes images of cultured SC-beta cell clusters (stem cell derived pancreatic beta cell clusters) that were microencapsulated within an alginate hydrogel.
Figure 15C:
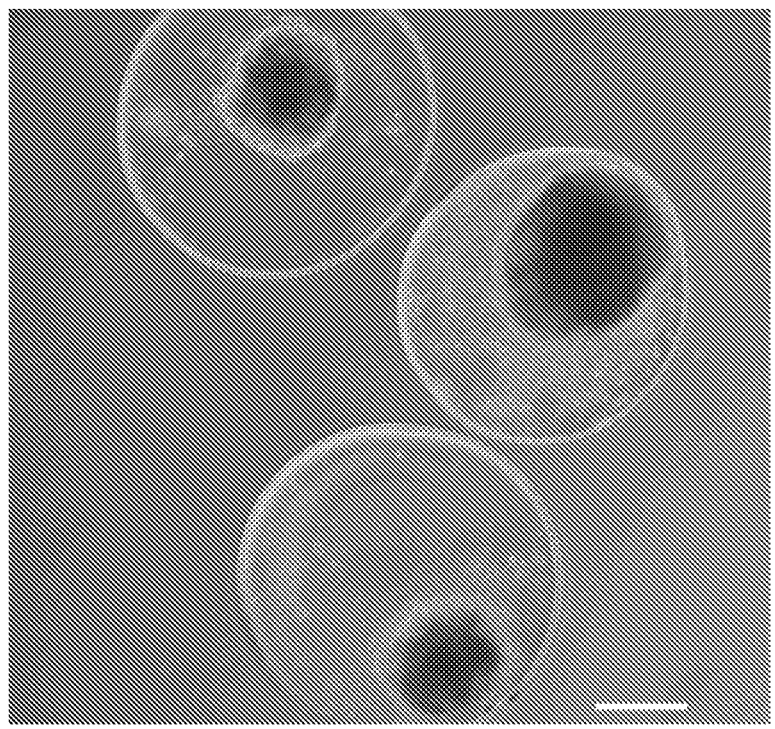
Figure 15D:
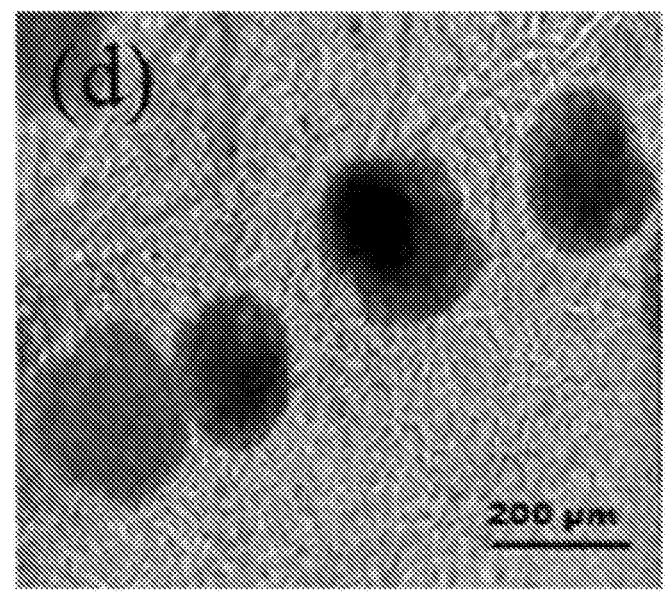
FIG. 15D is an image of SC-beta cell clusters cultured on a non-woven polymeric fiber sheet.

A further alternative to hydrogel macroencapsulation of islet cell clusters is use of non-woven polymeric fiber sheets and three-dimensional scaffolds comprising a first and a second non-woven polymeric fiber sheet, all of which comprise extracellular matrix proteins and mimic the in vivo environment (e.g., islets are surrounded by a capsule of extracellular matrix nanofibers in vivo) of pancreatic islet cell clusters (see FIGS. 15A, lower right panel, and 15D). The diameter of the fibers in such non-woven polymeric sheets are within an order of magnitude of the native pancreatic islet cell capsule fibers and these sheets and scaffolds have been integrated into a cartridge of the invention by, e.g., collecting formed fibers directly on the cartridge bodies. As described below, SC-beta cells cultured on such non-woven polymeric fiber sheets and scaffolds remain viable for more than 7 days and maintain protein expression of islet hormones for over a month.

Example 3: The Microfluidics Systems Comprising a Cartridge of the Invention Permit Improved Oxygenation and Improved Glucose Metabolism of Islet Cells Cultured Therein A COMSOL model was developed to validate the design of the cartridge chip by showing improved perfusion of the cells. This particular model was devised for an application of islet cells, using published parameter values for oxygen and glucose metabolism of islets.

Figure 16:
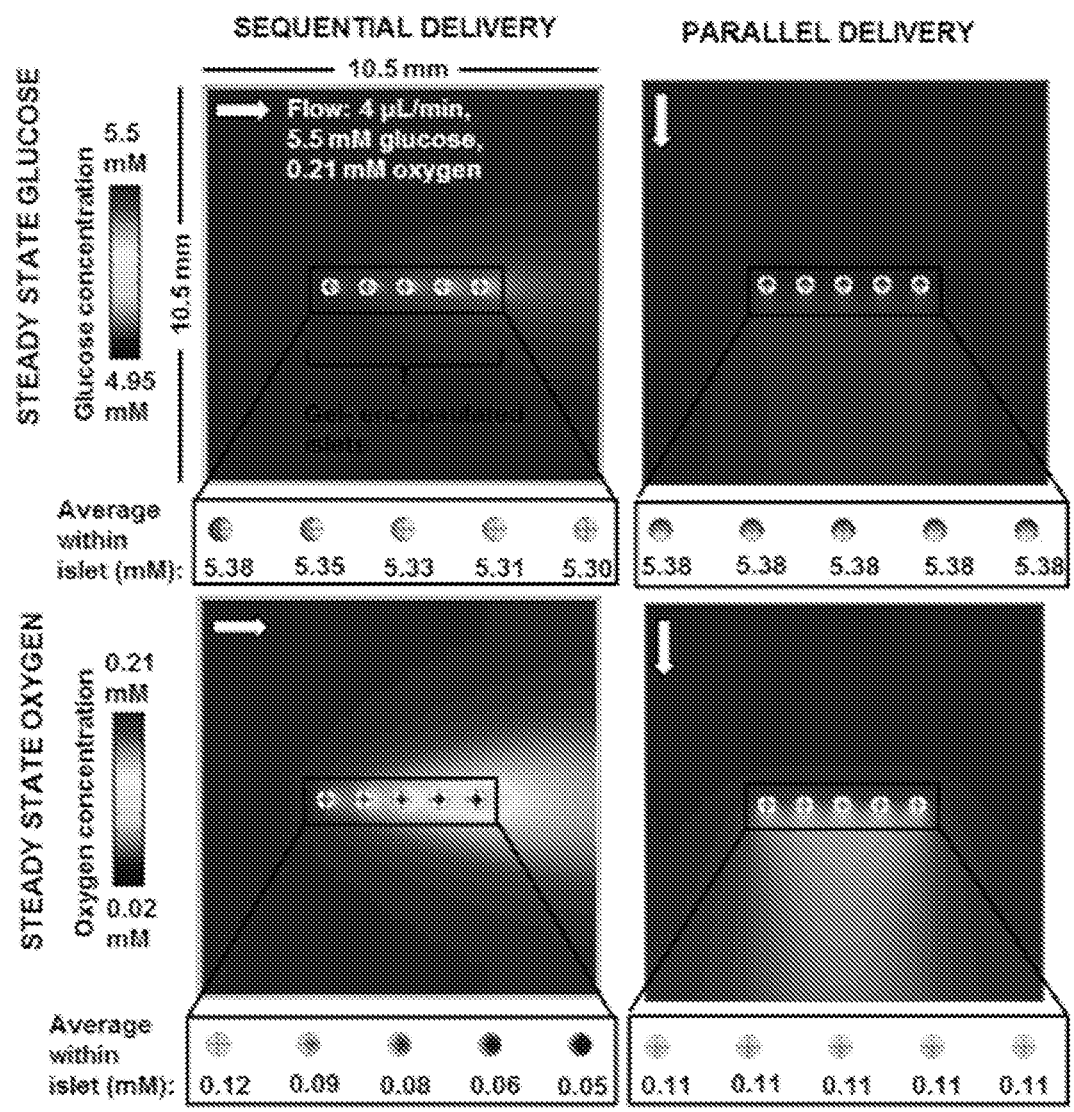
FIG. 16 includes 2-D graphs of steady state glucose levels for different flow geometries from a proof-of-concept COMSOL model comparing stead state oxygenation and glucose concentration for five simulated islets cell clusters with either sequential or parallel flow delivery to the cell clusters.

A simple proof of concept simulation was first conducted to demonstrate one of the core principles of the microfluidic design of the cartridge chip. In this simulation, five spherical islets of diameter 250 μm encased in a 125 μm thick hydrogel shell were placed within a 10.5 mm×10.5 mm×572 μm (L×W×D) channel and subjected to flow either sequentially (i.e. islets receiving flow one after another) or in parallel (i.e. islets receiving fresh flow simultaneously). The model was assessed for steady state glucose and oxygen concentrations in each of the two cases at a volumetric flow rate of 4 μL/min delivering 5.5 mM glucose and 0.21 mM oxygen to the hydrogel and islets with initial concentration values of 0 mM for both. As shown in FIG. 16, for both oxygen and glucose, parallel delivery (right side images) yielded a consistent internal concentration among the islets with less depletion than sequential delivery (left side images). These modeling results validate the cartridge and housing system, which is designed to deliver the medium in parallel, (e.g., with flow traveling radially across the cartridge surface from a central point the islets in the wells).

Example 4: Preparation of Non-Woven Polymeric Fiber Sheets

FIG. 17 shows a diagrammatic view of an exemplary pull spinning device, exemplary rotating collection mandrel, and exemplary method for fabrication of the non-woven polymeric fibers sheets for use in the scaffolds, cartridges, systems, and devices of the invention. As shown in FIG. 17, a solution of polycaprolactone (PCL) and gelatin was prepared by dissolving the polymers in hexafluoro-2-propanol to create a 10% solution (by weight). The solution was placed into a syringe pump and injected into a polymer reservoir to create a polymer deposit at a flow rate of about 0.2 mL/min. The solution was flung by a pull-spinning device and collected on a rotating mandrel. The non-woven polymeric fibers of the formed sheet deposited into the mandrel were analyzed for structural integrity using scanning electron microscope (SEM). The inset on the right side of FIG. 17 shows a scanning electron micrograph (SEM) of exemplary fibers of a non-woven polymeric fiber sheet prepared using the exemplary pull spinning device, the exemplary rotating collection mandrel, and the exemplary method (scale bar: 5 μm). In particular, the inset shows the structure and morphology of the fibers.

Figure 18A:
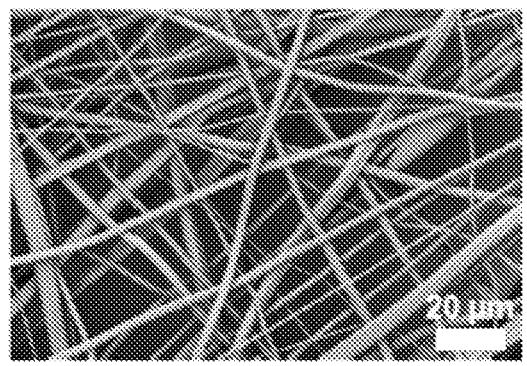
FIGS. 18A-C show scanning electron micrographs of fibers of non-woven polymeric fiber sheets (e.g., for fabrication of a three-dimensional scaffold as described herein) fabricated by pull-spinning using solutions comprising various polymer combinations, as indicated, and collection of the formed fibers on an exemplary rotating mandrel as depicted in FIG. 17.
Figure 18B:
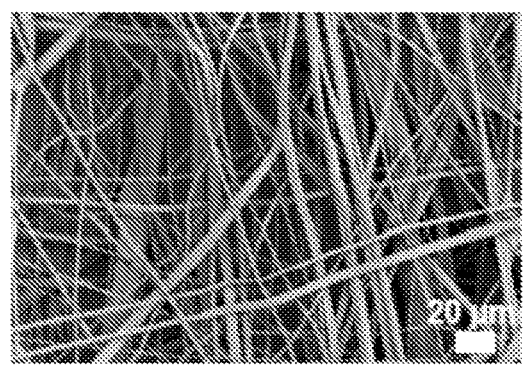
Figure 18C:
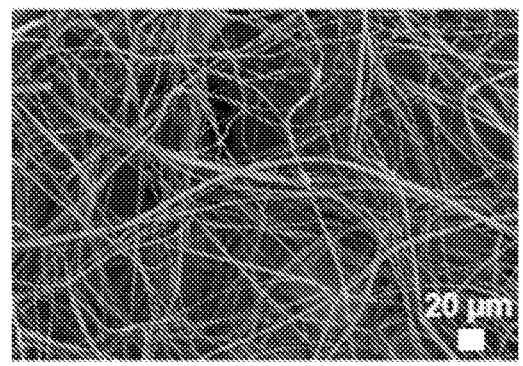

FIGS. 18A-C show scanning electron micrographs of fibers of non-woven polymeric fiber sheets generated using different polymer solutions and pull spinning of the solution into fibers collected on an exemplary rotating mandrel depicted in FIG. 17. In particular, FIG. 18A shows fibers from a solution containing a 50:50 mixture of PCL and gelatin, FIG. 18B shows fibers from a solution containing a 40:60 mixture of PCL and gelatin, and FIG. 18C shows fiber from a solution containing a 20:80 mixture of PCL and gelatin (scale bar: 20 μm). As can be seen from the side-by-side comparison, changing the PCL:gelatin ratio changes the diameter and/or the amount of coiling of the fibers. For instance, employing a 20:80 ratio of PCL:gelatin results in fibers that are thinner and more coiled than a 50:50 ratio of PCL:gelatin.

Example 5: Design and Construction of Scaffold Compositions

The non-woven polymeric fiber sheets prepared in accordance with Example 1 were used to prepare various scaffolds for culturing cells, as shown in FIG. 19. In particular, FIG. 19 shows an exemplary solid support for the three-dimensional scaffolds 400 having a top surface, a bottom surface, and a channel 402 extending from the top surface to the bottom surface of the solid support and one exemplary method to create a scaffold by folding a fiber sheet 404 over the solid support 400. In some embodiments, the first non-woven polymeric fiber sheet and the second non-woven polymeric fiber sheet can be the same non-woven polymeric fiber sheet and the first portion and the second portion can be different portions of the same non-woven polymeric fiber sheet. In some embodiments, the scaffolds can be designed with solid supports 400 that fit into standard tissue culture wells, e.g., the diameter of the solid support 400 is slightly less than the inner diameter of a 12-well tissue culture plate (e.g., about 19 mm) and the diameter of the channel 402 of the solid support 400 where cells can be seeded is equal to the inner diameter of a 96-well tissue culture plate (e.g., about 6.4 mm) or such that it slightly less than the inner diameter of a 96-well tissue culture plate or a 384-well tissue culture plate.

If the three-dimensional scaffolds are to be utilized in a microfluidics system comprising a cartridge, as described herein, for, e.g., high throughput studies (e.g., screening assays), the diameter of the solid support can be modified such that it slightly less than the inner diameter of a 96-well tissue culture plate or a 384-well tissue culture plate. The diameter or the shape/perimeter of the solid support can be modified to fit into a well of a cartridge body (e.g., the solid support may have a quadrant-shaped perimeter to fit into a quadrant-shaped well. In some embodiments, the non-polymeric fiber sheet, can be fabricated directly on the cartridge body using, e.g., a pull-spinning device.

Figure 20B:
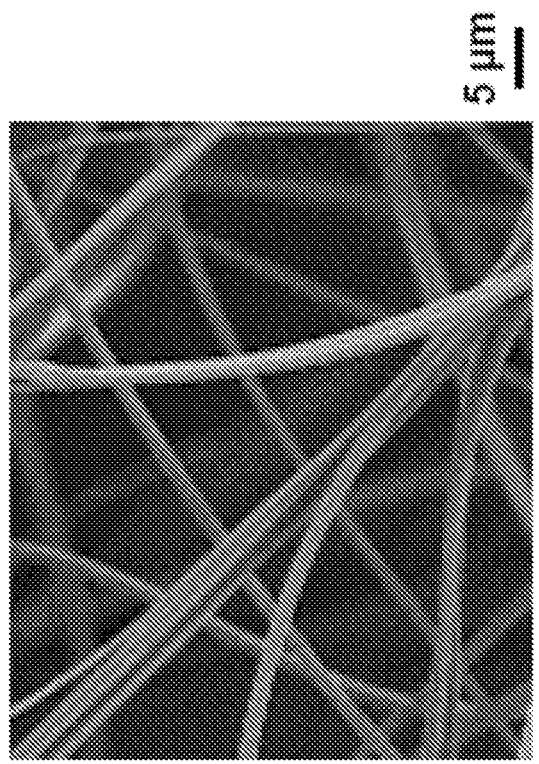
FIGS. 20A-B show a solid support covered by a non-woven polymeric fiber sheet with excess sheet to be used for covering the opposite side of the solid body support and a scanning electron micrograph of the fibers which make up the fiber sheet (scale bar: 5 μm).
Figure 20A:
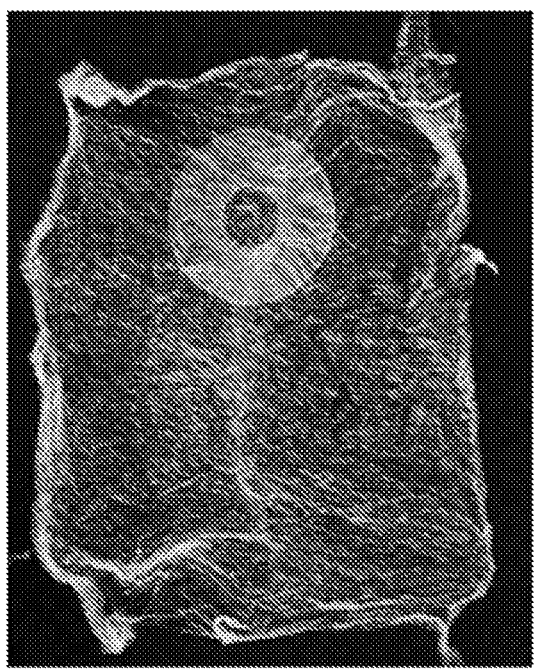

Example 6: Analysis of the Structural Features and Viability of Cultured Pancreatic Islet Cells Using the Scaffolds and Devices of the Invention FIGS. 20A-B show an exemplary solid support covered with an excess of a non-woven polymeric sheet and a scanning electron micrograph of fibers which are used to make the fiber sheets (scale bar: 5 μm). Any excess portions of the sheet can be cut with any suitable instrument. FIGS. 21A-E show photomicrographs of islet cells cultured on the scaffolds described herein (scale bar: 200 μm). A device including a three-dimensional scaffold was prepared. Non-woven polymeric fiber sheets and a solid support were prepared as described above. The non-woven polymeric fiber sheets were prepared by pull-spinning and were composed of PCL and gelatin at a ratio of 20:80, and the solid support was made of acrylate.

For structural and viability assays, the non-woven polymeric fiber sheets and exemplary solid support depicted in FIG. 19 and shown in FIG. 20A were placed in a 12-well culture dish and either left uncoated (FIG. 21E; no coat), coated with a 300 microgram/ml solution of MATRIGEL (FIG. 21C; Matrigel coat), or coated with a solution comprising a combination of collagen VI, laminin, and fibronectin (50 microgram/ml) (FIG. 21D; Islet ECM coat). One×10$^6$ human stem cell derived delta cells (SC-δ cells) were seeded onto each fiber sheet in the channel of each solid support. In the case of the uncoated scaffold, the cells and the solid body were then overlaid with a second portion of a second non-woven polymeric fiber sheet. For comparison purposes, 1×10$^6$ human stem cell derived delta cells (SC-δ cells) were also plated in a well of a 96-well tissue culture dish coated with MATRIGEL (FIG. 21A; Matrigel coat) or the cells were encapsulated with 11 mg/mL MATRIGEL prior to plating (FIG. 21B; Matrigel encapsulation). Standard culture conditions were used to maintain all cells for one week.

The morphology and the structural integrity of the seeded SC-δ cells were analyzed with a camera-coupled standard light microscope at different time points (e.g., at one day or seven days post-seeding). The results are shown in the photographs of FIG. 21A-E. It can be seen that after seven days from the seeding date, the cells seeded in control wells have spread and lack the cellular structure and morphology observed with freshly-seeded cells. For example, a comparison is made of cells seeded in control wells (FIGS. 21A-B) at day 1 and at day 7. In contrast, cells seeded in experimental wells (FIGS. 21C-D) form clusters and remain attached to scaffolds even after a week in culture. Especially, even after seven days of culture, the cells seeded in wells containing non-woven polymeric fiber scaffolds containing a coat of islet-specific extracellular matrix protein mixture (e.g., collagen VI, laminin and fibronectin) displayed a spherical cellular structure and an intact cellular morphology just like those displayed by freshly-seeded cells (compare cells of FIG. 21D at day 1 and at day 7). The results of the experiment demonstrate that the scaffold compositions of the instant invention permit islet cells to retain their cellular morphology and cellular structure even up to seven days after seeding. This protective effect was most pronounced when the scaffold compositions were coated with MATRIGEL or a composition of ECM proteins (see, e.g., FIGS. 21C-D).

Figure 22:
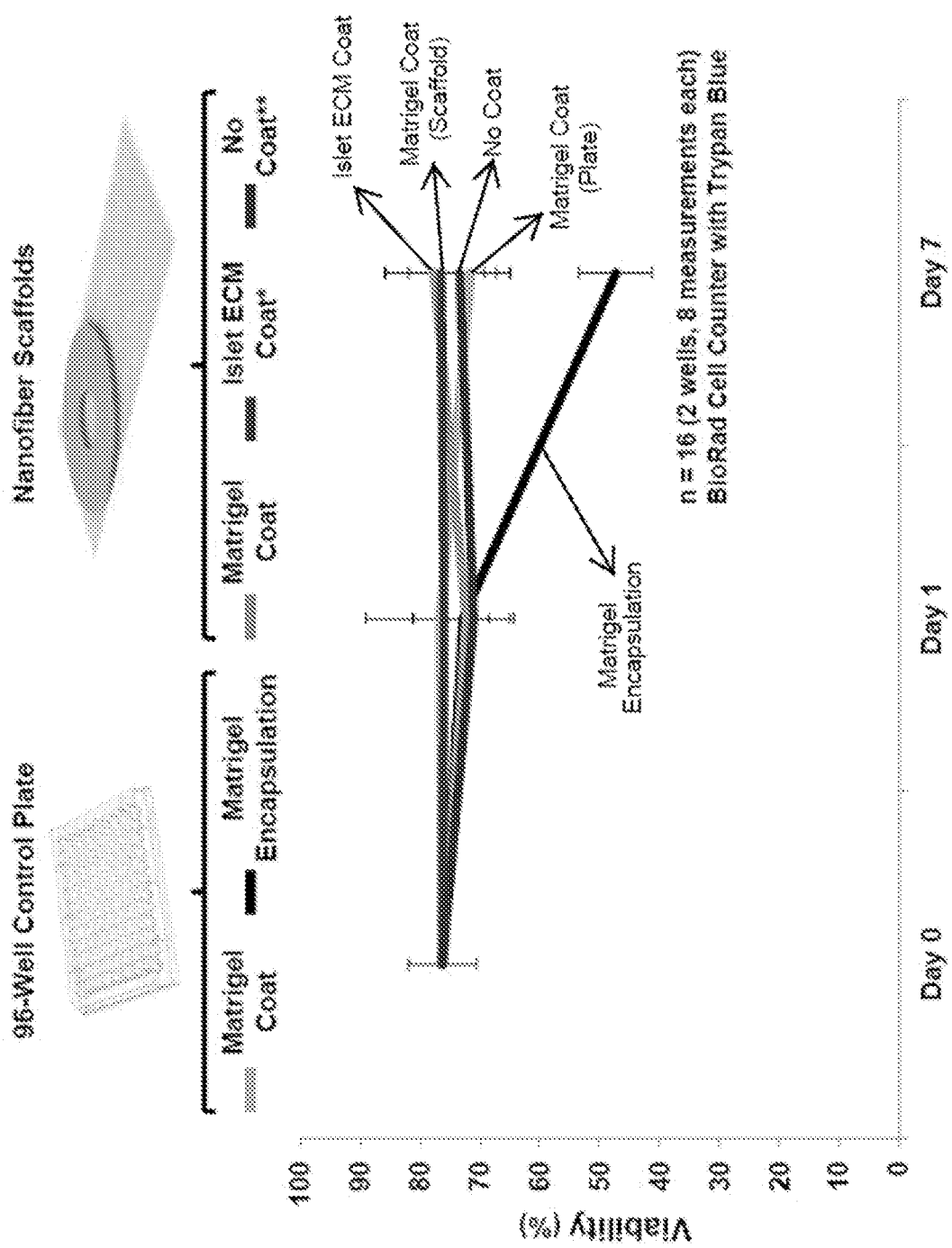
FIG. 22 shows a graph showing the viability of pancreatic islet cells cultured under the indicated conditions, and error bars indicating standard deviations (SD).

Cell viability was also assessed at day one and day seven post-seeding using standard techniques and instruments (e.g., using a trypan blue assay with a BIORAD cell counter). FIG. 22 shows a graph indicating the viability of pancreatic islet cells cultured under the various conditions discussed above, and error bars indicating standard deviations (SD). A baseline cell viability of about 78% was observed at day 0 (all samples), which plummeted to about 45% at day 7 in the case of cells seeded in control wells containing MATRIGEL encapsulation. Similarly, a loss of cell viability of about 10% was observed at day 7 with cells seeded in control wells containing MATRIGEL coating. In contrast, cells seeded in experimental wells including non-woven polymeric fiber scaffolds coated with either MATRIGEL or the composite of ECM proteins did not suffer loss of viability even after seven days of culture. Moreover, even the mere inclusion of naked scaffolds (i.e., scaffolds containing no coat) in the tissue culture wells conferred better cell viability at day 7 compared to the viability conferred by MATRIGEL coated wells, which result was surprising and unexpected.

Example 7: Long-Term Pancreatic Cell Viability and Pancreatic Alpha Cell Differentiation is Promoted by Culturing Cells on the Three-Dimensional Scaffolds of the Invention In order to further examine the benefits of the three-dimensional polymeric scaffolds to promote long-term cell viability in culture and promote islet alpha cell differentiation, 1×10⁶ human stem cell derived beta cells (SC-β cells) were seeded onto each fiber sheet in the channel of each solid support in e.g., a 12-well tissue culture plate and cultured using standard culture conditions. In parallel, 1×10⁶ human stem cell derived beta cells (SC-β cells) were placed into culture media in suspension and cultured under standard conditions, and 1×10⁶ human stem cell derived beta cells (SC-β cells) were placed in culture in a well of a 12-well tissue culture plate coated with a solution comprising a combination of collagen VI, laminin, and fibronectin (50 microgram/nil) and cultured under standard conditions. See FIG. 24.

Figures 23A, 23B:
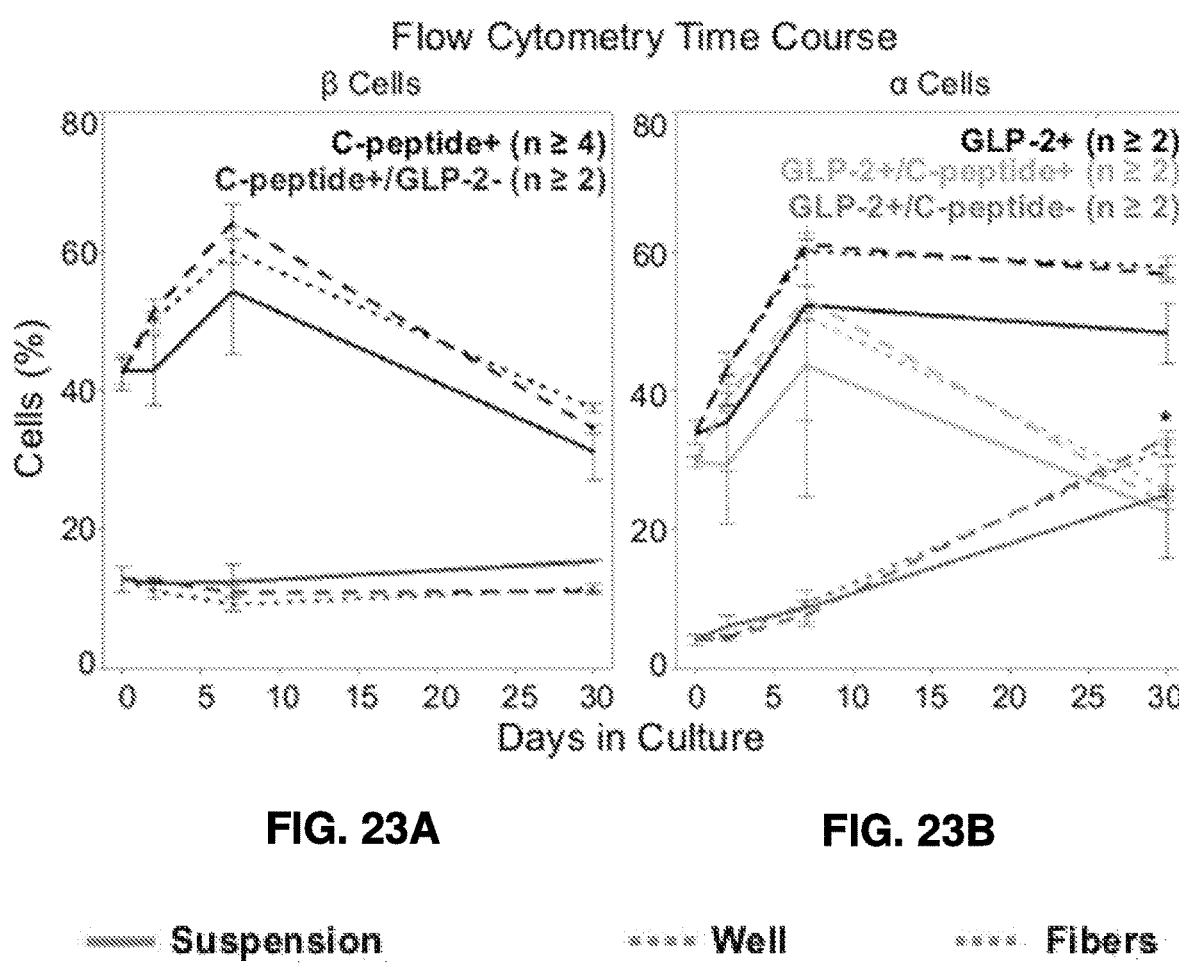
FIGS. 23A and 23B are graphs showing a flow cytometry time course analysis of islet cells cultured under the indicated conditions.

At days 1, 3, 7, and 30 post-seeding of the cells, aliquots of cells were removed from culture and stained with anti C-peptide antibodies in order to identify pancreatic beta cells in the culture (i.e. beta cells express C-peptide and alpha cells do not express C-peptide), and anti-GLP-2 antibodies in order to identify pancreatic alpha cells in the culture (i.e. beta cells no express GLP-2 and alpha cells do express GLP-2). The stained cells were subjected to flow cytometry and the results of these experiments are depicted in FIGS. 23A and 23B which demonstrate that the islet cells can be maintained in culture for over a month using the three-dimensional polymeric fiber scaffolds of the invention. Furthermore, FIG. 23B demonstrates that the ability of the three-dimensional polymeric fiber scaffolds of the invention to promote pancreatic alpha cell differentiation is superior to the ability of suspension growth.

Example 8: Pancreatic Islet Cell Viability and Functionality is Promoted by Encapsulating Pancreatic Islet Cell Clusters in Microspheres of a Hydrogel For use in the systems and cartridges of the present invention, in addition to or as alternative to non-woven polymeric fiber sheets and three-dimensional scaffolds, cells, such as pancreatic islet cell clusters, may be microencapsulated in a polymer, such as a hydrogel, e.g., alginate, via electrostatic droplet generation. For example, pancreatic islet cells are very sensitive to shear stress and microencapsulation of islet cells in a hydrogel provides protection from hydrodynamic forces, allows diffusion of nutrients and oxygen, and, furthermore, provides a medium in which additional extracellular matrix (ECM) proteins can be added to improve the health of the cells. Microencapsulation of cell clusters also enables cells to be exposed to a controlled and defined micro-environment whilst facilitating easier manipulation of cell number and placement within the systems and cartridges of the present invention.

More specifically, the micrometer scale of microencapsulated cells is within the diffusion limits of many small molecules such as nutrients and oxygen while the pores of the encapsulating alginate polymer are large enough to permit their transport. Indeed, mathematical modeling of the microencapsulated islet cells prepared as described below has indicated that oxygenation levels in such microencapsulated cell clusters (e.g., cell clusters encapsulated in alginate microsphere having a diameter of about 200 to about 600 μm) are adequate to maintain functionality in vitro, never dropping below 0.1 mol/m³ oxygen during glucose challenges (a 50% decrease in islet function has been reported in the literature at <0.05 mol/m³ oxygen). Furthermore, LIVE/DEAD imaging analysis has demonstrated that microencapsulation in alginate of pancreatic islet cell clusters promotes the maintenance of cell viability in vitro in short term culture (2 days) (FIGS. 15E-15K). In addition, glucose stimulated insulin secretion analysis demonstrated that alginate microencapsulated pancreatic islet cell clusters (e.g., microspheres having a diameter of about 200 to about 600 μm) have statistically significant higher levels of secreted insulin following glucose stimulation when cultured for either four days or seven days as compared to pancreatic islet cells that were not microencapsulated.

To prepare microencapsulated pancreatic islet cells clusters, SC-β clusters (stem-cell derived pancreatic beta cell clusters) were taken out of culture and washed with sterile calcium-free Krebs-Henseleit (KH) Buffer. After washing, SC-β clusters were allowed to settle and all of the supernatant was aspirated. The SC-β clusters were then re-suspended in sterile filtered 2% sodium alginate (UP MVG) (Viscosity<200 mPa·s, MW>200 kDa, NovaMatrix/FMC Biopolymer) in a ratio of 1:8 (cell to alginate volume). The alginate has a high guluronic acid:mannuronic acid ratio and is of GMP grade.

Figure 15L:
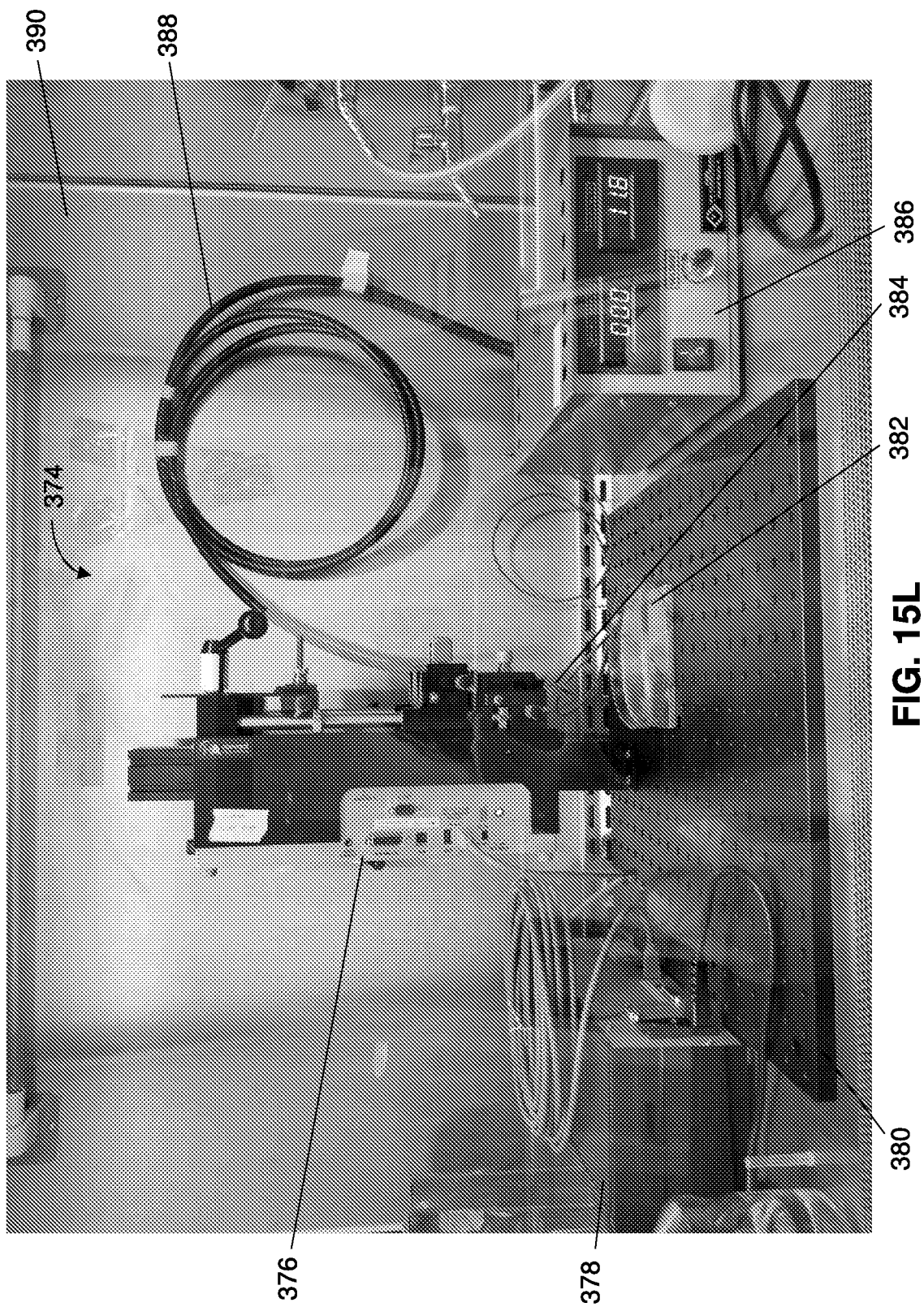
FIG. 15L is an exemplary microencapsulation rig used to microencapsulate SC-beta cell clusters.

The cell cluster suspension was then transferred to an electrostatic droplet generator set-up. FIG. 15L shows an exemplary rig 374 used in the process of microencapsulating SC-beta cell clusters. The rig 374 can include an inverted pump 376, a controller 378, a stand 380, a glass collector 382, a voltage converter 386, a blunt tip needle 384 connected to a voltage source, a co-axial cable 388, and a flow hood 390. In particular, the droplet generator set-up included an ES Series 0-100 kV, 20-watt high-voltage power generator (Gamma ES Series, Gamma High Voltage Research, FL, USA) which was connected to the tip of a blunt tipped needle (SAI Infusion Technologies, IL, USA). This needle was attached to a 3 mL Luer-lock syringe (BD, NJ, USA), which was in turn attached to a syringe pump (PHD ULTRA™ Remote Syringe Pump Programmable with Push/Pull Mechanism, Harvard Apparatus, MA, USA). The pump was orientated vertically by connection to a custom made remote stand. For formation of 500-800 μm diameter microspheres, an 18 G blunt tipped needle (SAI Infusion Technologies, IL, USA) was used with an applied voltage between 10-20 kV and a fluid flow rate of 0.2 mL/min.

Using this electrostatic droplet generator, microcapsules of SC-β clusters were prepared and cross-linked in a bath of 20 mM barium chloride. Supernatant from the settled microcapsules was discarded and the microcapsules were washed three times in CMRL 1066 media containing human albumin, ITS and antibiotics to remove excess barium. Microcapsules containing the SC-β clusters, one to two per microcapsule, were then sorted and placed in fresh CMRL 1066 medium and placed into culture until use. The Young's modulus of these micro-encapsulated spheres is in the range of between about 5 and about 10 kPa.

For glucose stimulated insulin secretion testing, microencapsulated SC-β clusters were washed with Krebs (Krb) buffer and were then pre-incubated in low (3.3 mM) glucose Krb for 1 hour to remove residual insulin. Microencapsulated clusters were washed two times in low glucose Krb, incubated in low-glucose Krb for 30 min, and the supernatant was collected. The microencapsulated islet cell clusters were then washed two times in low glucose Krb, incubated in (16.7 mM) high glucose Krb for 30 min, and the supernatant was collected. Finally, clusters were incubated in Krb containing 3.3 mM glucose and 30 mM KCl (depolarization challenge) for 30 min and then the supernatant was collected. Supernatant samples containing secreted insulin were processed using the Human Ultrasensitive Insulin ELISA (ALPCO Diagnostics).

The viability of microencapsulated SC-β clusters was assessed using a fluorescent LIVE/DEAD Cytotoxity Assay kit (Molecular Probes, Thermo Fisher Scientific). Specifically, 2 μM calcein AM and 4 μM ethidium homodimer-1 (EthD-1) solutions were employed to visualize the distribution of living and dead cells respectively.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

We claim:

1. A system, comprising:
   a housing including a first housing portion and a second housing portion forming a chamber therebetween, the housing including:
      an inlet for introduction of a medium into the system,
      an inlet channel fluidically connecting the inlet with the chamber,
      an outlet, and
      an outlet channel fluidically connecting the chamber with the outlet; and
   a cartridge configured to be disposed within the chamber, the cartridge including:
      a cartridge body having a first top surface and a second bottom surface facing away from the first top surface, the cartridge body defining a first plurality of channels disposed in the cartridge, each channel of the first plurality of channels extending through the cartridge body from the first top surface to the second bottom surface of the cartridge body; and
      at least one porous element disposed adjacent to the second bottom surface of the cartridge body at the first plurality of channels, the at least one porous element and the first plurality of channels forming a plurality of wells disposed in the cartridge, each well configured to hold one or more biological cells;
   wherein the housing and the cartridge are configured such that when the cartridge is disposed within the housing and a medium is introduced into the inlet, the medium flows through the inlet channel and into the chamber, and at least a first portion of the medium flows laterally in the chamber between the first top surface of the cartridge body and a chamber wall formed by a surface of the first housing portion opposite the first top surface of the cartridge body to the first plurality of channels, flows into the plurality of wells, through the first plurality of channels, past the second surface of the cartridge body, and out of the plurality of wells through the at least one porous element, and then flows through the outlet channel of the housing to the outlet of the housing.

2. The system of claim 1, wherein the outlet channel connects with a central portion of the chamber,
   wherein the cartridge body has a peripheral portion and a central portion that is disposed in the central portion of the chamber when the cartridge is held in the housing, and
   wherein the first plurality of channels are disposed in the peripheral portion of the cartridge body; and
   wherein the cartridge body and housing are configured such that when the cartridge is disposed within the housing and the medium is introduced into the inlet, the medium flows through the inlet channel and into the central portion of the chamber, and at least the first portion of the medium flows radially outward in the chamber between the first top surface of the cartridge body and the chamber wall formed by the surface of the first housing portion opposite the first top surface of the cartridge body from the central portion of the cartridge body to the first plurality of channels, flows into the plurality of wells, through the first plurality of channels, past the second surface of the cartridge body, and out of the plurality of wells through the at least one porous element, and then flows through the outlet channel of the housing to the outlet of the housing.

3. The system of claim 1, wherein the cartridge body further defines a second plurality of channels extending through the cartridge body from the first top surface to the second bottom surface of the cartridge body.

4. The system of claim 1, wherein the housing and the cartridge are configured such that when at least the first portion of the medium flows laterally in the chamber between the first top surface of the cartridge body and the chamber wall formed by the surface of the first housing portion opposite the first top surface of the cartridge body to the first plurality of channels, the medium flows into each of the first plurality of channels at substantially the same time.

5. A system, comprising:
   a housing including a first housing portion and a second housing portion forming a chamber therebetween, the housing including:
      an inlet for introduction of a medium into the system,
      an inlet channel fluidically connecting the inlet with the chamber,
      an outlet, and
      an outlet channel fluidically connecting the chamber with the outlet; and
   a cartridge configured to be disposed within the chamber, the cartridge including:
      a cartridge body having a first top surface and a second bottom surface facing away from the top surface, the first top surface defining a plurality of wells formed by a plurality of depressions in the first top surface, each well configured to hold one or more biological cells, the cartridge body defining a plurality of outer channels extending through the cartridge body from the first top surface to the second bottom surface of the cartridge body;
   wherein the housing and the cartridge are configured such that when the cartridge is disposed within the housing and a medium is introduced into the inlet, the medium flows through the inlet channel of the housing and into the chamber, and at least a first portion of the medium flows laterally between the first top surface of the cartridge body and a chamber wall formed by a surface of the first housing portion opposite the first top surface of the cartridge body to the plurality of wells, flows down into and up out of the plurality of wells, continues flowing laterally between the first top surface of the cartridge body and the chamber wall on to the plurality of outer channels, flows through the plurality of outer channels and past the second bottom surface of the cartridge body, and then flows through the outlet channel of the housing to the outlet of the housing.

6. The system of claim 5, wherein the outlet channel of the housing connects with a central portion of the chamber,
   wherein the cartridge body has a peripheral portion and a central portion that is disposed in the central portion of the chamber when the cartridge is held in the housing, and wherein the plurality of wells are disposed in the peripheral portion of the cartridge body; and wherein the cartridge body and housing are configured such that when the cartridge is disposed within the housing and the medium is introduced into the inlet, the medium flows through the inlet channel of the housing and into the central portion of the chamber, and at least the first portion of the medium flows radially outward between the first top surface of the cartridge body and the chamber wall from the central portion of the cartridge body to the plurality of wells, flows down into and up out of the first plurality of wells, continues flowing radially outward to the plurality of outer channels, flows through the plurality of outer channels and past the second bottom surface of the cartridge body, and then flows through the outlet channel of the housing to the outlet of the housing.

7. The system of claim 5, further comprising at least one three-dimensional scaffold for culturing pancreatic islet cells, brain tissue cells or adipocytes, the three-dimensional scaffold comprising:
   a first portion of a first non-woven polymeric fiber sheet;
   a second portion of a second non-woven polymeric fiber sheet overlaying the first portion, wherein the first non-woven polymeric fiber sheet and the second non-woven polymer fiber sheet include polymeric fibers comprising a biogenic polymer and a synthetic polymer; and
   pancreatic islet cells, brain tissue cells or adipocytes disposed between the first portion and the second portion;
   wherein at least one of the plurality of wells is configured to hold the three-dimensional scaffold.

8. The system of claim 7, further comprising a solid support for the three-dimensional scaffold, the solid support including:
   a top surface;
   a bottom surface facing away from the top surface; and
   a channel extending through the solid support from the top surface to the bottom surface of the solid support;
   wherein the first portion of the first non-woven polymeric fiber sheet is disposed on the bottom surface of the solid support;
   wherein the second portion of the second non-woven polymeric body is disposed on the top surface of the solid support;
   wherein the pancreatic islet cells, brain tissue cells or adipocytes are disposed in the channel of the solid support; and
   wherein at least one well in the plurality of wells is sized and configured to receive and hold the solid support.

9. A system, comprising:
   a housing including a first housing portion and a second housing portion forming a chamber therebetween, the housing including:
      an inlet for introduction of a medium including one or more biological cells into the system;
      an inlet channel fluidically connecting the inlet with a central portion of the chamber;
      an outlet;
      an outlet channel fluidically connecting the central portion of the chamber with the outlet; and
      a bypass channel fluidically connecting the inlet channel with the outlet channel and bypassing the central portion of the chamber; and
   a cartridge having a central portion and a peripheral portion and configured to be disposed within the chamber with the central portion of the cartridge in the central portion of the chamber, the cartridge including:
      a cartridge body having a first top surface and a second bottom surface facing away from the first top surface, the cartridge body defining a first plurality of channels disposed in the peripheral portion of the cartridge, each channel of the first plurality of channels extending through the cartridge body from the first top surface to the second bottom surface of the cartridge body; and
      at least one porous element disposed adjacent to the second bottom surface of the cartridge body at the first plurality of channels, the at least one porous element and the first plurality of channels forming a plurality of wells disposed in the peripheral portion of the cartridge, each well configured to hold the one or more biological cells;
   wherein the housing and the cartridge are configured such that when the cartridge is disposed within the housing and the medium including the one or more biological cells is introduced into the inlet, (i) at least a first portion of the medium and the one or more biological cells flows through the inlet channel and into the central portion of the chamber, at least one of the one or more biological cells lodges in a well of the plurality of wells, the first portion of the medium flows into the plurality of wells, through the first plurality of channels, past the second bottom surface of the cartridge body, and out of the plurality of wells through the at least one porous element, and then flows through the outlet channel of the housing to the outlet of the housing, and (ii) at least a second portion of the medium and the one or more biological cells flows through at least a portion of the inlet channel and into the bypass channel to bypass the plurality of wells of the cartridge and flows through the outlet channel of the housing to the outlet of the housing.

10. The system of claim 9, wherein the housing and cartridge are configured such that when no cells are disposed in the plurality of wells, a flow resistance of a first flow path from the inlet, through the inlet channel, through the first plurality of channels, out of the wells through the at least one porous element, through the outlet channel, and out the outlet is less than a flow resistance of a second flow path through the inlet, through inlet channel, through the bypass channel, through the outlet channel, and out the outlet.

11. A system, comprising:
   a housing including a first housing portion and a second housing portion forming a chamber therebetween, the housing including:
      an inlet for introduction of a medium including one or more biological cells into the system;
      an inlet channel fluidically connecting the inlet with a central portion of the chamber;
      an outlet;
      an outlet channel fluidically connecting a peripheral portion of the chamber with the outlet; and
      an alternate channel fluidically connecting the inlet channel with the outlet channel; and
   a cartridge having a central portion and a peripheral portion and configured to be disposed within the chamber with the central portion of the cartridge disposed in the central portion of the chamber and the peripheral portion of the cartridge disposed in the peripheral portion of the chamber, the cartridge including:
      a cartridge body having a first top surface and a second bottom surface facing away from the first top surface, the cartridge body defining a first plurality of channels disposed in the peripheral portion of the cartridge, each channel of the first plurality of channels extending through the cartridge body from the first top surface to the second bottom surface of the cartridge body; and at least one porous element disposed adjacent to the second bottom surface of the cartridge body at the first plurality of channels, the at least one porous element and the first plurality of channels forming a plurality of wells disposed in the peripheral portion of the cartridge, each well configured to hold the one or more biological cells;

wherein the housing and the cartridge are configured such that when the cartridge is disposed within the housing and the medium including the one or more biological cells is introduced into the inlet, (i) at least a first portion of the medium and the one or more biological cells flows through the inlet channel of the housing and into the central portion of the chamber, at least one of the one or more biological cells lodges in a well of the plurality of wells, the first portion of the medium flows into the plurality of wells, through the first plurality of channels, past the second bottom surface of the cartridge body, and out of the plurality of wells through the at least one porous element, and then flows through the outlet channel of the housing to the outlet of the housing, and (ii) at least a second portion of the medium and the one or more biological cells flows through the inlet channel into the central portion of the chamber and into the alternate channel to bypass the plurality of wells of the cartridge and flows through the outlet channel of the housing to the outlet of the housing.

12. The system of claim 1, wherein each channel of the plurality of first channels extends through the cartridge body parallel to a normal of the first top surface from the first top surface to the second bottom surface.

13. A method for culturing cells in a system, comprising:
providing the system of claim 1;
disposing one or more cells for culturing in at least one of the plurality of wells of the cartridge and disposing the cartridge in the chamber of the housing; and
providing suitable culture conditions and circulating a suitable culture medium through the system, thereby culturing the one or more cells.

14. A method for identifying a compound that modulates cell differentiation, cell viability, and/or cell function, the method comprising:
providing the system of claim 1 further comprising cells disposed in at least one of the plurality of wells of the cartridge;
contacting the cells with a test compound; and
determining the effect of the test compound on cell differentiation, cell viability, and/or cell function in the presence and absence of the test compound, wherein a modulation of cell differentiation, cell viability, and/or cell function in the presence of said test compound as compared to cell differentiation, cell viability, and/or cell function in the absence of said test compound indicates that said test compound modulates cell differentiation, cell viability, and/or function, thereby identifying a compound that modulates cell differentiation, cell viability, and/or function.

15. A method for identifying a compound useful for treating a disease or disorder, the method comprising:
providing the system of claim 1 further comprising suitable cells disposed in at least one of the plurality of wells of the cartridge;
contacting the cells with a test compound; and
determining the effect of the test compound on cell differentiation, cell viability, and/or cell function in the presence and absence of the test compound, wherein a modulation of cell differentiation, cell viability, and/or cell function in the presence of said test compound as compared to cell differentiation, cell viability, and/or cell function in the absence of said test compound indicates that said test compound modulates cell differentiation, cell viability, and/or function, thereby identifying a compound useful for treating the disease or disorder.

* * * * *